US006713477B1

(12) United States Patent
Scarlato et al.

(10) Patent No.: US 6,713,477 B1
(45) Date of Patent: Mar. 30, 2004

(54) HYDROXAMIC ACID DERIVATIVES

(75) Inventors: Gerard Robert Scarlato, La Jolla, CA (US); Sara Sabina Hadida Ruah, San Diego, CA (US); Tamiki Nishimura, Toyonaka (JP); Masashi Nakatsuka, Osaka (JP); Fumio Samizo, Amagasaki (JP); Yumiko Kamikawa, Nara (JP); Hitoshi Houtigai, Takatsuki (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/959,192

(22) PCT Filed: Apr. 19, 2000

(86) PCT No.: PCT/US00/10383

§ 371 (c)(1),
(2), (4) Date: Nov. 9, 2001

(87) PCT Pub. No.: WO00/63197

PCT Pub. Date: Oct. 26, 2000

Related U.S. Application Data

(60) Provisional application No. 60/129,933, filed on Apr. 19, 2000.

(51) Int. Cl.[7] .................... C07D 227/14; C07D 279/16; C07D 417/04; C07D 417/14; A61K 31/5415
(52) U.S. Cl. ................. 514/224.2; 514/227.5; 514/227.8; 514/228.2; 514/228.5; 514/367; 514/369; 544/47; 544/48; 544/49; 544/58.2; 548/171; 548/187
(58) Field of Search ................. 548/187, 171; 544/58.2, 47, 48, 49; 514/224.2, 227.5, 227.8, 228.2, 228.5, 367, 369

(56) References Cited

U.S. PATENT DOCUMENTS

| 3,873,535 A | 3/1975 | Worley et al. ........... 260/243 R |
| 3,910,904 A | 10/1975 | Worley ....................... 260/245 |
| 3,923,709 A | 12/1975 | Worley ....................... 260/240 |
| 4,584,300 A | 4/1986 | Iwao et al. .................. 514/255 |
| 4,755,509 A | 7/1988 | Teulon ....................... 514/224.2 |
| 4,771,050 A | 9/1988 | Meguro et al. ........... 514/224.2 |
| 5,496,817 A | 3/1996 | Kawashima et al. ..... 514/224.2 |

FOREIGN PATENT DOCUMENTS

| DE | 195 42 189 A | 5/1997 |
| EP | 0 606 046 A | 7/1994 |
| FR | 2 434 150 A | 3/1980 |
| WO | 96 20936 A | 7/1996 |
| WO | 96 33176 A | 10/1996 |

OTHER PUBLICATIONS

Pennington et al. (J. Am. Chem. Soc.; 1953; 75(1); 109–114).*
M. Fujita et al., Synthesis, pp. 599–604, 1988.
J.W. Worley et al., J. Org. Chem., 40(12) pp. 1731–1734 (1975).
H. Tawada et al., Chem. Pharm. Bull., 38(5) pp. 1238–1245 (1990).
G. Trapani et al., IL FARMACO, 50(2) pp. 107–112 (1995).
E.H. Karran et al., Annals of the Rheumatic Diseases, 54, pp. 662–669 (1995).
L.J. Bonassar et al., Arthritis & Rheumatism, 38(11), pp. 1678–1686 (1995).
J.G. Conway et al., J. Exp. Med., 182, pp. 449–457 (1995).
E.M. O'Byrne et al., Inflamm Res 44, Supplement 2, pp. S117–S118 (1995).
E. J. Lewis et al., British Journal of Pharmacology, 121, pp. 540–546 (1997).
G. Taraboletti et al., Journal of the National Cancer Institute, 87(4) pp. 293–298 (Feb. 15, 1995).
A.K. Hewson et al., Inflamm Res 44, pp. 345–349 (1995).

* cited by examiner

*Primary Examiner*—Bruck Kifle
(74) *Attorney, Agent, or Firm*—Birch, Stewart, Kolasch & Birch, LLP

(57) ABSTRACT

A hydroxamic acid derivative represented by formula (1) or a prodrug thereof, or a pharmaceutically acceptable salt thereof, which has a matrix metalo-proteinase inhibitor.

8 Claims, No Drawings

HYDROXAMIC ACID DERIVATIVES

This application is the national phase under 35 U.S.C. §371 of PCT International Application No. PCT/US00/10383 which has an International filing date of Apr. 19, 2000, which designated the United States of America and was published in English and which claims benefit of U.S. Provisional application No. 56/129,933 filed Apr. 19, 1999.

TECHNICAL FIELD

The present invention relates to hydroxamic acid derivatives useful as matrix metallo-proteinase inhibitors.

BACKGROUND ART

Extra cellular matrix, composition of connective tissue, is metabolized by a family of proteinases termed matrix metallo-proteinases. It is known that there exist 16 kinds of matrix metallo-proteinases such as collagenase (matrix metallo-proteinase-1: MMP-1), gelatinase A (matrix metallo-proteinase-2: MMP-2), stromelysin (metallo-proteinase-3: MMP-3), gelatinase B (matrix metallo-proteinase-9: MMP-9) and collagenase-3 (matrix metallo-proteinase-13: MMP-13). Extra cellular matrix is under tight control by the expression and secretion of these matrix metallo-proteinases or endogenous inhibitors such as tissue inhibitor of matrix metallo-proteinases in normal. There are many reports about relationships between diseases characterized by excessive tissue disruption and elevated activities of matrix metallo-proteinases derived form the breakdown of these control.

Elevated levels of matrix metallo-proteinases, particularly collagenase and stromelysin, have been detected in joints of osteoarthritic humans or that of rheumatoid arthritis (Arthr. Rheum., 33, 388–97 (1990); S. M. Krane et. al., "Modulation of matrix synthesis and in The Control of degradation in joint inflammation, The Control of Tissue Damage", A. B. Glauert (ed.), Elsevier Sci. Publ., Amsterdam, 1988, Ch. 14, pp 179–95; Clin. Chim. Acta, 185, 73–80(1989); Arthr. Rheum., 27, 305–312(1984); J. Clin. Invest., 84, 678–685 (1989)).

Secreted proteinases such as stromelysin, collagenase and gelatinase play an important role in processes involved in the movement of cells during metastatic tumor invasion. Indeed, there is also evidence that the matrix metallo-proteinases are overexpressed in certain metastatic tumor cell line. In this context, the enzyme functions to penetrate underlying basement membranes and allow the tumor cell to escape from the site of primary tumor formation and enter circulation (FEBS J., 5, 2145–2154(1991); Trends Genet., 6, 121–125(1990); Cancer Res., 46, 1–7(1986); Cell, 64, 327–336(1990); Cancer and Metastasis Rev., 9, 305–319 (1990)).

Both collagenase and stromelysin activities are observed in fibroblasts isolated from inflamed gingiva (J. Periodontal Res., 16, 417–424(1981)). Enzyme levels have been correlated to the severity of gum disease (J. Periodontal Res., 22, 81–88 (1987)).

Collagenase-3 (matrix metalloproteinase-13: MMP-13) is expressed in synovia of rheumatoid arthritis and chondrocyte of human osteoarthritis (J. Clin. Invest., 97, 2011–2019 (1996); J. Rheumatol., 23, 509–595(1996); J. Biol. Chem., 271, 23577–23581(1996); J. Clin. Invest., 97, 761–768 (1996)). MMP-13 has a strong enzyme activity against type II collagen and aggrecan. Thus, it is suggested that MMP-13 plays an important role in osteoarthritis and rheumatoid arthritis (J. Biol. Chem., 271, 1544–1550(1996); FEBS Lett., 380, 17–20(1996)). Therefore, inhibitors to matrix metallo-proteinase are useful as therapeutic agents or prophylactic drugs for joint diseases such as osteoarthritis, rheumatoid arthritis, metastasis of tumor cell and gingivitis.

Matrix metallo-proteinases are also concerned with conversion from the latent form of tumor necrosis factor-a to the mature form (Nature, 370, 555–557(1994)), degradation of α 1-antitrypsin (FEBS Lett., 279, 191–194(1991)) and processing of other matrix metallo-proteinases (Biochemistry, 29, 10261–10670(1990); J. Biol. Chem., 267, 21712–21719 (1992)). Therefore, inhibitors to matrix metalloproteinase are useful as anti-inflammatory agents.

WO 96/20936 disclose novel thiazolidin-4-one derivatives which inhibit platelet-activating factor and/or 5-lipoxygenase. But, it does not disclose the compounds can inhibit matrix metallo-proteinases.

DESCRIPTION OF THE INVENTION

The present invention is intended to provide novel compounds useful as matrix metallo-proteinase inhibitors.

The present inventors have earnestly examined and found that hydroxamic acid derivatives have excellent inhibition activity against matrix metallo-proteinases such as MMP-3, MMP-13 and the like. Thus, the present invention has been accomplished.

That is, the present invention is as follows:

(1) A hydroxamic acid derivative represented by the formula [1] or a prodrug thereof, or a pharmaceutically acceptable salt thereof:

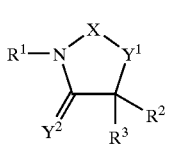

[1]

wherein
X is $C_1$–$C_2$ alkylene which is substituted by optionally substituted alkyl, optionally substituted cycloalkyl, optionally substituted heterocycloalkyl, optionally substituted aryl or optionally substituted heteroaryl; optionally substituted ortho-arylene; or optionally substituted ortho-heteroarylene;

$Y^1$ is —O—, —S—, —S(O)— or —S(O)$_2$—;

$Y^2$ is O, or S;

One of $R^1$ and $R^3$ is —(CHR$^4$)$_n$—(CR$^5$R$^6$)—CO—NHOH;

The other of $R^1$ and $R^3$ is hydrogen, optionally substituted alkyl, or optionally substituted cycloalkyl;

$R^2$ is hydrogen, optionally substituted alkyl, optionally substituted alkenyl, optionally substituted alkynyl, optionally substituted cycloalkyl, or optionally substituted hetero-cycloalkyl; or $R^2$ and $R^3$ may be taken together to be optionally substituted $C_1$–$C_{10}$ alkylidene;

$R^4$, $R^5$ and $R^6$ are independently hydrogen, optionally substituted alkyl, optionally substituted alkenyl optionally substituted alkynyl, optionally substituted alkoxy, optionally substituted alkylthio, optionally substituted cycloalkyl, optionally substituted heterocycloalkyl, optionally substituted aryl, or optionally substituted heteroaryl; or $R^5$ may be joined with $R^4$ or $R^6$ to form, with the carbon atom which they attach, optionally substituted cycloalkane or optionally substituted heterocycloalkane;

n is an integer of 0 to 4;

provided that when $R^2$ and $R^3$ are taken together to be optionally substituted $C_1$–$C_{10}$ alkylidene, X is not methylene substituted by a phenyl or a pyridyl wherein the phenyl and the pyridyl are optionally substituted by methyl or methoxy.

(2) A hydroxamic acid derivative according to (1) or a prodrug thereof, or a pharmaceutically acceptable salt thereof, wherein X is $C_1$–$C_2$ alkylene substituted by —Z—Ar; optionally substituted ortho-arylene; or optionally substituted ortho-heteroarylene;

Z is single bond or alkylene;

Ar is optionally substituted aryl or optionally substituted heteroaryl.

(3) A hydrozamic acid derivative according to (1) or a prodrug thereof, or a pharmaceutically acceptable salt thereof, wherein X is one of the groups represented by the formulae:

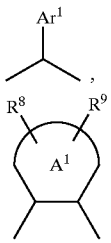

$Ar^1$ is optionally substituted aryl or optionally substituted heteroaryl;

$A^1$ is ortho-phenylene or monocyclic ortho-heteroarylene;

$R^8$ and $R^9$ are independently hydrogen or substituent.

(4) A hydroxamic acid derivative according to any one of (1)–(3) or a prodrug thereof, or a pharmaceutically acceptable salt thereof, wherein $Y^1$ is —S—, —S(O)— or —S(O)$_2$—.

(5) A hydroxamic acid derivative according to any one of (1)–(4) or a prodrug thereof, or a pharmaceutically acceptable salt thereof, wherein n is 0, 1 or 2.

(6) A hydroxamic acid derivative according to any one of (1)–(5) or a prodrug thereof, or a pharmaceutically acceptable salt thereof, wherein n is 0.

(7) A hydroxamic acid derivative according to (1) represented by the formula [2] or a prodrug thereof, or a pharmaceutically acceptable salt thereof:

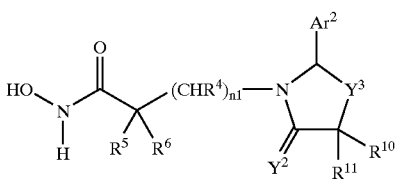

[2]

wherein $Y^2$, $R^4$, $R^5$ and $R^6$ are as defined in (1);

$Ar^2$ is optionally substituted phenyl; optionally substituted naphthyl; or optionally substituted mono or bicyclic heteroaryl;

$Y^3$ is —S—, —S(O)— or —S(O)$_2$—;

$R^{10}$ and $R^{11}$ are independently hydrogen or optionally substituted alkyl;

n1 is an integer of 0, 1 or 2.

(8) A hydroxamic acid derivative according to (7) or a prodrug thereof, or a pharmaceutically acceptable salt thereof, wherein n1 is 0.

(9) A hydroxamic acid derivative according to (1) represented by the formula [3] or a prodrug thereof, or a pharmaceutically acceptable salt thereof:

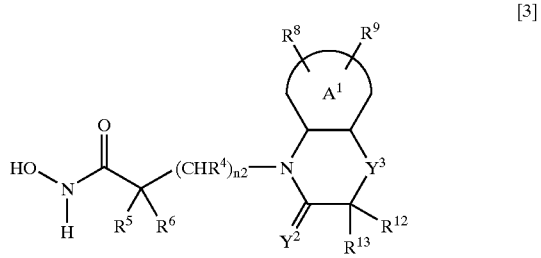

[3]

wherein $Y^2$, $R^4$, $R^5$ and $R^6$ are as defined in (1);

$A^1$, $R^8$, and $R^9$ are defined in (3);

$R^{12}$ and $R^{13}$ are independently hydrogen or optionally substituted alkyl;

$Y^3$ is —S—, —S(O)— or —S(O)$_2$—;

n2 is an integer of 0, 1 or 2.

(10) A hydroxamic acid derivative according to (1) represented by the formula [3'] or a prodrug thereof, or a pharmaceutically acceptable salt thereof:

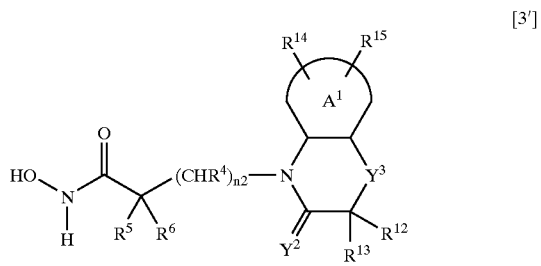

[3']

wherein $Y^2$, $R^4$, $R^5$ and $R^6$ are as defined in (1);

$A^1$ is defined in (3);

$Y^3$, n2, $R^{12}$ and $R^{13}$ are defined in (9);

$R^{14}$ is hydrogen or substituent;

$R^{15}$ is substituent.

(11) A hydroxamic acid derivative according to (9)–(10) or a prodrug thereof or a pharmaceutically acceptable salt thereof;

wherein n2 is 0, and $R^{12}$ and $R^{13}$ are independently hydrogen or substituted alkyl group.

(12) A hydroxamic acid derivative according to any one of claim 1–11 or a prodrug thereof, or a pharmaceutically acceptable salt thereof, wherein $Y^2$ is —O—.

(13) A pharmaceutical composition containing a hydroxamic acid derivative according to any one of (1)–(12) or a prodrug thereof, or a pharmaceutically acceptable salt thereof, and a pharmaceutically acceptable carrier or diluent.

(14) A method of inhibiting matrix metallo-proteinases which comprises treating the matrix metallo-proteinases with a hydroxamic acid derivative according to any one of (1)–(12) or a prodrug thereof, or a pharmaceutically acceptable salt thereof.

(15) A method of inhibiting matrix metallo-proteinases according to (14), wherein the matrix metallo-proteinases are matrix metallo-proteinase 3 and/or 13.

(16) A method of treating a disease associated with excess or undesired matrix metallo-proteinases which comprises administering an effective amount of a hydroxamic acid derivative according to any one of (1)–(12) or a prodrug thereof, or a pharmaceutically acceptable salt thereof, and a pharmaceutically acceptable carrier or diluent.

(17) A method of treating a disease associated with excess or undesired matrix metallo-proteinases according to (16), wherein the matrix metallo-proteinases are matrix metallo-proteinase 3 and/or 13.

(18) Use of a hydroxamic acid derivative according to any one of (1)–(12) or a prodrug thereof, or a pharmaceutically acceptable salt thereof, in the preparation of a medicament for treating a disease associated with excess or undesired matrix metallo-proteinases.

"Ortho-arylene" includes $C_6-C_{10}$ ortho-arylene. Typical examples are ortho-phenylene, 1,2-naphthalenediyl, 2,3-naphthalenediyl and the like. Preferable is ortho-phenylene.

"Ortho-heteroarylene" includes mono or bicyclic 5- or 6-membered ortho-heteroarylene containing 1 to 3 atoms selected independently from nitrogen atoms, sulfur atoms and oxygen atoms. Mono or bicyclic 5-membered ortho-heteroarylene includes, for example, monocyclic 5-membered ortho-heteroarylene containing 1 to 3 atoms selected independently from nitrogen atoms, sulfur atoms and oxygen atoms such as pyrrol-2,3-diyl, pyrrol-3,4-diyl, thiophen-2,3-diyl, thiophen-3,4-diyl, furan-2,3-diyl, imidazol-4,5-diyl, pyrazol-3,4-diyl, thiazol-2,3-diyl, oxazole-2,3-diyl, isothiazol-3,4-diyl, isoxazol-3,4-diyl and the like; bicyclic 5-membered ortho-heteroarylene containing 1 or 2 atoms selected independently from nitrogen atoms, sulfur atoms and oxygen atoms such as indol-2,3-diyl, benzofurandiyl, benzothiophendiyl and the like; and the like. Mono or bicyclic 6-membered ortho-heteroarylene includes, for example, monocyclic 6-membered ortho-heteroarylene containing 1 to 3 nitrogen atoms such as pyridin-2,3-diyl, pyridin-3,4-diyl, pyrazin-2,3-diyl, pyrimidin-4,5-diyl, pyridazin-3,4-diyl and the like; bicyclic 6-membered ortho-heteroarylene containing 1 to 3 nitrogen atoms such as quinolin-2,3-diyl, isoquinolin-3,4-diyl, naphthyridin-3,4-diyl, quinoxalin-2,3-diyl and the like; and the like. Preferable ortho-heteroarylene is monocyclic 5, or 6-membered ortho-heteroarylene.

"Aryl" includes $C_6-C_{10}$ aryl. Typical examples are phenyl, 1-naphthyl, 2-naphthyl and the like.

"Heteroaryl" includes, for example, mono or bicyclic 5- or 6-membered heteroaryl containing 1 to 5 atoms selected independently from nitrogen atoms, sulfur atoms and oxygen atoms, and the like. Mono or bicyclic 5-membered heteroaryl includes, for example, monocyclic 5-membered heteroaryl containing 1 to 5 atoms selected independently from nitrogen atoms, sulfur atoms and oxygen atoms such as pyrrolyl, thienyl, furyl, imidazolyl, pyrazolyl, isothiazolyl, isoxazolyl, furazanyl, oxazolyl, thiazolyl, triazolyl, tetrazolyl, and the like; bicyclic 5-membered heteroaryl containing 1 to 5 atoms selected independently from nitrogen atoms, sulfur atoms and oxygen atoms such as indolyl, isoindolyl, benzofuryl, benzothienyl, thieno[2,3-b]thienyl and the like; and the like. Mono or bicyclic 6-membered heteroaryl includes, for example, monocyclic 6-membered heteroaryl containing 1 to 5 nitrogen atoms such as pyridyl, pyrazinyl, pyrimidinyl, pyridazinyl, triazinyl and the like; bicyclic 6-membered heteroaryl containing 1 to 5 nitrogen atoms such as quinolyl, phthalazinyl, isoquinolyl, naphthyridinyl, quinoxalinyl and the like; and the like.

"Substituent" of the substituted aryl, the substituted heteroaryl, the substituted ortho-arylene and substituted ortho-heteroarylene, and "substituent" of $R^8$, $R^9$, and $R^{14}$ includes, for example, the following groups:

halogen; alkyl; alkenyl; alkynyl; halogenated alkyl; $-Z^1-Ar^3$; $-Z^1-Cy^1$; $-Z^1-N(Q^2)Q^1$; $-Z^1-N(Q^2)Ar^3$; $-Z^1-N(Q^2)Cy^1$; $-Z^1-NQ^4-C(NQ^3)N(Q^2)Q^1$; $-Z^1-NQ^4-C(NQ^3)N(Q^2)Ar^3$; $-Z^1-NQ^4-C(NQ^3)N(Q^2)Cy^1$; $-Z^1-NQ^3-CON(Q^2)Q^1$; $-Z^1-NQ^3-CON(Q^2)Ar^3$; $-Z^1-NQ^3CON(Q^2)Cy^1$; $-Z^1-NQ^2-COOQ^1$; $-Z^1-NQ^2-COOAr^3$; $-Z^1-NQ^2-COOCy^1$; $-Z^1-OCON(Q^1)Q^2$; $-Z^1-OCON(Q^2)Ar^3$; $-Z^1-OCON(Q^2)Cy^1$; $-Z^1-OCOOQ^1$; $-Z^1-OCOOAr^3$; $-Z^1-OCOOCy^1$; $-Z^1-NQ^2-COQ^1$; $-Z^1-NQ^2-COAr^3$; $-Z^1-NQ^2-COCy^1$; $-Z^1-NQ^2-SOQ^1$; $-Z^1-NQ^2-SOAr^3$; $-Z^1-NQ^2-SOCy^1$; $-Z^1-NQ^2-SO_2Q^1$; $-Z^1-NQ^2-SO_2Ar^3$; $-Z^1-NQ^2-SO_2Cy^1$; $-Z^1-OQ^1$; $-Z^1-OAr^3$; $-Z^1-O-Cy^1$; $-Z^1-OCOQ^1$; $-Z^1-OCOAr^3$; $-Z^1-OCOCy^1$; $-Z^1-COOQ^1$; $-Z^1-COOAr^3$; $-Z^1-COOCy^1$; $-Z^1-CON(Q^1)Q^2$; $-Z^1-CON(Q^2)Ar^3$; $-Z^1-CON(Q^2)Cy^1$; $-Z^1-CON(Q^2)OQ^1$; $-Z^1-CON(Q^2)OAr^3$; $-Z^1-CON(Q^2)OCy^1$; $-Z^1-COQ^1$; $-Z^1-COAr^3$; $-Z^1-CO-Cy^1$; $-Z^1-C(NQ^3)N(Q^1)Q^2$; $-C(NQ^3)N(Q^2)Ar^3$; $-Z^1-C(NQ^3)N(Q^2)Cy^1$; $-Z^1-SQ^1$; $-Z^1-SAr^3$; $-Z^1-S-Cy^1$; $-Z^1-SOQ^1$; $-Z^1-SOAr^3$; $-Z^1-SOCy^1$; $-Z^1-SO_2Q^1$; $-Z^1-SO_2Ar^3$; $-Z^1-SO_2Cy^1$; $-Z^1-SON(Q^1)Q^2$; $-Z^1-SON(Q^2)Ar^3$; $-Z^1-SON(Q^2)Cy^1$; $-Z^1-SO_2N(Q^1)Q^2$; $-Z^1-SO_2N(Q^2)Ar^3$; $-Z^1-SO_2N(Q^2)Cy^1$; $-Z^1-SO_3H$; $-Z^1-OSO_3H$; $-Z^1-NO_2$; $-Z^1-CN$; $-CHO$;

wherein $Z^1$ is single bond, alkylene, alkenylene or alkynylene; $Q^1$, $Q^2$, $Q^3$, $Q^4$ are independently hydrogen, alkyl, alkenyl, alkynyl, wherein the alkyl, the alkenyl and the alkynyl are optionally substituted by one or more groups selected from the following groups:

halogen; $-Ar^4$; $Cy^2$; $-N(R^{21})R^{22}$; $-N(R^{22})Ar^4$; $-N(R^{22})Cy^2$; $-NR^{24}-C(NR^{23})N(R^{22})R^{21}$; $-NR^{24}-C(NR^{23})N(R^{22})Ar^4$; $-NR^{24}-C(NR^{23})N(R^{22})Cy^2$; $-NR^{23}-CON(R^{22})R^{21}$; $-NR^{23}-CON(R^{22})Ar^4$; $-NR^{23}-CON(R^{22})Cy^2$; $-NR^{22}-COOR^{21}$; $-NR^{22}-COOAr^4$; $-NR^{22}-COOCy^2$; $-OCON(R^{22})R^{21}$; $-OCON(R^{22})Ar^4$; $-OCON(R^{22})Cy^2$; $-OCOOR^{21}$; $-OCOOAr^4$; $-OCOOCy^2$; $-NR^{22}-COR^{21}$; $-NR^{22}-COAr^4$; $-NR^{22}-COCy^2$; $-NR^{22}-SOR^{21}$; $-NR^{22}-SOAr^4$; $-NR^{22}-SOCy^2$; $-NR^{22}-SO_2R^{21}$; $-NR^{22}-SO_2Ar^4$; $-NR^{22}-SO_2Cy^2$; $-OR^{21}$; $-OAr^4$; $-OCy^2$; $-OCOR^{21}$; $-OCOAr^4$; $-OCOCy^2$; $-COOR^{21}$; $-COOAr^4$; $-COOCy^2$; $CON(R^{21})R^{22}$; $-CON(R^{22})Ar^4$; $-CON(R^{22})Cy^2$; $-CON(R^{22})OR^{21}$; $-CON(R^{22})OAr^4$; $-CON(R^{22})OCy^2$; $-COR^{21}$; $-COAr^4$; $-COCy^2$; $-SR^{21}$; $-SAr^4$; $-SCy^2$; $-SOR^{21}$; $-SOAr^4$; $-SOCy^2$; $-SO_2R^{21}$; $-SO_2Ar^4$; $-SO_2Cy^2$; $-SON(R^{22})R^{21}$; $-SON(R^{22})Ar^4$; $-SON(R^{22})Cy^2$; $-SO_2N(R^{22})R^{21}$; $-SO_2N(R^{22})Ar^4$; $-SO_2N(R^{22})Cy^2$; $-SO_3H$; $-OSO_3H$; $-NO_2$; $-CN$; $-CHO$;

or $Q^1$ may be Jointed with $Q^2$ or $Q^3$ to form, with the carbon atom which they attach, optionally substituted heterocycloalkane.

$R^{21}$, $R^{22}$, $R^{23}$, $R^{24}$, $R^{25}$, $R^{26}$, $R^{27}$, and $R^{28}$ are independently hydrogen, alkyl, alkenyl, alkynyl, or $R^{21}$ may be jointed with $R^{23}$, $R^{24}$ to form, with the carbon atom which they attach, heterocycloarlkane, or $R^{25}$ may be jointed with $R^{26}$, $R^{27}$ to form, with the carbon atom which they attach, heterocycloarlkane.

$Ar^3$ and $Ar^4$ are independently phenyl or heteroaryl, wherein the phenyl and the heteroaryl are optionally substituted by one or two groups selected from the following groups:

halogen; alkyl; alkenyl; alkynyl; halogenated alkyl; $-Z^2-N(R^{25})R^{26}$; $-Z^2-NR^{28}-C(NR^{27})N(R^{26})R^{25}$; $-Z^2-NR^{27}-CON(R^{26})R^{25}$; $-Z^2-NR^{26}-COR^{25}$; $-Z^2-OCON(R^{26})R^{25}$; $-Z^2-NR^{26}COR^{25}$; $-Z^2-NR^{26}SOR^{25}$; $-Z^2-NR^{26}-SO_2R^{25}$; $-Z^2-OR^{25}$; $-Z^2-COOR^{25}$; $-Z^2-OCOR^{25}$; $-Z^2-OCOOR^{25}$; $-Z^2-CON(R^{26})R^{25}$; $-Z^2-CON(R^{26})OR^{25}$; $-Z^2-COR^{25}$; $-Z^2-C(NR^{27})N(R^{26})R^{25}$; $-Z^2-SR^{25}$; $-Z^2-SOR^{25}$; $-Z^2-SO_2R^{25}$; $-Z^2-SON(R^{25})R^{26}$; $-Z^2-SO_2N(R^{26})R^{25}$; $-Z^2-SO_3H$; $-Z^2-OSO_3H$; $-Z^2-NO_2$; $-Z^2-CN$; $-CHO-O-CH_2-O-$; $-O-CH_2-CH_2-O-$; $-O-CH_2-CH_2-$, $-CH_2-CH_2-O-CO-$, $-CH_2-O-CO-$:

$Z^2$ is single bond, alkylene, alkenylene or alkynylene;

$Cy^1$ and $Cy^2$ are independently cycloalkyl, cycloalkenyl, heterocycloalkyl, or heterocycloalkenyl, wherein the cycloalkyl, the cycloalkenyl, the heterocycloalkyl, and the heterocycloalkenyl are optionally substituted by one or two groups which are the same as the substituent of the substituted phenyl as used in $Ar^3$ or $Ar^4$.

"Substituents" of $R^8$ and $R^9$ may also selected from the following groups:
$-O-CH_2-O-$; $-O-CH_2-CH_2-O-$; $-O-CH_2-CH_2-$, $-CH_2-CH_2-O-CO-$, $-CH_2-O-CO-$.

"Substituent" of $R^{15}$ includes, for example, the following groups:

$-Z^1-Ar^{3'}$; $-Z^1-Cy^{1'}$; $-Z^1-N(Q^1)Q^2$; $-Z^1-N(Q^2)Ar^3$; $-Z^1-N(Q^2)Cy^1$; $-Z^1-NQ^4-C(NQ^3)N(Q^2)Q^1$; $-Z^1-NQ^4-C(NQ^3)N(Q^2)Ar^3$; $-Z^1-NQ^4-C(NQ^3)N(Q^2)Cy^1$; $-Z^1-NQ^3-CON(Q^2)Q^1$; $-Z^1-NQ^3-CON(Q^2)Ar^3$; $-Z^1-NQ^3-CON(Q^2)Cy^1$; $-Z^1-NQ^2-COOQ^1$; $-Z^1-NQ^2-COOAr^3$; $-Z^1-NQ^2-COOCy^1$; $-Z^1-OCON(Q^1)Q^2$; $-Z^1-OCON(Q^2)Ar^3$; $-Z^1-OCON(Q^2)Cy^1$; $-Z^1-NQ^2-COQ^1$; $-Z^1-NQ^2-COAr^3$; $-Z^1-NQ^2-COCy^1$; $-Z^1-NQ^2-SOQ^1$; $-Z^1-NQ^2-SOAr^3$; $-Z^1-NQ^2-SOCy^1$; $-Z^1-NQ^2-SO_2Q^1$; $-Z^1-NQ^2SO_2Ar^3$; $-Z^1-NQ^2-SO_2Cy^1$; $-Z^1-OQ^{1'}$; $-Z^1-OCOQ^1$; $-Z^1-OCOAr^3$; $-Z^1-OCOCy^1$; $-Z^1-OCOOQ^1$; $-Z^1-OCOOAr^3$; $-Z^1-OCOOCy^1$; $-Z^1-COOQ^1$; $-Z^1-COOAr^3$; $-Z^1-COOCy^1$; $-Z^1-CON(Q^1)Q^2$; $-Z^1-CON(Q^2)Ar^3$; $-Z^1-CON(Q^2)Cy^1$; $-Z^1-CON(Q^1)OQ^2$; $-Z^1-CON(Q^2)OQ^2$; $-Z^1-CON(Q^2)OAr^3$; $-Z^1-CON(Q^2)OCy^1$; $-Z^1-COQ^1$; $-Z^1-COAr^3$; $-Z^1-CO-Cy^1$; $-Z^1-C(NQ^3)N(Q^1)Q^2$; $-Z^1-C(NQ^3)N(Q^2)Ar^3$; $-Z^1-C(NQ^3)N(Q^2)Cy^1$; $-Z^1-SQ^{1'}$; $-Z^1-SOQ^1$; $-Z^1-SOAr^3$; $-Z^1-SOCy^1$; $-Z^1-SO_2Q^1$; $-Z^1-SO_2Ar^3$; $-Z^1-SO_2Cy^1$; $-Z^1-SON(Q^1)Q^2$; $-Z^1-SON(Q^2)Ar^3$; $-Z^1-SON(Q^2)Cy^1$; $-Z^1-(Q^1)Q^2$; $-Z^1-SO_2N(Q^2)Ar^3$; $-Z^1-SO_2N(Q^2)-Cy^2$; $-CHO$;

wherein $Q^1$, $Q^2$, $Q^3$, $Q^4$, $R^{21}$, $R^{22}$, $R^{23}$, $R^{24, Z1}$, $Ar^3$, $Ar^4$, $Cy^1$ and $Cy^2$ are defined above.

$Q^{1'}$ is hydrogen, alkyl, alkenyl, or alkynyl, wherein the alkyl, alkenyl, and alkynyl are substituted by one or more groups selected from the following groups:
$-Ar^{4'}$; $-Cy^2$; $-N(R^{21})R^{22}$; $-N(R^{22})Ar^4$; $-N(R^{22})Cy^2$; $-NR^{24}-C(NR^{23})N(R^{22})R^{21}$; $-NR^{24}-C(NR^{23})N(R^{22})Ar^4$; $-NR^{24}-C(NR^{23})N(R^{22})Cy^2$; $-NR^{23}-CON(R^{22})R^{21}$; $-NR^{23}-CON(R^{22})Ar^4$; $-NR^{23}-CON(R^{22})Cy^2$; $-NR^{22}-COOR^{21}$; $-NR^{22}-COOAr^4$; $-NR^{22}-COOCy^2$; $-OCONR^{21}$; $-OCONAr^4$; $-OCONCy^2$; $-NR^{22}-COR^{21}$; $-NR^{22}-COAr^4$; $-NR^{22}-COCy^2$; $-NR^{22}-SOR^{21}$; $-NR^2-SOAr^{4}$; $-NR^{22}-SOCy^2$; $-NR^{22}-SO_2R^{21}$; $-NR^{22}-SO_2Ar^4$; $-NR^{22}-SO_2Cy^2$; $-OCOR^{21}$; $-OCOAr^4$; $-OCOCy^2$; $-COOR^{21}$; $COOAr^4$; $-COOCy^2$; $-OCOOR^{21}$; $-OCOOAr^4$; $OCOOCy^2$; $-CON(R^{21})R^{22}$; $-CON(R^{22})Ar^4$; $-CON(R^{22})Cy^2$; $-CON(R^{22})OR^{21}$; $-CON(R^{22})OAr^4$; $-CON(R^{22})OCy^2$; $-COR^{21}$; $-COAr^4$; $-COCy^2$; $-SOR^{21}$; $-SOAr^4$; $-SOCy^2$; $-SO_2R^{21}$; $-SO_2Ar^4$; $-SO_2Cy^2$; $-SON(R^{22})R^{21}$; $-SON(R^{22})Ar^4$; $-SON(R^2)Cy^2$; $-SO_2N(R^{22})R^{21}$; $-SO_2N(R^{22})Ar^4$; $-SO_2(R^{22})Cy^2$; $-CN$; $-CHO$; $-OH$; $-SH$ $Ar^{3'}$ and $Ar^{4'}$ are heteroaryl, wherein the heteroaryl are optionally substituted by one or two groups which are the same as the substituent of the substituted phenyl as used in $Ar^3$ or $Ar^4$.

$Cy^{1'}$ and $Cy^{2'}$ are heterocycloalkyl or heterocycloalkenyl, wherein the heterocycloalkyl and the heterocycloalkenyl is optionally substituted by one or two groups which are the same as the substituent of the substituted phenyl as used in $Ar^3$ or $Ar^4$.

The number of "substituent" of the substituted aryl, the substituted heteroaryl, the substituted ortho-arylene and substituted ortho-heteroarylene, and the number of "substituent" of $R^8$, $R^9$, $R^{14}$ and $R^{15}$ are one, two or three, preferably one or two.

"Alkyl" includes straight or branched $C_1$–$C_6$ alkyl. Typical examples are methyl, ethyl, propyl, 2-methylethyl, butyl, 2-methylpropyl, 1-methylpropyl, 1,1-dimethylethyl, 2,2-dimethylpropyl, pentyl, hexyl and the like.

"Halogenated alkyl" includes straight or branched $C_1$–$C_6$ alkyl substituted by one or more of halogens. Typical examples are trifluoromethyl, pentafluoroethyl, 2-chloroethyl, 3-bromopropyl, 5-fluoropentyl, 4-iodohexyl and the like.

"Alkoxy" includes straight or branched $C_1$–$C_6$ alkoxy. Typical examples are methoxy, ethoxy, propoxy, 2-methylethoxy, butoxy, 2-methylpropoxy, 1-methylpropoxy, 1,1-dimethylethoxy, 2,2-dimethylpropoxy, pentyloxy, hexyloxy, and the like.

"Alkylthio" includes straight or branched $C_1$–$C_6$ alkylthio. Typical examples are methylthio, ethylthio, propylthio, 2-methylethylthio, butylthio, 2-methylpropylthio, 1-methylpropylthio, 1,1-dimethylethlthio; 2,2-dimethylpropylthio, pentylthio, hexylthio, and the like.

"Alkenyl" includes straight or branched $C_2$–$C_6$ alkenyl. Typical examples are vinyl, allyl, 1-propenyl, 2-butenyl and the like.

"Alkynyl" includes straight or branched $C_2$–$C_6$ alkynyl. Typical examples are ethynyl, propargyl, 1-propynyl, 2-butynyl, pentynyl and the like.

"Alkylene" includes straight or branched $C_1$–$C_6$ alkylene. Typical examples are methylene, ethylene, trimethylene, 2-methyltrimethylene, tetramethylene, pentamethylene, hexamethylene and the like.

"Alkenylene" includes straight or branched $C_2$–$C_6$ alkenylene. Typical examples are vinylene, propenylene, 2-butenylene, 2-methyl-2-butenylene, 3-pentenylene, 3-hexenylene and the like.

"Alkynylene" includes straight or branched $C_2$–$C_6$ alkynylene. Typical examples are ethynylene, propynylene, 2-butynylene, 3-pentynylene, 2-methyl-3-pentynylene, 3-hexynylene and the like.

"$C_1$–$C_2$ alkylene" is methylene or ethylene.

"$C_1$–$C_{10}$ alkylidene" includes straight or branched $C_1$–$C_{10}$ alkylidene, preferably straight or branched $C_1$–$C_6$ alkylidene. Typical examples are methylidene, ethylidene, propylidene, butylidene, 2-methylbutylidene, hexylidene, octylidene, nonylidene, decylidene and the like. Preferable is methylidene.

"Cycloalkane" includes $C_3$–$C_8$ cycloalkane, which can be containing 0–2 carbonyl group. Typical examples are cyclopropane, cyclobutane, cyclopentane, cyclohexane, cycloheptane, cyclooctane, cyclohexanone and the like.

"Heterocycloalkane" includes, for example, 5- or 6-membered heterocycloalkane containing 1 to 3 atoms selected independently from nitrogen atoms, sulfur atoms and oxygen atoms, and the like. The sulfur atoms of "Heterocycloalkane" may be oxidized to form sulfoxide, or sulfone. "Heterocycloalkane" may also be containing 0–2 carbonyl groups. Typical examples of 5-membered heterocycloalkane containing 1 to 3 atoms selected independently from nitrogen atoms, sulfur atoms and oxygen atoms, are pyrrolidine, imidazolidine, pyrazolidine, tetrahydrofuran, tetrahydrothiophene, dioxolane, pyrrolidinone, and the like. Typical examples are 6-membered heterocycloalkane containing 1 to 3 atoms selected independently from nitrogen atoms, sulfur atoms and oxygen atoms, are piperidine, piperazine, morpholine, tetrahydropyrane, dioxane, thiomorpholine, 4-piperidone and the like.

"Cycloalkyl" includes $C_3$–$C_8$ cycloalkyl, which may contain 0–2 carbonyl group. Typical examples are cyclopropyl, cyclobutyl, cyclopentyl, cyclohexyl, cycloheptyl, cyclooctyl, cyclohexanone-4-yl and the like.

"cycloalkenyl" includes $C_3$–$C_8$ cycloalkenyl, which may contain 0–2 carbonyl group. Typical examples are cyclopentenyl, cyclohexenyl, cycloheptenyl, cyclooctenyl, cyclopenten-3-one-yl and the like.

"Heterocycloalkyl" includes, for example, 5- or 6-membered heterocycloalkyl containing 1 to 5 atoms selected independently from nitrogen atoms, sulfur atoms and oxygen atoms, and the like. The sulfur atoms of "Heterocycloalkyl" may be oxidized to form sulfoxide or sulfone. "Heterocycloalkyl" may also be containing 0–2 carbonyl groups. Typical examples are 5-membered heterocycloalkyl containing 1 to 3 atoms selected independently from nitrogen atoms, sulfur atoms and oxygen atoms, are pyrrolidinyl, 2-pyrrolidinone-1-yl, imidazolidinyl, pyrazolidinyl, tetrahydrofuryl, tetrahydrothienyl, diozolanyl and the like. Typical examples are 6-membered heterocycloalkyl containing 1 or 3 atoms selected independently from nitrogen atoms, sulfur atoms and oxygen atoms, are piperidyl, piperazinyl, morpholinyl, tetrahydropyranyl, dioxanyl, thiomorpholinyl, 4-piperidone-1-yl and the like.

"Heterocycloalkenyl" includes, for example, 5- or 6-membered heterocycloalkenyl containing 1 to 5 atoms selected independently from nitrogen atoms, sulfur atoms and oxygen atoms, and the like. The sulfur atoms of "Heterocycloalkenyl" may be oxidized to form sulfoxide or sulfone. "Heterocycloalkenyl" may also be containing 0–2 carbonyl groups. Typical examples are 5-membered heterocycloalkenyl containing 1 to 3 atoms selected independently from nitrogen atoms, sulfur atoms and oxygen atoms, are pyrrolinyl, imidazolinyl, pyrazolinyl, dihydrofuryl, 5-pyrazolone-4-yl and the like. Typical examples are 6-membered heterocycloalkyl containing 1 to 3 atoms selected independently from nitrogen atoms, sulfur atoms and oxygen atoms, are 2,3-dihydropyridyl-, 4-pyridone-1-yl and the like.

"Substituent" of the substituted alkyl, the substituted alkenyl, the substituted alkynyl, the substituted alkoxy, the substituted alkylthio, the substituted cycloalkyl, the substituted heterocycloalkyl, the cycloalkenyl, the substituted heterocycloalkenyl, the substituted cycloalkane, the substituted heterocycloalkane and the substituted $C_1$–$C_{10}$ alkylidene includes, for example, the following groups:

halogen; —$Ar^5$; —$Cy^3$; —$N(Q^5)Q^6$; —$N(Q^6)Ar^5$; —$N(Q^6)Cy^3$; —$NQ^8$—$C(NQ^7)N(Q^6)Q^5$; —$NQ^8$—$C(NQ^7)N(Q^6)Ar^5$; —$NQ^8$—$C(NQ^7)N(Q^6)Cy^3$; —$NQ^7$—$CON(Q^6)Q^5$; —$NQ^6$—$CON(Q^5)Ar^5$; —$NQ^7$—$CON(Q^6)Cy^3$; —$NQ^7$—$COOQ^6$; —$NQ^7$—$COOAr^5$; —$NQ^7$—$COOCy^3$; —$OCON(Q^6)Q^5$; —$OCON(Q^6)Ar^5$; —$OCON(Q^6)Cy^3$; $NQ^6$—$COQ^5$; —$NQ^6$—$COAr^5$; —$NQ^6$—$COCy^3$; —$NQ^6$—$SOQ^5$; —$NQ^6$—$SOAr^5$; —$NQ^6$—$SOCy^3$; —$NQ^6$—$SO_2Q^5$; —$NQ^6$—$SO_2Ar^5$; —$NQ^6$—$SO_2Cy^3$; —$OQ^5$; —$OAr^5$; —$OCy^3$; —$OCOQ^5$; —$OCOAr^5$; —$OCOCy^3$; —$COOQ^5$; —$COOAr^5$; —$COOCy^3$; —$OCOOQ^5$; —$OCOOAr^5$; —$OCOOCy^3$; —$CON(Q^6)Q^5$; —$CON(Q^6)Ar^5$; —$CON(Q^6)Cy^3$; —$CON(Q^6)OQ^5$; —$CON(Q^6)OAr^5$; —$CON(Q^6)OCy^3$; —$COQ^5$; —$COAr^5$; —$COCy^3$; —$SQ^5$; —$SAr^5$; —$SCy^3$; —$SOQ^5$—$SOAr^5$; —$SOCy^3$; —$SO_2Q^5$; —$SO_2Ar^5$; —$SO_2Cy^3$; —$SON(Q^6)Q^5$; —$SON(Q^6)Ar^5$; —$SON(Q^6)Cy^3$; —$SO_2N(Q^6)Q^5$; —$SO_2N(Q^6)Ar^5$; —$SO_2N(Q^6)Cy^3$; —$SO_3H$; —$NO_2$; —$CN$;

wherein $R^{29}$, $R^{30}$, $R^{31}$, and $R^{32}$ are independently hydrogen, alkyl, alkenyl, alkynyl;

$Q^5$, $Q^6$, $Q^7$, and $Q^8$ are independently hydrogen, alkyl, alkenyl and alkynyl wherein the alkyl, the alkenyl and the alkynyl are optionally substituted by one or more groups selected from the following group:

halogen; —$Ar^6$; $Cy^4$; —$N(R^{29})R^{30}$; —$N(R^{30})Ar^6$; —$N(R^{30})Cy^4$; —$NR^{32}$—$C(NR^{31})N(R^{30})R^{29}$; —$NR^{32}$—$C(NR^{31})N(R^{30})Ar^6$; —$NR^{32}$—$C(NR^{31})N(R^{30})Cy^4$; —$NR^{31}$—$CON(R^{30})R^{29}$; —$NR^{31}$—$CON(R^{30})Ar^6$; —$NR^{31}$—$CON(R^{30})Cy^4$; —$NR^{30}$—$COOR^{29}$; —$NR^{30}$—$COOAr^6$; —$NR^{30}$—$COOCy^4$; —$OCON(R^{30})R^{29}$; —$OCON(R^{30})Ar^6$; —$OCON(R^{30})Cy^4$; —$NR^{30}COR^{29}$; —$NR^{30}$—$COAR^6$; —$NR^{30}$—$COCy^4$; —$NR^{30}SOR^{29}$; —$NR^{30}$—$SOAR^6$; —$NR^{30}$—$SOCy^4$; —$NR^{30}$—$SO_2R^{29}$; —$NR^{30}$—$SO_2Ar^6$; —$NR^{30}$—$SO_2Cy^4$; —$OR^{25}$; —$OAr^6$; —$OCy^4$; —$COOR^{29}$; —$COOAr^6$; —$COOCy^4$; —$OCOR^{29}$; —$COAr^5$; —$OCOCy^3$; —$OCOOR^{29}$; —$OCOOAr^6$; —$Z^1$—$OCOOCy^4$; —$CON(R^{30})R^{29}$; —$CON(R^{30})Ar^6$; —$CON(R^{30})Cy^4$; —$CON(R^{30})OR^{29}$; —$CON(R^{30})OAr^6$; —$CON(R^{30})OCy^4$; —$COR^{29}$; —$COAr^6$; —$COCy^4$; —$SR^{29}$; —$SAr^6$; —$SCy^4$; —$SOR^{29}$; —$SOAr^6$; —$SOCy^4$; —$SO_2R^{29}$; —$SO_2Ar^6$; —$SO_2Cy^4$; —$SON(R^{30})R^{29}$; —$SON(R^{30})Ar^6$; —$SON(R^{30})Cy^4$; —$SO_2N(R^{30})R^{29}$; —$SO_2N(R^{30})Ar^6$; —$SO_2N(R^{30})Cy^4$; —$SO_3H$; —$NO_2$; —$CN$;

or $Q^5$ may be jointed with $Q^6$ or $Q^7$ to form, with the carbon atom which they attach, optionally substituted heterocycloalkane.

$Ar^5$ and $Ar^6$ are independently aryl or heteroaryl, wherein the aryl and the heteroaryl are optionally substituted by one or two groups which are the same as the "substituent" of the substituted aryl, the substituted heteroaryl, the substituted ortho-arylene and substituted ortho-heteroarylene, and "substituent" of $R^8$, $R^9$, and $R^{14}$;

$Cy^3$ and $Cy^4$ are independently cycloalkyl, cycloalkenyl, heterocycloalkyl, or heterocycloalkenyl, wherein the cycloalkyl, the cycloalkenyl, the heterocycloalkyl, and the heterocycloalkenyl are optionally substituted by one or two groups which are the same as the substituent of the substituted phenyl as used in $Ar^3$ or $Ar^4$.

The number of "substituent" of substituted alkyl is one to five, preferably one, two, or three.

When $R^1$ is —$(CHR^4)_n$—$(CR^5R^6)$—CO—NHOH in formula 1, —$(CHR^4)_{n1}$—$(CR^5R^6)$—CONHOH in formula 2, —$(CHR^4)_{n2}$—$(CR^5R^6)$—CO—NHOH in formula 3 and 3', and $R^5$ or $R^6$ are 1-substituted alkyl in formula 1, 2, 3, and 3', the substituents of $R^5$ or $R^6$ do not include the following groups:

—CON($Q^6$)$Q^5$; —CON($Q^6$)$Ar^5$; —CON($Q^6$)$Cy^3$—CON($Q^6$)OQ$^5$; —CON($Q^6$)OAr$^5$; —CON($Q^6$)OCy$^3$; —CO—$Q^5$ wherein $Q^5$, $Q^6$, $Ar^5$, and $Cy^3$ are described above.

"Halogen" includes fluorine, chlorine, bromine and iodine. Typical examples are chlorine and fluorine.

The preferable examples of —$(CHR^4)_n$—$(CR^5R^6)$—CO—NHOH as used in one of $R^1$ and $R^3$ in formula 1; —$(CHR^4)_{n1}$—$(CR^5R^6)$—CO—NHOH as used in formula 2; or —$(CHR^4)_{n2}$—$(CR^5R^6)$—CO—NHOH as used in formula 3 are

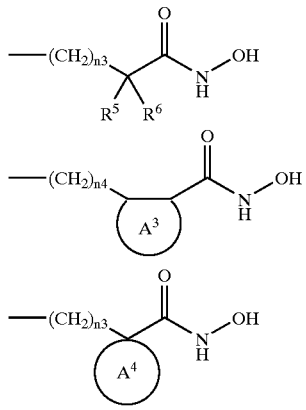

wherein $R^5$ is hydrogen, optionally substituted alkyl, optionally substituted cycloalkyl, and optionally substituted heterocycloalkyl, and more preferably hydrogen or optionally substituted alkyl;

n3 is an integer of 0 to 3; n4 is an integer of 0 to 2, and more preferable n3 and n4 is 0;

$A^3$ is cyclopentane or cyclohexane;

and $A^4$ is cyclopentane, cyclohexane, tetrahydropyrane, piperazine and the like.

The preferable $R^6$ in formula 1, 2, 3, and 3' is hydrogen or $C_1$-$C_3$ alkyl such as methyl, ethyl.

The more preferable example of $R^5$ in formula 2 is the optionally substituted alkyl. The functional groups of the "substituents" of substituted alkyl, such as hydroxy, carboxyl, amino, or thiol, may be protected with typical protective groups described in "protective groups in organic synthesis 2nd edition by W. Greene (John Wiley & Sons, INC.)".

The more preferable $R^5$ in formula 3 and 3' is hydrogen or alkyl such as methyl, ethyl, propyl, and isopropyl.

The preferable examples of the hydroxamic acid derivative represented by formula 1 are (1) the derivatives wherein $R^1$ is —$(CHR^4)_n$—$(CR^5R^6)$—CONHOH; and $R^3$ is hydrogen, or optionally substituted alkyl; and (2) the derivatives wherein $R^1$ is alkyl substituted by a) halogen, b) optionally substituted cycloalkyl, c) optionally substituted aryl, d) optionally substituted heterocycloalkyl or e) optionally substituted heteroaryl; and $R^3$ is —$(CHR^4)_n$—$(CR^5R^6)$—CONHOH;

wherein n, $R^4$, $R^5$, and $R^6$ are as defined above.

The preferable example of $R^2$ in formula 1; $R^{10}$ in formula 2; and $R^{12}$ in formula 3 and 3' are hydrogen or alkyl such as methyl and ethyl.

The preferable examples of the hydroxamic acid derivative represented by formula 2 are the derivatives wherein $R^{11}$ is hydrogen or optionally substituted alkyl, such as methyl, ethyl, propyl or butyl in which the "substituents" are selected from the following group;

—NQ$^6$—COOQ$^5$; —NQ$^6$—COOAr$^5$; —NQ$^6$—COOCy$^3$; —NQ$^6$—COQ$^5$; —NQ$^6$—COAr$^5$; —NQ$^6$—COCy$^3$; —NQ$^6$—SOQ$^5$; —NQ$^6$—SOAr$^5$; —NQ$^6$—SOCy$^3$; NQ$^6$—SO$_2$Q$^5$—; —NQ$^6$—SO$_2$Ar$^5$; —NQ$^6$—SO$_2$Cy$^3$; —COOQ$^5$—; —COOAr$^5$—; —COOCy$^3$—; —CON(Q$^6$)Q$^5$; —CON(Q$^6$)Ar$^5$; —CON(Q$^6$)Cy$^3$; —CON(Q$^6$)OQ$^5$; —CON(Q$^6$)OAr$^5$; —CON(Q$^6$)OCy$^3$; —COQ$^5$; —COAr$^5$; —COCy$^3$; —SO—Q$^5$; —SO—Ar$^5$; —SO—Cy$^3$; —SO$_2$—Q$^5$; —SO$_2$—Ar$^5$; —SO$_2$—Cy$^3$; —SON(Q$^6$)—Q$^5$; SON(Q$^6$)—Ar$^5$; SON(Q$^6$)—Cy$^3$; —SO$_2$N(Q$^6$)—Q$^5$; —SO$_2$N(Q$^6$)—Ar$^5$; —SO$_2$N(Q$^6$)Cy$^3$;

wherein $Ar^5$, $Cy^3$, $Q^5$ and $Q^6$ are described above.

The more preferable "substituents" are selected from the following group;

—COOQ$^5$; —COOAr$^5$; —COOCy$^3$; —CON(Q$^6$)Q$^5$; —CON(Q$^6$)Ar$^5$; —CON(Q$^6$)Cy$^3$; —CON(Q$^6$)OQ$^5$; —CON(Q$^6$)OAr$^5$; —CON(Q$^6$)OCy$^3$; —CO—Q$^5$; —CO—Ar$^5$; —CO—Cy$^3$; —COO—Q$^5$; —COO—Ar$^5$; —COO—Cy$^3$;

wherein $Ar^5$, $Cy^3$, $Q^5$ and $Q^6$ are described above.

The preferable example of the hydroxamic acid derivative represented by formula 3 and 3' are the derivatives wherein $R^{13}$ is optionally substituted alkyl, such as methyl, ethyl, or propyl. The "substituents" are selected from the following groups;

—Ar$^5$; —Cy$^3$; —O—Q$^9$; —OAr$^5$; —N(Q$^5$)Ar$^5$; —S—Q$^9$; —SAr$^5$;

wherein $Ar^5$, $Cy^3$, and $Q^5$ are described above;

$Q^9$ is alkyl, alkenyl or alkynyl wherein the alkyl, the alkenyl and the alkynyl are substituted by one or more groups selected from the following group:

—Ar$^6$; Cy$^4$; —OAr$^6$; —SAr$^6$;

wherein $Ar^6$, and $Cy^4$ are described above;

The preferable $Ar^5$ and $Ar^6$ in $R^{13}$ in formula 3 and 3' are optionally substituted phenyl or optionally substituted monocyclic heteroaryl such as pyridyl, thienyl, furyl and pyrrolyl. The preferable "substituents" are selected from the following groups;

halogen; halogenated alkyl; —$OQ^1$; —$OAr^3$; —$SQ^1$; or —$SAr^3$ wherein $Q^1$ and $Ar^3$ are as defined above.

The preferable positions of the substituents of the substituted phenyl and the substituted monocyclic heteroaryl in $R^{13}$ in formula 3 and 3' are m-position or p-position, especially p-position.

The preferable $Ar^2$ in formula 2 are optionally substituted phenyl, optionally substituted naphthyl, optionally substituted monocyclic heteroaryl, or optionally substituted bicyclic heteroaryl, wherein the "substituents" are selected from the following groups;

halogen, alkyl, halogenated alkyl, —$OQ^1$, —$OAr^3$, —$SQ^1$, —$SAr^3$, —$SOQ^1$, —$SOAr^3$, —$SO_2Q^1$, —$SO_2Ar^3$;

wherein $Ar^3$ and $Q^1$ are defined above.

The preferable positions of the substituent of the substituted phenyl and the substituted monocyclic heteroaryl as used in $Ar^2$ in formula 2 are n-position or p-position, especially p-position. More preferable $Ar^2$ in formula 2 are phenyl or monocyclic heteroaryl.

The preferable A1 in formula 3 and 3' are phenylene or monocyclic hteroarylene, such as pyrazole-3,4-diyl, imidazole-4,5-diyl, and thiophene-2,3-diyl.

When the A1 in formula 3 and 3' is phenylene, the preferable positions of $R^8$ or $R^9$ in formula 3, and $R^{14}$ or $R^{15}$ in formula 3' are 6th and/or 7th positions.

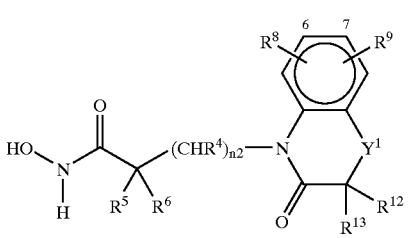

[3]

The hydroxamic acid derivatives can be prepared through three processes:

[A] cyclization process;
[B] substitution process;
[C] process of forming hydroxamic acid group.

The order of three processes may be the same as or different from the order [A], [B] and [C] as long as the hydroxamic acid derivatives can be prepared. And protective groups may be used through these processes to protect functional groups in the hydroxamic acid derivative. Protective groups include well known groups described in "Protective Groups Inorganic Syntheses" 2nd ed. T. W. Greene and P. G. M. Wuts, John Wiley & Sons, Inc. 1991.

[A] Cyclization Process (1) 5-Membered Ring

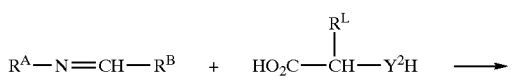

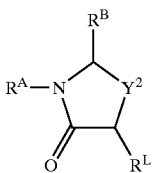

wherein $R^A$, $R^B$ and $R^L$ are independently hydrogen atom or substituent; and $Y^2$ is —O— or —S—.

5-Membered ring can be formed for example by cyclization reaction of imine with mercapto- or hydroxy-carboxylic acid by the same method as ones described in Chem. Rev., Vol.81, 175 (1981). One to 5 equivalents of mercapto- or hydroxy-carboxylic acid per equivalent of the imine is preferably used. In this reaction, dehydration agent such as molecular sieves 3A (MS 3A) or triethyl orthoformate may be added. Reaction solvent includes for example ether such as THF; halogenated hydrocarbon such as chloroform, dichloromethane; amide such as DMF, N-methylpyrrolidone; sulfone or sulfoxide such as tetramethylene solfone, DMSO; hydrocarbon such as benzene, toluene, xylene, heptane, hexane; or mixture thereof. Reaction temperature is usually 50° C. to boiling point of the solvent. The imine can be prepared by a conventional method.

(2) 6-Membered Ring

6-Membered ring can be formed for example by the same methods as ones described in EP 162776 A; Chem. Pharm. Bull., 39, 2888 (1991); ibid., 42, 1264 (1994); ibid., 44, 2055 (1996).

Method 1

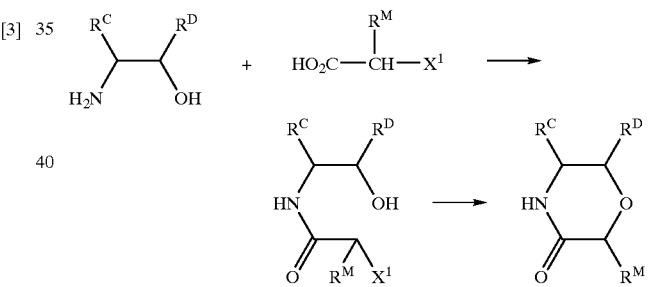

wherein $R^C$, $R^D$ and $R^M$ are independently hydrogen atom or substituent, or $R^C$—C—C—$R^D$ is optionally substituted ortho-arylene or optionally substituted ortho-heteroarylene; and $X^1$ is chlorine, bromine or iodine.

6-Membered ring can be formed by amidation reaction of hydroxy-amine with halo-carboxylic acid or halo-ester, followed by ether formation reaction. Amidation reaction can be performed by a conventional method such as dehydration method, mixed anhydride method, activated ester method and the like ("The Peptides Analysis, Synthesis, Biology", Vol.1, 2, 3, 5, ed. by E. Gross, J. Meinhofer Academic Press (1979)). Dehydration agent used in the dehydration method includes dicyclohexylcarbodiimide, N,N-dimethylaminopropyl-N'-ethylcarbodiimide, 2-ethoxy-1-ethoxycarbonyl-1,2-dihydroquinoline, O-(7-azabenzotriazol-1-yl)-1,1,3,3-tetramethyluronium hexafluorophosphate. Acylation agent used in mixed anhydride method includes isobutyl chloroformate, pivaloyl chloride and the like. Ether formation reaction can be carried out by a conventional method.

Method 2

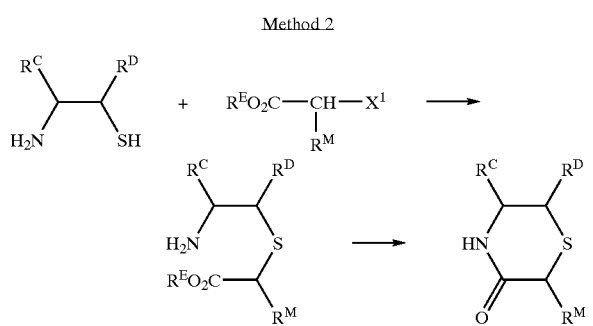

wherein $R^C$, $R^D$, $R^M$ and $X^1$ are as defined above; and $R^E$ is hydrogen or alkyl.

6-Membered ring can be formed by thioether formation reaction of mercaptoamine and halide, followed by amidation reaction. Thioether formation reaction may be performed in the presence of base such as $K_2CO_3$, NaOH and triethylamine. 2-Mercapto-anilines may be commercially available or can be prepared from 2-aminothiazoles, 2-methylthiazoles, or dithiazolium chloride by the same method as one described in Chem. Pharm. Bull., 39, 2888 (1991); ibid, 42, 1264 (1994); ibid, 44, 2055 (1996); J. Chem. Soc., 1948, 870. The amidation reaction can be carried out by heating in the presence of acid such as HCl, HBr, $H_2SO_4$, acetic acid and methanesulfonic acid, or by a conventional method described above.

Method 3

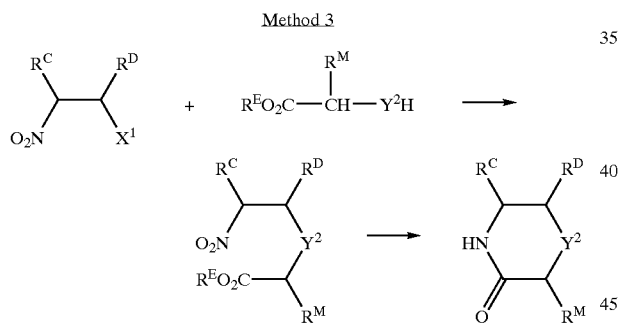

wherein $R^C$, $R^D$, $Y^2$, $R^E$, $R^M$ and $X^1$ are as defined above.

6-Membered ring can be formed by ether or thioether formation reaction of nitrohalide and thiol or alcohol, followed by reduction and amidation reaction. Ether or thioether formation reaction may be performed in the presence of base such as $K_2CO_3$, NaOH and triethylamine. Reduction may be carried out by a conventional method. Amidation reaction may be carried out by heating in the presence of acid or by a conventional method described above.

Method 4

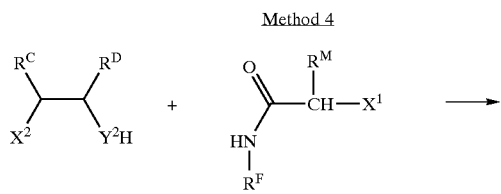

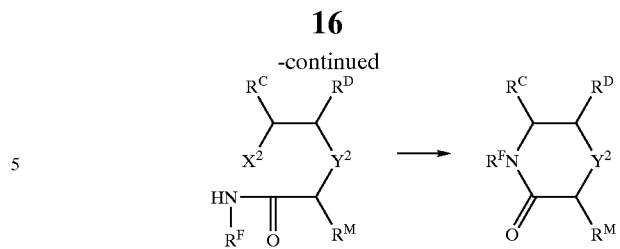

wherein $R^C$, $R^D$, $R^M$, $Y^2$ and $X^1$ are as defined above; and $X^2$ is chlorine, bromine or iodine; and $R^F$ is hydrogen or substituent.

6-Membered ring can be formed by ether or thioether formation reaction of alcohol or thiol and halide, followed by cyclization reaction. Ether or thioether formation reaction can be carried out by the method described above. Cyclization reaction can be performed in the presence of Pd catalyst by the same method as one described in J. Am. Chem. Soc., 119, 8451–8458 (1997). Base such as $Cs_2CO_3$ may be added in this reaction.

[B] Substitution Process (1) Substitution at the Position of $R^1$ in the Formula [1]

Introducing a substituent at the position of $R^1$ in the formula [1] can be performed for example by alkylation. Alkylation may be performed by reacting with corresponding alkyl halide, preferably alkyl iodide or bromide, in the presence of base such as NaH, NaOMe, potassium t-butoxide and $Na_2CO_3$. Reaction solvent is for example ether such as THF; amide such as DMF; sulfoxide such as DMSO or mixture thereof, preferably THF and DMF. Reaction temperature is usually 0° C. to 160° C.

(2) Substitution at the Position of $R^2$ and $R^3$ in the Formula [1]

Introducing substituent(s) at the position of $R^2$ and $R^3$ in the formula [1] can be performed for example by aldol reaction, Wittig reaction, alkylation, Michael reaction and the like.

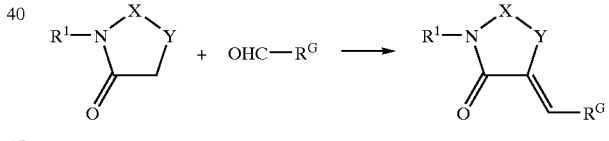

wherein $R^1$, X and Y are as defined above; and $R^G$ is hydrogen or substituent.

Aldol reaction may be performed by reacting with the corresponding aldehyde in the presence of base or acid (J. Med. Chem., 20, 729 (1977), EP 657444 (A), JP 7-233155 (A)).

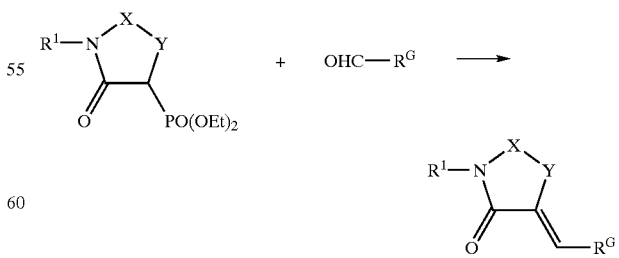

wherein $R^1$, X, Y and $R^G$ are as defined above.

Wittig reaction may be performed by reacting with the corresponding aldehyde (J. Org. Chem., 40, 1731 (1975), U.S. Pat. No. 3,873,535, U.S. Pat. No. 3,923,709).

(2) Introduction of Sulfoxide and Sulfone

Introduction of sulfoxide can be carried out by oxidizing thioether group with mild oxidizing agent such as hydrogen peroxide, sodium periodate and the like. Introduction of sulfone can be carried out by oxidizing thioether or sulfoxide with oxidizing agent such as m-chloroperbenzoic acid (m-CPBA) and potassium peroxymonosulfate.

[C] Process of Forming Hydroxamic Acid Group

Hydroxamic acid group can be formed for example by (1) amidation of ester group with hydroxylamine (J. Med. Chem., 40, 2525 (1997)) or (2) condensation of carboxylic acid group with protected hydroxylamine followed by deprotection (J. Med. Chem., 41, 1209 (1998); Ibid., 41, 1745 (1998); Ibid., 38, 2570 (1995)).

(1) Amidation of Ester Group With Hydroxylamine

—CO$_2$R$^H$+NH$_2$OH→—CONHOH wherein R$^H$ is optionally substituted alkyl such as methyl, ethyl and benzyl.

Preferred R$^H$ is methyl or ethyl. Two to 50 equivalents of hydroxylamine per equivalent of the ester group is preferably used. Reaction solvent is for example alcohol such as methanol, ethanol; amide such as DMF; sulfoxide such as DMSO; ketone such as acetone; water or mixture thereof, especially alcohol. Reaction temperature is usually 0° C. to 80° C.

(2) Condensation of Carboxylic Acid Group With Protected Hydroxylamine Followed by Deprotection

—CO$_2$H+NH$_2$OR$^J$→—CONHOH wherein R$^J$ is a protective group of hydroxylamine such as t-butyldimethylsilyl, trimethylsilyl, t-butyl, benzyl, 4-methoxybenzyl and tetrahydropyranyl.

Condensation of carboxylic acid group with protected hydroxylamine can be performed by a conventional method as described above. The protective group of the protected hydroxamic acid group can be removed by a conventional method ("Protective Groups in Organic Syntheses" 2nd ed. T. W. Greene and P. G. M. Wuts, John Wiley & Sons, Inc. 1991).

The prodrug of the hydroxamic acid derivative includes the prodrugs described in Chemistry and Industry, 1980, 435; Advanced Drug Discovery Reviews 3, 39(1989). The typical examples are biohydrolyzable esters such as acyloxymethyl esters, glycolates, lactates and morpholinoethyl ester of carboxyl group; hemiglutarates of phenolic hydroxyl group; N-morpholinomethyl amides; N-acyloxymethyl amines; N-ayloxyalkoxycarbonylamines.

The present invention includes every isomers such as diastereomers, enantiomers, and geometrical isomers, if the hydroxamic acid derivative has such isomers.

Method of optical resolution of a present invention compound or an intermediate thereof which has acidic group comprises steps of (1) a step of forming a salt of a compound of present invention or intermediate thereof and an optically active base;

(2) a step of recrystallization.

Examples of the solvent forming a salt are an alcohol solvent (such as methanol, ethanol 2-propanol and the like), an ether solvent (such as diethyl ether and the like), an aromatic hydrocarbon solvent (such as toluene and the like), an aprotic solvent (such as acetonitrile), and a mixture of the solvent described before. Examples of the optical active base are an organic amine (such as α-phenetylamine, quinine, quinidine, cinchonidine, cinchonine, strychnine, and the like), and the like.

Method of optical resolution of a present invention compound or an intermediate thereof which has basic group comprises steps of (1) a step of forming a salt of a compound of present invention or intermediate thereof and an optically active acid;

(2) a step of recrystallization.

Examples of the solvent forming a salt are an alcohol solvent (such as methanol, ethanol 2-propanol and the like), an ether solvent (such as diethyl ether and the like), an aromatic hydrocarbon solvent (such as toluene and the like), an aprotic solvent (such as acetonitrile), and a mixture of the solvent described before. Examples of the optical active acid are a monocarboxylic acid (such as mandelic acid, N-benzyl alanine, lactic acid and the like), a dicarboxylic acid (such as tartaric, acid, O-diisopropylidene tartaric acid, malic acid and the like), a sulfonic acid (such as camphor sulfonic acid, bromocamphor sulfonic acid and the like), and the like.

Temperature of forming the salt is selected from the range from about room temperature to about boiling point of the solvent. To increase the purity of optical isomer, it is preferable to heat the solution of salts to around the boiling point of solvent. A molar rate of optically active acid and the compound or the intermediate is selected from the range of about 0.5 to about 2.0, preferably around 1.0. If it is necessary to improve the optical purity, it is possible to repeat recrystallization in the solvent described before.

The present invention also includes solvates such as the hydrate and the like, of the hydroxamic acid derivative or the prodrug thereof, or the pharmaceutically acceptable salt thereof.

The pharmaceutically acceptable salts of the hydroxamic acid derivative or the prodrug thereof include, for example, salts with inorganic acids such as the hydrochloride, hydrobromide, sulfate, phosphate and the like; salts with organic acids such as the acetate, oxalate, citrate, lactate, tartrate, malonate, fumarate, maleate, mathanesulfonate and the like; salts with inorganic metals such as the lithium salt, sodium salt, potassium salt, magnesium salt, aluminum salt, barium salt and the like; salts with organic bases such as the ammonium salt, triethylammonium salt, tetrabutylammonium salt, pyridinium salt, pyrrolidinium salt, piperidinium salt and the like.

The hydroxamic acid derivatives or the prodrug thereof, or the pharmaceutically acceptable salt thereof of the present invention are useful as matrix metallo-proteinase inhibitors. Therefore, they may be used to treat or prevent a disease associated with excess or undesired matrix metalloproteinases.

The diseases associated with excess or undesired matrix metallo-proteinases include, for example, the following diseases:

Abnormal wound healing, acne, acute coronary syndrome, acute infection, AIDS, alcoholism, allergic conjunctivitis, allergic reactions, allergic rhinitis, ALS, Alzheimer's diseases, anaphylaxis, aneurysmal aortic disease, angina, angiofibromas, anorexia, aortic aneurysm, ARDS, aspirin-independent anti-thrombosis, asthma, atherosclerosis, atherosclerotic plaque rupture, atopic dermatitis, benign hyperplasia, bleeding, bone fractures, bronchitis, burns, cachexia, cancer, cardiac infarction, cardiac insufficiency, cardiomyopathy, cerebral hemorrhaging, cerebral ischemia, cerebral vascular dementia, CHF, chronic bronchitis, chronic dermal wounds, chronic obstructive pulmonary disease, cirrhosis, congestive heart failure, corneal injury, coronary thrombosis, Crohn's disease, cystic fibrosis, decubitis ulcer, diabetic peripheral neuropathy, diabetic retinopathy, diabetic ulcers, Duchenne's muscular dystrophy, emphysema, endometriosis, endosclerosis, epidermolysis bullosa, eye disorders, fibrosis, gastritis, gingivitis, glomerular diseases, glomerulonephritis, gout, graft rejection, gum disease, GVHD, Hashimoto's thyroiditis, head trauma, headaches, heart attacks, heart failure, hemangiomas, hemorrhage, hepatitis, hirsutism, Huntington's disease, hypertension, insulin resistance, interstitial nephritis, ischemia, ischemic heart disease, Kaposi's sarcoma, keratinization, keratitis, kidney failure, leishmaniasis, leprosy, leukemia, leukocyte infiltration, liver cirrhosis, loss of appetite, macular degeneration, malaria, mandibular joint disease, memory impairment, meningitis, migraine, miscarriage, multi-infarct dementia, multiple sclerosis, muscular dystrophy, myalgia, myasthenia gravis, myelinic degradation, myocardial infarction, myopia, neovascular glaucoma, neuroinfalmmation, ocular tumors, optic neuritis, osteoarthritis, osteopenia, Paget's disease, pain, pancreatitis, Parkinson's disease, periodontitis, peripheral vascular disease, polyarteritis nodositas, polychondritis, premature childbirth, premature rupture of fetal membranes, prion disease, proliferative retinopathies, proteinurea, pseudogout, psoriasis, pterygium, pulmonary emphysema, radiation damage, rattle snake bite, Reiter's syndrome, renal fibrosis, reocclusion, reperfusion injury, restenosis, scleritis, scleroderma, senile dementia, senility, sepsis, septic shock, Sharp syndrome, Sjoegren's syndrome, SLE, spondylosis, stenosis, sterility, stroke, system sclerosis, thrombosis, toxic effects of chemotherapy, toxic shock, tuberculosis, ulcerations (corneal, epidermal, gastric), ulcertive colitis, uremia, vasculitis, ventricular dilation, vesicular epidermolysis.

The hydroxamic acid derivative or the prodrug thereof, or the pharmaceutically acceptable salt thereof may be administered orally or parenterally. Pharmaceutical forms for oral administration include for example tablets, pills, capsules, powders, granules, suspensions, emulsions, syrups and the like. Pharmaceutical forms for parenteral administration include for example intravenous injections such as drops, intramuscular injections, subcutaneous injections, intranasal preparations, eye drops, suppository, percutaneous preparations such as ointments, creams, lotions, and the like.

The solid compositions such as tablets can be prepared by mixing the active compound with pharmaceutically acceptable conventional carriers or excipients such as lactose, sucrose, corn starch or the like; binders such as hydroxypropylcellulose, polyvinylpyrrolidone, hydroxypropylmethylcellulose or the like; disintegrating agents such as sodium carboxymethylcellulose, sodium starch glycolate or the like; lubricants such as stearic acid, magnesium stearate or the like; or preservatives or the like.

For parenteral administration, the active compound can be dissolved or suspended in a physiologically acceptable carrier such as water, saline, oil, dextrose solution or the like, which may contain auxiliary agents such as emulsifiers, stabilizers, salts for influencing osmotic pressure or buffers, if desired.

The dose for administration varies widely depending on the grade of the symptoms, the patient's age, body weight, sex, administration route, and the like. But the hydroxamic acid derivative is usually administered to an adult (ca. 60 kg) in a dose of approximately 1–1,000 mg, preferably 5–300 mg once or several times per day, by the oral route. By the parenteral route, the hydroxamic acid derivative is usually administered to an adult (ca. 60 kg) in a dose of approximately 0.1–200 mg, preferably 0.3–100 mg once or several times per day.

EXAMPLES

The present invention is explained below precisely with examples but is, of course, not limited by them. The mass and purity of the samples were determined by LC/MS using a column of 4.6×50 mm from YMC(ODS-A column). The flow rate through the column was 3.5 ml/minute. About 100 $\mu$l/min were split into the mass-spectrometer. The mass scan ranged from 200 to 700 amu. The determination of the purity of the samples was assigned through an UV detector (wavelengths: 220 and 254 nm). The gradient employed was from 10 to 99% of mobile phase B(0.035% of TFA in acetonitrile) during a period of 5 minutes (see table below).

| Duration (min) | Mobile Phase A | Mobile Phase B |
|---|---|---|
| 0.1 | 90 | 10 |
| 0.5 | 90 | 10 |
| 3.7 | 1 | 99 |
| 0.2 | 1 | 99 |
| 1 | 90 | 10 |
| 1 | 90 | 10 |

Solvent system:
Mobile phase A: 0.05% TFA in water
Mobile phase B: 0.035% TFA in acetonitrile Example 1

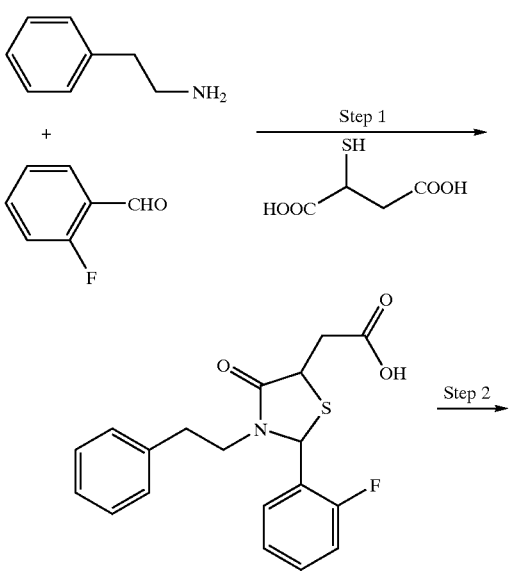

Step 1: 2-[2-(2-Fluorophenyl)-3-(2-phenylethyl)-4-oxo-thiazolidin-5-yl]-acetic Acid A solution of phenylethylamine (85 μl), 2-fluorobenzaldehyde (143 μl) and mercaptosuccinic acid (306 mg) and trimethyl orthoformate (0.5 mL) in THP (3 mL) was heated at 80° C. for 4 hrs. The reaction mixture was cooled, diluted with EtOAc (2 mL) and washed twice with 2 ml of 1N HCl. The organic layer was concentrated to give a residue that was used in the next step without further purification.

Step 2: 2-[2-(2-Fluorophenyl)-3-(2-phenylethyl)-4-oxo-thiazolidin-5-yl]-acetic Acid N-Hydroxyamide The residue from the previous step was dissolved in dry $CH_2Cl_2$ (1.5 mL) and pyridine (0.5 mL). Pentafluorophenyl trifluoroacetate (175 μl) was added and the mixture was stirred at room temperature for 1 hour. O-TBS-hydroxylamine (200 mg) was added and the agitation was continued at room temperature for 12 hours. The reaction was diluted with $CH_2Cl_2$ (3 mL) and quenched by adding 6N HCl (1.5 mL). The organic layer was washed with 2N HCl(2 mL). The crude reaction mixture was purified by HPLC.

The following compounds listed in the Table 1 were prepared in a similar manner.

TABLE 1

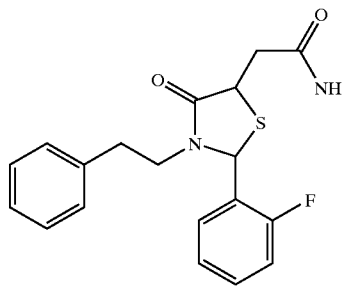

| Example No. | RR1 | RR2 | mol. weight | Mass (m/e) | HPLC rt (min) |
|---|---|---|---|---|---|
| 1 | —(CH2)2-Ph | —C6H4-2-F | 374.44 | 375.2, 342.2 | 3.05 |
| 2 | —CH(benzyl)CO2Me | —C6H2-5-Br-2,4-(OMe)2 | 553.43 | 555.2 | 3.25 |
| 3 | —(CH2)2-Ph | -4-Py | 357.43 | 358.0, 325.2 | 1.77 |
| 4 | -Benzyl | -2-Thiazolyl | 349.43 | 350.2, 317.0 | 2.73 |
| 5 | -Benzyl | —C6H4-4-CO2Me | 400.46 | 401.4, 368.2 | 3.13 |
| 6 | -Benzyl | -2-Furyl-5-Br | 411.28 | 413.0, 380.0, 265.2 | 3.19 |
| 7 | -Benzyl | (1-methyl-2-phenyl-5-methyl-pyrazol-3-one) | 452.54 | 453.0, 420.4 | 2.83 |
| 8 | —(CH2)2-Ph | -3-indolyl-5-OMe | 425.51 | 426.2, 279.0 | 2.87 |
| 9 | —CH2—C6H3-2-F, 4-Br | —C6H4-4-OMe | 469.33 | 469.2, 318.0 | 3.15 |
| 10 | —CH2CHCl(CH2)3Cl | —C6H3-2-NO2,3-OMe | 466.34 | 466.2, 433.2 | 3.35 |
| 11 | —(CH2)2—C6H4-4-Me | —C6H2-5-Br-2,4-(OMe)2 | 509.42 | 511.2, 448.0 | 3.66 |
| 12 | —(CH2)4-Ph | (3,4-dimethylthieno[2,3-b]thiophene) | 474.67 | 474.2, 441.4 | 3.02 |
| 13 | —(CH2)3-Ph | —C6H4-4-OMe | 400.50 | 401.2, 368.0 | 3.32 |
| 14 | —(CH2)3-Ph | 1-Naphthyl-4-NMe2 | 463.60 | 464.2, 293.0, 250.0 | 2.23 |
| 15 | —(CH2)3N(nBu)2 | -2-Furyl-5-(C6H4-4-Br) | 566.56 | 568.2 | 2.99, 3.08 |
| 16 | —CH2CH(Me)Ph | —C6H4-4-O—nBu | 442.58 | 443.0, 249.8 | 3.17 |
| 17 | —CH2C(Me)2CH2NMe2 | -2-Furyl-5-(C6H4-4-Cl) | 466.00 | 466.2 | 2.84 |
| 18 | —(CH2)2—C6H4-4-OH | -3-Pyrrolyl-4-CO2Et, 2,5-Me2, 1-Ph | 537.64 | 538.2, 505.2 | 3.36 |
| 19 | —(CH2)2—C6H4-4-OH | —C6H3-2,3-(OMe)2 | 432.50 | 433.2, 400.2 | 2.85 |
| 20 | —(CH2)—C6H3-3,4-(OMe)2 | -2-Furyl-5-(C6H4-4-Br) | 561.46 | 563.2, 528.2 | 3.71 |

Example 21

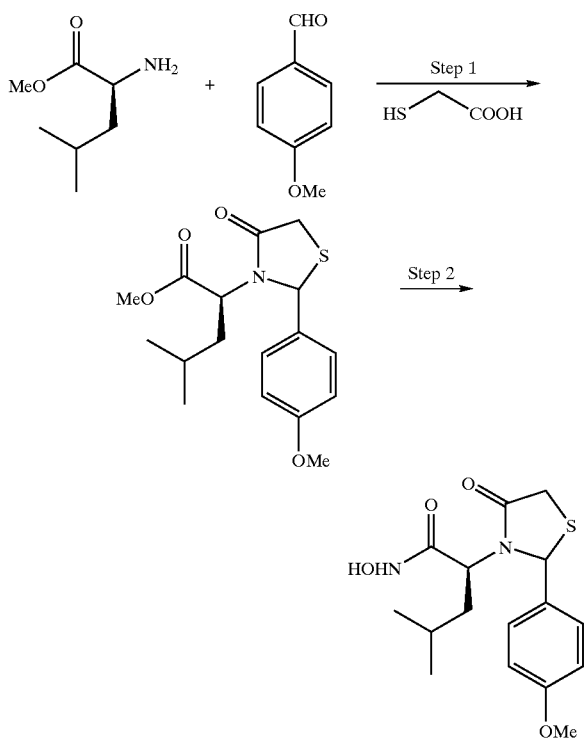

Step 1: 2-(4-Methoxyphenyl)-3-[(1S)-methoxycarbonyl-3-methylbutyl]-1,3-thiazolidine-4-one A solution of amino acid methyl ester (0.68 mmol) in 1 mL of THF was poured into a sealed tube containing molecular sieves 3A and a solution of the aldehyde (1.5 mmol) in dioxane (1 mL). The mixture was heated at 80° C. for 4 hours. Mercaptoacetic acid (17 µl, 2.5 mmol, 3.7 equiv.) was added to the mixture and the heating was continued for additional 12 hours. The reaction mixture was cooled down, diluted with EtOAc (2 mL) and filtered to remove the molecular sieves. The filtrate was washed twice with 2 mL of aq $Na_2CO_3$ and evaporated to give an oil that was used in the next step without further purification.

Step 2: 3-[(1S)-(N-Hydroxyaminocarbonyl)-3-methylbutyl]-2-(4-methoxyphenyl)-1,3-thiazolidine-4-one KOH (435 mg) and hydroxylamine.HCl (340.2 mg) were dissolved in MeOH (2.14 mL and 3.4 mL respectively) at room temperature. Once a solution was obtained the KOH solution was poured into the hydroxylamine solution at 0° C. and the mixture was maintained at this temperature for 1 hour. The precipitate (KCl) was filtered off, and the filtrate was poured into the solution of the methyl ester (0.68 mmol) in MeOH (2 mL) and stirring was continued for additional 3 hours. Acetic acid (0.5 ml) was added to the mixture and the volume of the reaction was reduced to one third. The resulting viscous solution was diluted with water (2 mL) and EtOAc (5 mL). The organic layer was separated, evaporated and purified by HPLC.

The following compounds listed in the Tables 2, 2' and 2" and Table 3 were prepared in a similar manner.

TABLE 2

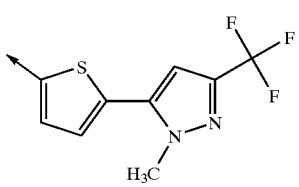

| Example No. | RR1 | RR2 | RR3 | mol. weight | Mass (m/e) | HPLC rt (min) |
|---|---|---|---|---|---|---|
| 21 | —iBu | —C6H4-4-OMe | —H | 338.43 | 339.0, 306.2, 278.4 | 2.93 |
| 22 | -Benzyl | —C6H4-2-Br | —H | 421.32 | 423.0, 390.0, 362.0 | 3.28 |
| 23 | -Benzyl | —C6H4-4-CF3 | —H | 410.42 | 411.2, 378.2, 350.0 | 3.42 |
| 24 | -Benzyl | —C6H3-3,4-methylenedioxy | —Me | 400.46 | 401.4, 368.4, 340.2 | 3.27 |
| 25 | -Benzyl | 2-Furyl-5-(C6H4-4-NO2) | —H | 453.48 | 453.8, 421.2, 393.2 | 3.44 |
| 26 | -Benzyl | (thienyl-pyrazole-CF3 structure) | —H | 496.53 | 497.0, 464.0, 436.2 | 3.63 |
| 27 | -Benzyl | —C6H4-4-n-pentyl | —H | 412.56 | 413.2, 380.2, 352.0 | 4.08 |
| 28 | -Benzyl | —C6H3-3-NO2, 4-Cl | —H | 421.86 | 422.2, 389.2, 361.4 | 3.49 |
| 29 | -Benzyl | —C6H4-4-CO2Me | —H | 400.46 | 401.0, 368.0, 340.0 | 3.16 |
| 30 | -Benzyl | —C6H4-4-CH2O-(Ph-4-NO2) | —H | 493.54 | 494.2, 461.2, 433.2 | 3.47 |
| 31 | -Benzyl | -4-Imidazolyl-5-Me | —H | 346.41 | 348.2 | 2.20 |
| 32 | -Benzyl | —C6H3-3-NO2, 4-S(C6H4-4-Br) | —H | 574.46 | 575.4 | 3.36 |
| 33 | —iBu | -2-Pyridyl-6-Me | —H | 323.42 | 324.2, 149.2 | 2.00 |
| 34 | —iBu | —C6H4-4-N(CH2CH2CN)2 | —H | 429.55 | 430.0, 369.0 | 2.86 |
| 35 | —CH2—C6H4-4-OH | -3-Furyl | —H | 348.38 | 349.4, 288.2 | 2.15 |
| 36 | —CH2—C6H4-4-OH | -2-Thienyl-5-Me | —H | 378.47 | 379.2, 346.0, 282.4 | 2.49 |
| 37 | —iPr | —CH(CN)—C6H4-4-Cl | —H | 367.86 | 369.2, 336.2 | 2.47 |

TABLE 2-continued
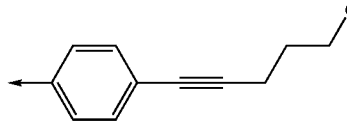
| Example No. | RR1 | RR2 | RR3 | mol. weight | Mass (m/e) | HPLC rt (min) |
|---|---|---|---|---|---|---|
| 38 | —CH2-3-indolyl | 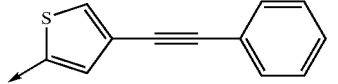 | —H | 461.59 | 462.2, 429.2, 401 | 3.32 |
| 39 | —CH2-3-indolyl | 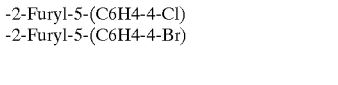 | —H | 487.60 | 488.0, 455.2 | 3.30 |
| 40 | —CH2-3-indolyl | -2-Furyl-5-(C6H4-4-Cl) | —H | 481.96 | 482.2, 449.0 | 3.19 |
| 41 | —CH2-3-indolyl | -2-Furyl-5-(C6H4-4-Br) | —H | 526.41 | 528.0, 495, 467 | 3.21 |
| 42 | —iBu | 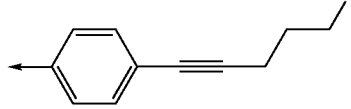 | —H | 388.53 | 389.2, 356, 328.2 | 3.62, 3.68 |
| 43 | —iBu |  | —H | 414.55 | 415.2, 382, 354.2 | 3.52 |
| 44 | —iBu |  | —H | 378.52 | 379.2, 346, 318.0 | 3.25 |
| 45 | —iBu | -2-Furyl-5-C6H4-3-CF3 | —H | 442.46 | 443.2, 410.2, 382 | 3.41 |
| 46 | —iBu | -2-Furyl-5-(C6H4-4-Cl) | —H | 408.91 | 409.2, 376, 348.2 | 3.40 |
| 47 | —iBu | -2-Furyl-5-(C6H4-4-Br) | —H | 453.36 | 455.2, 422, 394 | 3.44 |
| 48 | —iBu | -3-Py | —H | 309.39 | 310.2, 277, 249.2 | 1.37 |
| 49 | —iBu | -4-Py | —H | 309.39 | 3i0.2, 249.2 | 0.94 |
| 50 | —iBu | -2-Naphthyl-6-OMe | —H | 388.49 | 389.2, 356, 328.2 | 3.14 |
| 51 | —iBu | —C6H4-4-OH | —H | 324.40 | 325.2, 292, 264.0 | 2.71 |
| 52 | -Benzyl | 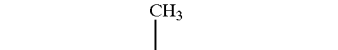 | —H | 384.46 | 385.2, 352.0, 324 | 3.14, 3.20 |
| 53 | -Benzyl |  | —H | 422.55 | 423.2, 390, 362.2 | 4.06 |
| 54 | -Benzyl | 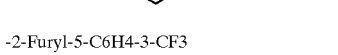 | —H | 448.57 | 449.0, 416.2, 388 | 3.97 |
| 55 | -Benzyl | -2-Furyl-5-(C6H4-4-Cl) | —H | 442.92 | 443.2 | 3.78 |
| 56 | -Benzyl | -2-Furyl-5-(C6H4-4-Br) | —H | 487.38 | 487.0, 454, 426 | 3.84 |
| 57 | -Benzyl | —C6H4-4-OH | —H | 358.42 | 359.2, 326, 298.2 | 2.79 |
| 58 | —iBu | —C6H3-3-F, 4-OMe | —H | 356.42 | 357.2, 324.2, 296.2 | 2.89 |
| 59 | —H | —C6H2-2,4,5-(OMe)3 | —H | 342.37 | 343.2, 282.0, 251.0 | 2.22 |

TABLE 2-continued

Structure: HOHNOC-C(RR1)-N(ring)-C(=O)-C(RR3)-S-C(RR2)- (thiazolidinone with hydroxamic acid)

| Example No. | RR1 | RR2 | RR3 | mol. weight | Mass (m/e) | HPLC rt (min) |
|---|---|---|---|---|---|---|
| 60 | —H | 5-(1-methyl-3-trifluoromethyl-pyrazolyl)-thiophen-2-yl | —H | 406.41 | 407.2, 374.0 | 2.89 |
| 61 | —(CH2)2-Ph | —C6H4-4-OMe | —H | 386.47 | 387.2, 354.2 | 3.31 |
| 62 | —CH2—C6H4-4-Ph | —C6H4-4-OMe | —H | 448.55 | 449.0, 416.2, 388.2 | 3.74 |
| 63 | —CH2-2-Naphthyl | —C6H4-4-OMe | —H | 422.51 | 423.2, 390.2, 316.2 | 3.55 |
| 64 | -Benzyl | —C6H4-4-OCHF2 | —H | 408.43 | 409.2, 348.2, 247.2 | 3.14 |
| 65 | -Benzyl | —C6H4-4-SO2Mo | —H | 420.51 | 421.2, 360.2, 286.2 | 2.63 |
| 66 | —iBu | —C6H4-4-Br | —H | 387.30 | 387.2, 326.0 | 3.30 |
| 67 | —Me | -2-Pyrrolyl-1-SO2—(C6H4-4-Me) | —H | 409.49 | 410.2, 377, 349.2 | 2.85 |
| 68 | —CH2-3-indolyl | —C6H4-4-OMe | —H | 411.48 | 412.2, 379.2, 351 | 3.12 |
| 69 | —CH2-3-indolyl | —C6H4-4-O-nBu | —H | 453.56 | 454.2, 421.2, 393 | 3.67 |
| 70 | —(CH2)2SCH3 | —C6H4-4-OMe | —H | 356.47 | 357.2, 324, 296.2 | 2.93 |
| 71 | —(CH2)2SCH3 | —C6H3-3-F, 4-OMe | —H | 374.46 | 375.0, 342, 314.2 | 2.90 |
| 72 | —CH2-cyclohexyl | —C6H4-4-OMe | —H | 378.49 | 379.2, 346, 318.0 | 3.41 |
| 73 | —CH2-cyclohexyl | —C6H4-4-O-nBu | —H | 420.58 | 421.2, 388, 360.2 | 4.05 |
| 74 | —CH2-cyclohexyl | —C6H3-3-F, 4-OMe | —H | 396.48 | 397.2, 364, 336.2 | 3.42 |
| 75 | —CH2S-benzyl | —C6H4-4-OMe | —H | 418.54 | 419.0, 386.2, 358 | 3.36 |
| 76 | —CH2S-benzyl | —C6H3-3-F, 4-OMe | —H | 436.53 | 437.2, 404.2, 376 | 3.39 |
| 77 | —CH2—C6H4-4-OH | —C6H4-4-OMe | —H | 388.45 | 389.2, 356, 328.2 | 2.73, 2.83 |
| 78 | —CH2—C6H4-4-OH | —C6H4-4-O-nBu | —H | 430.53 | 431.2, 398, 370.2 | 3.49 |
| 79 | —CH2O-tBu | —C6H4-4-OMe | —H | 368.46 | 369.2, 313.2, 280, 252.0 | 3.29 |
| 80 | —CH2O-tBu | —C6H3-3-F, 4-OMe | —H | 386.45 | 387.0, 331.2, 298, 270.2 | 3.33 |
| 81 | —nBu | —C6H4-4-OMe | —H | 338.43 | 339.2, 306, 278.0 | 3.18 |
| 82 | —nBu | —C6H4-4-Me | —H | 322.43 | 323.2, 290, 262.2 | 3.40 |
| 83 | —nBu | —C6H3-3-F, 4-OMe | —H | 356.42 | 357.2, 324, 296.2 | 3.21 |
| 84 | —CH2—C6H4-4-OH | -2-Furyl-5-(C6H4-3-NO2) | —H | 469.48 | 470.2, 437, 409.2 | 3.04 |
| 85 | —Ph | —C6H4-4-SMe | —H | 374.48 | 375.2, 342, 314.4 | 3.09 |
| 86 | —CH2—C6H4-4-OH | —C6H4-4-Cl | —H | 392.86 | 393.0, 360, 332.0 | 2.78, 2.90 |
| 87 | —iBu | —C6H4-4-Cl | —H | 342.85 | 343.2, 310, 282.2 | 3.10, 3.22 |
| 88 | —iBu | 5-(1-methyl-3-trifluoromethyl-pyrazolyl)-thiophen-2-yl | —H | 462.52 | 463.0, 430, 402.2 | 3.43 |
| 89 | —iBu | —C6H4-4-O(CH2)3NMe2 | —H | 409.55 | 410.2, 349.2 | 2.32, 2.45 |
| 90 | —iPr | —C6H4-4-OMe | —H | 324.40 | 325.2, 292.2, 264 | 3.11 |
| 91 | —iBu | —C6H3-3,4-methylenedioxy | —H | 352.41 | 353.2, 320.2, 292.2 | 3.15 |
| 92 | —iBu | —C6H4-4-OMe | —H | 338.43 | 339.2, 306.2, 278.2 | 3.18 |
| 93 | —Me | —C6H4-4-Br | —H | 345.22 | 347.0, 314.0, 286.0 | 3.05 |
| 94 | —CH(OH)CH3 | —C6H4-4-Cl | —H | 330.79 | 331.0, 298.0, 270.0 | 2.66 |
| 95 | —nBu | —C6H4-4-SMe | —H | 354.49 | 355.2, 322.2, 394.2 | 3.27 |
| 96 | —CH2O-iBu | —C6H4-4-O-nBu | —H | 410.54 | 411.2, 355.0, 322.2, 294.0 | 3.93 |
| 97 | —CH2-cyclohexyl | —C6H4-4-OPh | —H | 440.57 | 441.2, 408.2, 380.2 | 3.66 |
| 98 | —CH2-cyclohexyl | —C6H4-4-Ph | —H | 424.57 | 425.0, 392.0, 364.0 | 3.64 |
| 99 | —CH2-cyclohexyl | —Ph | —H | 348.47 | 349.2, 316.2, 288.2 | 3.21 |
| 100 | —Me | —C6H4-4-OPh | —H | 358.42 | 359.0, 326.0, 298.2 | 3.00 |
| 101 | —nBu | —C6H4-4-OPh | —H | 400.50 | 401.2, 368.2, 340.2 | 3.38 |
| 102 | —nBu | —C6H4-4-Ph | —H | 384.50 | 385.2, 352.2, 324.2 | 3.39 |
| 103 | —CH2-3-indolyl | —C6H4-4-OMe | —H | 411.48 | 412.2, 379.2, 351.2 | 2.90 |
| 104 | —Ph | —C6H4-4-OMe | —H | 358.42 | 359.0, 326.0, 298.2 | 2.80 |

TABLE 2-continued

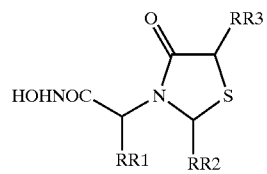

| Example No. | RR1 | RR2 | RR3 | mol. weight | Mass (m/e) | HPLC rt (min) |
|---|---|---|---|---|---|---|
| 105 | —CH2O-tBu | —C6H4-4-OMe | —H | 368.46 | 369.2, 313.2, 280.2, 252.0 | 2.96 |
| 106 | —nPr | —C6H4-4-OMe | —H | 324.40 | 325.2, 292.2, 264.0 | 2.71 |
| 107 | —CH2-(1-benzylimidazol-4-yl) | —C6H4-4-OMe | —H | 452.54 | 453.2, 420.2, 392.0 | 2.53 |
| 108 | —Me | —C6H4-4-OMe | —H | 296.35 | 297.2, 264.2, 236.2 | 2.41 |
| 109 | —CH2—C6H4-4-O-tBu | —C6H4-4-OMe | —H | 444.55 | 45.2, 412.2, 384.0, 328.2 | 3.26 |
| 110 | —nBu | —C6H4-4-OMe | —H | 338.43 | 339.2, 306.2, 278.2 | 2.88 |
| 111 | —CH2-3-indolyl | —C6H3-3-F, 4-OMe | —H | 429.47 | 430.2, 397.2, 369.2 | 2.90 |
| 112 | —nBu | —C6H4-4-Cl | —H | 342.85 | 343.2, 310.2, 282.2 | 3.11 |
| 113 | —(CH2)2SCH3 | —C6H4-4-OPh | —H | 418.54 | 419.0, 386.0, 358.0 | 3.06 |
| 114 | —CH2S-benzyl | —C6H4-3-Me | —H | 402.54 | 403.2, 370.0, 342.2 | 3.07 |
| 115 | —CH2S-benzyl | —C6H4-4-SMe | —H | 434.60 | 435.2, 402.2, 374.2 | 3.09 |
| 116 | —CH2S-benzyl | —C6H4-3-Cl | —H | 422.96 | 423.0, 390.0, 362.0 | 3.11 |
| 117 | —CH2S-benzyl | —C6H4-4-Cl | —H | 422.96 | 423.0, 390.0, 362.0 | 3.14 |
| 118 | —CH2S-benzyl | —C6H4-4-OPh | —H | 480.61 | 481.4, 448.2, 420.4 | 3.32 |
| 119 | —CH2O-tBu | —C6H4-4-SMe | —H | 384.52 | 385.2, 329.2, 296.2, 268.2 | 3.35 |
| 120 | —CH2-3-indolyl | —C6H4-4-F | —H | 399.45 | 400.2, 367.0, 339.2 | 3.74 |
| 121 | —CH2-3-indolyl | —C6H4-4-Cl | —H | 415.90 | 416.2, 383.0 | 3.95 |
| 122 | —CH2—C6H4-4-OH | —C6H4-4-SMe | —H | 404.51 | 405.2, 372.2, 344.0 | 3.59 |
| 123 | —CH2—C6H4-4-OH | —C6H4-4-SMe | —H | 404.51 | 405.2, 372.2, 344.0 | 2.91 |
| 124 | —CH2—C6H4-4-OH | —C6H4-4-OCF3 | —H | 442.42 | 443.2, 410.2, 382.2 | 3.12 |
| 125 | —CH2-3-indolyl | —C6H4-4-SMe | —H | 427.55 | 428.2, 395.2, 367.2 | 3.30 |
| 126 | —CH2-3-indolyl | —C6H4-4-F | —H | 399.45 | 400.2, 367.2, 339.2 | 3.20 |
| 127 | —Me | —C6H4-4-OPh | —H | 358.42 | 359.2, 326.2, 298.2 | 3.23 |
| 128 | —CH2—C6H4-4-OH | —C6H4-4-OPh | —H | 450.52 | 451.0, 418.0, 390.0 | 3.29 |
| 129 | —iBu | —C6H4-4-SMe | —H | 354.49 | 355.2, 322.2, 294.2 | 2.91 |
| 130 | —iBu | —C6H4-4-Cl | —H | 342.85 | 343.2, 310.2, 282.2 | 2.89 |
| 131 | —iBu | —C6H3-3-F, 4-OMe | —H | 356.42 | 357.0, 324.0, 296.2 | 2.90 |
| 132 | —iBu | —C6H4-4-Cl | —H | 342.85 | 343.2, 310.2, 282.2 | 3.03 |
| 133 | —iBu | —C6H4-4-Br | —H | 387.30 | 389.2, 356.2, 328.2 | 3.04 |
| 134 | -Benzyl | —C6H4-4-SMe | —H | 388.51 | 389.2, 356, 328.2 | 3.33, 3.37 |
| 135 | —iPr | —C6H4-4-nBu | —H | 350.48 | 351.2, 318, 290.0 | 3.42 |
| 136 | —(CH2)2SCH3 | —C6H4-4-SMe | —H | 372.53 | 373.0, 340, 312.0 | 2.96 |
| 137 | —(CH2)2SCH3 | —C6H4-4-Cl | —H | 360.88 | 361.0, 328, 300.0 | 3.01 |
| 138 | —(CH2)2SCH3 | —C6H4-4-Br | —H | 405.34 | 407, 374, 346.0, 298.2 | 3.04, 3.11 |
| 139 | —(CH2)2SCH3 | —C6H4-4-OPh | —H | 418.54 | 419.0, 386, 358.0, 310.2 | 3.30 |
| 140 | —nPr | —C6H4-4-SMe | —H | 340.47 | 341.2, 308, 280.0 | 2.97 |
| 141 | —nPr | —C6H4-4-Cl | —H | 328.82 | 329.2, 296, 268.0 | 2.94, 3.01 |
| 142 | —nPr | —C6H4-4-Br | —H | 373.27 | 375.0, 342, 314 | 2.98, 3.07 |
| 143 | —nPr | —C6H4-4-OPh | —H | 386.47 | 387.0, 354, 326.2 | 3.30 |
| 144 | —CH2-cyclohexyl | —C6H4-4-SMe | —H | 394.56 | 395.2, 362, 334.4 | 3.40 |
| 145 | —CH2-cyclohexyl | —C6H3-3-F, 4-OMe | —H | 396.48 | 397.2, 364, 336.2 | 3.26 |
| 146 | —CH2-cyclohexyl | —C6H4-4-F | —H | 366.46 | 367.0, 334, 306.2 | 3.29 |
| 147 | —CH2-cyclohexyl | —C6H4-4-Cl | —H | 382.91 | 383.0, 350, 322.2 | 3.44 |
| 148 | —CH2-cyclohexyl | —C6H4-4-Br | —H | 427.36 | 429.2, 396, 368.0 | 3.49 |
| 149 | —CH2-cyclohexyl | —C6H4-4-OPh | —H | 440.57 | 441.2, 308, 380.2 | 3.69 |
| 150 | —nBu | —C6H4-4-SMe | —H | 354.49 | 355.2, 322, 294.0 | 3.14 |
| 151 | —nBu | —C6H3-3-F, 4-OMe | —H | 356.42 | 357.0, 324, 296.2 | 2.96 |
| 152 | —nBu | —C6H4-4-F | —H | 326.39 | 327.2, 294, 266.0 | 3.00 |
| 153 | —nBu | —C6H4-4-Cl | —H | 342.85 | 343.0, 310, 282.0 | 3.15 |
| 154 | —nBu | —C6H4-4-Br | —H | 387.30 | 389.0, 356, 328.2 | 3.21 |
| 155 | —nBu | —C6H4-4-OPh | —H | 400.50 | 401.2, 368, 340.2 | 3.48 |
| 156 | —nBu | —C6H4-3-OCF3 | —H | 392.40 | 393.0, 360, 332.2 | 3.29 |
| 157 | —CH2-(1-benzylimidazol-4-yl) | —C6H4-4-F | —H | 440.50 | 441.4, 408.2 | 2.63 |
| 158 | —CH2-(1-benzylimidazol-4-yl) | —C6H4-4-Br | —H | 501.41 | 503.2 | 2.74, 2.80 |
| 159 | —CH2—C6H4-4-O-tBu | —C6H4-4-SMe | —H | 460.62 | 461.2, 428, 400.2 | 3.49 |
| 160 | —CH2—C6H4-4-O-tBu | —C6H3-3-F, 4-OMe | —H | 462.54 | 463.2, 430, 402.2, 346.0 | 3.35 |
| 161 | —CH2—C6H4-4-O-tBu | —C6H4-4-F | —H | 432.52 | 433.2, 400.2, 372, 316.2 | 3.35 |
| 162 | —CH2—C6H4-4-O-tBu | —C6H4-4-Cl | —H | 448.97 | 449.0, 416.2, 388, 332.0 | 3.51 |

TABLE 2-continued

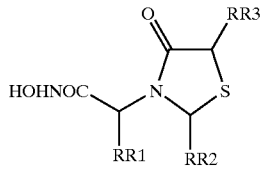

| Example No. | RR1 | RR2 | RR3 | mol. weight | Mass (m/e) | HPLC rt (min) |
| --- | --- | --- | --- | --- | --- | --- |
| 163 | —CH2—C6H4-4-O-tBu | —C6H4-4-Br | —H | 493.42 | 495.2, 462, 434.0, 378.0 | 3.34 |
| 164 | —CH2—C6H4-4-O-tBu | —C6H4-4-OPh | —H | 506.63 | 507.2, 474, 446.2, 390.0 | 3.75 |
| 165 | -Benzyl | —C6H4-4-SMe | —H | 388.51 | 389.0, 356, 328.2 | 3.20 |
| 166 | -Benzyl | —C6H4-4-Cl | —H | 376.86 | 377.0, 344, 316.2 | 3.22 |
| 167 | -Benzyl | —C6H4-4-Br | —H | 421.32 | 423.0, 390, 362.0 | 3.28 |
| 168 | -Benzyl | —C6H4-4-OPh | —H | 434.52 | 435.2, 402, 374.0 | 3.49 |
| 169 | —(CH2)4NHCO2-tBu | —C6H4-4-OMe | —H | 453.56 | 454.2, 398.2, 354.2 | 3.12 |
| 170 | —CH2CH2CO2-tBu | —C6H4-4-OMe | —H | 410.49 | 411.2, 355.2, 322.2 | 3.14 |
| 171 | —CH2-4-Imidazolyl | —C6H4-4-OMe | —H | 362.41 | 363.2, 302.2 | 2.02, 2.10 |
| 172 | —iPr | —C6H4-SMe | —H | 340.47 | 341.0, 308, 280.2 | 2.86 |
| 173 | —secBu | —C6H4-4-Cl | —H | 342.85 | 343.0, 310, 282.0 | 3.02 |
| 174 | —secBu | —C6H4-4-F | —H | 326.39 | 327.0, 294, 266.2 | 2.85 |
| 175 | —secBu | —C6H3-3-F, 4-OMe | —H | 356.42 | 357.2, 324, 296.2 | 2.89 |
| 176 | —secBu | —C6H4-4-SMe | —H | 354.49 | 355.2, 322.2, 294 | 3.32 |
| 177 | —(CH2)4NH2 | —C6H44-OMe | —H | 353.44 | 354.2, 321.2 | 2.16 |
| 178 | —(CH2)2CO2H | —C6H4-4-OMe | —H | 354.38 | 354.8, 337.2 | 2.62, 2.69 |
| 179 | —iPr | —C6H4-4-OPh | —H | 386.47 | 387.0, 354, 326.2 | 3.27 |
| 180 | —iPr | —C6H4-4-O-benzyl | —H | 400.50 | 401.2, 268, 340.0 | 3.31 |
| 181 | -Benzyl | —C6H4-4-Cl | —H | 376.86 | 377.2, 344, 316.2 | 3.22 |
| 182 | -Benzyl | —C6H4-4-Br | —H | 421.32 | 423.0, 390, 362.0 | 3.27 |
| 183 | -Benzyl | —C6H4-4-OPh | —H | 434.52 | 435.2, 402, 374.0 | 3.49 |
| 184 | —CH2O-tBu | —C6H4-4-Cl | —H | 372.87 | 373.0, 317.0, 284.0, 256 | 3.32 |
| 185 | —CH2O-tBu | —C6H4-4-Br | —H | 417.32 | 419.0, 363.0, 330, 302 | 3.38 |
| 186 | —CH2-(1-benzylimidazol-4-yl) | —C6H4-4-SMe | —H | 468.60 | 469.2 | 2.77 |
| 187 | —CH2-(1-benzylimidazol-4-yl) | —C6H4-4-Cl | —H | 456.95 | 457.2 | 2.76 |
| 188 | —CH2-(1-benzylimidazol-4-yl) | —C6H4-4-OCF3 | —H | 506.51 | 507.2, 474.2 | 2.95 |
| 189 | —CH2—C6H4-4-OH | —C6H3-3-F, 4-Cl | —H | 410.85 | 410.8, 350.2 | 2.79 |
| 190 | —CH2—C6H4-4-OH | -2-Thienyl-5-SMe | —H | 410.54 | 411.4, 349.8 | 2.83 |
| 191 | —CH2—C6H4-4-OH | —C6H3-3-F, 4-OMe | —H | 406.44 | 407.2, 374, 346.0 | 2.90 |
| 192 | —iBu | —C6H4-4-O-allyl | —H | 364.47 | 365.2, 332, 304.2 | 3.40 |
| 193 | —nBu | -2-Thienyl-5-Cl | —H | 348.87 | 349.0, 316, 288.0 | 3.41 |
| 194 | —nBu | ![benzodioxine] | —H | 366.44 | 367.2, 334.2, 306 | 2.95 |
| 195 | —nBu | 2-Benzofuranyl | —H | 348.42 | 349.2, 316, 288.2 | 3.31 |
| 196 | —CH2—C6H4-4-OH | —C6H4-4-Br | —H | 437.32 | 436.8, 404, 376.2 | 2.79 |
| 197 | -Benzyl | —C6H3-2-F, 5-OMe | —H | 390.44 | 391.0, 358.2, 330 | 2.92 |
| 198 | -Benzyl | -2-Furyl-5-(C6H4-2-Cl) | —H | 442.92 | 443.2, 410.2, 382 | 3.33 |
| 199 | -Benzyl | —C6H3-2-F, 4-OMe | —H | 390.44 | 391.0, 358.2, 330 | 2.91 |
| 200 | —iBu | —C6H3-2-F, 4-OMe | —H | 356.42 | 357.2, 324.4, 296 | 2.80 |
| 201 | —CH2—C6H4-4-OH | -2-Thienyl-4-Br | —H | 443.34 | 445.0, 383.8 | 2.70 |
| 202 | —CH2—C6H4-4-OH | -2-Thienyl-5-Br | —H | 443.34 | 444.8, 384 | 2.72 |
| 203 | —CH2—C6H4-4-OH | -2-Thienyl-5-Cl | —H | 398.89 | 399.0, 338.0 | 2.67 |
| 204 | —CH2—C6H4-4-OH | —C6H3-2-F, 4-Br | —H | 455.31 | 457.2, 396 | 2.91 |

TABLE 2'

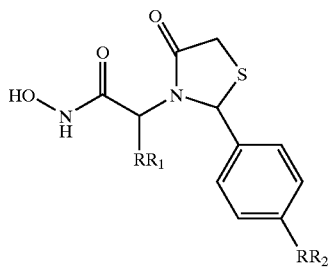

| Example No. | RR¹ | RR² | mol. weitht | Mass (m/e) | HPLC rt (min) |
|---|---|---|---|---|---|
| 447 | -Cyclohexyl | —OMe | 364.5 | 365.2, 332.2, 304 | 3.48 |
| 448 | -Cyclohexyl | —OMe | 364.5 | 365.2, 332.2, 304 | 3.58 |
| 449 | —iBu | —Cl | 342.8 | 343.0, 310, 282.2 | 3.09 |
| 450 | —iBu | —Cl | 342.8 | 343.0, 310, 282.2 | 3.13 |
| 451 | —iBu | —O—C6H4-4-F | 418.5 | 419.2, 386, 358.2 | 3.45 |
| 452 | —iBu | —O—C6H4-4-Cl | 434.9 | 435.2, 374.2 | 3.74 |
| 453 | —iBu | —Cl | 342.8 | 343.0, 310, 282.2 | 3.09 |
| 454 | —CH2-2-Imidazolyl | —Cl | 366.8 | 367.0, 334, 306 | 1.85 |
| 455 | —(CH2)3NHC(NH)NH2 | —Cl | 385.9 | 386.2, 353.0 | 2.26 |
| 456 | —(CH2)2CO-piperidino | —Cl | 425.9 | 426.2, 393, 365.0 | 2.82 |
| 457 | —(CH2)3NHCOOCH2Ph | —Cl | 478.0 | 478.2 | 3.16 |
| 458 | —(CH2)2CONMe2 | —Cl | 385.9 | 386.2, 353, 325.0 | 2.58 |
| 459 | —(CH2)3NHCOO-tBu | —Cl | 444.0 | 444.2, 388.2 | 3.29 |
| 460 | —iBu | —NEt2 | 379.5 | 380.2 | 3.49 |

TABLE 2"

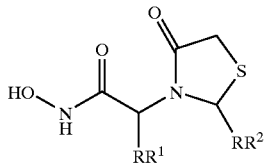

| Example No. | RR¹ | RR² | mol. weitht | Mass (m/e) | HPLC rt (min) |
|---|---|---|---|---|---|
| 461 | —iBu | -2-Thienyl | 314.4 | 315.0, | 3.29 |
| 462 | —iBu | -2-Thienyl-5-Br | 393.3 | 393.0, 360, | 3.59 |
| 463 | —iBu | -2-Thienyl-5-Br | 393.3 | 393.0, 360, | 3.58 |
| 464 | —iBu | -2-Thiazolyl | 315.4 | 316.0 | 2.89 |
| 465 | -Benzyl | -2-Thienyl | 348.4 | 349.0, 316, | 3.34 |
| 466 | -Benzyl | -2-Thienyl-5-Br | 427.3 | 429.0, 427, | 3.59 |

TABLE 3

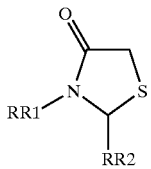

| Example No. | RR1 | RR2 | mol. weight | Mass (m/e) | HPLC rt (min) |
|---|---|---|---|---|---|
| 205 | —(CH2)3CONHOH | —C6H4-4-Br | 359.2 | 361.0, 328, 300 | 2.79 |
| 206 | —(CH2)3CONHOH | —C6H3-3,4-methylenedioxy | 324.4 | 325.2, 292, 264.2 | 2.46 |
| 207 | —(CH2)2CONHOH | —C6H4-4-OMe | 296.3 | 297.0, 264.0 | 2.30 |
| 208 | —CH(CO2Me)CH2CONHOH | —C6H4-4-Br | 403.3 | 405.0, 371.8, 344.0 | 3.07 |

Example 209

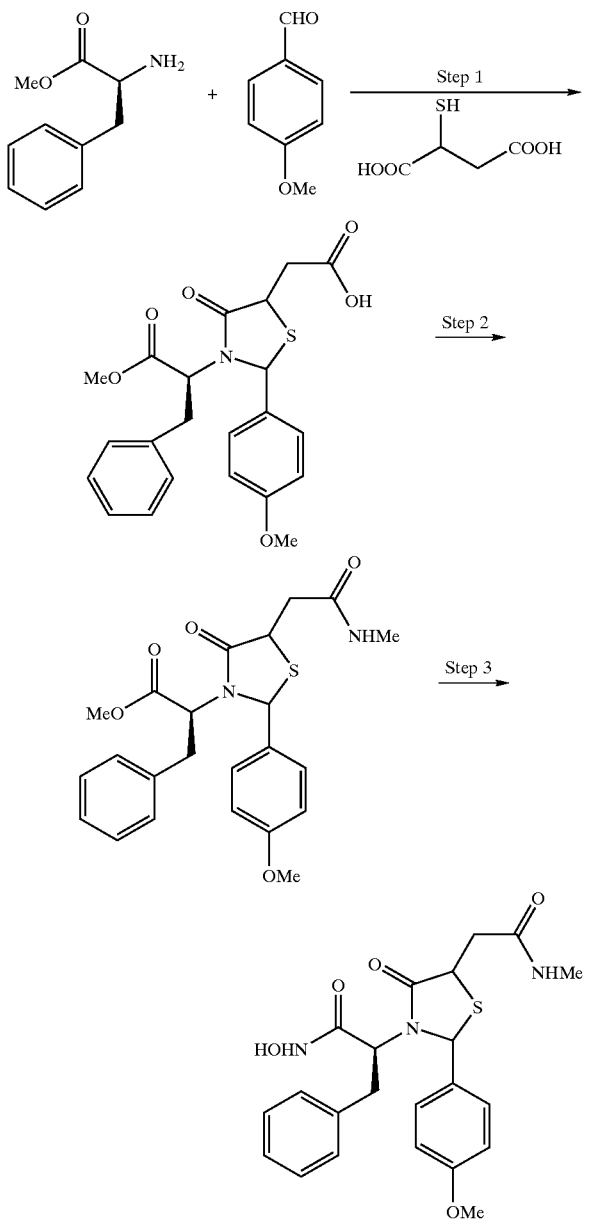

Step 1: 2-(4-Methoxyphenyl)-3-[(1S)-methoxycarbonyl-2-phenylethyl]-4-oxo-thiazolidin-5-yl)-acetic Acid A suspension of (L)-phenylalanine methyl ester (147 mg) and triethylamine (95 μl) in 1 mL of THF was stirred at room temperature for 5 minutes. The solution was filtrated and then poured into a sealed tube containing 3A molecular sieves and a solution of p-methoxybenzaldehyde (183 μl) in dioxane (1 ml). The mixture was heated at 80° C. for 4 hours. Mercaptosuccinic acid (375 mg) was added to the mixture and the heating was continued for an additional 12 hours. The reaction was cooled, diluted with EtOAc (2 mL) and filtered to remove the molecular sieves. The filtrate was washed twice with 2 ml of 1N HCl and evaporated to give a solid residue that was used in the next step without further purification.

Step 2: (2-(4-Methoxyphenyl)-3-[(1S)-methoxycarbonyl-2-phenylethyl]-4-oxo-thiazolidin-5-yl)-acetic Acid N-Methylamide The crude carboxylic acid from step 1, diisopropylethylamine (178 μl), HOBT (138 mg) and EDC.HCl (196 mg) were dissolved in $CH_2Cl_2$ (2 mL) and the reaction mixture was stirred at room temperature for 1 hour. Methylamine (254 μl, 8.03 M in ethanol) was added to the mixture and stirring was continued for an additional 12 hours. The reaction was diluted with $CH_2Cl_2$ (5 mL) and washed with 1N HCl (2×1.5 mL), water (1.5 mL) and brine (1.5 mL). The organic layer was concentrated in vacuo and the crude product was used in the next step.

Step 3: 2-[3-[(1S)-(N-Hydroxycarbamoyl)-2-phenylethyl]-2-(4-methoxyphenyl)-4-oxo-thiazolidin-5-yl]]-N-methylacetamide KOH (435 mg) and hydroxylamine.HCl (340 mg) were dissolved in MeOH (2.14 mL and 3.4 mL respectively) at room temperature. Once a solution was obtained, the KOH solution was poured into the hydroxylamine solution at 0° C. and the mixture was maintained at this temperature for 1 hour. The precipitate (KCl) was filtered off. The filtrate was added into the solution of the methyl ester (obtained in step 2) in MeOH (2 mL) and stirring was continued for an additional 3 hours. Acetic acid (0.5 mL) was added to the mixture and the volume of the reaction was reduced to one third. The resulting viscous solution was diluted with water (2 mL) and EtOAc (5 mL). The organic layer was separated, evaporated and purified by HPLC.

The following compounds listed in the Tables 4, 4' and 4" were prepared in a similar manner.

TABLE 4

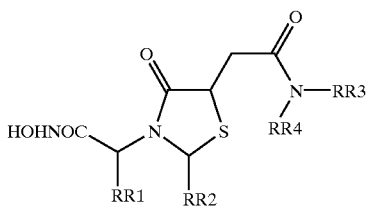

| Example No. | RR1 | RR2 | RR3 | RR4 | mol. weight | Mass (m/e) | HPLC rt (min) |
|---|---|---|---|---|---|---|---|
| 209 | -Benzyl | —C6H4-4-OMe | —H | —Me | 443.53 | 444.2, 411, 383.2 | 2.93, 2.99 |
| 210 | -Benzyl | —C6H4-4-OMe | —H | —OH | 445.50 | 447.2, 413.2, 386.2 | 3.01 |

TABLE 4-continued

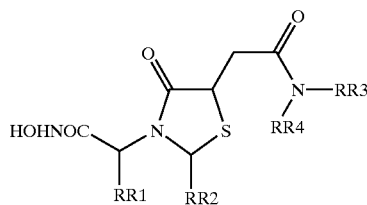

| Example No. | RR1 | RR2 | RR3 | RR4 | mol. weight | Mass (m/e) | HPLC rt (min) |
|---|---|---|---|---|---|---|---|
| 211 | -Benzyl | —C6H4-4-OMe | —H | —CH2-3-Py | 520.61 | 521.4, 460.2 | 2.82 |
| 212 | —iBu | —C6H4-4-OMe | —H | —CH2—C6H4-4-Me | 499.83 | 500.2, 467.4, 439 | 3.52 |
| 213 | —iBu | —C6H4-4-OMe | —H | —CH2—C6H4-4-Me | 499.63 | 500.2, 467.4, 439 | 3.58 |
| 214 | —iBu | —C6H4-4-OMe | —H | —CH2-3-furyl | 475.57 | 476.2, 443.2, 415 | 3.24 |
| 215 | —iBu | —C6H4-4-OMe | —H | —CH2-3-furyl | 475.57 | 426.2, 443.2, 415 | 3.28 |
| 216 | —iBu | —C6H4-4-OMe | —H | -Benzyl | 485.61 | 486.2, 453.2, 425 | 3.46 |
| 217 | —iBu | —C6H4-4-Cl | —H | —CH2-2-furyl | 479.99 | 480.2, 447.0, 419 | 3.42 |
| 218 | —iBu | —C6H4-4-Cl | —H | —CH2-2-furyl | 479.99 | 480.2, 447.0, 419 | 3.50 |
| 219 | —iBu | —C6H4-4-Cl | —H | —CH2-2-furyl | 479.99 | 480.2, 447.2, 419 | 3.50 |
| 220 | —iBu | —C6H4-4-Cl | —H | -Benzyl | 490.03 | 490.2, 457.2, 429 | 3.57 |
| 221 | —iBu | —C6H4-4-Cl | —H | -Benzyl | 490.03 | 490.2, 457.2, 429 | 3.64 |
| 222 | —iBu | —C6H4-4-Cl | —H | -Benzyl | 490.03 | 490.2, 457.2, 429 | 3.67 |
| 223 | —iBu | —C6H4-4-Cl | —H | -Cyclopentyl | 468.02 | 468.4, 435.2, 407 | 3.64 |
| 224 | —iBu | —C6H4-4-Cl | —H | -Cyclopentyl | 468.02 | 468.4, 435.2, 407 | 3.60 |
| 225 | —iBu | —C6H4-4-Cl | —H | -Cyclopentyl | 468.02 | 468.4, 435.2, 407 | 3.62 |
| 226 | —iBu | —C6H4-4-Cl | —H | —(CH2)2OMe | 457.98 | 458.2, 425.2, 397 | 3.17 |
| 227 | —iBu | —C6H4-4-Cl | —H | —(CH2)2OMe | 457.98 | 458.2, 425, 397 | 3.23 |
| 228 | —iBu | —C6H4-4-Cl | —H | —(CH2)2OMe | 457.98 | 458.2, 425, 397 | 3.23 |
| 229 | —iBu | —C6H4-4-OMe | —H | -iPentyl | 465.62 | 466.4, 433.2, 405 | 3.54 |
| 230 | —iBu | —C6H4-4-OMe | —H | -3-Isooxazolyl-5-Me | 476.56 | 477.2, 444.2 | 3.27 |
| 231 | —iBu | —C6H4-4-OMe | —H | —CH(Me)CH2OMe | 467.63 | 468.4, 435.2, 407 | 3.04 |
| 232 | —iBu | —C6H4-4-OMe | —H | -Cyclopentyl | 463.60 | 464.2, 431.2, 403 | 3.42 |
| 233 | —iBu | —C6H4-4-OMe | —H | -Cyclopentyl | 463.60 | 464.2, 431.2, 403 | 3.38 |
| 234 | —iBu | —C6H4-4-OMe | —H | —Et | 423.54 | 424.2, 391, 363.2 | 3.08 |
| 235 | —iBu | —C6H4-4-OMe | —H | —Et | 423.54 | 424.0, 391, 363.2 | 3.11 |
| 236 | —iBu | —C6H4-4-OMe | —H | -Allyl | 435.55 | 436.2, 403, 375.2 | 3.13 |
| 237 | —iBu | —C6H4-4-OMe | —H | -Allyl | 435.55 | 436.2, 403, 375.2 | 3.19 |
| 238 | —iBu | —C6H4-4-OMe | —H | —iBu | 451.59 | 452.2, 419.2, 391 | 3.47 |
| 239 | —iBu | —C6H4-4-OMe | —H | -Cyclohexyl | 477.63 | 478.2, 445.2, 417 | 3.58 |
| 240 | —iBu | —C6H4-4-OMe | —H | —iPr | 437.56 | 438.2, 405.2, 377 | 3.22 |
| 241 | —iBu | —C6H4-4-OMe | —H | —nPr | 437.56 | 438.2, 405, 377.2 | 3.22 |
| 242 | —iBu | —C6H4-4-OMe | —H | —nPr | 437.56 | 438.2, 405, 377.2 | 3.26 |
| 243 | —iBu | —C6H4-4-OMe | —H | —Ph | 471.58 | 472.2, 437.2, 411 | 3.49 |
| 244 | —iBu | —C6H4-4-OMe | —H | —Ph | 471.58 | 472.2, 739.2, 411 | 3.52 |
| 245 | —iBu | —C6H4-4-OMe | —H | -2-Py | 472.57 | 473.2, 412.2 | 2.84 |
| 246 | —iBu | —C6H4-4-OMe | —H | —(CH2)3OMe | 467.59 | 468.4, 435.2, 407 | 3.09 |
| 247 | —iBu | —C6H4-4-OMe | —H | —(CH2)3-1-(2-Me-piperidyl) | 534.72 | 450.2, 417.2, 389 | 3.21 |
| 248 | —iBu | —C6H4-4-OMe | —H | —(CH2)2OMe | 453.56 | 454.2, 421.2, 393 | 3.02 |
| 249 | —CH2—C6H4-4-O-tBu | —C6H4-4-Cl | —H | —CH2—C6H4-4-OMe | 626.18 | 626.4 | 3.90 |
| 250 | —CH2—C6H4-4-O-tBu | —C6H4-4-Cl | —H | —CH2—C6H4-4-OMe | 626.18 | 626.4, 593.4 | 4.06 |
| 251 | —CH2—C6H4-4-O-tBu | —C6H4-4-Cl | —H | —CH2—C6H4-4-OMe | 626.18 | 626.4, 593.2, 565 | 4.10 |
| 252 | —CH2—C6H4-4-O-tBu | —C6H4-4-Cl | —H | —CH2—C6H4-4-Me | 610.18 | 610.2, 577, 549.4 | 4.17 |
| 253 | —CH2—C6H4-4-O-tBu | —C6H4-4-Cl | —H | —CH2-3-Py | 597.14 | 597.2 | 3.24 |
| 254 | —CH2—C6H4-4-O-tBu | —C6H4-4-Cl | —H | -3-Isooxazolyl-5-Me | 587.10 | 587.2, 531.0, 470.2 | 3.79 |
| 255 | —CH2—C6H4-4-O-tBu | —C6H4-4-Cl | —H | -3-Isooxazolyl-5-Me | 587.10 | 587.2, 531, 470.2 | 3.88 |
| 256 | —CH2—C6H4-4-O-tBu | —C6H4-4-Cl | —H | —C(Me)2OMe | 578.13 | 578.2, 517.2 | 3.69 |
| 257 | —CH2—C6H4-4-O-tBu | —C6H4-4-Cl | —H | —C(Me)2OMe | 578.13 | 578.2, 545, 517.2 | 3.77 |
| 258 | —iBu | —C6H4-4-Cl | —H | —Ph | 476.00 | 476.0, 443.2, 415 | 3.77 |
| 259 | —iBu | —C6H4-4-Cl | —H | —iPr | 441.98 | 442.4, 409.2, 381 | 3.43 |
| 260 | —iBu | —C6H4-4-Cl | —H | —nPr | 441.98 | 442.4, 409, 381.2 | 3.45 |
| 261 | —iBu | —C6H4-4-Cl | —H | —iBu | 456.01 | 456.2, 423.2, 395 | 3.42 |
| 262 | —iBu | —C6H4-4-Cl | —H | -Allyl | 439.96 | 440.2, 407, 379.2 | 3.37 |
| 263 | —iBu | —C6H4-4-Cl | —H | —Et | 427.95 | 428.2, 395, 367.0 | 3.29 |
| 264 | —iBu | —C6H4-4-Cl | —H | —CH2-cyclopropyl | 453.96 | 454.2, 421.2, 393 | 3.49 |
| 265 | —iBu | —C6H4-4-Cl | —H | —CH2—C6H4-4-OMe | 520.05 | 520.4, 487.2, 459 | 3.64 |
| 266 | —iBu | —C6H4-4-Cl | —H | —CH2—C6H4-4-Me | 504.05 | 504.0, 471.2, 443 | 3.78 |
| 267 | —iBu | —C6H4-4-Cl | —H | -2-Py | 476.99 | 477.2, 416.2 | 3.12 |
| 268 | —iBu | —C6H4-4-Cl | —H | —(CH2)3-1-(2-Me-piperidyl) | 539.14 | 539.4 | 3.04 |
| 269 | —iBu | —C6H4-4-Cl | —H | —iPentyl | 470.04 | 470.2, 437.2, 409 | 3.75 |
| 270 | —iBu | —C6H4-4-Cl | —H | —(CH2)3OMe | 472.01 | 472.2, 439.2, 411 | 3.26 |
| 271 | —iBu | —C6H4-4-Cl | —H | —C(Me)2OMe | 472.01 | 472.2, 439.2, 411 | 3.34 |
| 272 | —iBu | —C6H4-4-Cl | —H | —(CH2)2-2-Py | 505.04 | 502.2, 472.2 | 2.93 |
| 273 | —iBu | —C6H4-4-Cl | —H | —CH2-3-Py | 491.01 | 491.2, 430.2 | 2.92 |
| 274 | —iBu | —C6H4-4-Cl | —H | -3-Isooxazolyl-5-Me | 480.97 | 481.2, 448.0, 420 | 3.44, 3.52 |
| 275 | —CH2—C6H4-4-O-tBu | —C6H4-4-Cl | —H | —Et | 534.08 | 534.2, 473.2 | 3.66 |

TABLE 4-continued

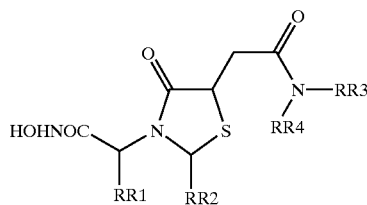

| Example No. | RR1 | RR2 | RR3 | RR4 | mol. weight | Mass (m/e) | HPLC rt (min) |
|---|---|---|---|---|---|---|---|
| 276 | —CH2—C6H4-4-O-tBu | —C6H4-4-Cl | —H | —Et | 534.08 | 534.2, 501, 473.2 | 3.67, 3.72 |
| 277 | —CH2—C6H4-4-O-tBu | —C6H4-4-Cl | —H | —Et | 534.08 | 534.2, 501, 473.2 | 3.73 |
| 278 | —CH2—C6H4-4-O-tBu | —C6H4-4-Cl | —H | -Allyl | 546.09 | 546.2, 485.2 | 3.70 |
| 279 | —CH2—C6H4-4-O-tBu | —C6H4-4-Cl | —H | -Allyl | 546.09 | 546.2, 513, 485.2 | 3.76 |
| 280 | —CH2—C6H4-4-O-tBu | —C6H4-4-Cl | —H | -Cyclohexyl | 588.17 | 588.2, 527.4 | 4.17 |
| 281 | —CH2—C6H4-4-O-tBu | —C6H4-4-Cl | —H | —iPr | 548.11 | 548.4, 487.2 | 3.78 |
| 282 | —CH2—C6H4-4-O-tBu | —C6H4-4-Cl | —H | —iPr | 548.11 | 548.4, 515, 487.2 | 3.88 |
| 283 | —CH2—C6H4-4-O-tBu | —C6H4-4-Cl | —H | —nPr | 548.11 | 548.4, 515, 487.2 | 3.88 |
| 284 | —CH2—C6H4-4-O-tBu | —C6H4-4-Cl | —H | —nPr | 548.11 | 548.4, 487.2 | 3.77 |
| 285 | —CH2—C6H4-4-O-tBu | —C6H4-4-Cl | —H | -2-Py | 583.11 | 583.2, 522.4 | 3.53 |
| 286 | —CH2—C6H4-4-O-tBu | —C6H4-4-Cl | —H | -2-Py | 583.11 | 583.2, 522.4 | 3.52 |
| 287 | —CH2—C6H4-4-O-tBu | —C6H4-4-Cl | —H | -2-Py | 583.11 | 583.2, 522.4 | 3.42 |
| 288 | —CH2—C6H4-4-O-tBu | —C6H4-4-Cl | —H | —Ph | 582.12 | 582.2, 549, 521.4 | 4.08 |
| 289 | —CH2—C6H4-4-O-tBu | —C6H4-4-Cl | —H | —CH2-cyclopropyl | 560.12 | 560.2, 527, 499.2 | 3.92 |
| 290 | —CH2—C6H4-4-O-tBu | —C6H4-4-Cl | —H | —CH2-cyclopropyl | 560.12 | 560.2, 499.2 | 3.80 |
| 291 | —CH2—C6H4-4-O-tBu | —C6H4-4-Cl | —nPr | —nPr | 590.19 | 590.4, 529.2 | 4.39 |
| 292 | —CH2—C6H4-4-O-tBu | —C6H4-4-Cl | —H | -4-Py | 583.11 | 583.2 | 3.30 |
| 293 | —CH2—C6H4-4-O-tBu | —C6H4-4-Cl | —H | -4-Py | 583.11 | 583.2, 527.2 | 3.25 |
| 294 | —CH2—C6H4-4-O-tBu | —C6H4-4-Cl | —H | -Benzyl | 596.15 | 596.2, 563, 535.2 | 4.05 |
| 295 | —CH2—C6H4-4-O-tBu | —C6H4-4-Cl | —H | -Cyclopentyl | 574.14 | 574.4, 513.4 | 4.06 |
| 296 | —CH2—C6H4-4-O-tBu | —C6H4-4-Cl | —H | —iPentyl | 576.16 | 576.4, 543, 515.2 | 4.17 |
| 297 | —CH2—C6H4-4-O-tBu | —C6H4-4-Cl | —H | —(CH2)3OMe | 578.13 | 578.2, 517.2 | 3.64 |
| 298 | —CH2—C6H4-4-O-tBu | —C6H4-4-Cl | —H | —(CH2)3OMe | 578.13 | 578.2, 517.2 | 3.74 |
| 299 | —CH2—C6H4-4-O-tBu | —C6H4-4-Cl | —H | —(CH2)3-1-(2-Me-piperidyl) | 645.27 | 645.4 | 3.22 |
| 300 | —CH2—C6H4-4-O-tBu | —C6H4-4-Cl | —H | —(CH2)2-2-Py | 611.17 | 611.2 | 3.15 |
| 301 | —CH2—C6H4-4-O-tBu | —C6H4-4-Cl | —H | —(CH2)2-2-Py | 611.17 | 611.2 | 3.26 |
| 302 | —CH2—C6H4-4-O-tBu | —C6H4-4-Cl | —H | —CH2-2-furyl | 586.11 | 586.2, 525.2 | 3.98 |
| 303 | —CH2—C6H4-4-O-tBu | —C6H4-4-Cl | —H | —CH2-2-furyl | 586.11 | 586.2, 553, 525.2 | 3.85, 3.90 |
| 304 | —CH2—C6H4-4-O-tBu | —C6H4-4-Cl | —H | —CH2-2-furyl | 586.11 | 586.2, 525.2 | 3.80 |
| 305 | —iBu | —C6H4-4-Cl | —nPr | —nPr | 484.06 | 484.2, 451, 423 | 4.03 |
| 306 | —iBu | —C6H4-4-Cl | —nPr | —nPr | 484.06 | 484.2, 451.0 | 4.02 |
| 307 | -Benzyl | —C6H4-4-Cl | —H | —Me | 443.53 | 444.2, 411, 383.2 | 2.85 |
| 308 | -Benzyl | —C6H4-4-OMe | —H | —CH2—C6H4-4-OMe | 549.65 | 550.4, 489.2 | 3.46 |
| 309 | -Benzyl | —C6H4-4-OMe | —H | —CH2—C6H4-4-OMe | 549.65 | 550.4, 517.4, 489 | 3.51 |
| 310 | —iBu | —C6H4-4-OMe | —H | —CH2-cyclopropyl | 449.57 | 450.2, 417.2, 389 | 3.21 |
| 311 | —iBu | —C6H4-4-OMe | —H | —CH2-cyclopropyl | 449.57 | 450.2, 417.2, 389 | 3.30 |
| 312 | —iBu | —C6H4-4-OMe | —H | —CH2—C6H4-4-OMe | 515.63 | 516.2, 483.2, 455 | 3.45 |
| 313 | —iBu | —C6H4-4-OMe | —H | —CH2—C6H4-4-OMe | 515.63 | 516.2, 483.2, 455 | 3.39, 3.44 |
| 314 | —CH2—C6H4-4-O-tBu | —C6H4-4-Cl | —H | —iBu | 562.13 | 562.4, 501.2 | 4.07 |
| 315 | —CH2—C6H4-4-O-tBu | —C6H4-4-Cl | —H | —(CH2)2OMe | 564.11 | 564.2, 503.2 | 3.58 |
| 316 | —CH2—C6H4-4-O-tBu | —C6H4-4-Cl | —H | —(CH2)2OMe | 564.11 | 564.2, 503.2 | 3.72 |
| 317 | —iBu | —C6H4-4-Cl | —H | —(CH2)3SMe | 488.07 | 488.2, 455.2, 427 | 3.52 |
| 318 | —iBu | —C6H4-4-Cl | —H | —(CH2)3SMe | 488.07 | 488.2, 455.2, 427 | 3.52 |
| 319 | —CH2—C6H4-4-O-tBu | —C6H4-4-Cl | —H | —(CH2)3SMe | 594.20 | 594.2, 533.2 | 3.96 |
| 320 | —CH2—C6H4-4-O-tBu | —C6H4-4-Cl | —H | —nBu | 562.13 | 562.2, 501.2 | 3.95 |
| 321 | —CH2—C6H4-4-O-iBu | —C6H4-4-Cl | —H | —nBu | 562.13 | 562.2, 529, 501.2 | 3.99 |
| 322 | —CH2—C6H4-4-O-tBu | —C6H4-4-Cl | —H | —nBu | 562.13 | 562.2, 501.2 | 4.04 |
| 323 | —iBu | —C6H4-4-Cl | —H | -Cyclohexyl | 482.05 | 482.2, 449.2, 421 | 3.82 |
| 324 | —CH2—C6H4-4-O-tBu | —C6H4-4-OMe | —H | —Me | 515.63 | 516, 483, 455 | 3.43 |
| 325 | —CH2—C6H4-4-O-tBu | —C6H4-4-Cl | —H | —Me | 520.05 | 520.4, 459.2 | 3.51 |
| 326 | —CH2—C6H4-4-O-tBu | —C6H4-4-Cl | —H | —Me | 520.05 | 520.4, 487, 459.2 | 3.63 |
| 327 | —CH2—C6H4-4-O-tBu | —C6H4-4-OMe | —H | —iPentyl | 571.74 | 572.4, 539, 511.4 | 3.91, 3.97 |
| 328 | —CH2—C6H4-4-O-tBu | —C6H4-4-OMe | —H | —(CH2)3OMe | 573.71 | 574.4, 513.4 | 3.49 |
| 329 | —CH2—C6H4-4-O-tBu | —C6H4-4-OMe | —H | —(CH2)3OMe | 573.71 | 574.4, 541, 513.4 | 3.54 |
| 330 | —CH2—C6H4-4-O-tBu | —C6H4-4-OMe | —H | —(CH2)3-1-(2-Me-pipridyl) | 640.85 | 641.4 | 3.21, 3.25 |
| 331 | —CH2—C6H4-4-O-tBu | —C6H4-4-OMe | —H | —(CH2)2-2-Py | 606.75 | 607.2, 574.2 | 3.27 |
| 332 | —CH2—C6H4-4-O-tBu | —C6H4-4-OMe | —H | —(CH2)2-2-Py | 606.75 | 607.2 | 3.10, 3.14 |
| 333 | —CH2—C6H4-4-O-tBu | —C6H4-4-OMe | —H | —CH2-2-furyl | 581.69 | 582.2, 549, 521.4 | 3.68, 3.73 |
| 334 | —CH2—C6H4-4-O-tBu | —C6H4-4-OMe | —H | -Benzyl | 591.73 | 592.4, 559, 531.2 | 3.80, 3.87 |
| 335 | —CH2—C6H4-4-O-tBu | —C6H4-4-OMe | —H | -4-Py | 578.69 | 579.2, 518.2 | 3.22 |
| 336 | —CH2—C6H4-4-O-tBu | —C6H4-4-OMe | —H | -Cyclopentyl | 569.73 | 570.4, 537, 509.4 | 3.78, 3.85 |
| 337 | —CH2—C6H4-4-O-tBu | —C6H4-4-OMe | —H | -Cyclopentyl | 569.73 | 570.4, 537, 509.4 | 3.85 |
| 338 | —CH2—C6H4-4-O-tBu | —C6H4-4-OMe | —H | —(CH2)2OMe | 559.69 | 560.2, 527.2, 499 | 3.42, 3.48 |
| 339 | —CH2—C6H4-4-O-tBu | —C6H4-4-OMe | —H | —(CH2)3SMe | 589.78 | 590.2, 557.2, 529 | 3.68 |
| 340 | —CH2—C6H4-4-O-tBu | —C6H4-4-OMe | —H | —nBu | 557.71 | 558.2, 525, 497.4 | 3.81 |

TABLE 4-continued

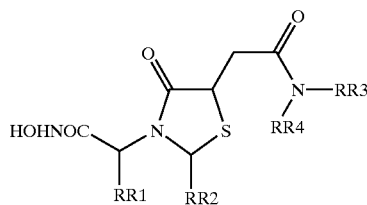

| Example No. | RR1 | RR2 | RR3 | RR4 | mol. weight | Mass (m/e) | HPLC rt (min) |
|---|---|---|---|---|---|---|---|
| 341 | —CH2—C6H4-4-O-tBu | —C6H4-4-OMe | —H | —nBu | 557.71 | 558.2, 525, 497.4 | 3.84 |
| 342 | —CH2—C6H4-4-O-tBu | —C6H4-4-OMe | —H | —(CH2)3SMe | 589.78 | 590.2, 557, 529.2 | 3.78 |
| 343 | —CH2—C6H4-4-O-tBu | —C6H4-4-OMe | —H | —C(Me)2OMe | 573.71 | 574.4, 541, 513.4 | 3.61 |
| 344 | —CH2—C6H4-4-O-tBu | —C6H4-4-OMe | —H | -3-Isooxazolyl-5-Me | 582.68 | 583.2, 522 | 3.63 |
| 345 | —CH2—C6H4-4-O-tBu | —C6H4-4-OMe | —H | —C(Me)2OMe | 573.71 | 574.4, 541, 513.4 | 3.52, 3.59 |
| 346 | —CH2—C6H4-4-O-tBu | —C6H4-4-OMe | —H | -3-Isooxazolyl-5-Me | 582.68 | 583.2, 550, 522.2 | 3.70 |
| 347 | —CH2—C6H4-4-O-tBu | —C6H4-4-OMe | —H | —CH2-4-Py | 592.72 | 593.4 | 3.20, 3.26 |
| 348 | —CH2—C6H4-4-O-tBu | —C6H4-4-OMe | —H | —Et | 529.68 | 530.2, 497, 469.4 | 3.44 |
| 349 | —CH2—C6H4-4-O-tBu | —C6H4-4-OMe | —H | —Et | 529.68 | 530.2, 497, 469.4 | 3.53 |
| 350 | —CH2—C6H4-4-O-tBu | —C6H4-4-OMe | —H | -Allyl | 541.67 | 542.4, 509, 481.4 | 3.52 |
| 351 | —CH2—C6H4-4-O-tBu | —C6H4-4-OMe | —H | -Allyl | 541.67 | 542.4, 509, 481.2 | 3.60 |
| 352 | —CH2—C6H4-4-O-tBu | —C6H4-4-OMe | —H | —iBu | 557.71 | 558.2, 525, 497.4 | 3.73 |
| 353 | —CH2—C6H4-4-O-tBu | —C6H4-4-OMe | —H | —iBu | 557.71 | 558.2, 525, 497.4 | 3.80 |
| 354 | —CH2—C6H4-4-O-tBu | —C6H4-4-OMe | —H | -Cyclohexyl | 583.75 | 584.2, 551, 523 | 3.89, 3.95 |
| 355 | —CH2—C6H4-4-O-tBu | —C6H4-4-OMe | —H | —iPr | 543.69 | 544.4, 511, 483.4 | 3.58 |
| 356 | —CH2—C6H4-4-O-tBu | —C6H4-4-OMe | —H | —iPr | 543.69 | 544.4, 511, 483.4 | 3.64 |
| 357 | —CH2—C6H4-4-O-tBu | —C6H4-4-OMe | —H | —nPr | 543.69 | 544.4, 511, 483.4 | 3.58, 3.65 |
| 358 | —CH2—C6H4-4-O-tBu | —C6H4-4-OMe | —H | —nPr | 543.69 | 544.4, 511, 483.4 | 3.65 |
| 359 | —CH2—C6H4-4-O-tBu | —C6H4-4-OMe | —H | —Ph | 577.71 | 578.2, 545.2, 517 | 3.86 |
| 360 | —CH2—C6H4-4-O-tBu | —C6H4-4-OMe | —H | —2-Py | 578.69 | 579.2, 518.2 | 3.22 |
| 361 | —CH2—C6H4-4-O-tBu | —C6H4-4-OMe | —H | —2-Py | 578.69 | 579.2, 518.2 | 3.29 |
| 362 | —CH2—C6H4-4-O-tBu | —C6H4-4-OMe | —H | —CH2-cyclopropyl | 555.70 | 556.2, 523, 495.4 | 3.62, 3.69 |
| 363 | —CH2—C6H4-4-O-tBu | —C6H4-4-OMe | —H | —CH2-cyclopropyl | 555.70 | 556.2, 523, 495.4 | 3.70 |
| 364 | —CH2—C6H4-4-O-tBu | —C6H4-4-OMe | —H | —CH2—C6H4-4-OMe | 621.76 | 622.4, 589, 561 | 3.73, 3.81 |

TABLE 4'

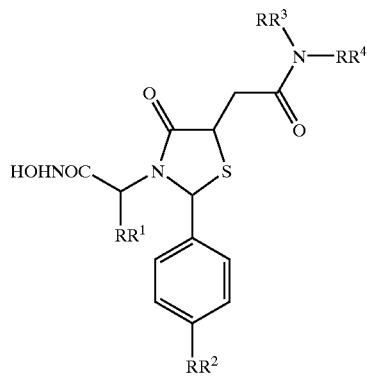

| Example No. | RR$^1$ | RR$^2$ | RR$^3$ | RR$^4$ | mol. weitht | Mass (m/e) | HPLC rt (min) |
|---|---|---|---|---|---|---|---|
| 467 | -Benzyl | —Cl | —H | -Benzyl | 524.0 | 524.2, 491.2, 463 | 4.59 |
| 468 | -Benzyl | —Cl | —H | -Benzyl | 524.0 | 524.2, 491, 463.2 | 4.57 |
| 469 | -Benzyl | —Cl | —H | -Benzyl | 524.0 | 524.2, 491, 463.2 | 4.51 |
| 470 | -Benzyl | —Cl | —H | -Benzyl | 524.0 | 524.2, 491, 463.2 | 4.49 |
| 471 | -Benzyl | —OMe | —nPr | —nPr | 513.7 | 514.4, 481.2, 453 | 4.60 |
| 472 | -Benzyl | —OMe | —nPr | —nPr | 513.7 | 514.2, 481, 453 | 4.75 |
| 473 | -Benzyl | —OMe | —H | —iBu | 485.6 | 486.2, 453, 425.2 | 4.44 |
| 474 | -Benzyl | —OMe | —H | —iBu | 485.6 | 486.2, 453.2, 425 | 4.30 |
| 475 | -Benzyl | —OMe | —H | —(CH2)3OMe | 501.6 | 502.2, 469, 441.4 | 4.19 |
| 476 | -Benzyl | —OMe | —H | —(CH2)3OMe | 501.6 | 502.2, 469, 441.4 | 4.14 |
| 477 | -Benzyl | —OMe | —H | —(CH2)3OMe | 501.6 | 502.2, 469, 441.4 | 4.19 |
| 478 | -Benzyl | —Cl | —H | -3-Isooxazolyl-5-Me | 515.0 | 515.2, 482, 454.2 | 4.17 |
| 479 | -Benzyl | —OMe | —H | —iPr | 471.6 | 472.2, 439, 411.2 | 4.32 |
| 480 | -Benzyl | —OMe | —H | —iPr | 471.6 | 472.2, 439.4, 411 | 4.27 |

TABLE 4'-continued

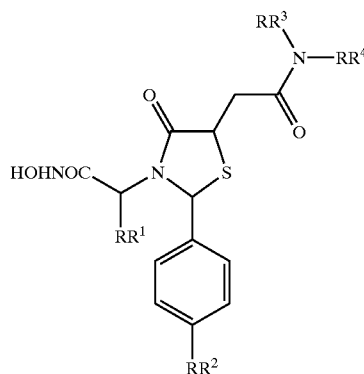

| Example No. | RR¹ | RR² | RR³ | RR⁴ | mol. weitht | Mass (m/e) | HPLC rt (min) |
|---|---|---|---|---|---|---|---|
| 481 | -Benzyl | —OMe | —H | —iPr | 471.6 | 472.2, 439.2, 411 | 4.28 |
| 482 | -Benzyl | —OMe | —H | —iPentyl | 504.1 | 504.2, 471, 443.2 | 4.32 |
| 483 | -Benzyl | —Cl | —H | —iPentyl | 504.1 | 504.2, 471.2, 443 | 4.46 |
| 484 | -Benzyl | —OMe | —H | —C(Me)2OMe | 501.6 | 502.2, 469, 441.4 | 3.88 |
| 485 | -Benzyl | —OMe | —H | —C(Me)2OMe | 501.6 | 502.4, 469, 441.4 | 3.94 |
| 486 | -Benzyl | —OMe | —H | —C(Me)2OMe | 501.6 | 502.4, 469, 441.4 | 3.95 |
| 487 | -Benzyl | —Cl | —H | -3-Isooxazolyl-5-Me | 515.0 | 515.2, 472, 454.2 | 4.15 |
| 488 | -Benzyl | —Cl | —H | -3-Isooxazolyl-5-Me | 515.0 | 515.0, 482, 454.2 | 5.24 |
| 489 | -Benzyl | —OMe | —H | —CH2-cyclopropyl | 483.6 | 484.2, 451.2, 423 | 4.04 |
| 490 | -Benzyl | —OMe | —H | —CH2-cyclopropyl | 483.6 | 484.2, 451.2, 423 | 4.11 |
| 491 | -Benzyl | —OMe | —H | —CH2-cyclopropyl | 483.6 | 484.2, 451.2, 423 | 4.17 |
| 492 | -Benzyl | —OMe | —H | —Ph | 505.6 | 506.2, 47.3, 445.2 | 4.26 |
| 493 | -Benzyl | —OMe | —H | —Ph | 505.6 | 506.2, 473, 445.2 | 4.28 |
| 494 | -Benzyl | —OMe | —H | -Allyl | 489.6 | 470.2, 437, 409.2 | 3.98 |
| 495 | —CH2-cyclohexyl | —Cl | —H | —Et | 468.0 | 468.4, 435.2, 407 | 4.52 |
| 496 | —CH2-cyclohexyl | —Cl | —H | —iPr | 482.0 | 482.2, 449.2, 421 | 4.61 |
| 497 | —CH2-cyclohexyl | —Cl | —H | —iPr | 482.0 | 482.2, 449, 421.2 | 4.63 |
| 498 | —CH2-cyclohexyl | —Cl | —H | —nPr | 482.0 | 482.4, 449, 421.2 | 4.65 |
| 499 | —CH2-cyclohexyl | —Cl | —H | —nPr | 482.0 | 482.2, 449, 421.2 | 4.62 |
| 500 | —CH2-cyclohexyl | —Cl | —H | —Ph | 516.1 | 516.2, 483, 455.2 | 3.84 |
| 501 | —CH2-cyclohexyl | —Cl | —H | —CH2—C6H4-4-OMe | 560.1 | 560.2, 527.2, 499 | 3.91 |
| 502 | —CH2-cyclohexyl | —Cl | —H | —CH2—C6H4-4-OMe | 560.1 | 560.2, 527.4, 499 | 3.76 |
| 503 | —CH2-cyclohexyl | —Cl | —H | —CH2-cyclopropyl | 494.1 | 494.4, 461, 433.2 | 3.61 |
| 504 | —CH2-cyclohexyl | —Cl | —H | -2-Py | 517.1 | 517.4, 456.2 | 3.17 |
| 505 | —CH2-cyclohexyl | —Cl | —H | -2-Py | 517.1 | 517.2, 456.2 | 3.13 |
| 506 | —CH2-cyclohexyl | —Cl | —H | —CH2—C6H4-4-Me | 544.1 | 544.2, 511, 483.4 | 3.97 |
| 507 | —CH2-cyclohexyl | —Cl | —H | —(CH2)3OMe | 512.1 | 512.2, 479, 451.2 | 3.41 |
| 508 | —CH2-cyclohexyl | —Cl | —H | -3-Isooxazolyl-5-Me | 521.0 | 521.2, 488, 460.2 | 3.65 |
| 509 | —CH2-cyclohexyl | —Cl | —H | -3-Isooxazolyl-5-Me | 521.0 | 521.4, 488, 460.2 | 3.67 |
| 510 | —CH2-cyclohexyl | —Cl | —H | —CH2-3-Py | 531.1 | 531.2, 470.2 | 2.81 |
| 511 | —CH2-cyclohexyl | —Cl | —H | —CH2-3-Py | 531.1 | 531.2, 470.2 | 2.60 |
| 512 | —CH2-cyclohexyl | —Cl | —H | —(CH2)3OMe | 512.1 | 512.2, 479, 451.2 | 3.42 |
| 513 | -Benzyl | —OMe | —Me | —(CH2)2NMe2 | 514.6 | 515.2 | 3.92 |
| 514 | —CH2-cyclohexyl | —Cl | —H | —(CH2)2-2-Py | 545.1 | 545.2, 484.4 | 2.84 |
| 515 | —CH2-cyclohexyl | —Cl | —H | —(CH2)2-2-Py | 545.1 | 545.2, 484.2 | 2.86 |
| 516 | —CH2-cyclohexyl | —Cl | —H | —CH2-2-furyl | 520.1 | 520.4, 487, 459.2 | 3.66 |
| 517 | —CH2-cyclohexyl | —Cl | —H | —CH2-2-furyl | 520.1 | 520.4, 487, 459.2 | 3.65 |
| 518 | —CH2-cyclohexyl | —Cl | —H | -Benzyl | 530.1 | 530.2, 497, 469.4 | 3.83 |
| 519 | —CH2-cyclohexyl | —Cl | —H | —Me | 454.0 | 454.2, 421, 393.2 | 3.25 |
| 520 | —CH2-cyclohexyl | —Cl | —H | —nBu | 496.1 | 496.4, 463, 435.2 | 3.78 |
| 521 | —CH2-cyclohexyl | —Cl | —H | —(CH2)3SMe | 528.1 | 528.2, 495, 467.2 | 3.70 |
| 522 | —CH2-cyclohexyl | —Cl | —H | —(CH2)2OMe | 498.0 | 498.2, 465, 437.2 | 3.34 |
| 523 | —CH2-cyclohexyl | —OMe | —H | -3-Isooxazolyl-5-Me | 516.6 | 517.4, 484, 456.2 | 4.46 |
| 524 | —CH2-cyclohexyl | —OMe | —H | -3-Isooxazolyl-5-Me | 516.6 | 517.2, 484, 456.2 | 4.42 |
| 525 | —CH2-cyclohexyl | —OMe | —H | —CH2-2-furyl | 515.6 | 516.2, 483, 455.2 | 4.40 |
| 526 | —CH2-cyclohexyl | —OMe | —H | —(CH2)2-2-Py | 540.7 | 541.2, 508.4 | 4.01 |
| 527 | —CH2-cyclohexyl | —OMe | —H | —(CH2)3-1-(2-Me-piperidyl) | 574.8 | 575.6 | 3.98 |
| 528 | —CH2-cyclohexyl | —OMe | —H | —(CH2)3OMe | 507.7 | 508.4, 475, 447.2 | 4.34 |
| 529 | —CH2-cyclohexyl | —OMe | —H | —(CH2)3OMe | 507.7 | 508.4, 475.2, 447 | 4.29 |
| 530 | —CH2-cyclohexyl | —OMe | —H | -Benzyl | 525.7 | 526.2, 493, 465.2 | 4.58 |
| 531 | —CH2-cyclohexyl | —OMe | —H | -Benzyl | 525.7 | 526.2, 493.4, 465 | 4.56 |
| 532 | —CH2-cyclohexyl | —OMe | —nPr | —nPr | 519.7 | 520.4, 487, 459 | 4.83 |
| 533 | —CH2-cyclohexyl | —OMe | —H | —CH2-2-furyl | 515.6 | 516.2, 483, 455.2 | 4.48 |
| 534 | -Benzyl | —Cl | —H | —iPentyl | 504.1 | 504.0, 471, 443.2 | 4.33 |
| 535 | -Benzyl | —Cl | —H | —iPentyl | 504.1 | 504.2, 471, 443.2 | 4.40 |
| 536 | —CH2-cyclohexyl | —OMe | —H | -Cyclopentyl | 503.7 | 504.2, 471.2, 443 | 4.51 |
| 537 | —CH2-cyclohexyl | —OMe | —H | -4-Py | 512.6 | 513.4, 452.2 | 4.04 |

TABLE 4'-continued

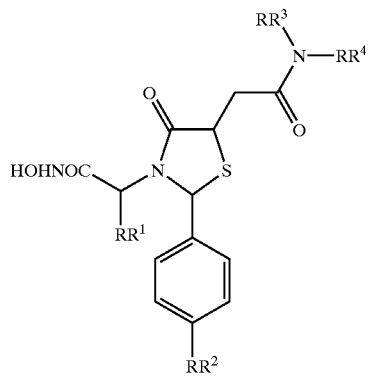

| Example No. | RR$^1$ | RR$^2$ | RR$^3$ | RR$^4$ | mol. weitht | Mass (m/e) | HPLC rt (min) |
|---|---|---|---|---|---|---|---|
| 538 | —CH2-cyclohexyl | —OMe | —H | -4-Py | 512.6 | 513.4, 452.2 | 4.01 |
| 539 | —CH2-cyclohexyl | —OMe | —H | —(CH2)3SMe | 523.7 | 524.4, 491.2, 463 | 4.49 |
| 540 | —CH2-cyclohexyl | —OMe | —H | —(CH2)2OMe | 493.6 | 494.4, 461.2, 433 | 4.34 |
| 541 | —CH2-cyclohexyl | —OMe | —H | —(CH2)2OMe | 493.6 | 494.4, 461.2, 433 | 4.27 |
| 542 | —CH2-cyclohexyl | —OMe | —H | -Cyclopentyl | 503.7 | 504.2, 471.2, 443 | 4.56 |
| 543 | —CH2-cyclohexyl | —OMe | —H | —nBu | 491.7 | 492.4, 459.4, 431 | 4.54 |
| 544 | —CH2-cyclohexyl | —OMe | —H | —Me | 449.6 | 450.2, 417, 389.4 | 3.88 |
| 545 | —CH2-cyclohexyl | —OMe | —H | —Et | 463.6 | 464.2, 431.2, 403 | 4.32 |
| 546 | —CH2-cyclohexyl | —OMe | —H | —Et | 463.6 | 464.2, 431.2, 403 | 4.36 |
| 547 | —CH2-cyclohexyl | —OMe | —H | -Allyl | 475.6 | 476.2, 443.2, 415 | 4.41 |
| 548 | —CH2-cyclohexyl | —OMe | —H | —iBu | 491.7 | 492.4, 459.4, 431 | 4.47 |
| 549 | —CH2-cyclohexyl | —OMe | —H | —iBu | 491.7 | 492.4, 459.4, 431 | 4.51 |
| 550 | —CH2-cyclohexyl | —OMe | —H | —iBu | 491.7 | 492.4, 459.4, 431 | 4.56 |
| 551 | —CH2-cyclohexyl | —OMe | —H | -Cyclohexyl | 517.7 | 518.4, 485.2, 457 | 4.62 |
| 552 | —CH2-cyclohexyl | —OMe | —H | -Cyclohexyl | 517.7 | 518.4, 485.2, 457 | 4.69 |
| 553 | —CH2-cyclohexyl | —OMe | —H | —iPr | 477.6 | 478.2, 445.2, 417 | 4.40 |
| 554 | —CH2-cyclohexyl | —OMe | —H | —iPr | 477.6 | 478.2, 445.2, 417 | 4.45 |
| 555 | —CH2-cyclohexyl | —OMe | —H | —nPr | 477.6 | 478.2, 445.2, 417 | 4.41 |
| 556 | —CH2-cyclohexyl | —OMe | —H | —nPr | 477.6 | 478.2, 445.2, 417 | 4.46 |
| 557 | —CH2-cyclohexyl | —OMe | —H | —Ph | 511.6 | 512.4, 479, 451.2 | 4.61 |
| 558 | —CH2-cyclohexyl | —OMe | —H | -2-Py | 512.6 | 513.4, 452.2 | 4.13 |
| 559 | —CH2-cyclohexyl | —OMe | —H | -2-Py | 512.6 | 513.4, 452.2 | 4.18 |
| 560 | —CH2-cyclohexyl | —OMe | —H | —CH2-cyclopropyl | 489.6 | 490.4, 457.2, 429 | 4.46 |
| 561 | —CH2-cyclohexyl | —OMe | —H | —CH2-cyclopropyl | 489.6 | 490.4, 457.2, 429 | 4.50 |
| 562 | —CH2-cyclohexyl | —OMe | —H | —CH2—C6H4-4-OMe | 555.7 | 556.2, 523, 495.4 | 4.52 |
| 563 | —CH2-cyclohexyl | —OMe | —H | —CH2—C6H4-4-OMe | 555.7 | 556.2, 523, 495.4 | 4.56 |
| 564 | —CH2-cyclohexyl | —OMe | —H | —CH2—C6H4-4-OMe | 555.7 | 556.2, 523, 495.4 | 4.57 |
| 565 | —CH2-cyclohexyl | —OMe | —H | —CH2—C6H4-4-Me | 539.7 | 540.4, 507, 479.2 | 4.62 |
| 566 | —CH2-cyclohexyl | —OMe | —H | —CH2—C6H4-4-Me | 539.7 | 540.4, 507.4, 479 | 4.65 |
| 567 | —CH2-cyclohexyl | —OMe | —H | —CH2—C6H4-4-Me | 539.7 | 540.4, 507.4, 479 | 4.68 |
| 568 | —CH2-cyclohexyl | —OMe | —H | —CH2-3-Py | 526.7 | 527.2, 466.4 | 4.00 |
| 569 | -Benzyl | —Cl | —Me | —(CH2)2NMe2 | 519.1 | 519.4 | 3.95 |
| 570 | -Benzyl | —Cl | —H | —iPr | 476.0 | 476.0, 443, 415.4 | 4.34 |
| 571 | -Benzyl | —Cl | —H | —iPr | 476.0 | 476.0, 443, 415.2 | 4.42 |
| 572 | -Benzyl | —Cl | —H | —iPr | 476.0 | 476.2, 443.2, 415 | 4.48 |
| 573 | -Benzyl | —Cl | —nPr | —nPr | 518.1 | 518.2, 485.2, 457 | 4.65 |
| 574 | -Benzyl | —Cl | —nPr | —nPr | 518.1 | 518.2, 485, 457.2 | 4.81 |
| 575 | -Benzyl | —OMe | —H | —CH2—C6H4-4-Me | 533.7 | 534.2, 501, 473.2 | 4.58 |
| 576 | -Benzyl | —Cl | —H | —nBu | 490.0 | 490.2, 457, 429.2 | 4.57 |
| 577 | -Benzyl | —Cl | —H | —nBu | 490.0 | 490.2, 457, 429.2 | 4.64 |
| 578 | -Benzyl | —OMe | —H | —nPr | 471.6 | 472.2, 439.2, 411 | 4.32 |
| 579 | -Benzyl | —OMe | —H | —nPr | 471.6 | 472.2, 439, 411.2 | 4.37 |
| 580 | -Benzyl | —OMe | —H | —nPr | 471.6 | 472.2, 439, 411.2 | 4.38 |
| 581 | -Benzyl | —OMe | —H | —(CH2)3-1-(2-Me-piperidyl) | 568.7 | 569.4 | 3.98 |
| 582 | -Benzyl | —OMe | —H | -Benzyl | 519.6 | 520.4, 487, 459.2 | 4.37 |
| 583 | -Benzyl | —Cl | —H | -Cyclohexyl | 516.1 | 516.2, 483, 455.2 | 4.67 |
| 584 | -Benzyl | —OMe | —H | —nBu | 485.6 | 486.2, 453, 425.2 | 4.30 |
| 585 | -Benzyl | —Cl | —H | —CH2-2-furyl | 514.0 | 514.2, 481, 453.2 | 4.51 |
| 586 | -Benzyl | —OMe | —H | -Cyclohexyl | 511.6 | 512.4, 479, 451.2 | 4.54 |
| 587 | -Benzyl | —OMe | —H | —CH2-2-furyl | 509.6 | 510.2, 477, 449.2 | 4.39 |
| 588 | -Benzyl | —Cl | —H | —CH2-cyclopropyl | 488.0 | 488.2, 455, 427.2 | 4.49 |
| 589 | -Benzyl | —Cl | —H | —CH2-cyclopropyl | 488.0 | 488.2, 455.2, 427 | 4.56 |
| 590 | -Benzyl | —Cl | —H | -Allyl | 474.0 | 474.2, 441, 413.2 | 4.43 |
| 591 | -Benzyl | —Cl | —H | -Allyl | 474.0 | 474.2, 441.2, 413 | 4.45 |
| 592 | -Benzyl | —Cl | —H | —nPr | 476.0 | 476.2, 443.2, 415 | 4.50 |
| 593 | -Benzyl | —OMe | —H | —Et | 457.6 | 458.2, 425, 397.2 | 4.19 |
| 594 | -Benzyl | —Cl | —H | -Cyclohexyl | 516.1 | 516.2, 483, 455.2 | 4.60 |

TABLE 4'-continued

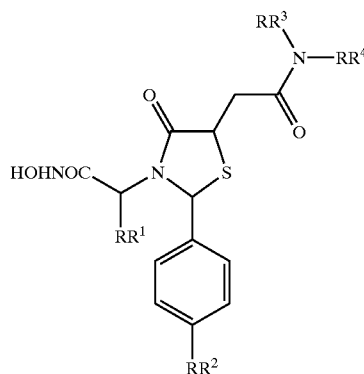

| Example No. | RR¹ | RR² | RR³ | RR⁴ | mol. weitht | Mass (m/e) | HPLC rt (min) |
|---|---|---|---|---|---|---|---|
| 595 | -Benzyl | —OMe | —H | —CH2—C6H4-4-OMe | 549.7 | 550.4, 517.4, 489 | 4.40 |
| 596 | -Benzyl | —OMe | —H | —CH2—C6H4-4-OMe | 549.7 | 550.2, 517.4, 489 | 4.37 |
| 598 | -Benzyl | —OMe | —H | -Benzyl | 519.6 | 520.4, 487, 459.2 | 4.41 |
| 599 | -Benzyl | —Cl | —H | —Et | 462.0 | 462.2, 429, 401.2 | 4.24 |
| 600 | -Benzyl | —Cl | —H | —Et | 462.0 | 462.2, 429, 401.2 | 4.33 |
| 601 | -Benzyl | —OMe | —H | —(CH2)2OMe | 487.6 | 488.2, 455, 427.2 | 4.07 |
| 602 | -Benzyl | —OMe | —H | —(CH2)2OMe | 487.6 | 488.2, 455.2, 427 | 4.11 |
| 603 | -Benzyl | —OMe | —H | —nBu | 485.6 | 486.2, 453, 425.2 | 4.37 |
| 604 | -Benzyl | —OMe | —H | —nBu | 485.6 | 486.2, 453, 425.2 | 4.38 |
| 605 | -Benzyl | —OMe | —H | —nBu | 485.6 | 486.2, 453.2, 425 | 4.51 |
| 606 | -Benzyl | —Cl | —H | —nPr | 476.0 | 476.2, 443, 415.2 | 4.38 |
| 607 | -Benzyl | —Cl | —H | —Ph | 510.0 | 510.2, 477, 449.0 | 4.65 |
| 608 | -Benzyl | —Cl | —H | —(CH2)3OMe | 506.0 | 506.2, 473, 445.2 | 4.36 |
| 609 | -Benzyl | —Cl | —H | —iBu | 490.0 | 490.2, 457, 429.2 | 4.56 |
| 610 | -Benzyl | —Cl | —H | —iBu | 490.0 | 490.2, 457.2, 429 | 4.63 |
| 611 | -Benzyl | —Cl | —H | —(CH2)3SMe | 522.1 | 522.4, 489, 461.2 | 4.56 |
| 612 | -Benzyl | —Cl | —H | —(CH2)3OMe | 506.0 | 506.2, 473, 445.2 | 4.28 |
| 613 | -Benzyl | —Cl | —H | —C(Me)2OMe | 506.0 | 506.2, 473, 445.2 | 4.39 |
| 614 | -Benzyl | —Cl | —H | —CH2—C6H4-4-OMe | 554.1 | 554.2, 421, 493.4 | 4.60 |
| 615 | -Benzyl | —Cl | —H | —CH2—C6H4-4-OMe | 554.1 | 554.2, 521, 493.2 | 4.52 |
| 616 | -Benzyl | —Cl | —H | —(CH2)3-1-(2-Me-piperidyl) | 573.2 | 573.4 | 4.09 |
| 617 | -Benzyl | —OMe | —H | -4-Me-3-isoxazolyl | 510.6 | 511.2, 478, 450.2 | 4.31 |
| 618 | -Benzyl | —OMe | —H | —iPentyl | 499.6 | 500.2, 467, 439.4 | 4.44 |
| 619 | -Benzyl | —OMe | —H | —iPentyl | 499.6 | 500.2, 467, 439.4 | 4.46 |
| 620 | -Benzyl | —OMe | —H | —iPentyl | 499.6 | 500.2, 467, 439.4 | 4.51 |
| 621 | -Benzyl | —OMe | —H | —iPentyl | 499.6 | 500.2, 467.4, 439 | 4.60 |
| 622 | -Benzyl | —Cl | —H | —C(Me)2OMe | 506.0 | 506.2, 473, 445.2 | 4.32 |
| 623 | -Benzyl | —Cl | —H | —iBu | 490.0 | 490.2, 457, 429.2 | 4.51 |
| 624 | -Benzyl | —OMe | —H | —Et | 457.6 | 458.2, 425, 397.2 | 4.13 |
| 625 | -Benzyl | —Cl | —H | —CH2-2-furyl | 514.0 | 514.2, 481, 453.2 | 4.45 |
| 626 | -Benzyl | —Cl | —H | —(CH2)2OMe | 492.0 | 492.2, 459, 431.2 | 4.24 |
| 627 | -Benzyl | —Cl | —H | —(CH2)2OMe | 492.0 | 492.2, 459, 431.2 | 4.29 |
| 628 | -Benzyl | —OMe | —H | -4-Me-3-isoxazolyl | 510.6 | 511.2, 478, 450.2 | 4.25 |
| 629 | -Benzyl | —Cl | —H | —nPr | 476.0 | 476.2, 443, 415.4 | 4.46 |
| 630 | -Benzyl | —Cl | —H | -Allyl | 474.0 | 474.2, 441, 413.2 | 4.35 |
| 631 | -Benzyl | —OMe | —H | -Cyclohexyl | 511.6 | 512.4, 479, 451.2 | 4.47 |
| 632 | -Benzyl | —Cl | —H | —CH2-cyclopropyl | 488.0 | 488.2, 455, 427.2 | 4.47 |
| 633 | -Benzyl | —OMe | —H | —CH2-2-furyl | 509.6 | 510.2, 477, 449.2 | 4.40 |
| 634 | —Ph | —Cl | —H | —Et | 447.9 | 446.0, 415, 387 | 4.15 |
| 635 | —Ph | —Cl | —H | -2-Py | 497.0 | 497.2 | 4.14 |
| 636 | —Ph | —Cl | —H | -2-Py | 497.0 | 497.2 | 4.18 |
| 637 | —Ph | —Cl | —H | —CH2—C6H4-4-Me | 524.0 | 524.2, 491.2, 463 | 4.64 |
| 638 | —Ph | —Cl | —H | —(CH2)3OMe | 492.0 | 492.2, 459.2, 431 | 4.26 |
| 639 | —Ph | —Cl | —H | -Allyl | 460.0 | 460.0, 427.2, 399 | 4.36 |
| 640 | -Benzyl | —OMe | —H | —(CH2)3SMe | 517.7 | 518.2, 485, 457.2 | 4.40 |
| 641 | -Benzyl | —Cl | —H | —CH2-3-Py | 525.0 | 525.2, 464.2 | 4.02 |
| 642 | -Benzyl | —Cl | —H | —(CH2)2-2-Py | 539.1 | 539.2, 478.2 | 4.02 |
| 643 | -Benzyl | —Cl | —H | -2-Py | 511.0 | 511.2, 450.0 | 4.20 |
| 644 | -Benzyl | —OMe | —H | —(CH2)2-2-Py | 534.6 | 535.2, 474.2 | 3.89 |
| 645 | -Benzyl | —Cl | —H | —(CH2)2-2-Py | 539.1 | 539.2 | 3.94 |
| 646 | -Benzyl | —Cl | —H | -Cyclopentyl | 502.0 | 502.2, 469, 441.2 | 4.50 |
| 647 | -Benzyl | —Cl | —H | -Cyclopentyl | 502.0 | 502.2, 469, 441.2 | 4.60 |
| 648 | -Benzyl | —OMe | —H | -Cyclopentyl | 497.6 | 498.2, 465, 437.2 | 4.38 |
| 649 | -Benzyl | —OMe | —H | -Cyclopentyl | 497.6 | 498.2, 465, 437.2 | 4.45 |
| 650 | -Benzyl | —OMe | —H | -2-Py | 506.6 | 507.2, 446.2 | 4.00 |
| 651 | -Benzyl | —OMe | —H | -2-Py | 506.6 | 507.2, 446.2 | 4.02 |
| 652 | -Benzyl | —OMe | —H | —(CH2)3SMe | 517.7 | 518.2, 485, 457.2 | 4.38 |

TABLE 4'-continued

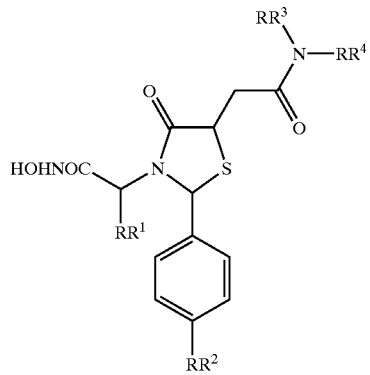

| Example No. | RR¹ | RR² | RR³ | RR⁴ | mol. weitht | Mass (m/e) | HPLC rt (min) |
|---|---|---|---|---|---|---|---|
| 653 | —Ph | —OMe | —H | -Cyclohexyl | 497.6 | 498.2, 465.2, 437 | 4.48 |
| 654 | —Ph | —OMe | —H | —iPr | 457.6 | 458.2, 425.2, 397 | 4.25 |
| 655 | —Ph | —OMe | —H | —Ph | 491.6 | 492.2, 459.2, 431 | 4.47 |
| 656 | —Ph | —OMe | —H | -2-Py | 492.6 | 493.4, 460.2 | 4.04 |
| 657 | —Ph | —OMe | —H | -2-Py | 492.6 | 493.4, 460.2 | 4.10 |
| 658 | —Ph | —OMe | —H | —CH2-cyclopropyl | 469.6 | 470.2, 437.2, 409 | 4.30 |
| 659 | —Ph | —OMe | —H | —CH2—C6H4-4-Me | 519.6 | 520.4, 487.2, 459 | 4.48 |
| 660 | —Ph | —OMe | —H | -3-Isooxazolyl-5-Me | 496.5 | 497.2, 464.2, 436 | 4.30 |
| 661 | —Ph | —OMe | —H | —C(Me)2OMe | 487.6 | 488.2, 455.2, 427 | 4.24 |
| 662 | —Ph | —OMe | —H | —(CH2)3OMe | 487.6 | 488.2, 455.2, 427 | 4.15 |
| 663 | —Ph | —OMe | —H | —(CH2)2-2-Py | 520.6 | 521.4, 488.2 | 3.92 |
| 664 | —Ph | —OMe | —H | —CH2-2-furyl | 495.6 | 496.2, 463.2, 435 | 3.11 |
| 685 | —Ph | —OMe | —H | -Cyclopentyl | 483.6 | 484.2, 451.2, 423 | 3.18 |
| 666 | —Ph | —OMe | —H | —(CH2)2OMe | 473.6 | 474.2, 441.4, 413 | 2.81 |
| 667 | —Ph | —OMe | —H | —(CH2)3SMe | 503.6 | 504.0, 471.2, 443 | 3.14 |
| 668 | —Ph | —OMe | —H | —(CH2)3-Ph | 533.7 | 534.2, 501.2, 473 | 3.46 |
| 669 | —Ph | —Cl | —H | —iBu | 476.0 | 476.0, 443.2, 415 | 3.43 |
| 670 | —Ph | —Cl | —H | -Cyclohexyl | 502.0 | 502.2, 469.2, 441 | 3.60 |
| 671 | —Ph | —Cl | —H | —iPr | 462.0 | 462.2, 429.2, 401 | 3.26 |
| 672 | —Ph | —Cl | —H | —Ph | 496.0 | 496.2, 463.2, 435 | 3.59 |
| 673 | —Ph | —Cl | —H | —iPentyl | 490.0 | 490.2, 457.2, 429 | 3.58 |
| 674 | —Ph | —Cl | —H | —(CH2)3-1-(2-Me-piperidyl) | 559.1 | 559.2 | 2.81 |
| 675 | —Ph | —Cl | —H | —(CH2)3-1-(2-Me-piperidyl) | 559.1 | 559.2 | 2.89 |
| 676 | —Ph | —Cl | —H | —(CH2)-2-Py | 525.0 | 525.2, 492.2 | 2.72 |
| 677 | —Ph | —Cl | —H | -4-Py | 497.0 | 497.2, 436.2 | 2.79 |
| 678 | —Ph | —Cl | —H | -Cyclopentyl | 488.0 | 488.2, 455.2, 427 | 3.56 |
| 679 | —Ph | —Cl | —H | —(CH2)2OMe | 478.0 | 478.2, 445.2, 417 | 3.10 |
| 680 | —Ph | —Cl | —H | —CH2-cyclopropyl | 474.0 | 474.2, 441.2, 413 | 3.48 |
| 681 | —Ph | —Cl | —H | —CH2—C6H4-4-OMe | 540.0 | 540.2, 507.2, 479 | 3.60 |
| 682 | —Ph | —Cl | —H | —CH2-2-furyl | 500.0 | 500.2, 467.2, 439 | 3.51 |
| 683 | —iBu | —Cl | —H | —Me | 413.9 | 414.2, 381, 353.2 | 2.96 |
| 684 | —iBu | —Cl | —H | —Me | 413.9 | 414.2, 381, 353.2 | 3.02 |
| 685 | —iBu | —Cl | —H | —Me | 413.9 | 414.2, 381, 353.0 | 3.11 |
| 686 | —iBu | —Cl | —H | —CH2-2-furyl | 480.0 | 480.2, 447.0, 419 | 3.21 |
| 687 | —iBu | —Cl | —H | —CH2-2-furyl | 480.0 | 480.2, 447.0, 419 | 3.28 |
| 688 | —iBu | —Cl | —H | —CH2-2-furyl | 480.0 | 480.2, 447.2, 419 | 3.30 |
| 689 | —iBu | —F | —H | —CH2-2-furyl | 463.5 | 464.2, 431, 403.2 | 3.06 |
| 690 | —iBu | —F | —H | —(CH2)2OMe | 441.5 | 442.4, 409, 381.2 | 2.89 |
| 691 | —iBu | —F | —H | —Me | 397.5 | 398.2, 365, 337.2 | 2.85 |
| 692 | —iBu | —F | —H | —H | 383.4 | 384.2, 351, 323.2 | 2.75 |
| 693 | —iBu | —H | —H | —CH2-2-furyl | 445.5 | 446.2, 413, 385.2 | 3.21 |
| 694 | —iBu | —H | —H | —(CH2)2OMe | 423.5 | 424.0, 391, 363.2 | 2.87 |
| 695 | —iBu | —H | —H | —Me | 379.5 | 380.2, 347, 319.2 | 2.82 |
| 696 | —iBu | —O—C6H4-4-F | —H | —CH2-2-furyl | 555.6 | 556.2, 523, 495.4 | 3.25 |
| 697 | —iBu | —O—C6H4-4-F | —H | —(CH2)2OMe | 533.6 | 534.2, 501.2 | 2.98 |
| 698 | —iBu | —O—C6H4-4-F | —H | —Me | 489.6 | 490, 457.2 | 2.97 |
| 699 | —iBu | —Cl | —H | —CH2-2-furyl | 480.0 | 480.2, 447.0, 419 | 2.91 |
| 700 | —iBu | —Cl | —H | —Me | 413.9 | 414.2, 381, 353.0 | 2.49 |
| 701 | —iBu | —Cl | —H | —H | 399.9 | 400.2, 367, 339.0 | 2.52 |
| 702 | —iBu | —Cl | —H | —(CH2)2OMe | 458.0 | 458.0, 425, 397.2 | 2.67 |
| 703 | —iBu | —O—C6H4-4-Cl | —H | —CH2-2-furyl | 572.1 | 572.2, 539.2, 511 | 3.44 |
| 704 | —iBu | —O—C6H4-4-Cl | —H | —(CH2)2OMe | 550.1 | 550.2, 493.4, 460.2 | 3.22 |
| 705 | —iBu | —O—C6H4-4-Cl | —H | —Me | 506.0 | 506.2, 473, 445.2 | 3.16 |

TABLE 4''

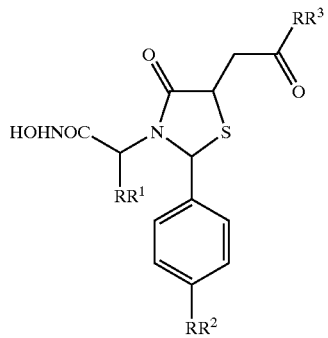

| Example No. | RR¹ | RR² | RR³ | mol. weitht | Mass (m/e) | HPLC rt (min) |
|---|---|---|---|---|---|---|
| 706 | -Benzyl | —Cl | 4-methyl-1,4-diazepan-1-yl | 531.1 | 531.2, 470.2 | 3.97 |
| 707 | -Benzyl | —OMe | -piperidino | 497.6 | 498.2, 465.2, 437 | 4.18 |
| 708 | -Benzyl | —OMe | -piperidino | 497.6 | 498.2, 485.2, 437 | 4.19 |
| 709 | -Benzyl | —OMe | -piperidino | 497.6 | 498.2, 465.2, 437 | 4.24 |
| 710 | —CH2-cyclohexyl | —Cl | -morpholino | 510.1 | 510.2, 477.2, 449 | 3.40 |
| 711 | —CH2-cyclohexyl | —Cl | -piperidino | 508.1 | 508.4, 475.2, 447 | 3.94 |
| 712 | —CH2-cyclohexyl | —Cl | -piperidino | 508.1 | 508.4, 475.2, 447 | 3.77 |
| 713 | —CH2-cyclohexyl | —Cl | -1-pyrrolidinyl | 494.1 | 494.4, 461.2, 433 | 3.64 |
| 714 | —CH2-cyclohexyl | —Cl | -piperidino | 508.1 | 508.4, 475.2, 447 | 3.85 |
| 715 | —CH2-cyclohexyl | —OMe | -morpholino | 505.6 | 506.2, 473.2, 445 | 4.32 |
| 716 | —CH2-cyclohexyl | —OMe | -morpholino | 505.6 | 506.2, 473.2, 445 | 4.29 |
| 717 | —CH2-cyclohexyl | —OMe | -1-pyrrolidinyl | 489.6 | 490.4, 457.2, 439 | 4.46 |
| 718 | —CH2-cyclohexyl | —OMe | -1-pyrrolidinyl | 489.6 | 490.4, 457.2, 429 | 4.40 |
| 719 | —CH2-cyclohexyl | —OMe | -piperidino | 503.7 | 504.4, 471.2, 443 | 4.59 |
| 720 | —CH2-cyclohexyl | —OMe | -piperidino | 503.7 | 504.4, 471.2, 443 | 4.62 |
| 721 | -Benzyl | —OMe | 4-methyl-1,4-diazepan-1-yl | 526.7 | 521.4 | 3.85 |
| 722 | -Benzyl | —OMe | 4-methyl-1,4-diazepan-1-yl | 526.7 | 527.4 | 3.90 |
| 723 | -Benzyl | —Cl | -1-pyrrolidinyl | 488.0 | 488.2, 455.2, 427 | 4.37 |
| 724 | -Benzyl | —Cl | -1-pyrrolidinyl | 488.0 | 488.2, 455, 427.2 | 4.48 |
| 725 | -Benzyl | —OMe | -morpholino | 499.6 | 500.2, 467.4, 439 | 4.11 |
| 726 | -Benzyl | —Cl | -piperidino | 502.0 | 502.2, 469, 441.2 | 4.50 |
| 727 | -Benzyl | —Cl | -piperidino | 502.0 | 502.2, 469, 441.4 | 4.60 |
| 728 | -Benzyl | —Cl | -morpholino | 504.0 | 504.0, 471, 443.2 | 4.29 |
| 729 | -Benzyl | —OMe | -1-pyrrolidinyl | 483.6 | 484.2, 451.2, 423 | 4.34 |

Example 365

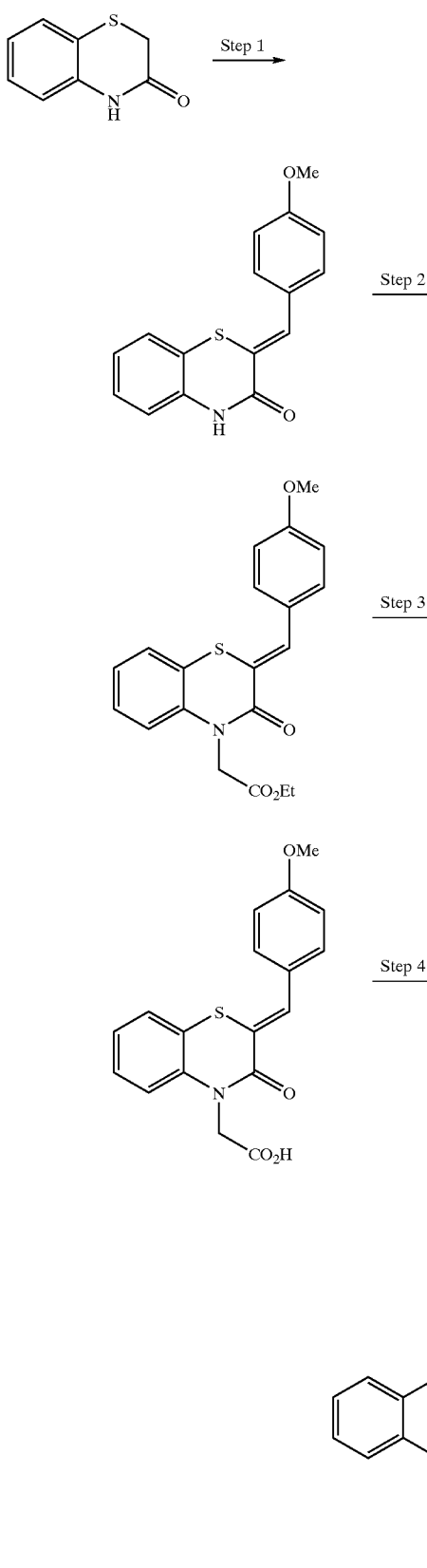

Step 1: 2H-2(Z)-(4-Methoxybenzylidene)-1,4-benzothiazin-3(4H)-one

A mixture of 2H-1,4-benzothiazin-3(4H)-one (5 g), p-anisaldehyde (6.6 g), and sodium methoxide (11.63 g) in 260 mL of DHF was heated to reflux for 15 hrs. The reaction mixture was cooled down to r.t., and water was added. The resulting precipitate was filtered and washed with water and ethanol to give the product.

Step 2: 2H-2(Z)-(4-Methoxybenzylidene)-4-(N-ethoxycarbonylmethyl)-1,4-benzothiazin-3(4H)-one To a DMF (60 mL) solution of 2H-2(Z)-(4-methoxybenzylidene)-1,4-benzothiazin-3(4H)-one (1.4 g), NaH (160 mg) was added at 4° C. After 1 hr's stirring, ethyl bromoacetate (684 mg) was added and the reaction mixture was warmed to room temperature. After 2 hrs' additional stirring, the reaction mixture was added ethyl bromoacetate (68 mg) and left at r.t. overnight. The reaction mixture was added 5% $KHSO_4$ aq. and extracted with EtOAc. The organic layer was washed with sat. $NaHCO_3$ aq. and brine, and dried over $MgSO_4$ and concentrated under reduced pressure. The residue was purified by silica gel column chromatography to give the product.

Step 3: 2H-2(Z)-(4-Methoxybenzylidene)-1,4-benzothiazin-3(4H)-one-4-yl-acetic Acid 2-2(Z)-(4-methoxybenzylidene)-4-(N-ethoxycarbonylmethyl)-1,4-benzothiazin-3(4H)-one (1.4 g) was dissolved in ethanol (20 mL) and THF (20 mL). 5N NaOH aq. was added to the solution at room temperature and stirred for 3 hrs. The reaction mixture was added 5% $KHSO_4$ aq. and extracted with EtOAc. The organic layer was washed with brine, dried over $MgSO_4$ and concentrated under reduced pressure to give the product.

Step 4: 2H-2(Z)-(4-Methoxybenzylidene)-1,4-benzothiazin-3(4H)-one-4-yl-acetic Acid N-Hydroxylamide Isobutyl chloroformate (477 mg) was added dropwise to a THF (40 mL) solution of 2H-2(Z)-(4-methoxybenzylidene)-1,4-benzothiazin-3(4H)-one-4-yl-acetic acid (1.19 g) and N-methylmorpholine (353 mg) at −15 to −20° C. THF (10 ml) solution of O-TBDMS-hydoxylamine (565 mg) was added after additional 5 minutes' stirring. The mixture was warmed to r.t. with stirring, and stood overnight. The reaction mixture was quenched with sat. $Na_2CO_3$ aq. and extracted with EtOAc. The organic layer was washed with 1N HCl and brine, dried over $MgSO_4$ and concentrated under reduced pressure. The residue was purified by recrystallization from mixed solvent of THF and hexane to give 1.2 g of the hydroxamic acid as colorless solid.

$^1$H-NMR (DMSO-$d_6$, δ) 1.82 (s, 3H), 4.60 (s, 1.6H), 4.88 (s, 0.4H), 7.07 (d, J=8.8 Hz, 2H), 7.04–7.11 (m, 1H), 7.27 (dt, J=1.4 Hz, 8.2 Hz, 1H), 7.38 (dd, J=1.1 Hz, 7.7 Hz, 1H), 7.68 (d, J=8.8 Hz, 2H), 7.73 (s, 1H), 8.98 (s, 0.8H), 9.43 (s, 0.2H), 10.3 (s, 0.2H), 10.8 (s, 0.8H).

The following compounds listed in the Table 5 were prepared in a similar manner.

TABLE 5

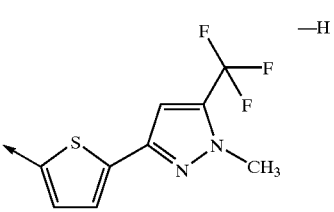

| Example No. | RR1 | RR2 | RR3 | mol. weight | Mass (m/e) | HPLC rt (min) |
|---|---|---|---|---|---|---|
| 365 | —C6H4-4-OMe | —H | —H | 356.4 | 357.0, 324.0, 296.2 | 3.05 |
| 366 | —C6H4-4-OEt | —H | —H | 370.4 | 371.0, 338.0 | 3.43 |
| 367 | —C6H4-4-SMe | —H | —H | 372.5 | 373.2, 339.8 | 3.46 |
| 368 | —C6H4-4-OPh | —H | —H | 418.5 | 419.0, 386.0 | 3.40 |
| 369 | —C6H4-4-O-nBu | —H | —H | 398.5 | 399.2, 366.2 | 3.84, 3.91 |
| 370 | —C6H4-4-OMe | —H | —Cl | 390.8 | 391.0, 358.0 | 3.26 |
| 371 | —C6H4-4-OMe | —CF3 | —H | 424.4 | 425.0, 392.0 | 3.35 |
| 372 | —C6H4-4-O-benzyl | —H | —H | 432.5 | 433.2, 400.2 | 3.54 |
| 373 | —C6H4-4-O-nPr | —H | —H | 384.5 | 385.2, 352.2 | 3.42 |
| 374 | —C6H4-4-OCHF2 | —H | —H | 392.4 | 393.0, 360.0 | 3.18, 3.26 |
| 375 | —C6H4-3-OMe | —H | —H | 356.4 | 357.2, 324.2 | 2.92 |
| 376 | —C6H3-3,4-Cl2 | —H | —H | 395.3 | 395.0, 362.0 | 3.29 |
| 377 | —C6H4-2-OMe | —H | —H | 356.4 | 357.2, 324.2 | 2.43, 2.56 |
| 378 | -2-Py | —H | —H | 327.4 | 328.2, 267.0 | 1.46, 1.92 |
| 379 | -2-Pyrrolyl-1-(C6H3-2,6-Cl2) | —H | —H | 460.3 | 459.8, 427.0 | 3.48 |
| 380 | —C6H3-3,5-(OMe)2 | —H | —H | 386.4 | 387.0, 354.2 | 3.00 |
| 381 | —C6H3-2-O-benzyl, 3-OMe | —H | —H | 462.5 | 463.2, 430.2, 374.0 | 3.22 |
| 382 | —C6H2-2-F, 4,5-(OMe)2 | —H | —H | 404.4 | 404.5, 372.2 | 2.80 |
| 383 | —C6H2-2-F, 3-CN, 4-NMe2 | —H | —H | 412.4 | 413.0, 380.2 | 3.00 |
| 384 | —C6H2-2,3,4-(OMe)3 | —H | —H | 416.5 | 417.0, 384.0, 297.2 | 2.81, 2.91 |
| 385 | —C6H3-3,5-(CF3)2 | —H | —H | 462.4 | 462.8, 402.2 | 3.45 |
| 386 | —C6H4-4-F | —H | —H | 344.4 | 345.0, 312.2 | 3.30 |
| 387 | —C6H4-4-Me | —H | —H | 340.4 | 341.0, 308.2 | 3.44 |
| 388 | —Ph | —H | —H | 326.4 | 327.0, 294.0 | 3.23 |
| 389 | -2-Furyl-5-(C6H4-4-Br) | —H | —H | 471.3 | 471.0, 438.0, 371.2 | 4.03 |
| 390 | 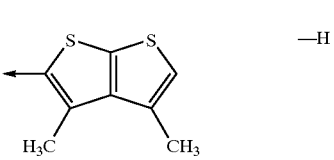 | —H | —H | 480.5 | 482.0, 420.0 | 3.28 |
| 391 |  | —H | —H | 416.5 | 417.2, 384.0 | 3.42 |
| 392 | —C6H4-4-O(3,4-Cl2-benzyl) | —H | —H | 501.4 | 501.0, 470.2 | 3.73 |
| 393 | —C6H4-4-Ph | —H | —H | 402.5 | 403.2, 370.2 | 3.42 |
| 394 | -3-Pyrrolidyl-4-CO2Et, 2,5-Me2, 1-Ph | —H | —H | 491.65 | 492.2, 459.2 | 3.72 |
| 395 | —C6H4-4-CF3 | —H | —H | 394.4 | 395.2, 362.2, 315.4 | 3.53, 3.60 |
| 396 | —C6H4-4-iBu | —H | —H | 382.5 | 383.2, 350.2 | 4.02 |
| 397 | —C6H4-4-(1-pyrrolidinyl) | —H | —H | 395.5 | 396.2, 363.2 | 3.68 |
| 398 | -2-Furyl-5-(C6H4-3-NO2) | —H | —H | 437.4 | 438.2, 405.0 | 3.35 |
| 399 | -2-Thienyl-3-Br | —H | —H | 411.3 | 413.0, 380.0 | 3.14 |
| 400 | —C6H4-4-(CH=CH—Ph) | —H | —H | 428.5 | 429.0, 396.0 | 3.68 |
| 401 | —nPentyl | —H | —H | 320.4 | 321.2, 288.2 | 3.38 |
| 402 | —C6H4-4-SCF3 | —H | —H | 426.4 | 427.0, 394.0 | 3.55 |
| 403 | —C6H4-4-SO2Me | —H | —H | 404.5 | 405.0, 372.0 | 2.64, 2.72 |
| 404 | -1-Naphthyl-4-OMe | —H | —H | 406.55 | 407.0, 374.0 | 3.33, 3.41 |

Example 405

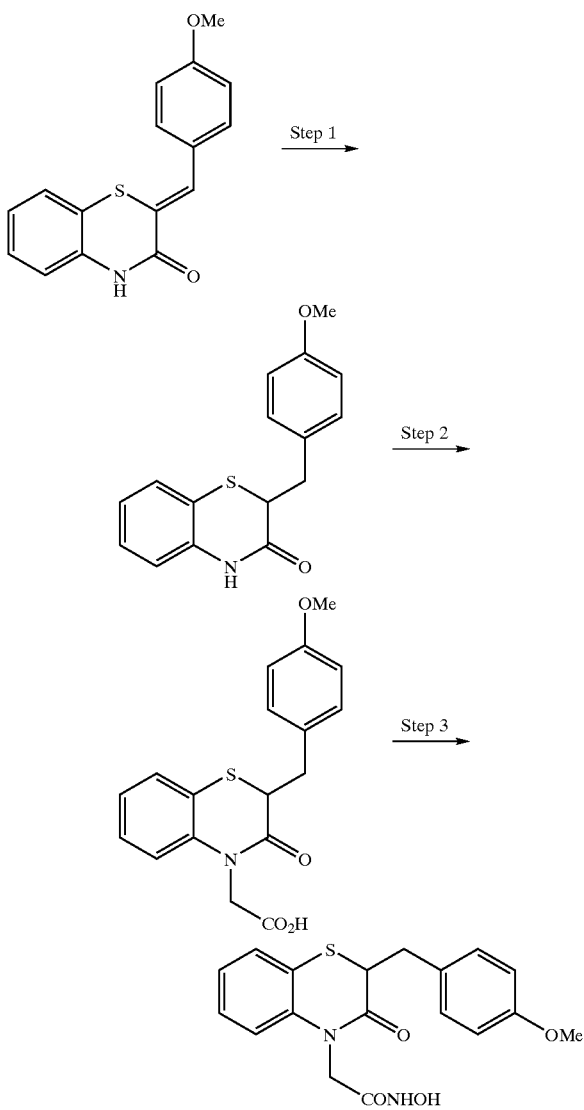

Step 1: 2H-2-(4-Methoxybenzyl)-1,4-benzothiazin-3(4H)-one 2H-2(Z)-(4-methoxybenzylidene)-1,4-benzothiazin-3 (4H)-one (142 mg) was dissolved in MeOH (5 mL) and THF (20 mL). 10% Pd/C (350 mg) was added. The reaction mixture was vigorously stirred at r.t. for 4 hours under $H_2$. The catalyst was removed by filtration, and the filtrate was concentrated under reduced pressure. The residue was purified by preparative thin layer chromatography on silica gel (EtOAc/toluene, 1/4) to give the product as a white solid (133.5 mg).

Step 2: 2H-2-(4-Methoxybenzyl)-1,4-benzothiazin-3(4H)-one-4-yl-acetic Acid

To a solution of 2H-2-(4-methoxybenzyl)-1,4-benzothiazin-3(4H)-one (428 mg) in DMF (20 mL), NaH (66 mg, 60% in oil) was added. After 1 hour's stirring, ethyl bromoacetate (263 mg, 1.57 mmol) was slowly added. The reaction mixture was stirred at r.t. overnight. The solvent was removed under reduced pressure and the residue was dissolved in EtOAc and washed with 1N HCl, 5% $Na_2CO_3$ aq., and brine. The organic layer was dried over $Na_2SO_4$ and concentrated. The crude product was used in the following step without purification.

To a solution of ethyl ester (515 mg) in MeOH (10 mL), 1N NaOH (2.58 mL) was slowly added at 0° C. After 30 minutes' stirring, the mixture was warmed to room temperature and left overnight. The reaction mixture was concentrated under reduced pressure. The residue was dissolved in 5% $Na_2CO_3$ aq., and washed with $Et_2O$. The aqueous layer was acidified with 4N HCl, and the product a was extracted with EtOAc. The organic layer was dried over $Na_2SO_4$ and concentrated to give the acetic acid (451 mg, 88%) as a white solid.

Step 3: 2H-2-(4-Methoxybenzyl)-1,4-benzothiazin-3(4H)-one-4-yl-acetic Acid N-Hydroxyamide The acetic acid (343 mg), obtained as above, was dissolved in $CH_2Cl_2$ (4 mL) and pyridine (4 mL) and pentafluorophenyl trifluoroacetate (560 mg) was added. After 3 hours' stirring, O-TBDMS-hydoxylamine (736 mg) was added. The reaction mixture was stirred at r.t. overnight. The solvent was removed and the residue was dissolved in EtOAc. The organic layer was washed with 1N HCl and brine, dried over $Na_2SO_4$ and concentrated under reduced pressure. The residue was purified by preparative thin layer chromatography on silica gel ($CHCl_3$/MeOH, 10/1) to give hydroxamic acid (323 mg) as a pale orange solid.

$^1$H-NMR (DMSO-$d_6$, δ) 2.69 (1H, m), 3.16 (1H, m), 3.76 (3H, s), 3.83 (1H, m), 4.52 (2H, m), 6.87 (2H, d, J=7.0), 7.09–7.18 (4H, m), 7.33–7.40 (2H, m), 9.06 (1H, br-s), 10.83 (1H, s).

Example 406

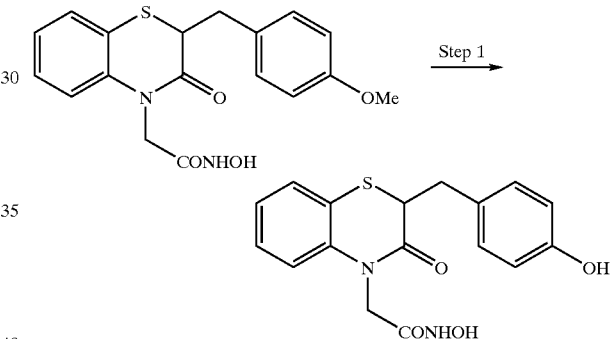

Step 1: 2H-2-(4-Hydroxybenzyl)-1,4-benzothiazin-3(4H)-one-4-yl-acetic Acid N-Hydroxyamide 2H-2-(4-methoxybenzyl)-1,4-benzothiazin-3(4H)-one-4-yl-acetic acid N-hydroxyamide (373 mg) was dissolved in $CH_2Cl_2$ (10 ml). $BBr_3$ (3M solution in $CH_2Cl_2$, 5 ml) was added and the reaction mixture was stirred at r.t. overnight. The solvent was removed under reduced pressure, and the residue was dissolved in EtOAc. The organic layer was washed with 1N HCl and brine, dried over $Na_2SO_4$ and concentrated under reduced pressure. The residue was purified by preparative thin layer chromatography on silica gel ($CHCl_3$/MeOH, 10/1) to give hydroxamic acid (161 mg) as a pale yellow solid.

$^1$H-NMR (DMSO-$d_6$, δ) 2.58 (1H, m), 3.06 (1H, m), 3.75 (1H, s), 4.37–4.83 (2H, m), 6.66 (2H, d, J=7.86 Hz), 6.97–7.13 (4H, m), 7.27–7.38 (2H, m), 8.99 (1H, s), 9.26 (1H, s), 10.77 (1H, s).

Example 407

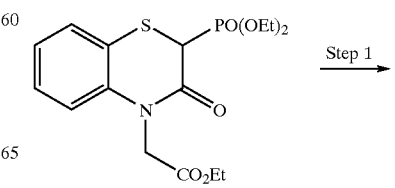

-continued

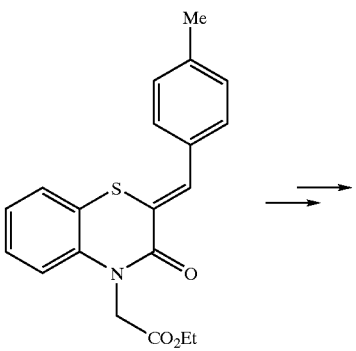

→

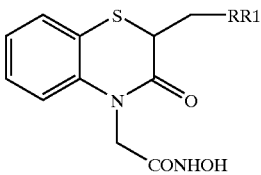

Step 1: Ethyl [2H-2Z-(4-methybenzylidene)-1,4-benzothiazin-3(4H)-one-4-yl]acetate To a stirred solution of p-tolualdehyde (48 mg) and 2H-2-diethylphosphonyl-1,4-benzothiazine-3(4H)-one-4-yl-acetic acid ethyl ester (78 mg) in ethanol (3 mL), which was prepared by Worley's method (J. Org. Chem., 40, 1731 (1975)), was added a solution of sodium ethoxide (28 mg, 0.42 mmol) in ethanol (1 mL). The reaction mixture was stirred at r.t. overnight. The solvent was removed under reduced pressure. The residue was dissolved in EtOAc and washed with sat. $NaKCO_3$ aq., 1N HCl, and brine. The organic layer was dried over $Na_2SO_4$ and concentrated. The residue was purified by preparative thin layer chromatography on silica gel ($CHCl_3$/MeOH, 15/1) to give a yellow solid (37 mg,. 52%).

This compound was converted to 2H-2-(4-Methylbenzyl)-1,4-benzothiazin-3(4H)-one-4-yl-acetic acid N-hydroxyamide by the reactions analogous to those described in Example 405.

The following compounds listed in the Tables 6 and 6' were prepared in a similar manner.

TABLE 6

| Example No. | RR1 | NMR: $^1$H-NMR(DMSO-d6; δ) |
|---|---|---|
| 407 | —C6H4-4-Me | 2.27(3H, s), 2.65(1H, m), 3.15(1H, m), 3.83(1H, m), 4.43(1H, d, J=16Hz), 4.51(1H, d, J=16Hz), 7.04–7.14(6H, m), 7.28–7.38(2H, m), 8.98(1H, s), 10.76(1H, s) |
| 408 | -2-Py | 2.91(1H, m), 3.33(1H, m), 4.12(1H, m), 4.48(2H, s), 7.05–7.11(2H, m), 7.24–7.37(4H, m), 7.73(1H, t, J=7.5Hz), 8.49(1H, d, J=4.05Hz), 9.03(1H, s), 10.90(1H, s) |
| 409 | —C6H4-4-OPh | 2.72(1H, m), 3.17(1H, m), 3.87(1H, m), 4.49(2H, m), 6.90–7.65(13H, m), 9.01(1H, s), 10.80(1H, s) |
| 410 | —Ph | 2.70(1H, m), 3.20(1H, m), 3.88(1H, m), 4.48(2H, m), 7.05–7.38(9H, m), 8.98(1H, s), 10.76(1H, s) |
| 411 | —C6H4-2-Me | 2.22(3H, s), 2.69(1H, m), 3.16(1H, m), 3.85(1H, m), 4.49(2H, s), 7.06–7.16(6H, m), 7.29–7.40(2H, m), 9.00(1H, s), 10.78(1H, s) |
| 412 | —C6H4-3-Me | 2.27(3H, s), 2.65(1H, m), 3.17(1H, m), 3.85(1H, m), 4.43(1H, d, J=16Hz), 4.52(1H, d, J=16Hz), 6.98–7.19(6H, m), 7.28–7.38(2H, m), 8.99(1H, s), 10.78(1H, s) |
| 413 | —C6H4-2-Me | 2.92(1H, m), 3.35(1H, m), 3.91(1H, m), 4.49(2H, m), 7.06–7.17(2H, m), 7.30–7.72(6H, m), 9.02(1H, s), 10.80(1H, s) |
| 414 | —C6H4-2-OMe | 2.67(1H, m), 3.18(1H, m), 3.76(3H, s), 3.79(1H, m), 4.42(1H, d, J=16Hz), 4.53(1H, d, J=16Hz), 6.87 (1H, m), 6.96(1H, d, J=8.25Hz), 7.07–7.14(3H, m), 7.21–7.37(3H, m), 8.99(1H, s), 10.79(1H, s) |
| 415 | —C6H4-3-OMe | 2.66(1H, m), 3.17(1H, m), 3.73(3H, s), 3.87(1H, m), 4.44(1H, d, J=16Hz), 4.51(1H, d, J=16Hz), 6.76–6.79(3H, m), 7.04–7.19(3H, m), 7.28–7.38(2H, m), 8.99(1H, s), 10.77(1H, s) |
| 416 | —C6H4-4-OEt | 1.31(3H, m), 2.64(1H, m), 3.09(1H, m), 3.79(1H, m), 3.98(2H, m), 4.46(2H, m), 6.82(2H, d, J=6.78Hz), 7.04–7.12(4H, m), 7.27–7.37(2H, m), 8.99(1H, s), 10.77(1H, s) |
| 417 | —C6H3-3,4-(OMe)2 | 2.62(1H, m), 3.12(1H, m), 3.71(3H, m), 3.72(3H, s), 3.84(1H, m), 4.47(2H, s), 6.68(1H, m), 6.83(2H, m), 7.04–7.14(2H, m), 7.28–7.39(2H, m), 8.98(1H, s), 10.77(1H, s) |
| 418 | —C6H4-4-Bu | 0.89(3H, t, J=7Hz), 1.30(2H, m), 1.54(2H, m), 2.54(2H, m), 2.66(1H, m), 3.14(1H, m), 3.83(1H, m), 4.47 (2H, m), 6.95–7.13(5H, m), 7.28–7.38(3H, m), 8.99(1H, S), 10.77(1H, s) |

TABLE 6-continued

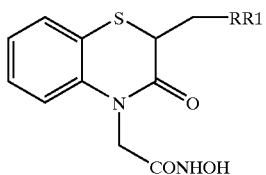

| Example No. | RR1 | NMR: ¹H-NMR(DMSO-d6; δ) |
|---|---|---|
| 419 | —C6H4-4-Ph | 2.77(1H, m), 3.25(1H, m), 3.93(1H, m), 4.49(2H, m), 7.05–7.16(2H, m), 7.30–7.48(7H, m), 7.58(2H, d, J=7.14Hz), 7.65(2H, d, J=8.25Hz), 8.99(1H, s), 10.78(1H, s) |
| 420 | —(CH2)2-Ph | 1.64–1.81(m, 2H), 2.56(m, 2H), 3.61(m, 3H), 4.38(d, J=16Hz, 1H), 4.50(d, J=16Hz, 1H), 7.02–7.07(m, 2H), 7.07–7.18(m, 3H), 7.18–7.30(m, 3H), 7.39(m, 1H), 8.96(s, 0.8H), 9.34(s, 0.2H), 10.3(s, 0.2H), 10.7(s, 0.8H) |
| 421 | —C6H4-4-O(CH2)2OH | 2.56(1H, m), 3.05(1H, m), 3.74(1H, m), 3.83–3.92(4H, m) 4.40(2H, m), 6.76(2H, d, J=8.22Hz), 6.97–7.06(4H, m), 7.21–7.30(2H, m), 8.92(1H, s). 10.70(1H, s) |
| 422 | —C6H4-4-NEt2 | 1.06(6H, t, J=7Hz), 2.54(1H, m), 3.05(1H, m), 3.26–3.34(4H, m), 3.74(1H, m), 4.47(2H, m), 6.55(2H, d, J=8Hz), 6.97(2H, d, J=8Hz), 7.04–7.13(2H, m), 7.27–7.38(2H, m), 8.98(1H, s), 10.77(1H, s) |
| 423 | -3-Py | 2.77(1H, m), 3.18(1H, m), 3.96(1H, m), 4.48(2H, m), 6.96–7.14(2H, m), 7.29–7.40(3H, m), 7.68(1H, d, J=7.71Hz), 8.42(2H, m), 9.00(1H, s), 10.78(1H, s) |
| 424 | -4-Py | 2.75(1H, m), 3.20(1H, m), 4.01(1H, m), 4.47(2H, m), 7.06–7.15(2H, m), 7.28(2H, d, J=5.67Hz), 7.32–7.40(2H, m), 8.46(2H, d, J=5.67Hz), 9.00(1H, s), 10.78(1H, s) |
| 425 | —C6H4-4-Cl | 2.73(1H, m), 3.16(1H, m), 3.90(1H, m), 4.47(2H, m), 7.05–7.14(2H, m), 7.24–7.38(6H, m), 8.99(1H, s), 10.78(1H, s) |
| 426 | —C6H4-4-Br | 2.72(1H, m), 3.14(1H, m), 3.90(1H, m), 4.47(2H, m), 7.05–7.14(2H, m), 7.20(2H, d, J=8.25Hz), 7.29–7.39(2H, m), 7.47(2H, d, J=8.25Hz), 8.99(1H, s), 10.78(1H, s) |

TABLE 6'

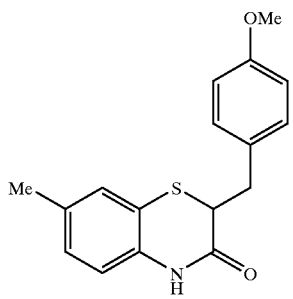

| Example No. | RR¹ | NMR: ¹H-NMR(DMSO-d6; δ) |
|---|---|---|
| 754 | —O—C6H4-4-F | 2.71(1H, dd, J=9.0, 14Hz), 3.16(1H, dd, J=5.9, 14Hz), 3.85(1H, dd, J=5.9, 9.0Hz), 4.48(1.6H, br-s), 4.67(0.2H, d, J=18Hz), 4.88(0.2H, d, J=18Hz), 6.88(2H, d, J=8.4Hz), 6.95–7.39(10H, m), 8.98(0.8H, s), 9.36(0.2H, s), 10.33(0.2H, s), 10.77(0.8H, s) |
| 755 | —F | 2.73(1H, m), 3.16(1H, m), 3.88(1H, m), 4.47(2H, m), 6.96–7.14(4H, m), 7.24–7.39(4H, m), 8.99(1H, s), 10.78(1H, s) |
| 756 | —CF3 | 2.85(1H, m), 3.27(1H, m), 3.98(1H, m), 4.48(2H, m), 7.06–7.16(2H, m), 7.30–7.40(2H, m), 7.48(2H, J=8.07Hz), 7.64(2H, J= 8.07Hz), 8.99(1H, s), 10.79(1H, s) |

Example 427

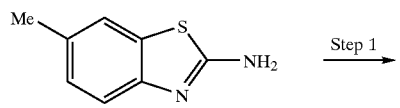 Step 1

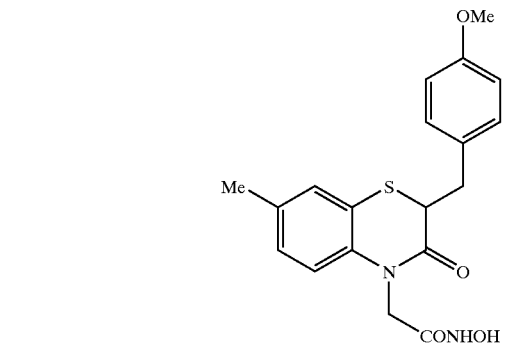

Step 1: 2H-2-(4-Methoxybenzyl)-7-methyl-1,4-benzothiazin-3(4H)-one

A mixture of 2-amino-6-methylbenzothiazole (657 mg) in 20% NaOH aq. (10 ml) was heated at 180° C. in an autoclave for 5 hours. The mixture was cooled to 80° C. and a solution of 2-bromo-3-(4-methoxyphenyl)propionic acid (1.088 g) in 104 NaOH ag. (10 mL) was added and the temperature was maintained at 80° C. for 1 hour. The mixture was cooled to r.t. and concentrated under reduced pressure. The residue was dissolved in AcOH (40 mL) and heated at 100° C. for 4 hours. The reaction mixture was cooled to r.t. and concentrated under reduced pressure. The residue was dissolved in EtOAc and washed with water and 5% $Na_2CO_3$ aq. The organic layer was dried over $Na_2SO_4$ and concentrated. The residue was purified by recrystallization from $Et_2O$ and hexane to give a white solid (805 mg).

Step 2: 2H-2-(4-Methoxylbenzyl)-7-methyl-1,4-benzothiazin-3(4H)-one-4-yl-acetic Acid N-Hydroxyamide The product of Step 1 was converted to hydroxamic acid as described in Example 405 (step 2 and 3).

The following compounds listed in the Tables 7, 7' and 7" were prepared in a similar manner.

TABLE 7

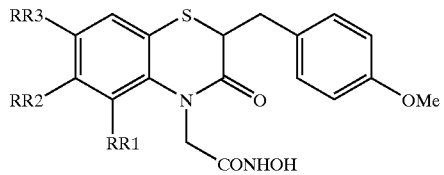

| Example No. | RR1 | RR2 | RR3 | NMR ¹H-NMR (DMSO-d6; δ) |
|---|---|---|---|---|
| 427 | —H | —H | —Me | 2.29(3H, s), 2.68(1H, m), 3.15(1H, m), 3.77(3H, s), 3.81(1H, m), 4.45(1H, d, J=16Hz), 4.51(1H, d, J=16Hz), 6.88(2H, d, J=8.07Hz), 7.04–7.22 (5H, m), 9.02(1H, s), 10.80 (1H, s) |
| 428 | —Me | —H | —H | 2.40(3H, s), 2.71(1H, m), 3.21(1H, m), 3.69(1H, m), 3.76(3H, s), 4.19(2H, br-s), 6.87(2H, d, J=7.86Hz), 7.02–7.28(5H, m), 8.90(1H, bs), 10.60(1H, s) |
| 429 | —Cl | —H | —H | 2.73(1H, m), 3.19(1H, m), 3.76(3H, s), 3.84(1H, m), 4.43(2H, s), 6.87–6.90(2H, d, J=8.61Hz), 7.13–7.19 (3H, m), 7.44–7.48(2H, m), 8.89(1H, bs), 10.63(1H, s) |
| 430 | —OMe | —H | —H | 2.66(1H, m), 3.17(1H, m), 3.68(1H, m), 3.72(3H, s), 3.80(3H, s), 4.20(1H, d, J=15Hz), 4.40(1H, d, J=15Hz), 6.84(2H, d, J=8.25Hz), 6.95–7.15(5H, m), 8.76(1H, bs), 10.40(1H, s) |
| 431 | —H | —Me | —Me | 2.16(3H, s), 2.21(3H, s), 2.62(1H, m), 3.08(1H, m), 3.72(3H, s), 3.73(1H, m), 4.43(2H, s), 6.83(2H, d, J=8.61Hz), 6.93(1H, s), 7.10–7.13(3H, m), 8.98(1H, s), 10.74(1H, s) |
| 432 | —H | —H | —F | 2.70(1H, m), 3.16(1H, m), 3.77(3H, s), 3.90(1H, m), |

TABLE 7-continued

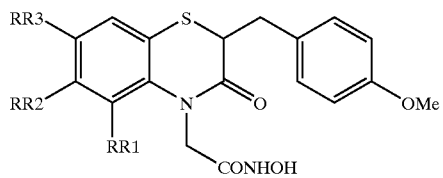

| Example No. | RR1 | RR2 | RR3 | NMR ¹H-NMR (DMSO-d6; δ) |
|---|---|---|---|---|
|  |  |  |  | 4.47(1H, d, J=16Hz), 4.54 (1H, d, J=16Hz), 6.88(2H, d, J=8.61Hz), 7.16–7.22 (4H, m), 7.36(1H, d, J=7.68 Hz), 9.05(1H, bs), 10.82(1H, s) |

TABLE 7'

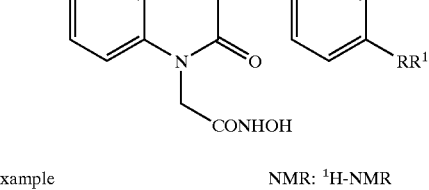

| Example No. | RR¹ | RR² | NMR: ¹H-NMR (DMSO-d6; δ) |
|---|---|---|---|
| 757 | —OMe | —NO2 | 2.69(1H, dd, J=9.14Hz), 3.08(1H, dd, J=6.14Hz), 3.71(3H, s), 3.99(1H, dd, J=6.9Hz), 4.5–5.0(2H, m), 6.82(2H, d, J=8.6Hz), 7.13 (2H, d, J=8.6Hz), 7.34(1H, d, J=9Hz), 8.14(1H, dd, J=2.6, 9Hz), 8.24(1H, d, J=2.6Hz), 9.02, 9.42(1H, bs), 10.42, 10.83(1H, bs). |
| 758 | —OMe | —SO2Me | 2.78(1H, dd, J=8.8Hz, 14 Hz), 3.19(1H, dd, J=6.14 Hz), 3.31(3H, s), 3.68(3H, s), 4.03(1H, dd, J=6, 8.8 Hz), 4.63–5.05(2H, m), 6.92 (2H, d, J=8.5Hz), 7.22(2H, d, J=8.5Hz), 7.44(1H, d, J=8.6Hz), 7.88(1H, dd, J=2, 8.6Hz), 7.97(1H, d, J=2Hz), 9.09, 9.56(1H, bs), 10.48, 10.92(1H, bs). |
| 759 | —OCF3 | —SO2Me | 2.85(1H, m), 3.19(1H, m), 3.22(3H, s), 4.06(1H, dd, J= 6.5, 8Hz), 4.54–4.99(2H, m), 7.30(5H, m), 7.80(1H, d, J=8.6Hz), 7.92(1H, s), 9.43, 9.01(1H, bs), 10.83, 10.41(1H, bs). |

TABLE 7"

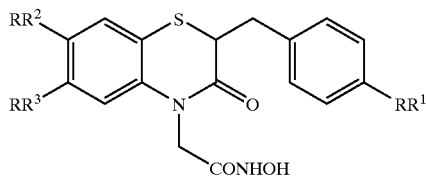

| Example No. | RR¹ | RR² | RR³ | mol. weight | Mass(m/e) | HPLC rt (min) |
|---|---|---|---|---|---|---|
| 760 | —H | —H | —NMe2 | 371.5 | 372.2, 339.2 | 2.29 |
| 761 | —H | —H | —CF3 | 396.4 | 396.8, 364.0, 336 | 3.00 |
| 762 | —OCF3 | —H | —SO2Me | 490.5 | 491.1, 458.0 | 2.71 |
| 763 | —OCF3 | —H | —H | 412.4 | 413.2, 380.2, 352 | 3.11 |
| 764 | —OCF3 | —CF3 | —H | 480.4 | 481.2, 448.0 | 3.20 |
| 765 | —H | —Me | —Me | 356.4 | 357.0, 324.2 | 2.97 |
| 766 | —OCF3 | —H | —F | 430.4 | 431.2, 398.0 | 2.99 |
| 767 | —H | —H | —OMe | 358.4 | 359.2, 326.2, 298 | 2.74 |
| 768 | —H | —H | —SO2Me | 406.5 | 407.2, 374.0, 446 | 2.46 |
| 769 | —OCF3 | —Me | —Me | 440.4 | 441.4, 408.2 | 3.17 |
| 770 | —H | —H | —Me | 342.4 | 343.0, 310.2 | 2.84 |
| 771 | —H | —H | —F | 346.4 | 347.4, 314.0 | 3.11 |
| 772 | —H | —H | —OEt | 372.4 | 372.9, 340.2 | 3.23 |
| 773 | —H | —H | —Cl | 362.8 | 363.2, 330.2 | 2.97 |
| 774 | —OCF3 | —H | —Cl | 446.8 | 446.9, 414.2 | 3.16 |
| 775 | —H | —H | —NO2 | 373.4 | 374.0, 341.0 | 2.76 |
| 776 | —H | —H | —Br | 407.3 | 407.0, 374.0, 346 | 3.37 |

Example 433

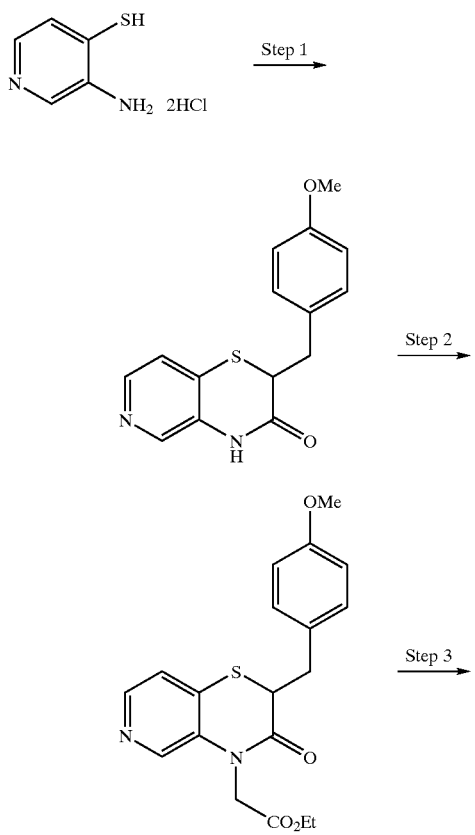

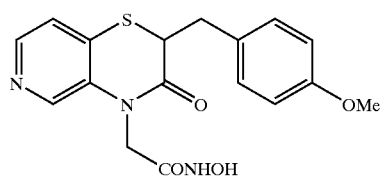

Step 1: 2H-2-(p-Methoxybenzyl)-1,4-pyrido[3,4-e]thiazin-3(4H)-one

To a mixture of 3-Amino-4-mercaptopyridine.2HCl (400 mg) and 2-bromo-3-(p-methoxyphenyl)propionic acid (520 mg) in DMF (8 mL) was added K₂CO₃ (1.38 gr) and the mixture was stirred for 3 hrs at r.t. EDC.HCl (800 mg) and 1-hydroxybenzotriazole (900 mg) were added to the reaction mixture and the stirring was continued overnight. The reaction mixture was diluted with aq. NaHCO₃ and extracted with EtOAc 3 times. The combined organic layers were washed with aq. NaHCO₃, aq. NaH₂PO₄ and brine. Column chromatography on silica gel (eluent; CHCl₃/MeOH=40/1) gave the product as a white solid (390 mg).

Step 2: 2H-2-(p-Methoxybenzyl)-1,4-pyrido[3,4-e]thiazin-3(4H)-one-4-yl-acetic Acid Ethyl Ester To a THF (15 mL) solution of 2H-2-(p-methoxybenzyl)-1,4-pyrido[3,4-e]thiazin-3(4H)-one (385 mg) was added NaH (60% in oil, 39 mg) at 0° C., and the mixture was stirred for 30 min. at the same temperature and for 30 min at r.t. After the reaction mixture was cooled to 0° C., ethyl bromoacetate (164 μL) was added and the reaction mixture was stirred for 3 hrs at r.t. The reaction was quenched by the addition of aq. NaH₂PO₄ and extracted with EtOAc several times. Column chromatography on silica gel (eluent; CHCl₃/EtOAc=5/1) gave the product almost quantitatively as a colorless oil.

Step 3: 2H-2-(p-Methoxybenzyl)-1,4-pyrido[3,4-e]thiazin-3(4H)-one-4-yl-acetic Acid N-Hydroxyamide The compound obtained above was treated with 5N NaOH (0.8 mL) in MeOH (8 mL) for 1 hr at r.t. The reaction mixture was concentrated in vacuo, diluted with water and the pH was adjusted to 5.2 by 1N HCl. Lyophilization gave the corresponding carboxylic acid as a white powder.

The white powder in $CH_2Cl_2$ (15 mL) and pyridine (0.8 mL) was treated with pentafluorophenyl trifluoroacetate (400 μL) for 3 hrs at r.t., and the resulting mixture was treated with O-TMS-hydroxylamine (320 μL) and stirred overnight at r.t. The reaction mixture was concentrated in vacuo and the residue was dispersed in water and cyclohexane. The white precipitate was filtered and purified on silica gel (eluent: $CHCl_3$/MeOH=20/1), affording the product as a white solid. (315 mg)

NMR ($d_6$-DMSO, δ): 2.70 (1H, dd, J=14.3, 9.0), 3.11 (1H, dd, J=14.3, 6.1), 3.72 (3H, s), 3.99 (1H, dd, J=9.0, 6.1), 4.57 (2H, s), 6.83 (2H, d, J=8.6), 7.13 (2H, d, J=8.6), 7.42 (1H, d, J=5.1), 8.18 (1H, d, J=5.1), 8.35 (1H, s), 9.00 (1H, s), 10.81 (1H, s).

Example 434

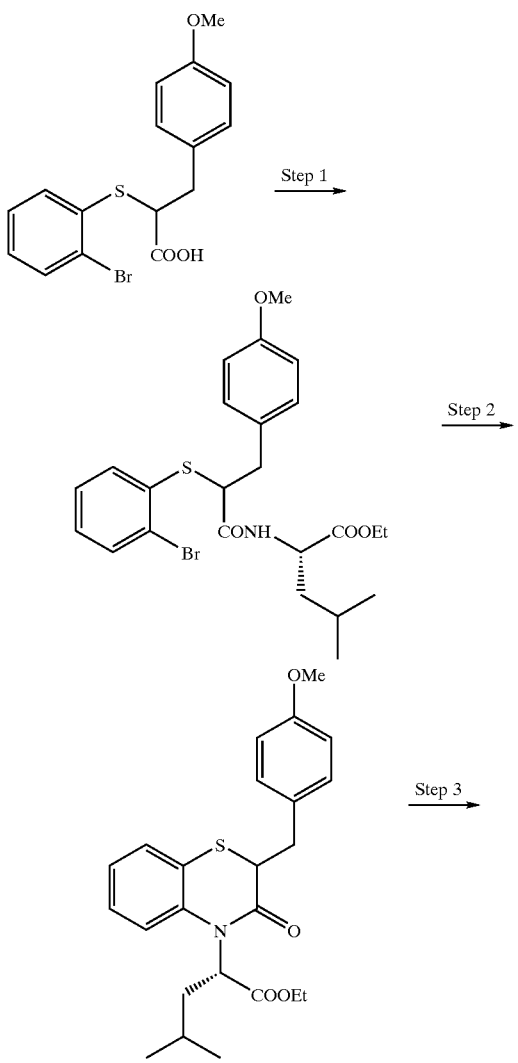

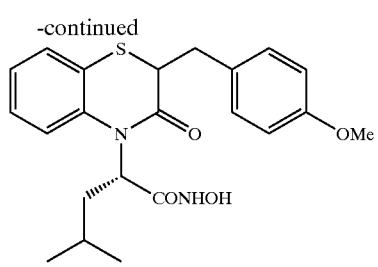

Step 1: Ethyl (2S)-2-[2'-(2-bromophenyl)thio-3'-(4-methoxyphenyl)propanoyl]amino-4-methylpentanoate To a solution of 2-(2-bromophenyl)thio-3-(4-methoxyphenyl)propanoic acid (1.102 g) and L-leucine ethyl ester.HCl (704 mg) in DMF (10 mL), HOBt (551 mg) and EDC.HCl (690 mg) were added. The reaction mixture was stirred at r.t. overnight. The solvent was removed under reduced pressure. The residue was dissolved in EtOAc and washed with 1N HCl, 5% $Na_2CO_3$ aq. and brine. The organic layer was dried over $Na_2SO_4$ and concentrated to give the pure product as a pale yellow oil (1.561 g, quant.).

Step 2: Ethyl (2S)-2-[2H-2-(4-Methoxybenzyl)-1,4-benzothiazin-3(4H)-one-4-yl]-4-methylpentanoate The product obtained in Step 1 (763 mg), $Pd_2(dba)_3 \cdot CHCl_3$ (78 mg), P(o-tolyl)$_3$ (92 mg), and $Cs_2CO_3$ (977 mg) in toluene (12 mL) were heated to 100° C. in a culture tube (PYREXPLUS®) under nitrogen for 40 hrs. The reaction mixture was then cooled to r.t., diluted with EtOAc, filtered, and the filtrate was concentrated under reduced pressure. The residue was purified by preparative thin layer chromatography on silica gel (toluene/EtOAc, 20/1) to give the product as a pale yellow oil (274 mg).

Step 3: (2S)-2-[2H-2-(4-Methoxybenzyl)-1,4-benzothiazin-3(4H)-one-4-yl]-4-methylpentanoic Acid N-Hydroxyamide To a solution of the compound obtained in Step 2 (274 mg) in ethanol (5 mL) and THF (5 mL), 1N NaOH (2.56 mL) was slowly added at 0° C. After 30 minutes' stirring, the mixture was warmed to room temperature and left over 1 day. The reaction mixture was concentrated under reduced pressure and the residue was dissolved in EtOAc and washed with 1N HCl. The organic layer was dried over $Na_2SO_4$ and concentrated. The crude acid was used in the following step. The acid (204 mg) was dissolved in $CH_2Cl_2$ (3 mL) and pyridine (3 mL) and pentafluorophenyl trifluoroacetate (716 mg) was added. After 3 hours' stirring, O-TBDMS-hydoxylamine (452 mg) was added. The reaction mixture was stirred at r.t. overnight. The solvent was removed under reduced pressure, and the residue was dissolved in EtOAc. The organic layer was washed with 1N HCl and brine, and dried over $Na_2SO_4$ and concentrated under reduced pressure. The residue was purified by preparative thin layer chromatography on silica gel (toluene/EtOAc=1/1) to give the hydroxamic acid (208 mg) as a pale orange solid.

The following compounds listed in the Table 8 were prepared in a similar manner.

TABLE 8

| Example No. | RR1 | NMR: ¹H-NMR(DMSO-d6; δ) |
|---|---|---|
| 434 | (S) —iBu | 0.57–0.77(6H, m), 1.00(1H, m), 1.70 (1.5H, m), 2.02(0.5H, m), 2.58(0.5H, m), 2.79(0.5H, m), 3.02(0.5H, m), 3.35 (0.5H, m), 3.72(1.5H, s), 3.73(1.5H, s), 3.78(1H, m), 5.14(0.5H, m), 5.56(0.5H, m), 6.82–6.88(2H, m), 7.03–7.46 (6H, m), 8.94(0.5H, s), 9.00(0.5H, s), 10.68(0.5H, s), 10.79(0.5H, s) |
| 435 | (R) —iBu | 0.57–0.77(6H, m), 1.00(1H, m), 1.73 (1.5H, m), 2.02(0.5H, m), 2.59(0.5H, m), 2.76(0.5H, m), 3.02(0.5H, m), 3.42 (0.5H, m), 3.72(1.5H, s), 3.73(1.5H, s), 3.78(1H, m), 5.16(0.5H, m), 5.56(0.5H, m), 6.82–6.88(2H, m), 7.06–7.46(6H, m), 8.94(0.5H, s), 9.00(0.5H, s), 10.68 (0.5H, s), 10.79(0.5H, s) |
| 436 | (S) —iPr | 0.43(3H, m), 0.96(3H, m), 2.26(0.5H, m), 2.45(0.5H, m), 2.80(1H, m), 3.17 (1H, m), 3.71(1.5H, s), 3.73(1.5H, s), 3.80(1H, m), 4.77(0.5H, d, J=10.9Hz), 4.94(0.5H, d, J=10.9Hz), 6.81–6.87(2H, m), 6.94–7.42(6H, m), 9.05(1H, bs), 10.81(1H, m) |
| 437 | (S) —Me | 1.27(1.5H, d, J=7.32Hz), 1.39(1.5H, d, J=6.96Hz), 2.59(0.5H, m), 2.70(0.5H, m), 3.02(0.5H, m), 3.34(0.5H, m), 3.72 (1.5H, s), 3.73(1.5H, s), 3.82(1H, m), 5.08(0.5H, m), 5.49(0.5H, m), 6.82–6.88(2H, m), 7.03–7.41(6H, m), 8.86 (0.5H, s), 8.95(0.5H, s), 10.56(0.5H, s), 10.70(0.5H, s) |
| 438 | (R) —Me | 1.27(1.5H, d, J=7.32Hz), 1.39(1.5H, d, J=6.96Hz), 2.59(0.5H, m), 2.71(0.5H, m), 3.00(0.5H, m), 3.34(0.5H, m), 3.72 (1.5H, s), 3.73(1.5H, s), 3.78(1H, m), 5.08(0.5H, m), 5.49(0.5H, m), 6.82–6.88(2H, m), 7.03–7.41(6H, m), 8.86 (0.5H, s), 8.95(0.5H, s), 10.56(0.5H, s), 10.70(0.5H, s) |

Example 439

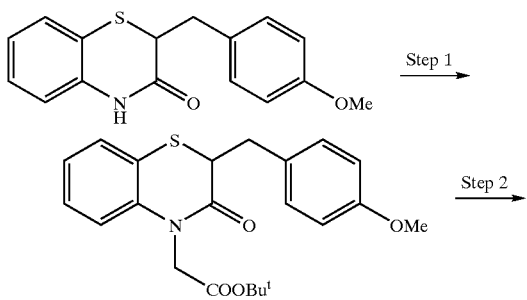

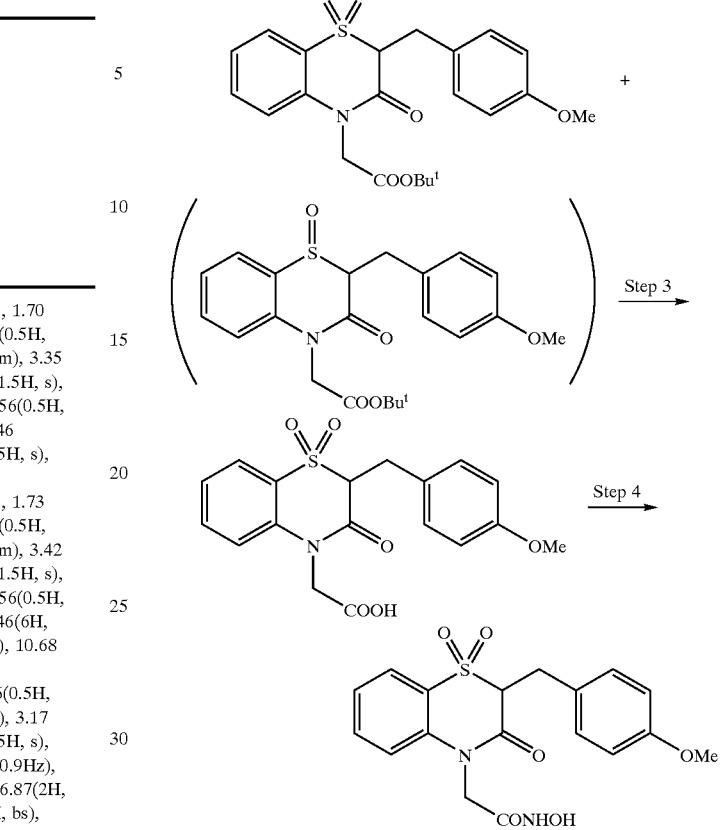

Step 1: 2H-2-(4-Methoxybenzyl)-1,4-benzothiazin-3(4H)-one-4-yl-acetic Acid t-Butyl Ester To a solution of 2H-2-(4-methoxybenzyl)-1,4-benzothiazin-3(4H)-one (2 g) in THF (20 mL), NaH (304 mg) and subsequently t-butyl bromoacetate (1.13 mL) were added at 0–5° C. The mixture was stirred at the same temperature for 5 minutes and at r.t. for 30 minutes. The reaction was quenched by adding 150 mL of water, and extracted with EtOAc. The organic layer was washed with brine, and dried over MgSO₄ and concentrated under the reduced pressure, and residue was purified by silica gel column chromatography (Eluent: Hexane:EtOAc=10:1) to give 3.0 g of the product as oil.

Step 2: 2H-2-(4-Methoxybenzyl)-1,4-benzothiazin-3(4H))-one-4-yl-acetic Acid t-Butyl Ester 1-Oxide and 1,1-dioxide Product in Step 1 (500 mg) was dissolved in MeOH (10 mL) and m-CPBA (432 mg) was added at 0–5° C. The mixture was stirred at the same temperature for 5 min. and warmed to r.t. After stirred for 1 hour, 100 mL of water was added and extracted with EtOAc. The organic layer was washed with sat. NaHCO₃ aq. and brine, and dried over MgSO₄ and concentrated under the reduced pressure, and the residue was purified with silica gel column chromatography (Eluent: Hexane:EtOAc=5:1) to give 270 mg of 1,1-dioxide and 370 mg of 1-oxide as oil.

Step 3: 2H-2-(4-Methoxybenzyl)-1,4-benzothiazin-3(4H)-one-4-yl-acetic Acid 1,1-Dioxide To the sulfone of Step 2 (270 mg), was added TFA (2 mL) at 0–5° C. The mixture was warmed to r.t. and stirred for 2 hrs. 100 mL of Et₂O was added and the resulting precipitate was filtered and washed with Et₂O, giving 245 mg of the corresponding acid.

Step 4: 2H-2-(4-Methoxybenzyl)-1,4-benzothiazin-3(4H)-one-4-yl-acetic Acid N-Hydroxyamide 1,1-Dioxide The product of Step 3 was converted to hydroxamic acid by the method described in Example 405, giving 95.6 mg of the product as colorless solid.

$^1$H-NMR (DMSO-$d_6$, δ) 3.06 (1H, dd, J=8.6 Hz, 14.6 Hz), 3.21 (1H, dd, J=4.0 Hz, 14.6 Hz), 3.70 (3H, s), 4.51 (1H, d, J=17 Hz), 4.57 (1H, d, J=17 Hz), 4.99 (1H, dd, J=4.0 Hz, 8.6 Hz), 6.80 (2H, d, J=8.4 Hz), 7.20 (2H, d, J=8.4 Hz), 7.38 (2H, m), 7.78 (1H, t, J=7.3 Hz), 7.88 (2H, d, J=7.1 Hz), 9.03 (0.8H, bs), 9.42 (0.2H, bs), 10.43 (0.2H, bs), 10.79 (0.8H, bs).

Example 440

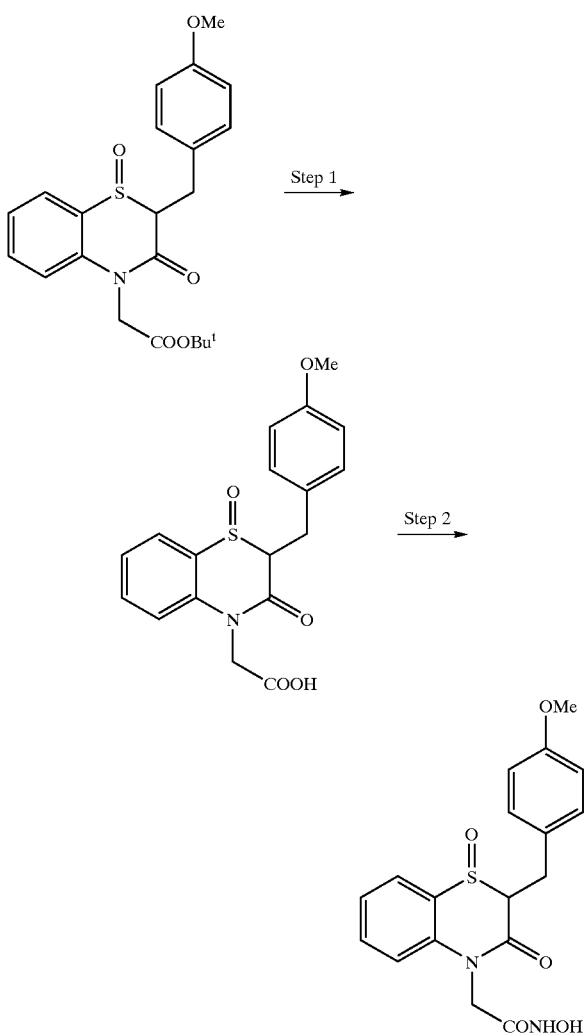

Step 1: 2H-2-(4-Methoxybenzyl)-1,4-benzothiazin-3(4H)-one-4-yl-acetic Acid 1-Oxide The product (290 mg) was obtained as colorless precipitate from the sulfoxide (370 mg) of Example 439 (Step 2) by the method described in Example 439 (Step 3).

Step 2: 2H-2-(4-Methoxybenzyl)-1,4-benzothiazin-3(4H)-one-4-yl-acetic Acid N-Hydroxyamide 1-Oxide The product of Step 1 was converted to hydroxamic acid as described in Example 439 to give 95 mg of the product.

$^1$H-NMR (DMSO-$d_6$, δ) 3.09 (1H, m), 3.49 (1H, b), 3.76 (3H, m), 4.40–5.00 (3H, m), 6.30–6.50 (2H, m), 7.00–7.50 (4H, m), 7.60–7.90 (2H, m), 9.04–9.45 (1H, m), 10.78–10.87 (1H, m).

Example 441

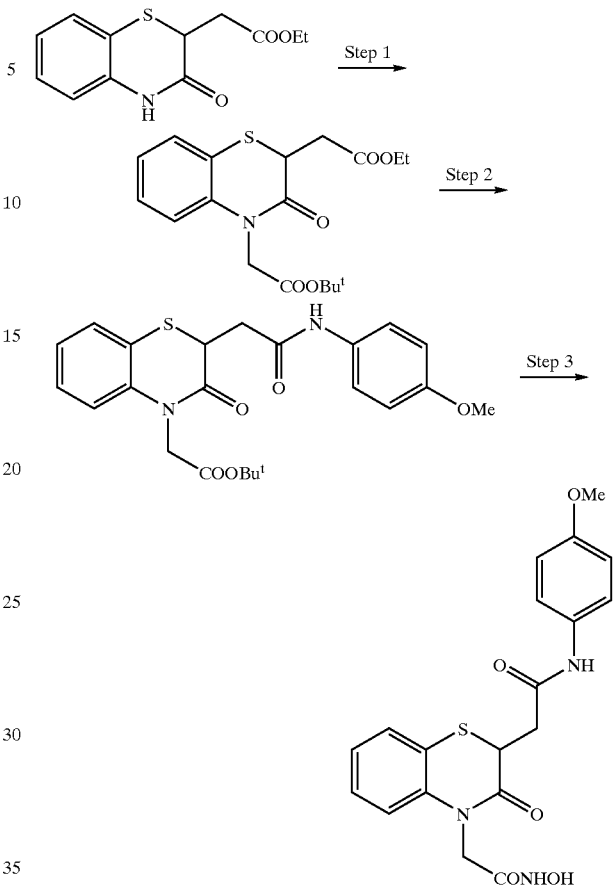

Step 1: 2H-2-(Ethoxycarbonylmethyl)-1,4-benzothiazin-3(4H)-one-4-yl-acetic Acid t-Butyl Ester To a solution of 2H-2-(ethoxycarbonylmethyl)-1,4-benzothiazin-3(4H)-one (2 g) in THF (20 mL) was added sodium hydride (335 mg), and t-butyl bromoacetate (1.23 mL) was added dropwise at 0–5° C. The mixture was stirred for 5 min. at the same temperature and for 30 minutes at r.t. 150 mL of water was added and extracted with EtOAc. The organic layer was washed with brine, and dried over MgSO$_4$ and concentrated under the reduced pressure to give 3.1 g of the product as oil.

Step 2: 2H-2-[N'-(4-Methoxyphenyl)carbamoylmethyl]-1,4-benzothiazin-3(4H)-one-4-yl-acetic Acid t-Butyl Ester To a solution of the product of step 1 in MeOH (20 ml), 1N NaOH (7.96 ml) was added at 0° C. Stirring was continued for 3 hrs. The reaction mixture was diluted with water, and washed with Et$_2$O. The aqueous layer was acidified with 1N HCl and the product was extracted with EtOAc. The organic layer was dried over Na$_2$SO$_4$ and concentrated to give the corresponding acetic acid (2.79 g) as oil.

To the solution of the acetic acid (200 mg) in DMF (20 ml), 4-anisidine (77 mg) and EDC.HCl (119 mg) were added at 0° C. Stirring was continued for 5 hours. The reaction mixture was diluted with water and extracted with EtOAc. The organic layer was washed with 1N HCl, sat. NaHCO$_3$ and brine, dried over MgSO$_4$ and concentrated under the reduced pressure. The residue was purified with silica gel column chromatography (Eluent: Hexane:EtOAc=3:1) to give the product (220 mg).

Step 3: 2H-2-[N'-(4-Methoxyphenyl)-carbamoylmethyl]-1,4-benzothiazin-3(4H)-one-4-yl-acetic Acid N-Hydroxylamide The product of Step 2 was converted to the hydroxamic acid as described in Example 439 to give 141 mg of the product.

The following compounds listed in the Table 9 were prepared in a similar manner.

Step 1: 2H-2-(4-Methoxybenzyl)-1,4-benzoxazin-3(4H)-one

To a solution of 2-bromo-3-(4-methoxyphenyl)propionic acid (1.6 g) in DMF (10 ml), 2-aminophenol (731 mg), EDC.HCl (1.54 g), and HOBt (500 mg) were added at 0° C. Stirring was continued for 2 hrs. The reaction mixture was diluted with water and extracted with EtOAc. The organic layer was washed with 1N HCl, sat. NaHCO$_3$ and brine,

TABLE 9

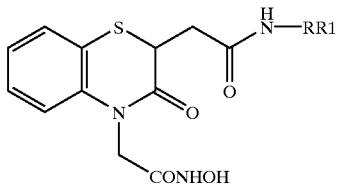

| Example No. | RR1 | NMR: $^1$H-NMR(DMSO-d6; δ) |
|---|---|---|
| 441 | —C6H4-4-OMe | 2.55(1H, dd, J=15Hz, 8.8Hz), 2.94(1H, dd, J=15Hz, 5.5Hz), 3.70(3H, s), 4.01Hz(1H, dd, J=8.6Hz, 5.5Hz), 4.34–4.76(2H, m), 6.86(2H, d, J=9.0Hz), 7.08(2H, m), 7.31 (1H, m), 7.43(3H, m), 8.97, 9.37(1H, s), 9.91, 9.95(1H, s), 10.34, 10.79(1H, s). |
| 442 | —CH2—C6H4-4-OMe | 2.42(1H, dd, J=9.0Hz, 15Hz), 2.81(1H, dd, J=5.0Hz, 15Hz), 3.71(3H, s), 3.95(1H, m), 4.17(2H, m), 4.33–4.76(2H, m), 6.87(2H, d, J=8.6Hz), 7.05–7.41(6H, m), 8.46(1H, t, J=5.6Hz), 8.97, 9.39(1H, s), 10.33, 10.79 (1H, s). |
| 443 | —(CH2)2—C6H4-4-OMe | 2.30(1H, dd, J=9.5Hz, 15Hz), 2.64(3H, m), 3.22(2H, m), 3.70(3H, s), 3.89(1H, m), 4.33–4.74(2H, m), 6.83(2H, d, J=8.4Hz), 7.07–4.41(6H, m), 8.08(1H, m), 8.97, 9.37(1H, s), 10.34, 10.79(1H, s). |

Example 444

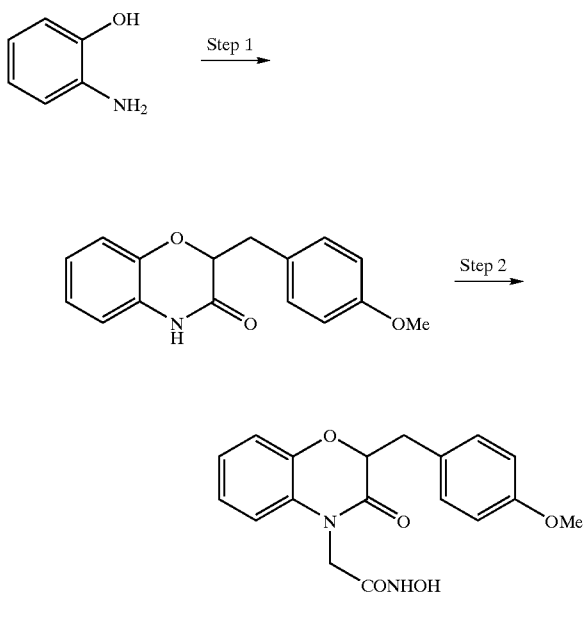

dried over MgSO$_4$ and concentrated under reduced pressure. The residue was purified with silica gel column chromatography (Eluent: Hexane:EtOAc=5:1).

To a solution of the obtained crystal (547 mg) in DMF (3 ml), K$_2$CO$_3$ (300 mg) was added at 0° C. Stirring was continued at room temperature for 2 hrs. The reaction mixture was diluted with water and extracted with EtOAc. The organic layer was washed with brine, dried over MgSO$_4$ and concentrated under reduced pressure. The residue was purified with silica gel column chromatography (Eluent: Toluene:EtOAc=6:1). 266 mg of the product was obtained as oil.

Step 2: 2H-2-(4-Methoxybenzyl)-1,4-benzoxazin-3(4H)-one-4-yl-acetic Acid N-Hydroxyamide The compound obtained in Step 1 (266 mg) was converted to the hydroxamic acid derivative by the method described above and 152 mg of the product was obtained as colorless precipitate.

$^1$H-NMR (DMSO-d$_6$, δ) 2.90 (1H, dd, J=9.0 Hz, 14 Hz), 3.06 (1H, dd, J=4.2 Hz, 14 Hz), 3.71 (3H, s), 4.41 (1H, d, J=16 Hz), 4.47 (1H, d, J=16 Hz), 4.83 (1H, dd, J=4.2 Hz, 9.0 Hz), 6.89 (2H, d, J=8.6 Hz), 6.89–7.03 (4H, m), 7.15 (2H, d, J=8.6 Hz), 8.98, (0.8H, bs), 9.40 (0.2H, bs), 10.35 (0.2H, bs), 10.80 (0.8H, bs).

Example 445

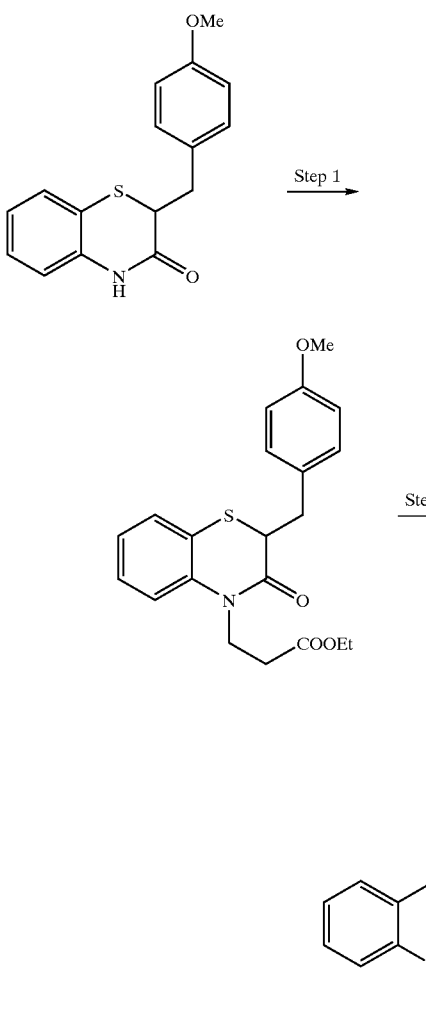

Step 1: 3-[2H-2-(4-Methoxybenzyl)-1,4-benzothiazin-3(4H)-one-4-yl]propanoic Acid To a solution of 2H-2-(4-methoxybenzyl)-1,4-benzothiazin-3(4H)-one (570 mg) in THF (20 mL), NaOH powder (84 mg) was added. After 10 minutes' stirring, ethyl acrylate (600 mg) was slowly added. The reaction mixture was stirred at room temperature for 5 hours. The solvent was removed under reduced pressure and the residue was acidified with 4N HCl. The product was extracted with EtOAc and the organic layer was dried over $Na_2SO_4$ and concentrated. The crude product was used in the following step without purification.

To a solution of the ethyl ester in MeOH (20 mL), 1N NaOH (2.0 mL) was slowly added. The mixture was stirred at r.t. overnight and concentrated under reduced pressure. The residue was dissolved in water, and the aqueous solution was washed with $Et_2O$ and acidified with 4N HCl. The product was extracted with EtOAc. The organic layer was dried over $Na_2SO_4$ and concentrated to give the propanoic acid (618 mg) as a white solid.

Step 2:
The product of Step 1 was converted to hydroxamic acid by the method described in example 405 (step 3 and 4).

$^1$H-NMR (DMSO-$d_6$, δ) 2.30 (2H, m), 2.63 (1H, m), 3.03 (1H, m), 3.72 (3H, s), 3.77 (1H, m), 4.11 (2H, m), 6.84 (2H, d, J=8.04 Hz), 7.06–7.11 (3H, m), 7.32–7.42 (3H, m), 8.82 (1H, s), 10.53 (1H, s).

Example 446

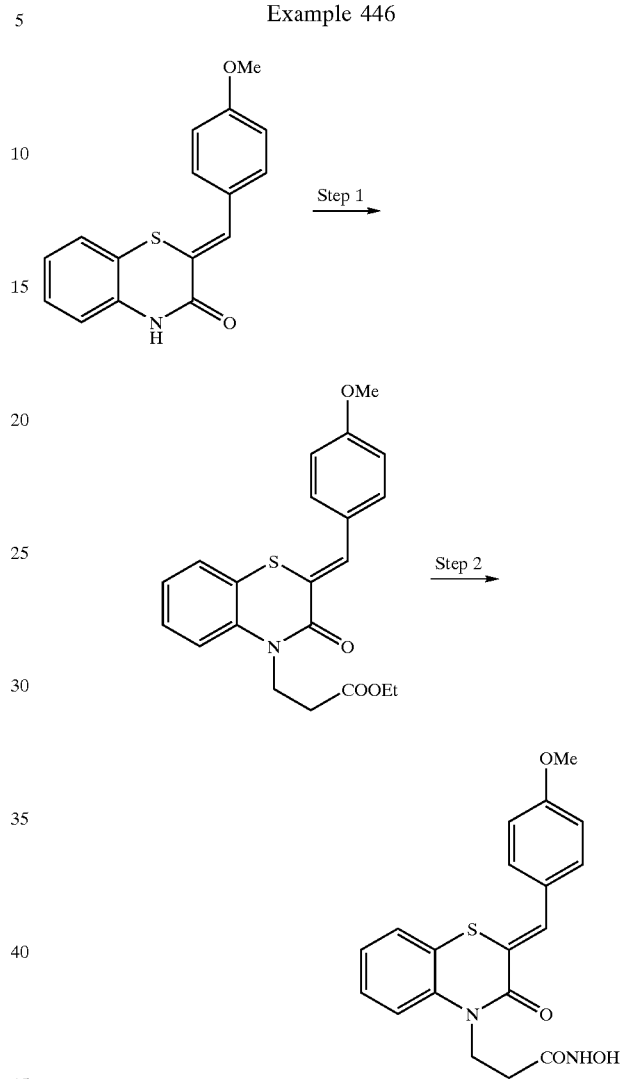

3-[2H-2-(4-Methoxybenzylidene)-1,4-benzothiazin-3(4H)-one-4-yl]propanoic Acid N-Hyroxylamide The reaction procedure of Step 1 and 2 were similar to the example 445 (Step 1 and 2).

LC-MS: MS (m/e) 371.0, 338.0, 296.2 (M.W.=370.4); Retention Time=3.07 min.

Example 730

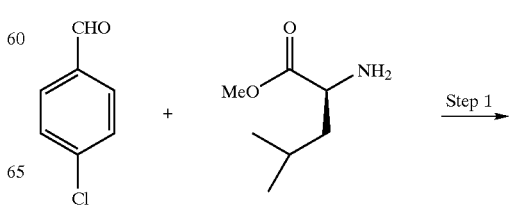

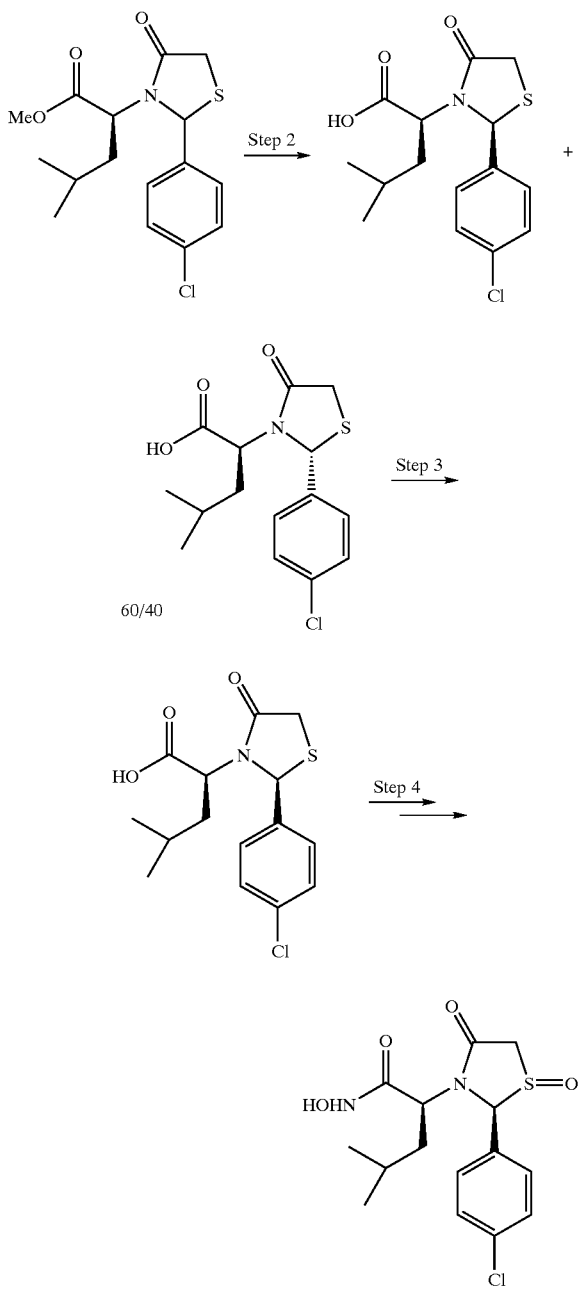

Step 1: 4-Methyl-2-(S)-[2-(RS)-(4-chlorophenyl)-4-oxo-thiazolidin-3-yl]-pentanoic Acid Methyl Ester A suspension of (L)-leucine methyl ester (10 g, 55 mmol) and triethylamine (7.7 ml, 55 mmol) in 120 ml of dioxane was stirred at room temperature for 5 minutes. 3 Å molecular sieves were added followed by p-chlorobenzaldehyde (17 g, 121 mmol). The mixture was heated at 80° C. for 4 hrs. Mercaptoacetic acid (14.2 ml, 203.5 mmol) was added to the mixture and the heating was continued for an additional 12 hrs. The reaction mixture was cooled to room temperature, and diluted with ethyl acetate (40 ml) and water (30 ml). The reaction mixture was filtered to remove the molecular sieves. The organic layer was diluted with ethyl acetate (100 ml), washed twice with 60 ml of saturated solution of sodium carbonate, twice with aqueous 1N HCl and once with water. The organic layer was dried with MgSO$_4$ and evaporated to give a residue that was carried out to the next step without further purification.

Step 2: 4-Methyl-2-(S)-[2-(RS)-(4-chlorophenyl)-4-oxo-thiazolidin-3-yl]-pentanoic Acid The residue obtained in step 1 was dissolved in dioxane (50 ml). 30 ml of saturated solution of LiOH were added and the mixture was stirred at room temperature for 3 h (analytical LC/MS showed no traces of starting material). The mixture was acidified with conc. HCl until acidic pH and diluted with ethyl acetate (50 ml). The 2 layers were separated and the aqueous layer was extracted 3 times with ethyl acetate (30 ml). The organic layers were combined, dried with MgSO$_4$, filtered and evaporated to give an oil that solidified upon standing. The reaction mixture was further purified column by chromatography with hexane-ethyl acetate (from 95:5 to 1:1) to give 14.4 g (yield for 2 steps: 80%) of the desired product as a 60:40 mixture of diastereoisomers.

Step 3: Separation of Diastereoisomers

The mixture of pure acids obtained in Step 2 was dissolved in refluxing toluene. Upon cooling 2 g of the minor isomer crystallized out of the mixture and were used for further transformations.

Step 4: 4-Methyl-2-(S)-[2-(S)-(4-chlorophenyl)-1,4-dioxo-thiazolidin-3-yl]-pentanoic Acid N-Hydroxyamide The crystal obtained in Step 3 (500 mg, 1.52 mmol) was dissolved in methanol (200 ml). A solution of sodium periodate (326 mg, 1.5 mmol) in 25 ml of water was added and the heterogeneous mixture was stirred at room temperature for 3 days. When no starting material was observed by LC/MS, the reaction mixture was concentrated to 80% of its volume, acidified with acetic acid (2 ml) and diluted with water (10 ml) and ethyl acetate (25 ml). The 2 layers were separated and the water layer extracted 2 additionnal times with ethyl acetate (2×20 ml). The organic layers were combined, dried with MgSO$_4$, evaporated under dryness to give the product as a white solid that was taken to the next step without purification.

To a solution of the product in 5 ml of CH$_2$Cl$_2$(DCM) and 2 ml of pyridine was added pentafluorophenol trifluoroacetate (914 ml, 5.32 mmol). The solution was stirred at room temperature for 1 h. O-(tert-Butyldimethylsilyl)-hydroxylamine (1.2 g, 7.6 mmol) in 2 ml of CH$_2$Cl$_2$ was added to the activated ester and the mixture was stirred at room temperature for an additional 12 h. The reaction mixture was acidified with HCl (to cleave the TBDMS protective group) and stirred at room temperature for 1 h. After dilution with DCM (4 ml) and water (2 ml), the 2 layers were separated, the organic layer dried with MgSO$_4$, filtered and evaporated to give an oil that was dissolved in DMSO (3 ml) and purified by reverse phase HPLC. The Product (141 mg, 26%) was obtained with 98% purity.

The following compounds listed in the Table 13 were prepared in a similar manner.

TABLE 13

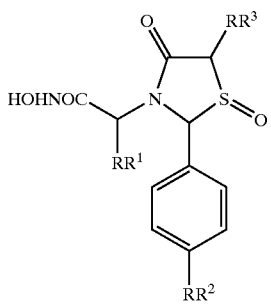

| Example No. | RR¹ | RR² | RR³ | mol. weitht | Mass(m/e) | HPLC rt (min) |
|---|---|---|---|---|---|---|
| 730 | —iBu | —Cl | —H | 358.8 | 359.2, 326.0, 298 | 1.99 |
| 731 | —iBu | —O—C6H4-4-Cl | —CH2CONH(CH2)2OMe | 566.1 | 566.2, 508.2, 475.2 | 3.05 |
| 732 | —iBu | —F | —H | 342.4 | 343.0, 310.2, 282 | 1.98 |
| 733 | —iBu | —O—C6H4-4-F | —H | 434.5 | 435.2, 402.2, 374 | 2.76 |
| 734 | —iBu | —O—C6H4-4-F | —H | 434.5 | 435.2, 402.2, 374 | 2.75 |
| 735 | —iBu | —Cl | —H | 358.8 | 359.2, 326.0, 298 | 2.24 |
| 736 | —iBu | —O—C6H4-4-Cl | —H | 450.9 | 451.0, 418.0 | 3.21 |
| 737 | —iBu | —H | —H | 324.4 | 325.2, 292.2, 264 | 1.91 |
| 738 | —iBu | —O—C6H4-4-Cl | —CH2CONHCH2-2-furyl | 588.1 | 588.2, 509.2 | 3.12 |
| 739 | —iBu | —O—C6H4-4-Cl | —CH2CONHCH2-2-furyl | 588.1 | 588.2 | 3.14 |
| 740 | —iBu | —O—C6H4-4-Cl | —CH2CONH(CH2)2OMe | 566.1 | 566.2, 509.2, 476.0 | 2.88 |
| 741 | —iBu | —O—C6H4-4-Cl | —CH2CONH(CH2)2OMe | 566.1 | 566.2, 509.2, 476.0 | 3.15 |
| 742 | —iBu | —Cl | —CH2CONHCH2-2-furyl | 496.0 | 496.2 | 3.10 |
| 743 | —iBu | —Cl | —CH2CONHMe | 429.9 | 430.2 | 2.81 |
| 744 | —iBu | —Cl | —CH2CONHMe | 429.9 | 430.2 | 2.43 |
| 745 | —iBu | —Cl | —CH2CONH(CH2)2OMe | 474.0 | 474.2, 417.2 | 2.86 |
| 746 | —iBu | —Cl | —CH2CONH2 | 415.9 | 416.2, 483.0 | 2.35 |
| 747 | —iBu | —Cl | —CH2CONH2 | 415.9 | 416.2 | 2.61 |

Example 748

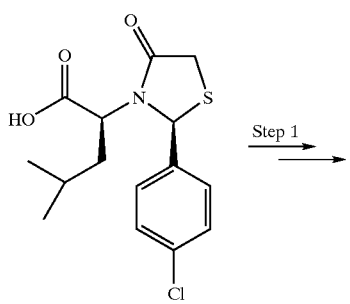

Step 1

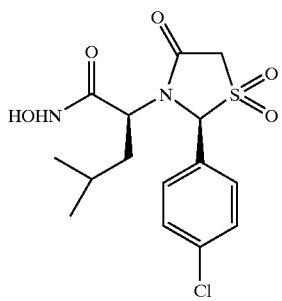

Step 1: 4-Methyl-2-(S)-[2-(S)-(4-chlorophenyl)-1,1,4-trioxothiazolidin-3-yl]-pentanoic Acid N-Hydroxyamide The crystal obtained from Example 730, Step 3 (100 mg, 0.30 mmol) was dissolved in acetic acid (2 ml). A solution of potassium permanganate (66.4 mg, 0.42 mmol) in 2 ml of water was added dropwise during a period of 1 hour at 0° C. The mixture was stirred at room temperature and followed by LC/MS. After 1 h, no starting material was observed; the color of the reaction was removed with $NaHS_2O_3$, diluted with water and extracted with EtOAc. The 2 layers were separated and the water layer extracted 2 additional times with ethyl acetate (2×20 ml). The organic layers were combined, dried with $MgSO_4$, evaporated under dryness to give the product as a white solid that was taken to the next step without purification.

To a solution of this solid in 1 ml of DCM and 0.5 ml of pyridine was added pentafluorophenol trifluoroacetate (231 ml, 1.34 mmol). The solution was stirred at room temperature for 1 h. O-(tert-Butyldimethylsilyl)-hydroxylamine (270 mg, 1.83 mmol) in 1 ml of DCM was added to the activated ester and the mixture was stirred at room temperature for an additional 12 h. The reaction was acidified with HCl (to cleave the TBDMS protective group) and stirred at room temperature for 1 h. After dilution with DCM (4 ml) and water (2 ml), the 2 layers were separated, the organic layer dried with $MgSO_4$, filtered and evaporated to give an oil that was dissolved in DMSO (2 ml) and purified by reverse phase HPLC to yield the hydroxamic acid as a white solid.

The following compounds listed in the Table 14 were prepared in a similar manner.

TABLE 14

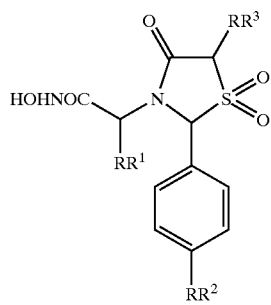

| Example No. | RR¹ | RR² | RR³ | mol. weitht | Mass (m/e) | HPLC rt (min) |
|---|---|---|---|---|---|---|
| 748 | —iBu | —Cl | —H | 374.8 | 375.0, | 2.37 |
| 749 | —iBu | —O—C6H4-4-Cl | —CH2CONH2 | 524.0 | 524.2, | 2.71 |
| 750 | —iBu | —O—C6H4-4-Cl | —CH2CONH(CH2)2OMe | 582.1 | 582.2, | 3.36 |
| 751 | —iBu | —Cl | —CH2CONH(CH2)2OMe | 490.0 | 490.2, | 2.81 |
| 752 | —iBu | —O—C6H4-4-F | —H | 450.5 | 451.0, | 3.22 |
| 753 | —iBu | —O—C6H4-4-Cl | —H | 466.9 | 467.2, | 3.38 |

Example 777

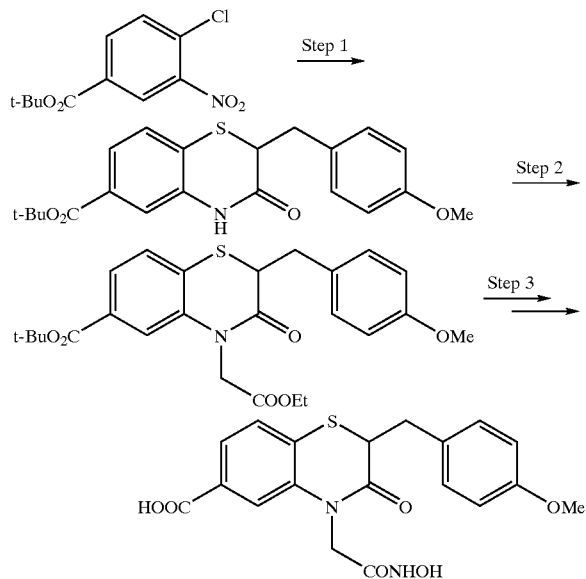

Step 1: t-Butyl 2H-2-(4-Methoxybenzyl)-1,4-benzo-thiazin-3(4H)-one-6-carboxylate To 2-mercapto-3-(4-methoxyphenyl)propionic acid (14 g) in ethanol (100 ml), t-butyl 4-chloro-3-nitrobenzoate (17 g), and potassium fluoride (3.8 g) were added at 0° C. Potassium carbonate (9.1 g) was slowly added at 0° C. and the mixture was heated under reflux for 7 hrs. The solvent was removed under the reduced pressure and the residue was diluted with water. The solution was washed with $Et_2O$ and extracted with EtOAc. The organic layer was washed with brine, and dried over $MgSO_4$ and concentrated under the reduced pressure. The solution of the residue in MeOH (120 ml) was added dropwise to the suspension of Fe powder (11.4 g) in MeOH (50 ml)-$NH_4Cl$aq. (17.6 g/80 ml of water) at r.t. The mixture was stirred at 80° C. for 3 hrs. AcOH (50 ml) was added to the reaction mixture, and the stirring was continued for 3 hrs at 80° C. The reaction mixture was cooled to room temperature, poored into ice-water, and extracted with EtOAc. The organic layer was washed with brine, dried over $MgSO_4$ and concentrated under the reduced pressure. The residue was purified with silica gel column chromatography (eluent: hexane/EtOAc, 8/1,5/1,3/1) to give the product as oil. This was crystalized from EtOAc-Hexane to give a colorless crystal (12.7 g).

Step 2: Ethyl 6-t-Butoxycarbonyl-2H-2-(4-methoxy-benzyl)-1,4-benzothiazin-3(4H)-one-4-yl-acetate To sodium hydride (3.32 g) suspended with THF (30 mL)was added a solution of the product of Step 1 (30.5 g) in THF (240 mL), and ethyl bromoacetate (13.1 mL) were added dropwise at 0–5° C. The mixture was warmed to r.t. and left at r.t. overnight. Saturated aqueous ammonium chloride was added and extracted with EtOAc. The organic layer was washed with water and brine, dried over $MgSO_4$, and concentrated under the reduced pressure to give 37 g of the product as oil.

Step 3: 6-Carboxyl-2H-2-(4-methoxybenzyl)-1,4-benzo-thiazin-3(4H)-one-4-yl-acetic Acid N-Hydroxyamide To a solution of ethyl 6-t-butoxycarbonyl-2H-2-(4-methoxy-benzyl)-1,4-benzothiazin-3(4H)-one-4-yl-acetate (3 g) was added 5N-aqueous sodium hydroxide (1.44 mL) at r.t. and stirred for 4 hr at r.t. The reaction mixture was concentrated under reduced pressure. 5% $KHSO_4$ aq. was added, and extracted with EtOAc. The organic layer was washed with brine, and dried over $MgSO_4$ and concentrated under reduced pressure to give 6-t-butoxycarbonyl-2H-2-(4-methoxy-benzyl)-1,4-benzothiazin-3(4H)-one-4-yl acetic acid as oil. Isobutyl chloroformate (1.04 g) was added dropwise to a THF (30 ml) solution of 6-t-butoxycarbonyl-2H-2-(4-Methoxy-benzyl)-1,4-benzo-thiazin-3(4H)-one-4-yl acetic acid and N-methylmorpholine (769 mg) at −15 to −20° C. O-TMS-hydoxylamine (1.09 g) was added after additional 15 minutes' stirring. The mixture was warmed to r.t. with stirring, and stood overnight. The reaction mixture was quenched with sat.$NaHCO_3$ aq. and extracted with EtOAc. The organic layer was washed with 1N HCl, sat-.$NaHCO_3$ aq. and brine, dried over $MgSO_4$ and concentrated under reduced pressure to give 2.25 g of 6-t-butoxycarboxyl-2H-2-(4-methoxybenzyl)-1,4-benzothiazin-3(4H)-one-4-ylacetic acid N-hydroxyamide as pale yellow oil. 5%-ethanedithiol in TFA (10 mL) was added to dissolve 6-t-butoxycarboxyl-2H-2-(4-methoxybenzyl)-1,4-benzo-thiazin-3(4H)-one-4-ylacetic acid N-hydroxyamide, and stood at r.t. for 2 hrs. Toluene (10 mL) was added and concentrated under reduced pressure. The residue was purified by recrystallization from mixed solvent of THF and hexane to give 1.2 g of the hydroxamic acid as colorless solid.

The following compounds listed in the Tables 15, and 15' were prepared in a similar manner.

TABLE 15

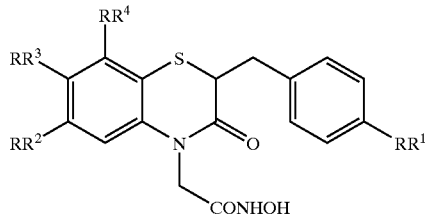

| Example No. | RR¹ | RR² | RR³ | RR⁴ | NMR: $^1$H-NMR(DMSO-d6; δ) |
|---|---|---|---|---|---|
| 777 | —OMe | —COOH | —H | —H | 2.68(1H, dd, J=9.0, 14Hz), 3.13(1H, dd, J=6.2, 14Hz), 3.72(3H, s), 3.90(1H, dd, J=6.2, 9.0Hz), 4.50(1.6H, br-s), 4.69(0.2H, d, J=19Hz), 4.91(0.2H, d, J=19 Hz), 6.83(2H, d, J=8.4Hz), 7.13(2H, d, J=8.4Hz), 7.48(1H, d, J=7.9Hz), 7.61(1H, dd, J=1.3, 7.9Hz), 7.66(1H, d, J=1.3Hz), 9.04(0.8H, s), 9.44(0.2H, s), 10.39(0.2H, s), 10.80(0.8H, s) |
| 778 | —Cl | —CH2CO2H | —H | —H | 2.73(1H, dd, J=9.2, 14.5Hz), 3.17(1H, dd, J=6, 14.5Hz), 3.57(2H, s), 3.89(1H, dd, J=6, 9.2Hz), 4.38–4.81(2H, m), 6.98(1H, d, J=8Hz), 7.06(1H s) 7.2–7.5(5H, m), 8.9–9.7(1H, bs), 10.78, 10.34(1H, bs). |
| 779 | —C6H4-4-Cl | —H | —H | —H | 2.76(1H, m), 3.23(1H, m), 3.91(1H, m), 4.4–5.0(2H, m), 7.12(2H, m), 7.35(4H, m), 7.50(2H, d, J=8.7Hz), 7.59 (2H, d, J=8.3Hz), 7.68(2H, d, J=8.7Hz), 8.98, 9.38 (1H, bs), 10.35, 10.78(1H, bs). |
| 780 | —C6H4-4-F | —H | —H | —H | 2.76(1H, dd, J=9.2, 14.3Hz), 3.23(1H, dd, J=6.0, 14.3 Hz), 3.93(1H, dd, J=6.0, 9.2Hz), 4.4–5.0(2H, m), 7.0–7.4(8H, m), 7.56(2H, d, J=8.1Hz), 7.70(2H, m), 8.99, 9.38(1H, bs), 10.34, 10.78(1H, bs). |
| 781 | —O—C6H4-4-Cl | —H | —H | —H | 2.72(1H, dd, J=9.1, 14Hz), 3.17(1H, dd, J=5.9, 14Hz), 3.87(1H, dd, J=5.9, 9.0Hz), 4.45(0.8H, d, J=16Hz), 4.50 (0.8H, d, J=16Hz), 4.68(0.2H, d, J=18Hz), 4.88(0.2H, d, J=18Hz), 6.94(2H, d, J=8.5Hz), 7.01(2H, d, J=8.5Hz), 7.07(1H, td, J=0.9, 7.6Hz), 7.13(1H, d, J=8.0Hz), 7.25 (2H, d, J=8.5Hz), 7.31(1H, td, J=1.3, 8.0Hz), 7.38(1H, dd, J=1.3, 7.6Hz), 7.42(2H, d, J=8.9Hz), 8.99(0.8H, s), 9.40(0.2H, s), 10.34(0.2H, s), 10.74(0.8H, s) |
| 782 | —H | —CO2H | —H | —H | 2.73(1H, m), 3.20(1H, m), 3.98(1H, m), 4.46(2H, m), 7.21–7.42(5H, m), 7.50(1H, d, J=8.07Hz), 7.62(1H, d, J=8.04Hz), 7.67(1H, s), 9.06(1H, s), 10.84(1H, s) |
| 783 | —O—C6H4-4-Cl | —COO-tBu | —H | —H | 1.55(9H, s), 2.75(1H, dd, J=8, 8.14Hz), 3.15(1H, dd, J= 6.1, 14Hz), 3.96(1H, dd, J=6.1, 8.8Hz), 4.48(0.8H, d, J= 17Hz), 4.56(0.8H, d, J=17Hz), 4.68(0.2H, d, J=18Hz), 4.96(0.2H, d, J=18Hz), 6.93(2H, d, J=8.4Hz), 7.00(2H, d, J=9.0Hz), 7.25(2H, d, J=8.4Hz), 7.42(2H, d, J=9.0 Hz), 7.50(1H, d, J=8.1Hz), 7.58(1H, dd, J=1.5, 8.1Hz), 7.64(1H, br-s), 9.04(0.8H, d), 9.44(0.2H, s), 10.42(0.2H, s), 10.85(0.8H, s) |
| 784 | —O—C6H4-4-Cl | —CO2H | —H | —H | 2.77(1H, dd, J=9, 0.14Hz), 3.19(1H, dd, J=5.9, 14Hz), 3.95(1H, m), 4.52(1.6H, br-s), 4.69(0.2H, d, J=18Hz), 4.95(0.2H, d, J=18Hz), 6.92(2H, d, J=8.4Hz), 7.00 (2H, d, J=9.0Hz), 7.25(2H, d, J=8.4Hz), 7.40(2H, d, J=9.0Hz), 7.48(1H, d, J=8.1Hz), 7.62(1H, dd, J=1.7, 8.1Hz), 7.67(1H, br-s), 9.05(0.8H, s), 9.44 (0.2H, s), 10.39(0.2H, s), 10.84(0.8H, s), 12.37(1H, s) |
| 786 | —H | —COONa | —H | —H | 2.73(1H, m), 3.20(1H, m), 3.98(1H, m), 4.46(2H, m), 7.21–7.42(5H, m), 7.50(1H, d, J=8.07Hz), 7.62(1H, d, J=8.04Hz), 7.67(1H, s), 9.06(1H, s), 10.84(1H, s) |
| 787 | —Cl | —CO2H | —H | —H | 2.75(1H, dd, J=14.1, 9.0Hz), 3.14(1H, dd, J=14.3Hz, 6.2Hz), 3.99(1H, dd, J=8.6Hz, 6.2Hz), [4.49(S), 4.87 (d, J=17.9Hz), 4.90(d, J=17.9Hz)] 2H, 7.24(2H, d, J=8.6Hz), 7.32(2H, d, J=8.6Hz), 7.48(1H, d, J=8.0Hz), 7.60(1H, d, J=8.1Hz, 1.5Hz), 7.65(1H, d, J=1.5Hz), 9.44(1H, br), [10.80(br), 10.38(s)] 1H, 13.02(1H, br) |

TABLE 15-continued

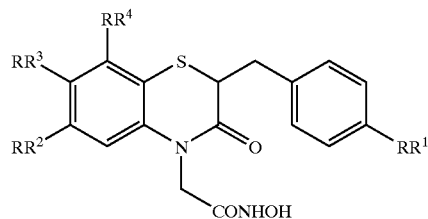

| Example No. | RR$^1$ | RR$^2$ | RR$^3$ | RR$^4$ | NMR: $^1$H-NMR(DMSO-d6; δ) |
|---|---|---|---|---|---|
| 788 | —OCF3 | —CO2H | —H | —H | 2.81(1H, dd, J=8.8, 14.5Hz), 3.20(1H, dd, J=6.4, 14.5 Hz), 4.04(1H, dd, J=6.4, 8.8Hz), 4.5–4.9(2H, m), 7.26 (2H, d, J=8Hz), 7.36(2H, d, J=8Hz), 7.52(1H, m), 7.61 (1H, dd, J=1.5, 8Hz), 7.66(1H, d, J=1.5Hz), 9.46, 9.06 (1H, bs), 10.86, 10.43(1H, bs), 13.19(1H, bs). |
| 789 | —OMe | —NO2 | —H | —H | 2.722(1H, m), 3.089(1H, dd, J=6.4, 14.4Hz), 3.716(3H, s), 4.032(1H, m), 4.544–5.02(2H, m), 6.82(2H, d, J=8.6 Hz), 7.12(2H, d, J=8.6Hz), 7.68(1H, d, J=8.4Hz), 7.91 (1H, dd, J=8, 4.2Hz), 7.99(1H, d, J=2Hz), 9.09, 9.48 (1H, bs), 10.48, 10.91(1H, bs). |
| 790 | —OMe | —CN | —H | —H | 2.68(1H, dd, J=9.2, 14.3Hz), 3.09(1H, dd, J=6.4, 14.3 Hz), 3.72(3H, s), 3.96(1H, dd, J=6.4, 9.2Hz), 4.5–5.0 (2H, m), 6.82(2H, d, J=8.7Hz), 7.12(2H, d, J=8.7Hz), 7.52(1H, d, J=8.3Hz), 7.59(2H, m), 9.01, 9.37(1H, bs), 10.38, 10.86(1H, bs). |
| 791 | —H | —NO2 | —H | —H | 2.75(1H, dd, J=9.2, 14Hz), 3.17(1H, dd, J=6.2, 14Hz), 4.08(1H, dd, J=6.2, 9.2Hz), 4.5–5.0(2H, m), 7.10–7.30 (5H, m), 7.65(1H, d, J=8.6Hz), 7.90(1H, dd, J=2.2, 8.6 Hz), 8.00(1H, d, J=2.2Hz), 9.05–9.47(1H, bs), 10.45, 10.89(1H, bs). |
| 792 | —H | —H | —H | —COONa | 2.68(1H, dd, J=8.3, 14Hz), 3.16(1H, dd, J=10, 14Hz), 3.41(1H, m), 4.23(0.8H, d, J=16Hz), 4.55(0.8H, d, J=17 Hz), 4.65(0.2H, d, J=18Hz), 4.76(0.2H, d, J=17Hz), 6.99 (1H, d, J=8.1Hz), 7.00–7.30(6H, m), 7.40(1H, d, J=7.5 Hz), 9.02(0.6H, s), 9.48(0.1H, s), 10.29(0.2H, s), 10.77 (0.8H, s) |
| 793 | —OMe | —N(SO2Me)COO-iBu | —H | —H | 0.75(6H, d, J=8.4Hz), 1.81(1H, m), 2.61(1H, dd, J=9.5, 14.5Hz), 3.07(1H, dd, J=5.9, 14.5Hz), 3.57(3H, s), 3.71 (3H, s), 3.78(3H, m), 4.41–4.90(2H, m), 6.83(2H, d, J= 8.3Hz), 7.10(3H, m), 7.20(1H, m), 7.44(1H, d, J=8.3 Hz), 8.98, 9.36(1H, bs), 10.28, 10.75(1H, bs). |
| 794 | —OMe | —SO2Me | —H | —H | 2.70(1H, dd, J=9, 4.14Hz), 3.12(1H, dd, J=6.2, 14Hz), 3.24(3H, s), 3.73(3H, s), 3.96(1H, dd, J=6.2, 9.4Hz), 4.58(1.6H, br-s), 4.79(0.2H, d, J=18Hz), 4.97(0.2H, d, J=18Hz), 6.83(2H, d, J=8.6Hz), 7.13(2H, d, J=8.6 Hz), 7.63–7.68(2H, m), 7.73(1H, dd, J=1.5, 8.1Hz), 9.07 (0.7H, s), 9.46(0.3H, s), 10.41(0.3H, s), 10.86(0.7H, s) |
| 795 | —H | —O—CH2CONHOH | —H | —H | 2.67(1H, dd, J=9.5Hz, 14.5Hz), 3.17(1H, dd, J=4, 14.5 Hz), 3.81(1H, dd, J=4, 9.5Hz), 4.45–4.85(4H, m), 6.80 (2H, m), 7.30(6H, m), 8.95, 9.35(2H, bs), 10.28, 10.75 (2H, bs). |
| 796 | —OMe | —H | —O—CH2OMe | —H | 2.64(1H, m), 3.12(1H, dd, J=5.5, 14Hz), 3.35(3H, s), 3.71(3H, s), 3.78(1H, m), 4.33–4.76(2H, m), 5.15(2H, s), 6.82(2H, d, J=8.6Hz), 6.88–7.13(5H, m), 8.63, 8.95(1H, bs), 10.30, 10.73(1H, bs). |
| 797 | —OMe | —H | —O—CH2COOH | —H | 2.59(1H, dd, J=9, 3.14Hz), 3.11(1H, dd, J=6.14Hz), 3.14 (3H, s), 3.78(1H, dd, J=6, 9.3Hz), 4.30–4.80(2H, m), 4.66(2H, s), 6.88(4H, m), 7.04(1H, d, J=9Hz), 7.12(2H, d, J=8.4Hz), 9.34, 8.96(1H, bs), 10.73, 10.30(1H, bs). |

TABLE 15'

| Example No. | Structure | NMR: $^1$H-NMR(DMSO-d6; δ) |
|---|---|---|
| 988 | (structure: thieno-benzothiazine with HOOC, Cl-benzyl, CONHOH) | 2.80(1H, m), 3.14(1H, dd, J=6.3, 14.1Hz), 4.11(1H, m), 4.39–4.90(2H, m), 7.24 (2H, d, J=8.4Hz), 7.34(2H, d, J=8.4Hz), 7.55(1H, s), 9.01, 9.35(1H, bs), 10.36, 10.78(1H, bs), 13.44(1H, bs). |

Example 798

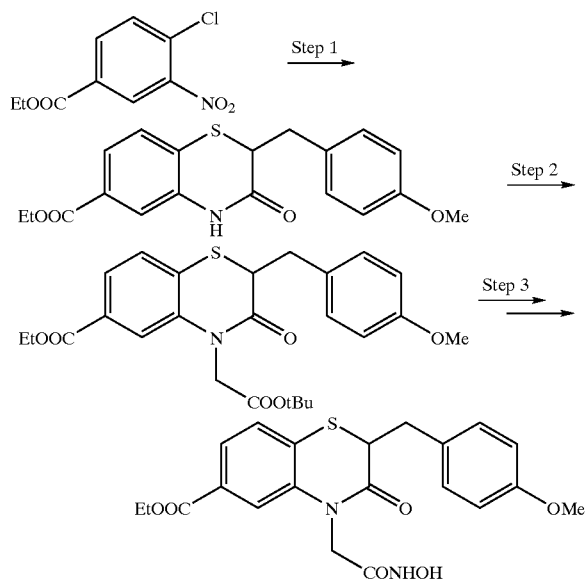

Step 1: Ethyl 2H-2-(4-Methoxybenzyl)-1,4-benzothiazin-3(4H)-one-6-carboxylate

Ethyl 4-chloro-3-nitrobenzoate (8 g) was dissolved in ethanol (100 mL) and potassium carbonate (9.67 g) was added. Ethanol (50 mL) solution of 3-(4-methoxyphenyl)-2-mercaptopropanoic acid (7.43 g) was added at 4° C., and potassium fluoride (2.0 g) was added. The reaction mixture was heated under reflux for 3 hrs, and concentrated under reduced pressure. 1N-hydrochloric acid was added and extracted with EtOAc. The organic layer was washed with brine, dried over MgSO$_4$ and concentrated under reduced pressure. The residue was dissolved in AcOH (100 mL), and added to the suspension of Fe (6.1 g) in AcOH (50 mL) at 60–70° C. The reaction mixture was filtered and precipitate was washed with AcOH. Filtrate was added to water, and precipitate was collected and washed with mixed solvent of THF and hexane to give 5.9 g of the product as white solid.

Step 2: t-Butyl 6-Ethoxycarboxyl-2H-2-(4-Methoxybenzyl)-1,4-benzothiazin-3(4H)-one-4-yl-acetate To sodium hydride (3.3 g) suspended in THF (30 mL) was added a solution of ethyl 2H-2-(4-methoxybenzyl)-1,4-benzothiazin-3(4H)-one-6-carboxylate (3 g) in THF (250 mL), and t-butyl bromoacetate (1.7 ml) was added dropwise at 0–5° C. The mixture was warmed to r.t. and left at r.t. overnight. Saturated aqueous ammonium chloride was added and extracted with EtOAc. The organic layer was washed with water and brine, and dried over MgSO$_4$ and concentrated under the reduced pressure. The residue was purified by silica gel column chromatography to give 3.9 g of the product as oil.

Step 3: 6-Carboxy-2H-2-(4-methoxybenzyl)-1,4-benzothiazin-3(4H)-one-4-yl-acetic Acid N-Hydroxyamide The product of Step 2 was converted to hydroxamic acid by the method described in example 777 (step 3).

The following compounds listed in the Tables 16 and 16' were prepared in a similar manner.

TABLE 16

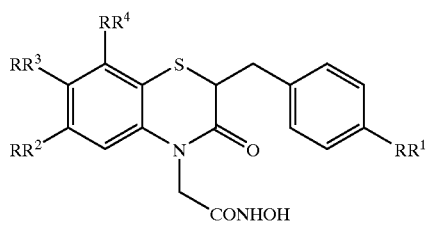

| Example No. | RR$^1$ | RR$^2$ | RR$^3$ | RR$^4$ | NMR: $^1$H-NMR(DMSO-d6; δ) |
|---|---|---|---|---|---|
| 798 | —OMe | —CO2Et | —H | —H | 1.32(3H, t, J=7.0Hz), 2.68(1H, dd, J=9.2, 14Hz), 3.11(1H, dd, J=5.9, 14Hz), 3.72(3H, s), 3.91(1H, m), 4.32(2H, q, J=7.0Hz), 4.55(1.6H, br-s), 4.70(0.2H, d, J=18Hz), 4.93(0.2H, d, J=18Hz), 6.83(2H, d, J=8.4Hz), 7.13(2H, d, J=8.4Hz), 7.51(1H, d, J=7.9Hz), 7.63(1H, dd, J=1.5, 7.9Hz), 7.66(1H, br-s), 9.06(0.8H, s), 9.46(0.2H, s), 10.42(0.2H, s), 10.86(0.8H, s) |
| 799 | —H | —H | —H | —CO2Et | 1.30(3H, t, J=7.2Hz), 2.69(1H, dd, J=8.4, 14Hz), 3.16(1H, dd, J=6.4, 14Hz), 3.74(1H, dd, J=6.4, 8.4Hz), 4.24–4.64(2H, m), 4.44(0.8H, d, J=16Hz), 4.52(0.8H, d, J=17Hz), 4.71(0.2H, d, |

TABLE 16-continued

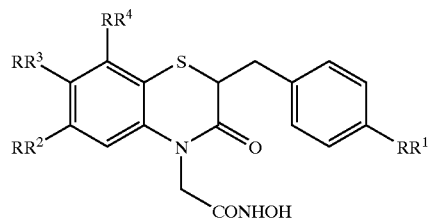

| Example No. | RR¹ | RR² | RR³ | RR⁴ | NMR: ¹H-NMR(DMSO-d6; δ) |
|---|---|---|---|---|---|
|  |  |  |  |  | J=17Hz), 4.87(0.2H, d, J=18Hz), 7.16–7.28(5H, m), 7.37–7.41(2H, m), 7.64(1H, m), 9.00 (0.8H, s), 9.38(0.2H, s), 10.35(0.2H, s), 10.80(0.8H, s) |
| 800 | —H | —CO2Et | —H | —H | 1.31(3H, t, J=7Hz), 2.71(1H, m), 3.18(1H, m), 3.97(1H, m), 4.31(2H, dd, J=7.14, 14.10Hz), 4.51(2H, m), 7.19–7.30(5H, m), 7.51(1H, d, J=8.07Hz), 7.62(1H, d, J=8.04Hz), 7.68(1H, s), 9.05(1H, br-s), 10.84(1H, s) |

TABLE 16'

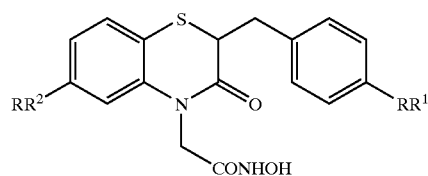

| Example No. | RR¹ | RR² | NMR: ¹H-NMR(DMSO-d6; δ) |
|---|---|---|---|
| 989 | —OH | —CO2Et | 1.32(3H, t, J=7.1Hz), 2.61(1H, dd, J=9.3Hz, 14Hz), 3.05(1H, dd, J=6.0 Hz, 14Hz), 3.86(1H, dd, J=6.0Hz, 9.3Hz), 4.32(2H, q, J=7.1Hz), 4.50 (1.6H, br-s), 4.69(0.2H, d, J=19Hz), 4.93(0.2H, d, J=19Hz), 6.65(2H, d, J=8.4Hz), 6.99(2H, d, J=8.4Hz), 7.52(1H, d, J=8.1Hz), 7.63(1H, dd, 1.6Hz, 8.1Hz), 7.69(1H, d, J=1.6Hz), 9.05(0.8H, s), 9.26(1H, s), 9.45 (0.2H, s), 10.41(0.2H, s), 10.85(0.8H, s) |
| 990 | —Cl | —C(CH3)2—COOEt | 1.12(3H, t, J=7.2Hz), 1.48(6H, s), 2.74(1H, m), 3.18(1H, dd, m), 3.90(1H, m), 4.06(2H, q, J=7.2Hz), 4.38–4.90(2H, m), 6.83–7.15(2H, m), 7.26 (2H, d, J=8.4Hz), 7.32(3H, m), 9.02, 9.42(1H, bs), 10.37, 10.81(1H, bs) |
| 991 | —OCF3 | —CO2Et | 1.32(3H, t, J=7.0Hz), 2.81(1H, dd, J=8.8Hz, 14Hz), 3.19(1H, dd, J=6.2 Hz, 14Hz), 4.04(1H, dd, J=6.2Hz, 8.8Hz), 4.32(2H, q, J=7.0Hz), 4.49 (0.8H, d, J=17Hz), 4.55(0.8H, d, J=17Hz), 4.70(0.2H, d, J=18Hz), 4.94 (0.2H, d, J=18Hz), 7.25(2H, d, J=8.0Hz), 7.36(2H, d, J=8.0Hz), 7.53 (1H, d, J=8.1Hz), 7.63(1H, dd, 1.3Hz, 8.1Hz), 7.69(1H, br-s), 9.06(0.8H, s), 9.46(0.2H, s), 10.44(0.2H, s), 10.87(0.8H, s) |
| 992 | —OMe | —COO-iPr | 1.31(6H, t, J=6.2Hz), 2.66(1H, dd, J=9.2Hz, 14Hz), 3.08(1H, dd, J=5.9 Hz, 14Hz), 3.71(3H, s), 3.90(1H, dd, J=5.9Hz, 9.2Hz), 4.48(0.8H, d, J=17 Hz), 4.53(0.8H, d, J=17Hz), 4.68(0.2H, d, J=18Hz), 4.96(0.2H, d, J=18 Hz), 5.11(1H, m), 6.82(2H, d, J=8.6Hz), 7.11(2H, d, J=8.6Hz), 7.50(1H, d, J=8.1Hz), 7.60(1H, dd, 1.5Hz, 8.1Hz), 7.66(1H, d, J=1.5Hz), 9.04(0.8H, s), 9.45(0.2H, s), 10.41(0.2H, s), 10.85(0.8H, s) |
| 993 | —OMe | ![structure] | 1.20–1.45(6H, m), 1.58(3H, d, J=5.3Hz), 1.58–1.68(2H, m), 1.75–1.88(2H, m), 2.67(1H, m), 3.12(1H, m), 3.72(3H, s), 3.92(1H, m), 4.51–4.80(2.8H, m), 4.95(0.2H, d, J=18Hz), 6.75–6.89(3H, m), 7.12(2H, d, J=8.2Hz), 7.53(1H, m), 7.61(1H, m), 7.73(1H, nr-s), 9.06(0.8H, s), 9.46(0.2H, s), 10.41(0.2H, s), 10.86(0.8H, s) |

Example 801

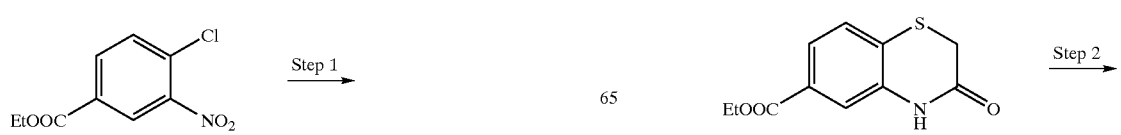

-continued

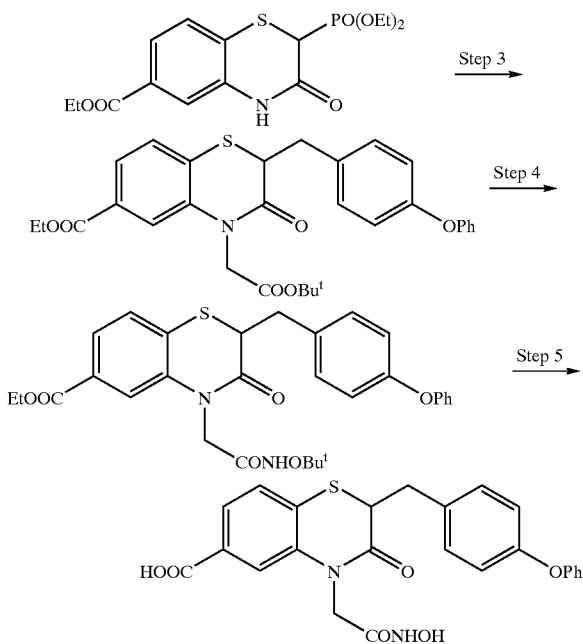

Step 1: 6-Ethoxycarbonyl-2H-1,4-benzothiazin-3(4H)-one

To a mixture of thioglycolic acid (10.75 g) and $K_2CO_3$ (65.00 g) in DMF (300 mL), a solution of ethyl 4-chloro-3-nitrobenzoate (28.12 g) in DMF (100 ml) was added and heated at 80° C. The mixture was stirred at 80° C. for 6 hrs. The solid of $K_2CO_3$ was filtered off, and the filtrate was concentrated under reduced pressure. To the residue, diethyl ether (50 mL) and water (100 mL) was added and the yellow solid product was collected by filtration. The product was acidified with 4N HCl and extracted with ethyl acetate. The organic layer was dried over $Na_2SO_4$ and concentrated. The product (27.634 g, 83%) was used in the following step.

To a solution of the product (12.956 g) in THF (300 mL), 10% Pd/C (13.00 g) was added. The reaction mixture was vigorously stirred at r.t. for 9 hrs under $H_2$. The catalyst was removed by filtration, and the filtrate was concentrated under reduced pressure. To a solution of the crude product (9.345 g) and HOBt (5.88 g) in DMF (200 mL), EDC.HCl (7.37 g) was added. The reaction mixture was stirred at r.t. overnight. The solvent was removed under reduced pressure. The residue was dissolved in ethyl acetate and washed with 1N HCl, 5% $Na_2CO_3$ aq., and brine. The organic layer was dried over $Na_2SO_4$ and concentrated. The residue was purified by recrystallization from diethyl ether and hexane to give the product (8.502 g, 79% in 2 steps) as a white solid.

Step 2: 6-Ethoxycarbonyl-2H-2-diethylphosphoryl-1,4-benzothiazin-3(4H)-one

To a solution of the 6-ethoxycarbonyl-2H-1,4-benzothiazin-3(4H)-one (8.432 g) in dichloromethane (80 mL), sulfuryl chloride (4.79 g) was added dropwise. The reaction mixture was stirred at r.t. for 6 hours. The solvent was removed under reduced pressure. The residue was purified by recrystallization from chloroform and hexane to give the product (8.80 g, 91%) as a white solid.

A mixture of 6-ethoxycarbonyl-2H-2-chloro-1,4-benzothiazin-3(4H)-one (8.724 g) and triethyl phosphate (11.74 g) was heated at 120° C. and stirred for 10 hrs. The solvent was removed under reduced pressure. The residue was purified by recrystallization from THF and diethyl ether to give the product (10.534 g, 88%) as a pale yellow solid.

Step 3: t-Butyl 6-Ethoxycarbonyl-2H-2-(4-phenoxybenzyl)-1,4-benzothiazin-3(4H)-one-4-ylacetate To a stirred solution of p-phenoxybenzaldehyde (796 mg) and 6-ethoxycarbonyl 2H-2-diethylphosphoryl-1,4-benzothiazine-3(4H)-one (1.00 g) in 80% ethanol aq. (10 mL) and THF (10 mL), a solution of sodium ethoxide (400 mg) in ethanol (5 mL) was added dropwise. The reaction mixture was stirred at r.t. overnight. The solvent was removed under reduced pressure. To the residue, ethyl acetate (5 ml) and water (10 ml) was added and the solid product was collected by filtration. After drying under reduced pressure, the product (980 mg, 88%) was given as a yellow solid.

To a solution of 6-ethoxycarbonyl-2H-2-(4-phenoxybenzylidene)-1,4-benzothiazin-3(4H)-one (980 mg) was dissolved in methanol (40 mL) and THF (40 mL), 10% Pd/C (1.00 g) was added. The reaction mixture was vigorously stirred at r.t. for 4 hrs under $H_2$. The catalyst was removed by filtration, and the filtrate was concentrated under reduced pressure. The product (936 mg, 95%) was used in the following step without purification.

To a solution of 6-ethoxycarbonyl-2H-2-(4-phenoxybenzyl)-1,4-benzothiazin-3(4H)-one (925 mg) in DMF (15 mL), potassium t-butoxide (495 mg) was added at r.t. After 20 minutes' stirring, t-buthyl bromoacetate (645 mg) was slowly added. The reaction mixture was stirred at r.t. overnight. The solvent was removed under reduced pressure and the residue was dissolved in ethyl acetate and washed with water. The organic layer was dried over $Na_2SO_4$ and concentrated. The residue was purified with silica gel column chromatography (eluent: toluene/ethyl acetate, 30/1) to give the product (677 mg, 58%).

Step 4: 6-Ethoxycarbonyl-2H-2-(4-phenoxybenzyl)-1,4-benzothiazin-3(4H)-one-4-ylacetic Acid N-t-Butoxyamide t-Butyl 6-ethoxycarbonyl-2H-2-(4-phenoxybenzyl)-1,4-benzothiazin-3(4H)-one-4-ylacetate (677 mg) was dissolved in TFA (10 mL). The mixture was stirred r.t. for 2 hrs. The solvent was removed under reduced pressure. The residue was purified with silica gel column chromatography (eluent: chloroform/methanol, 10/1) to give the product (428 mg, 71%).

Isobutyl chloroformate (133 mg) was added dropwise to a THF (10 ml) solution of 6-ethoxycarbonyl-2H-2(Z)-(4-phethoxybenzylidene)-1,4-benzothiazin-3(4H)-one-4-ylacetic acid (422 mg) and N-methylmorpholine (98 mg) at −5° C. A solution of O-t-butyl-hydoxylamine hydrochloride (133 mg) and N-methylmorpholine (107 mg) in THF (2 mL) was added dropwise after additional 20 minutes' stirring. The mixture was warmed to r.t. with stirring, and stood overnight. The reaction mixture was concentrated under reduced pressure, acidified with 0.5N citric acid, and extracted with ethyl acetate. The organic layer was dried over $Na_2SO_4$ and concentrated under reduced pressure. The residue was purified with silica gel column chromatography (eluent: chloroform/methanol, 5/1) to give the product (260 mg, 54%).

Step 5: 6-Carboxy-2H-2-(4-phenoxybenzyl)-1,4-benzothiazin-3(4H)-one-4-ylacetic Acid N-Hydroxyamide To a solution of 6-ethoxycarbonyl-2-2-(4-phenoxybenzyl)-1,4-benzothiazin-3(4H)-one-4-ylacetic acid N-t-butoxyamide (256 mg) in ethanol (5 mL) and THF (5 mL), 1N NaOH (560 uL) was slowly added at 0° C. After 30 minutes' stirring, the mixture was warmed to room temperature and left overnight. The reaction mixture was concentrated under reduced pressure and acidified with 1N citric acid, and the product was extracted with ethyl acetate. The organic layer was dried over $Na_2SO_4$ and concentrated. The crude product (241 mg) was used in the following step without purification.

6-Carboxy-2H-2-(4-phenoxybenzyl)-1,4-benzothiazin-3(4H)-one-4-ylacetic acid N-t-butoxyamide (124 mg) was dissolved in TFA (10 mL). The mixture was stirred at r.t. for 2 days. The solvent was removed under reduced pressure. The residue was purified by preparative thin layer chromatography on silica gel (eluent: chloroform/methanol, 5/1) to give the hydroxamic acid (99 mg, 46% in 2 steps).

The following compounds listed in the Tables 17, 17', and 17" were prepared in a similar manner.

TABLE 17

| Example No. | RR$^1$ | NMR: $^1$H-NMR(DMSO-d6; δ) |
|---|---|---|
| 801 | —OPh | 2.75(1H, m), 3.16(1H, m), 3.96(1H, m), 4.51(2H, m), 6.90(2H, d, J=8.25 Hz), 6.99(2H, d, J=8.61Hz), 7.15 (1H, m), 7.24(2H, d, J=8.43Hz), 7.36–7.42(2H, m), 7.49(1H, d, 8.04 Hz), 7.60–7.66(2H, m), 9.06(1H, br-s), 10.84(1H, s) |
| 802 | —O-Pentyl | 0.89(3H, t, J=7Hz), 1.36(4H, m), 1.68 (2H, m), 2.68(1H, m), 3.13(1H, m), 3.90–3.94(3H, m), 4.51(2H, m), 6.82 (2H, d, J=8.43Hz), 7.11(2H, d, J= 8.40Hz), 7.49(1H, d, J=8.04Hz), 7.61 (1H, d, J=8.04Hz), 7.66(1H, s), 9.05 (1H, s), 10.83(1H, s) |
| 803 | —F | 2.77(1H, m), 3.17(1H, m), 4.00(1H, m), 4.51(2H, m), 7.10(2H, t, J=8.79 Hz), 7.27(2H, m), 7.50(1H, d, J=8.07 Hz), 7.62(1H, d, J=8.07Hz), 7.67(1H, s), 9.05(1H, s), 10.84(1H, s) |

TABLE 17'

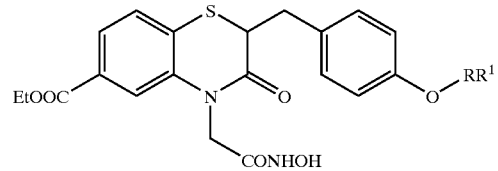

| Example No. | RR$^1$ | NMR: $^1$H-NMR(CDCl3; δ) |
|---|---|---|
| 994 | —C6H3-3,4-methylenedioxy | 1.41(t, J=7.2Hz, 3H), 2.81(m, 1H), 3.14(m, 1H), 3.70(m, 1H), 4.40(q, J=7.2Hz, 2H) 4.48(d, J=16Hz, 1H), 4.73(d, J=16Hz, 1H), 5.97(s, 2H), 6.49(dd, J=2.4, 8.4Hz, 1H), 6.57(d, J=2.4Hz, 1H), 6.76(d, J=8.4Hz, 1H), 6.88(m, 2H), 7.05(m, 2H), 7.44(d, J=8.0Hz, 1H), 7.78(m, 1H), 8.10(m, 1H), 9.00 br, 1H) |
| 995 | —C6H4-3-F | 1.41(t, J=6.9Hz, 3H), 2.84(m, 1H), 3.18(m, 1H), 3.73(m, 1H), 4.40(q, J=6.9Hz, 2H) 4.50(d, J=15.6 Hz, 1H), 4.73(d, J=15.6Hz, 1H), 6.70(m, 1H), 6.76–6.82(m, 2H), 6.96(m, 2H), 7.11(m, 2H), 7.28(m, 1H), 7.45(d, J=8.0Hz, 1H), 7.78(m, 1H), 8.09(br, 1H), 9.10(br, 1H) |
| 996 | —C6H4-3-OMe | 1.41(t, J=7.2Hz, 3H), 2.81(m, 1H), 3.18(m, 1H), 3.71(m, 1H), 3.78(s, 3H), 4.39(q, J=7.2Hz, 2H) 4.51 (d, J=16Hz, 1H), 4.72(d, J=16Hz, 1H), 6.56–6.60(m, 2H), 6.65(m, 1H), 6.94(m, 2H), 7.08(m, 2H), 7.22(m, 1H), 7.43(d, J=8.0Hz, 1H), 7.49(br, 1H), 7.76(d, J=8.0Hz, 1H), 8.06(br, 1H), 9.15(br, 1H) |
| 997 | —C6H4-4-SO2Me | 1.41(t, J=7.2Hz, 3H), 2.88(m, 1H), 3.06(m, 3H), 3.20(m, 1H), 3.75(m, 1H), 4.40(q, J=7.2Hz, 2H) 4.50 (d, J=16Hz, 1H), 4.74(d, J=16Hz, 1H), 7.00(m, 2H), 7.08(m, 1H), 7.18(m, 2H), 7.45(d, J=8.0Hz, 1H), 7.78(d, J=8.0Hz, 1H), 7.89(m, 2H) 8.09(m, 1H), 9.03(br, 1H) |

TABLE 17"

| Example No. | RR¹ | NMR: ¹H-NMR(DMSO-d6; δ) |
|---|---|---|
| 998 | —O-4-pyridyl | 2.82(1H, dd, J=14.2, 8.8Hz, benzylic C—H), 3.22(1H, dd, J=14.2, 6.1Hz, another benzylic C—H), 4.02(1H, dd, J=8.8, 6.1Hz, H—C—S), 4.52(2H, s, CH2CO), 6.88 & 8.45(2H+2H, dd, J= 4.7, 1.5, 3,5- & 2.6-H's of pyridine), 7.08 & 7.34(2H+2H, d, J=8.5), 7.51(1H, d, J=8.0), 7.63(1H, dd, J=8.0, 1.4) 7.68(1H, d, J=1.4), 9.06 & 10.86(1H+1H, s, NH—OH), 13.2(1H, br s, CO2H) |
| 999 | —O—C6H3-3,4-methylenedioxy | 2.72(m, 1H), 3.14(m, 1H), 3.95(m, 1H), 4.51+4.69+4.92(2H, NCH2CO), 6.03(s, 2H), 6.47(dd, J=2.4, 8.2Hz, 1H), 6.71(d, J=2.4Hz, 1H), 6.83(m, 2H), 6.91(d, J=8.2Hz, 1H), 7.20(m, 2H), 7.49 (d, J=8.0Hz, 1H), 7.61(dd, J=1.6, 8.0Hz, 1H), 7.65(d, J=1.6Hz, 1H), 9.05+9.45(s, 1H), 10.40+10.84(s, 1H) 13.14(br, 1H) |
| 1000 | —O—C6H4-3-CF3 | 2.78(m, 1H), 3.19(m, 1H), 4.00(m, 1H), 4.52+4.71+4.92(2H, NCH2CO), 7.05(m, 2H), 7.23–7.33 (m, 4H), 7.43–7.53(m, 2H), 7.59–7.64(m, 2H), 7.67(m, 1H), 9.05+9.46(s, 1H), 10.41+10.85 (s, 1H), 13.17(br, 1H) |
| 1001 | —O—C6H4-3-F | 2.77(m, 1H), 3.18(m, 1H), 3.99(m, 1H), 4.15+4.70+4.92(2H, NCH2CO), 6.79(m, 1H), 6.84(m, 1H), 6.94–7.01(m, 3H), 7.27(m, 2H), 7.41(m, 1H), 7.51(d, J=8.0Hz, 1H), 7.62(dd, J=1.6, 8.0Hz, 1H), 7.66(d, J=1.6Hz, 1H), 9.05+9.46(s, 1H), 10.41+10.84(s, 1H), 13.14(br, 1H) |
| 1002 | —SO2—C6H4-4-OMe | 2.84(m, 1H), 3.23(m, 1H), 3.82(s, 3H), 4.06(m, 1H), 4.49+4.78+4.90(2H, NCH2CO), 7.10–7.14 (m, 2H), 7.46–7.51(m, 3H), 7.59(m, 1H), 7.66(m, 1H), 7.81–7.90(m, 4H), 9.06+9.46(s, 1H), 10.42+10.84(s, 1H), 13.10(br, 1H) |
| 1003 | —O—C6H4-3-OMe | 2.75(m, 1H), 3.16(m, 1H), 3,74(s, 3H), 3.98(m, 1H), 4.52+4.70+4.92(2H, NCH2CO), 6.52(m, 1H), 6.57(m, 1H), 6.72(m, 1H), 6.92(m, 2H), 7.22–7.31(m, 3H), 7.51(d, J=8Hz, 1H), 7.62(dd, J=4.8Hz, 1H), 7.66(m, 1H), 9.05+9.45(s, 1H), 10.41+10.85(s, 1H), 13.18(br, 1H) |
| 1004 | —O—C6H4-4-SO2Me | 2.81(m, 1H), 3.19(S, 3H), 3.40(m, 1H), 4.02(m, 1H), 4.52+4.73+4.95(2H, NCH2CO), 7.06(m, 2H), 7.13(m, 2H), 7.33(m, 2H), 7.51(d, J=8Hz, 1H), 7.62(dd, J=1.6, 8Hz, 1H), 7.67(d, J=1.6 Hz, 1H), 7.91(m, 2H), 9.05+9.46(s, 1H), 10.41+10.85(s, 1H), 13.19(br, 1H) |

Example 804

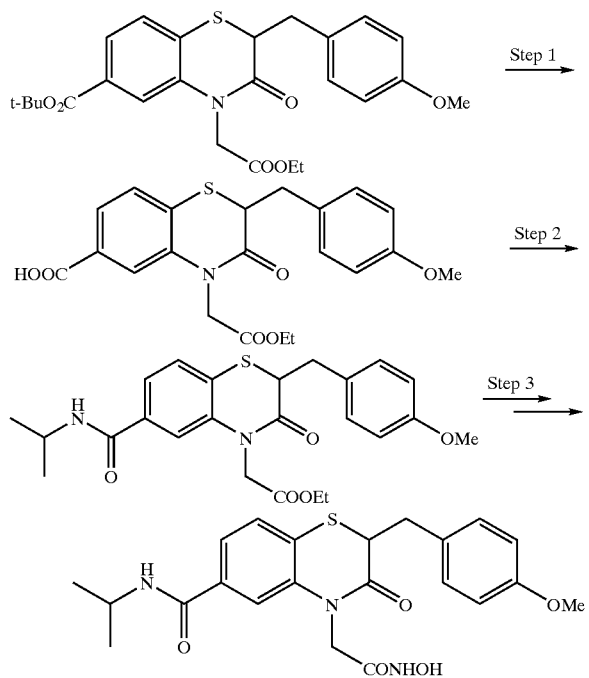

Step 1: Ethyl 6-Carboxy-2H-2-(4-methoxybenzyl)-1,4-benzothiazin-3(4H)-one-4-ylacetate Ethyl 6-t-butoxycarbonyl-2H-2-(4-methoxybenzyl)-1,4-benzothiazin-3(4H)-one-4-ylacetate (32.9 g) was dissolved in 5%-ethanedithiol in TFA (100 mL) and stood at r.t. for 1.5 hrs. Toluene (100 mL) was added and concentrated under reduced pressure. The residue was washed with mixed solvent of ether and hexane to give 30.2 g of ethyl 6-carboxy-2H-2-(4-methoxybenzyl)-1,4-benzothiazin-3 (4H)-one-4-ylacetate as pale yellow solid.

Step 2: Ethyl 6-Isopropylcarbamoyl-2H-2-(4-methozybenzyl)-1,4-benzothiazin-3(4H)-one-4-ylacetate Ethyl 6-carboxyl-2H-2-(4-methoxybenzyl)-1,4-benzothiazin-3(4H)-ylacete (2 g) was dissolved in dichloromethane (20 mL), and oxalyl chloride (1.22 g) was added at 4° C. 1 drop of DMF was added and warmed to r.t., and stirred for 3 hrs. Toluene (20 mL) was added and concentrated under reduced pressure. This acid chloride was dissolved in dichloromethane (15 mL), and added to dichloromethane (10 mL) solution of diisopropylamine (299 mg) and triethylamine (511 mg) at 4° C. The reaction mixture was stirred for 4 hrs at r.t., diluted with 5% KHSO₄ aq., and extracted with ethyl acetate. The organic layer was washed with sat. NaHCO₃ aq. and brine, and dried over MgSO₄ The solution was concentrated under reduced pressure. The residue was purified by silica gel column chromatography to give 1.47 g of ethyl 6-isopropylcarbamoyl-2H-2-(4-methoxy-benzyl)-1,4-benzothiazin-3(4H)-one-4-ylacetate as pale yellow oil.

Step 3: 6-Isopropylcarbamoyl-2H-2-(4-methoxybenzyl)-1,4-benzothiazin-3(4H)-one-4-ylacetic Acid N-Hydroxyamide The product of Step 2 was converted to hydroxamic acid by the method described in example 777 (step 3).

The following compounds listed in the Table 18 were prepared in a similar manner.

TABLE 18

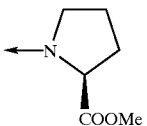

| Example No. | RR¹ | RR² | NMR: ¹H-NMR(DMSO-d6; δ) |
|---|---|---|---|
| 804 | —OMe | —NHiPr | 1.17(6H, d, J=6.6Hz), 2.85(1H, dd, J=9.4, 14Hz), 3.10(1H, dd, J=6.1, 14Hz), 3.73(3H, s), 3.85(1H, dd, J=6.1, 9.4Hz), 4.09(1H, m), 4.53(1.6H, br-s), 4.70(0.2H, d, J=18Hz), 4.93(0.2H, d, J=18Hz), 6.83(2H, d, J=8.6Hz), 7.12(2H, d, J=8.3Hz), 7.44(1H, d, J=8.1Hz), 7.53–7.56 (2H, m), 8.27(1H, d, J=7.7Hz), 9.02(0.8H, s), 9.44(0.2H, s), 10.34(0.2H, s), 10.80(0.8H, s) |
| 805 | —H | 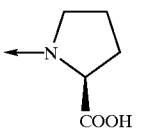 (N-pyrrolidine-COOMe) | 1.88(3H, m), 2.27(1H, m), 2.74(1H, m), 3.19(1H, m), 3.56(2H, m), 3.67(3H, s) 3.94(1H, m), 4.49(3H, m), 7.24–7.29(7H, m), 7.46(1H, d, J=8.04Hz), 9.04(1H, s), 10.82(1H, s) |
| 806 | —H | (N-pyrrolidine-COOH) | 1.91(3H, m), 2.26(1H, m), 2.74(1H, m), 3.21(1H, m), 3.53(2H, m), 3.94(1H, m), 4.39(1H, m), 4.50(2H, m) 7.23–7.28(7H, m), 7.45(1H, d, J=7.68Hz), 9.00(1H, br-s), 10.81(1H, s) |
| 807 | —H | -Piperadino-4-COO-tBu | 1.41(9H, s), 2.74(1H, m), 3.23(1H, m), 3.31–3.39(8H, m), 3.94(1H, m), 4.51(2H, m), 7.09–7.29(7H, m), 7.44(1H, d, J=8.04Hz), 9.02(1H, s), 10.79(1H, s) |
| 808 | —H | -Piperadino | 2.74(1H, m), 3.15–3.26(5H, m), 3.68(4H, m), 3.94(1H, m), 4.53(2H, m), 7.14–7.29(7H, m), 7.46(1H, d, J=7.86Hz), 9.03(1H, s), 10.87(1H, s) |
| 809 | —H | —NH2 | 2.66(1H, dd, J=9.5, 14Hz), 3.14(1H, dd, J=5.7, 14Hz), 3.88(1H, dd, J=5.7, 9.5Hz), 4.48 (1.6H, br-s), 4.68(0.2H, d, J=18Hz), 4.87(0.2H, d, J=18Hz), 7.14–7.25(5H, m), 7.25–7.41 (2H, m), 7.50(1H, d, J=7.9Hz), 7.56(1H, br-s), 8.00(1H, br-s), 8.06(0.8H, s), 9.37(0.2H, s), 10.29(0.2H, s), 10.72(0.8H, s) |
| 810 | —OMe | —NH2 | 2.63(1H, dd, J=9.3, 14Hz), 3.12(1H, dd, J=5.9, 14Hz), 3.72(3H, s), 3.86(1H, dd, J=5.9, 9.3Hz), 4.53(1.4H, br-s), 4.72(0.3H, d, J=17Hz), 4.93(0.3H, d, J=17Hz), 6.84(2H, d, J=8.6 Hz), 7.12(2H, d, J=8.6Hz), 7.42–7.45(2H, m), 7.54–7.81(2H, m), 8.05(1H, br-s), 9.01(0.7H, s), 9.42(0.3H, s), 10.34(0.3H, s), 10.78(0.7H, s) |
| 811 | —H | —NH—(S)—CH(Me)COOH | 1.40(3H, d, J=7.3Hz), 2.70(1H, m), 3.18(1H, m), 3.93(1H, m), 4.41(1H, m), 4.52(0.8H, d, J=18Hz), 4.57(0.8H, d, J=18Hz), 4.73(0.2H, dd, J=18Hz), 4.94(0.2H, dd, J=18Hz), 7.20–7.25 (3H, m), 7.25–7.31(2H, m), 7.46–7.64(3H, m), 8.76(1H, dd, J=1.8, 7.3Hz), 9.04(0.8H, s), 9.45(0.2H, s), 10.36(0.2H, s), 10.80(0.8H, s), 12.6(1H, s) |
| 812 | —OMe | —(S)—NHCH(Me)COO-t-Bu | 1.38(3H, d, J=8.1Hz), 1.42(9H, s), 2.61(1H, m), 3.10(1H, m), 3.72(3H, s), 3.87(1H, dd, J=6.2, 9.2Hz), 4.34(1H, m), 4.53(1.6H, br-s), 4.69(0.2H, m), 4.94(0.2H, d, J=18Hz), 6.84 (2H, d, J=8.3Hz), 7.12(2H, d, J=8.3Hz), 7.43–7.59(3H, m), 8.73(1H, d, J=6.4Hz), 9.02 (0.8H, s), 9.44(0.2H, s), 10.34(0.2H, s), 10.79(0.8H, s) |
| 813 | —OMe | —NH—(S)—CH(Me)COOH | 1.40(3H, d, J=7.3Hz), 2.58–2.69(1H, m), 3.04–3.14(1H, m), 3.72(3H, s), 3.87(1H, dd, J=6.1, 9.1Hz), 4.41(1H, m), 4.53(1.6H, br-s), 4.69(0.2H, dd, J=13, 18Hz), 4.94(0.2H, dd, J=13.18 Hz), 6.84(2H, d, J=8.6Hz), 7.12(2H, d, J=8.6Hz), 7.45–7.60(3H, m), 8.74(1H, d, J=7.1 Hz), 9.03(0.8H, s), 9.44(0.2H, s), 10.36(0.2H, s), 10.80(0.8H, s), 12.58(1H, s) |
| 814 | —OMe | —NH-cyclopentyl | 1.53(4H, br-s), 1.70(2H, br-s), 1.89(2H, br-s), 2.65(1H, dd, J=9.4, 14Hz), 3.10(1H, dd, J=5.9, 14Hz), 3.73(3H, s), 3.85(1H, dd, J=5.9, 9.4Hz), 4.21(1H, m), 4.53(1.6H, br-s), 4.71(0.2H, d, J=18Hz), 4.94(0.2H, d, J=18Hz), 6.84(2H, d, J=8.4Hz), 7.12(2H, d, J=8.4Hz), 7.40–7.55 (3H, m), 8.33(1H, d, J=7.3Hz), 9.03(0.8H, s), 9.46(0.2H, s), 10.36(0.2H, s), 10.81(0.8H, s) |
| 815 | —OMe | —NH-cyclopropyl | 0.53–0.59(2H, m), 0.680.74(2H, m), 2.65(1H, dd, J=9.4, 14Hz), 2.71(1H, m), 3.10(1H, dd, J=5.7, 14Hz), 3.72(3H, s), 3.86(1H, dd, J=5.7, 9.4Hz), 4.52(1.6H, br-s), 4.71(0.2H, d, J=17Hz), 4.92(0.2H, d, J=17Hz), 6.83(2H, d, J=8.6Hz), 7.12(2H, d, J=8.6Hz), 7.40–7.54(3H, m), 8.50(1H, d, J=3.9Hz), 9.02(0.8H, s), 9.45(0.2H, s), 10.36(0.2H, s), 10.79(0.8H, s) |
| 804 | —H | —NHEt | 1.12(3H, t, J=7.14Hz), 2.71(1H, m), 3.15–3.33(3H, m), 3.93(1H, m), 4.53(2H, m), 7.20–7.31 (5H, m), 7.44–7.58(3H, m), 8.55(1H, m), 9.03(1H, s), 10.80(1H, s) |
| 817 | —OMe | —NHC(Me)2CH2OH | 1.31(6H, s), 2.65(1H, dd, J=9.4.14Hz), 3.09(1H, dd, J=5.7, 14Hz), 3.73(3H, s), 3.74–3.90 (3H, m), 4.53(1.4H, br-s), 4.67(0.3H, d, J=18Hz), 4.91(0.3H, d, J=18Hz), 6.84(2H, d, J=8.6 Hz), 7.11(2H, d, J=8.6Hz), 7.43(1H, d, J=8.4Hz), 7.53(1H, d, J=8.4Hz), 7.61(1H, br-s), 9.03 (0.7H, s), 9.45(0.3H, s), 10.36(0.3H, s), 10.81(0.7H, s) |
| 818 | —OMe | —(S)—NHCH(iPr)CH2OH | 0.87–0.96(6H, m), 1.57(1H, m), 2.65(1H, m), 3.08(1H, m), 3.52(2H, br-s), 3.72(3H, s), 3.81 (1H, m), 4.54(1.6H, br-s), 4.74(0.2H, dd, J=6.8.18Hz), 4.95(0.2H, dd, J=12.18Hz), 8.84 (2H, d, J=7.8Hz), 6.87(1H, s), 7.13(2H, m), 7.45(1H, d, J=7.7Hz), 7.59(1H, br-s), 7.60 (1H, d, J=8.4Hz), 8.07(1H, d, J=8.1Hz), 9.03(0.8H, s), 9.49(0.2H, s), 10.37(0.2H, s), 10.81(0.8H, s) |
| 819 | —OMe | —NHMe | 2.64(1H, dd, J=9, 14Hz), 2.77(3H, d, J=4.4Hz), 3.09(1H, dd, J=5.8.14Hz), 3.71(3H, s), 3.86 (1H, dd, J=5.8, 9Hz), 4.50–4.93(2H, m), 6.82(2H, d, J=8.6Hz), 7.11(2H, d, J=8.6Hz), 7.46(2H, m), 7.55(1H, s), 8.50(1H, m), 9.44, 9.01(1H, bs), 10.78, 10.34(1H, bs). |

TABLE 18-continued

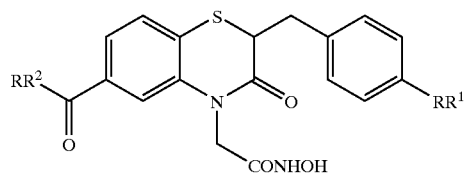

| Example No. | RR¹ | RR² | NMR: ¹H-NMR(DMSO-d6; δ) |
|---|---|---|---|
| 820 | —Cl | —NH-cyclopropyl | 0.51–0.56(2H, m), 0.66–0.73(2H, m), 2.72(1H, dd, J=14.3Hz, 9.3Hz), 2.76–2.84(1H, m), 3.12 (1H, dd, J=14.4Hz, 6.4Hz), 3.93(1H, dd, J=8.9Hz, 6.4Hz), [4.50(S), 4.62(d, J=17.7Hz), 4.84 (d, J=17.7Hz)] 2H, 7.23(2H, d, J=8.4Hz), 7.32(2H, d, J=8.4Hz), 7.43(1H, d, J=8.1Hz), 7.48(1H, dd, J=8.2Hz, 1.8Hz), 7.53(1H, d, J=1.8Hz.), 8.49(1H, d, J=4.1Hz), [9.01(br), 9.43(s)] 1H,(10.78(br), [10.35(s)] 1H. |
| 821 | —Cl | —NHCH2-2-furyl | 2.73(1H, dd, J=14.4, 8.8Hz), 3.14(1H, dd, J=14.3Hz, 6.6Hz), 3.94(1H, dd, J=8.9Hz, 6.4Hz), 4.46(2H, d, J=5.4Hz), [4.51(S), 4.72(d, J=17.9Hz), 4.95(d, J=17.9Hz)] 2H, 6.27(1H, dd, J=3.1Hz, 0.5Hz), 6.39(1H, dd, J=3.1Hz, 1.8Hz), 7.23(2H, d, J=8.4Hz), 7.32(2H, d, J=8.4 Hz), 7.45(1H, d, J=7.9Hz), 7.55(1H, dd, J=8.9Hz, 1.5Hz), 7.57(1H, d, J=1.8Hz) 7.60(1H, m), [9.01(br), 9.42(s)] 1H, 9.04(1H, t, J=5.4Hz), [10.78(br), 10.35(s)] 1H. |
| 822 | —Cl | —NHCH2CF3 | 2.74(dd, J=14.4, 9.1Hz, 1H), 3.12(dd, J=14.3Hz, 6.6Hz, 1H), 3.96(dd, J=8.9Hz, 6.4Hz, 1H), 4.10(dd, J=10.5Hz, 6.4Hz, 2H), [4.52(S), 4.72(d, J=17.9Hz), 4.95(d, J=17.9Hz)] 2H, 7.23 (d, J=8.4Hz, 2H), 7.32(d, J=8.2Hz, 2H), 7.49(d, J=8.0Hz, 1H), 7.57(dd, J=8.0Hz, 1.0Hz, 1H), 7.63(d, J=1.0Hz, 1H), [9.01(br), 9.44(s)] 1H, 9.15(t, J=6.4Hz, 1H), [10.79(br), 10.36(s)] 1H. |
| 823 | —Cl | —NH(CH2)2OH | 2.72(dd, J=14.1, 9.1Hz, 1H), 3.12(dd, J=13.9Hz, 6.2Hz, 1H), 3.46–3.50(m, 2H), 3.28–3.32 (m, 2H), 3.94(dd, J=8.7Hz, 6.2Hz, 1H), [4.51(s), 4,72(d, J=17.9Hz), 4.95(d, J=17.9Hz)] 2H, 4.88(br, 1H), 7.28(d, J=8.4Hz, 2H), 7.32(d, J=8.4Hz, 2H), 7.44(d, J=8.0Hz, 1H), 7.53(dd, J=8.0Hz, 1.4Hz, 1H), 7.58(d, J=1.0Hz, 1H), 8.54(t, J=5.6Hz, 1H), [9.00(br), 9.42(s)]1H, [10.78 (br), 10.34(s)] 1H. |
| 824 | —Cl | —NH2 | 2.73(dd, J=13.9, 8.9Hz, 1H), 3.13(dd, J-14.1Hz, 6.1Hz, 1H), 3.94(dd, J=8.9Hz, 6.2Hz, 1H),(4.51(S), 4.72(d, J=17.9Hz), 4.90(d, J=17.9Hz)) 2H, 7.23(d, J=8.4Hz, 2H), 7.32(d, J=8.4Hz, 2H), 7.44(d, J=8.0Hz, 1H), 7.54(dd, J=8.0Hz, 1.5Hz, 1H), 7.59(d, J=1.0Hz, 1H), 8.04(br, 2H), [8.99(br), 9.41(s)] 1H, [10.76(br), 10.34(s)] 1H. |
| 825 | —Cl | —NH(CH2)2NEt2 | 1.21(t, J=7.1Hz, 6H), 2.74(dd, J=14.1, 9.1Hz, 1H), 3.13(dd, J=14.6Hz, 6.7Hz, 1H), 3.17–3.27 (m, 6H), 3.50–3.70(m, 2H), 3.97(dd, J=8.7Hz, 6.4Hz, 1H), [4.51(S), 4.69(d, J=17.3Hz), 4.93 (d, J-17.3Hz)] 2H, 7.24(d, J=8.4Hz, 2H), 7.34(d, J=8.3Hz, 2H), 7.51(d, J=8.0Hz, 1H), 7.55(d, J=8.0Hz, 1H), 7.61(s, 1H), 8.84(t, J=5.1Hz, 1H), 9.39(br, 1H), [10.84(br), 10.37(s)] 1H. |
| 826 | —Cl | (N-ethyl-2-pyrrolidinylmethylamino) | 1.11(t, J=7.1Hz, 3H), 1.50–2.20(m, 2H), 2.73(dd, J=14.1, 8.8Hz, 1H), 3.06–3.17(m, 2H), 3.45–3.52(m, 1H), 3.54–3.64(m, 2H), 4.10–4.40(m, 5H), 3.95(t, J=6.4Hz, 1H), [4.49(S), 4.72(d, J=17.3Hz), 4.92(d, J=17.3Hz)] 2H, 7.23(d, J=8.2Hz, 2H), 7.32(d, J=8.4Hz, 2H), 7.51(d, J=8.0Hz, 1H), 7.55(d, J=8.0Hz, 1H), 7.60(s, 1H), 8.90(br, 1H), 9.20(br, 1H), [10.82 (br), 10.36(s)] 1H. |
| 827 | —Cl | (2-hydroxy-2-methylpropanamide) | 1.59(s, 6H), 2.73(dd, J=14.1, 8.8Hz, 1H), 3.11(m, 2H), 3.92(t, J=6.3Hz, 1H), [4.51(S), 4.72 (d, J=17.3Hz), 4.92(d, J=17.3Hz)] 2H, 7.23(d, J=8.2Hz, 2H), 7.32(d, J=8.4Hz, 2H), 7.44(d, J=7.8Hz, 2H), 7.53(s, 1H), 7.54(d, J=8.0Hz, 1H), 8.30(br, 1H), 10.79(br, 1H). |
| 828 | —Cl | —NH(CH2)3NMe2 | 1.80–1.90(m, 2H), 2.73(dd, J=14.1, 8.8Hz, 1H), 2.77(s, 6H), 3.05–3.10(m, 2H), 3.12(dd, J=13.9Hz, 6.4Hz, 1H), 3.27–3.36,(m, 2H), 3.94(dd, J=8.8Hz, 6.4Hz, 1H), [4.50(S), 4.68(d, J=17.2Hz), 4.92(d, J=17.4Hz)] 2H, 7.23(d, J=8.2Hz, 2H), 7.32(d, J=8.4Hz, 2H), 7.50(d, J=8.0Hz, 1H), 7.53(d, J=8.0Hz, 1H), 7.58(s, 1H), 8.70(t, J=5.6Hz, 1H), 9.46(br, 1H), [10.82 (br), 10.35(s)] 1H. |
| 829 | —Cl | —NH(CH2)3-1-imidazolyl | 2.04–2.10(m, 2H), 2.73(dd, J=14.1, 8.8Hz, 1H), 3.12(dd, J=13.9Hz, 6.3Hz, 1H), 3.26–3.31, (m, 2H), 3.93(dd, J=8.8Hz, 6.4Hz, 1H), 4.21–4.26(m, 2H), [4.50(S), 4.68(d, J=17.3Hz), 4.91 (d, J=17.3Hz)] 2H, 7.23(d, J=8.2Hz, 2H), 7.32(d, J=8.4Hz, 2H), 7.47(d, J=8.0Hz, 1H), 7.55(d, J=8.0Hz, 1H), 7.57(s, 1H), 7.69(dd, J=1.65Hz, J=1.65Hz, 1H), 7.81(dd, J=1.65Hz, J=1.65Hz, 1H), 8.64(t, J=5Hz, 1H), 9.13(s, 1H), [10.81(br), 10.35(s)] 1H. |
| 830 | —Cl | —NH—(S)—CH(Me)COOH | 1.38(d, J=7.5Hz, 3H), 2.66–2.75(m, 1H), 3.04–3.18(m, 1H), 3.95(dd, J=8.8Hz, 6.6Hz, 1H), 4.40(dd, J=6.9Hz, 6.4Hz, 1H), [4.52(S), 4.66–4.84(m), 4.88–4.96(m)] 2H, 7.23(d, J=8.2Hz, 2H), 7.32(d, J=8.3Hz, 2H), 7.47(d, J=8.4Hz, 1H), 7.58–7.63(m 2H), 8.75(d, J=6.4Hz, 1H), 9.45(br, 1H), [10.78(br), 10.35(s)] 1H. |
| 831 | —Cl | —NH—(R)—CH(Me)COOH | 1.38(d, J=7.3Hz, 3H), 2.72(dd, J=14.6Hz, 8.4Hz, 1H), 3.06–3.18(m, 1H), 3.95(dd, J=8.9Hz, 6.4Hz, 1H), 4.36–4.45(m, 1H), [4.52(S), 4.66–4.84(m), 4.88–4.96(m)] 2H, 7.23(d, J=8.2Hz, 2H), 7.32(d, J=8.3Hz, 2H), 7.47(d, J=8.2Hz, 1H), 7.58–7.63(m 2H), 8.75(d, J=8.4Hz, 1H), 9.44(br, 1H), [10.79(br), 10.35(s)] 1H. |
| 832 | —Cl | (5-oxopyrrolidin-3-ylamino) | 2.30–2.46(m, 2H), 2.70(dd, J=13.9Hz, 9.3Hz, 1H), 3.08(dd, J=13.7Hz, 6.2Hz, 1H), 3.95(dd, J=8.9Hz, 6.4Hz, 1H), 4.23(dd, J=16Hz, 9.8Hz, 1H), 4.39(dd, J=17Hz, 9.9Hz, 1H), [4.47(S), 4.62–4.73(m), 4.85–4.93(m)] 2H, 4.65–4.71(m, 1H), 7.19(d, J=8.2Hz, 2H), 7.28(d, J=8.2Hz, 2H), 7.48(d, J=7.9Hz, 1H), 7.50(d, J=8.6Hz, 1H), 7.56(s, 1H), 9.03–9.06(m, 2H), 9.40(br, 1H), [10.75(br), 10.32(s)] 1H. |

TABLE 18-continued

| Example No. | RR¹ | RR² | NMR: ¹H-NMR(DMSO-d6; δ) |
|---|---|---|---|
| 833 | —Cl | (cyclopropyl-NH-C(=O)-C(CH2CH2)-N-OH) | 0.938(d, J=3.6Hz, 2H), 1.31(d, J=3.6Hz, 2H), 2.71(dd, J=13.9Hz, 8.2Hz, 1H), 3.06–3.16(m, 1H), 3.87–3.96(m, 1H), [4.44(d, J=16Hz), 4.53(d, J=16Hz), 4.60–4.73(m), 4.88–4.97 (m)] 2H, 7.23(d, J=8.4Hz, 2H), 7.32(d, J=8.3Hz, 2H), 7.42(d, J=7Hz, 1H), 7.47(d, J=7Hz, 1H), 7.60(s, 1H), 8.88(s, 1H), 8.89(br, 1H), 9.44(br, 1H), [10.77(br), 10.34(br)] 1H, [10.62 (br), 11.28(br)] 1H. |

Example 835

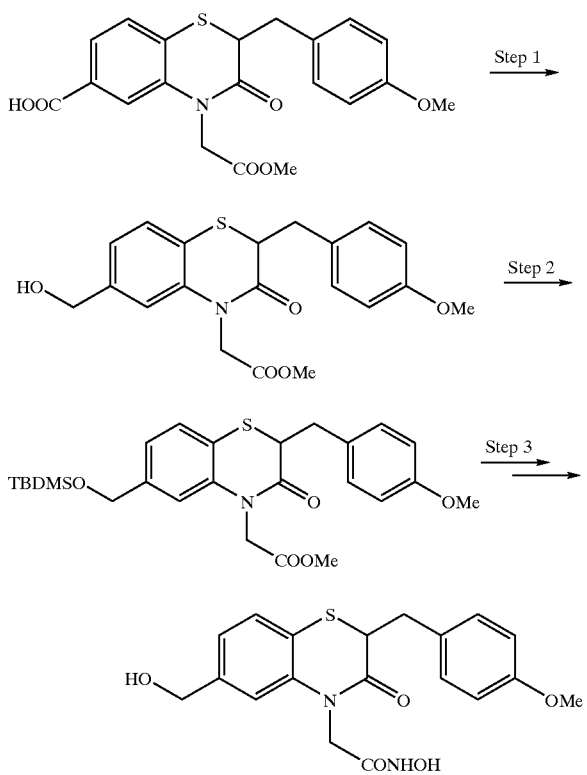

Step 1: Methyl 6-Hydroxymethyl-2H-2-(4-methoxybenzyl)-1,4-benzothiazin-3(4H)-one-4-ylacetate

Ethyl chloroformate (3.475 g) was added dropwise to a THF (30 mL) solution of methyl 6-carboxy-2H-2-(4-methoxybenzyl)-1,4-benzothiazin-3(4H)-one-4-ylacetate (2.795 g) and triethylamine (3.241 g) at 0° C. A solution of sodium borohydride (3.160 g) in water (5 mL) was added dropwise after additional 1 hour's stirring. The reaction mixture was stirred at 0° C. for 1 hr. The reaction mixture was quenched with acetic acid and concentrated under reduced pressure. The residue was dissolved in ethyl acetate and washed with water. The organic layer was dried over Na₂SO₄ and concentrated. The residue was purified with silica gel column chromatography (eluent: toluene/EtOAc, 4/1) to give the product (2.294 g, 79%).

Step 2: Methyl 6-t-Butyldimethylsiloxymethyl-2H-2-(4-methoxybenzyl)-1,4-benzothiazin-3(4H)-one-4-ylacetate

To a solution of methyl 6-hydroxymethyl-2H-2-(4-methoxybenzyl)-1,4-benzothiazin-3(4H)-one-4-ylacetate (2.294 g) and imidazole (1.612 g) in DMF (30 mL), a solution of TBDMSCl (2.665 g) in DMF (5 ml) was slowly added. The reaction mixture was stirred at r.t. for 2 days and quenched with water. The solvent was removed under reduced pressure, and the residue was dissolved in chloroform, dried over Na₂SO₄, and concentrated. The residue was purified with silica gel column chromatography (eluent: toluene/EtOAc, 50/1) to give the product (2.966 g, quant.).

Step 3: 6-Hydroxymethyl-2H-2-(4-methoxybenzyl)-1,4-benzothiazin-3(4H)-one-4-ylacetic Acid N-Hydroxyamide

To a solution of the methyl ester (2.966 g) in methanol (20 mL), 1N NaOH (8.86 mL) was slowly added at 0° C. After 30 minutes' stirring, the mixture was warmed to room temperature and left overnight. The reaction mixture was concentrated under reduced pressure. The residue was dissolved in ethyl acetate and water. After the pH was adjusted to 6 with acetic acid, the product was extracted with EtOAc. The organic layer was dried over Na₂SO₄ and concentrated to give the product (1.208 g, 42%) as a white solid.

Isobutyl chloroformate (373 mg) was added dropwise to a THF (10 mL) solution of 6-t-butyldimethylsiloxymethyl-2H-2-(4-methoxybenzyl)-1,4-benzothiazin-3(4H)-one-4-ylacetic acid (1.208 g) and N-methylmorpholine (276 mg) at −5° C. THF (1 mL) solution of O-TMS-hydoxylamine (313 mg) was added after additional 20 minutes' stirring. The mixture was stirred at −5° C. for 2 hrs, gradually warmed to r.t. with stirring, and stood overnight. The reaction mixture was quenched with water and extracted with EtOAc. The organic layer was washed with 1N HCl and brine, dried over Na₂SO₄ and concentrated under reduced pressure. The residue was purified with silica gel column chromatography (eluent: chloroform/methanol, 10/1) to give the hydroxamic acid (645 mg, 70%) as a white powder.

The following compounds listed in the Table 19 were prepared in a similar manner.

TABLE 19

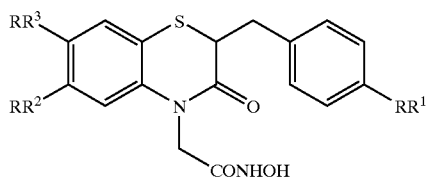

| Example No. | RR$^1$ | RR$^2$ | RR$^3$ | NMR: $^1$H-NMR(DMSO-d6; δ) |
|---|---|---|---|---|
| 835 | —OMe | —CH2OH | —H | 2.63(1H, m), 3.10(1H, m), 3.72(3H, s), 3.77(1H, m), 4.45–4.49(4H, m), 5.28(1H, m), 6.84(2H, d, J=8.43Hz), 7.02(1H, d, J=8.07Hz), 7.10–7.13(3H, m), 7.31(1H, d, J=7.89Hz), 8.99(1H, s), 10.76 (1H, s) |
| 836 | —OMe | —H | —CH2OH | 2.65(1H, m), 3.10(1H, m), 3.72(3H, s), 3.78(1H, m), 4.42–4.45(4H, m), 5.21(1H, m), 6.84(2H, d, J=8.25Hz), 7.07–7.14(3H, m), 7.23(1H, d, J=8.43Hz), 7.28(1H, s), 8.97(1H, s), 10.75(1H, s) |
| 837 | —OPh | —H | —CH2OH | 2.71(1H, m), 3.16(1H, m), 3.85(1H, m), 4.43–4.46(4H, m), 6.91(2H, d, J=8.61Hz), 7.00(2H, d, J=7.71Hz), 7.07–7.16(2H, m), 7.22–7.25(3H, m), 7.30(1H, s), 7.37–7.42(2H, m), 8.98(1H, s), 10.76 (1H, s) |
| 838 | —Cl | —CH2OH | —H | 2.72(1H, dd, J=9.0, 14Hz), 3.14(1H, dd, J=6.2, 14Hz), 3.85(1H, dd, J=6.2, 9.0Hz), 4.44(1.6H, br-s), 4.49(2H, d, J=5.2Hz), 4.63(0.2H, d, J=18Hz), 4.87(0.2H, d, J=18Hz), 7.03(2H, d, J=7.8Hz), 7.11(1H, br-s), 7.24(2H, d, J=8.4Hz), 7.30–7.34(3H, m), 9.01(0.8H, s), 9.45(0.2H, s), 10.35(0.2H, s), 10.80(0.8H, s) |
| 839 | —OH | —CH2OH | —H | 2.58(1H, dd, J=9.5Hz, 14Hz), 3.07(1H, dd, J=5.7Hz, 14Hz), 3.79(1H, dd, J=5.7Hz, 9.5Hz), 4.69 (3.8H, br-s), 4.84(0.2H, d, J=18Hz), 6.65(2H, d, J=8.4Hz), 6.98(2H, d, J=8.4Hz), 7.15(1H, dd, J=1.3Hz, 8.0Hz), 7.25(br-s, 1H), 7.35(1H, d, J=8.0Hz), 9.01(s, 1H), 9.26(0.8H, s), 9.40(0.2H, s), 10.35(0.2H, s), 10.79(0.8H, s) |

Example 840

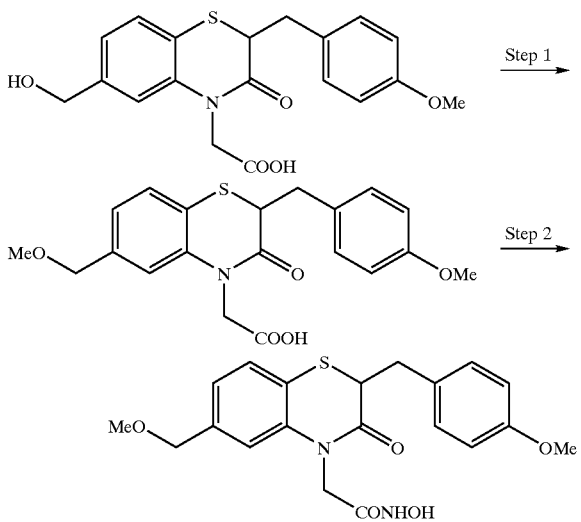

Step 1: 6-Methoxymethyl-2H-2-(4-methoxybenzyl)-1,4-benzothiazin-3(4H)-one-4-ylacetic Acid To a solution of methyl 6-hydrozymethyl-2H-2-(4-methoxybenzyl)-1,4-benzothiazin-3(4H)-one-4-yl-acetate (335 mg) and tetra-n-buthylammonium iodide (133 mg) in toluene (10 mL), 50% NaOH aq. (5 mL) was added. After 30 minutes' stirring, dimethyl sulfate (1.47 g) was slowly added. The reaction mixture was vigorously stirred at r.t. overnight. The solvent was removed under reduced pressure, and the residue was acidified with 4N HCl and extracted with ethyl acetate. The organic layer was dried over Na$_2$SO$_4$ and concentrated. The crude product (346 mg) was used in the following step without purification.

Step 2: 6-Methoxymethyl-2H-2-(4-methoxybenzyl)-1,4-benzothiazin-3(4H)-one-4-ylacetic Acid N-Hydroxyamide The crude product (305 mg) of step 1 was dissolved in dichloromethane (4 mL) and pyridine (3 mL) and pentafluorophenyl trifluoroacetate (664 mg) was added. After 3 hours stirring, O-TBDMS-hydoxylamine (465 mg) was slowly added. The reaction mixture was stirred at r.t. overnight. The solvent was removed and the residue was dissolved in EtOAc. The organic layer was washed with 1N HCl and water, dried over Na$_2$SO$_4$ and concentrated under reduced pressure. The residue was purified with preparative thin layer chromatography on silica gel (EtOAc) to give the hydroxamic acid (190 mg, 60% in 2 steps) as a pale orange solid.

$^1$H-NMR (DMSO-d$_6$, δ); 2.65 (1H, m), 3.10 (1H, m), 3.30 (3H, s), 3.72 (3H, m), 3.80 (1H, m), 4.39 (2H, m), 4.46 (2H, m), 6.84 (2H, d, J=8.61 Hz), 7.02 (1H, d, J=8.25 Hz), 7.12 (3H, m), 7.34 (1H, d, J=7.89 Hz), 9.00 (1H, s), 10.77 (1H, s).

Example 841

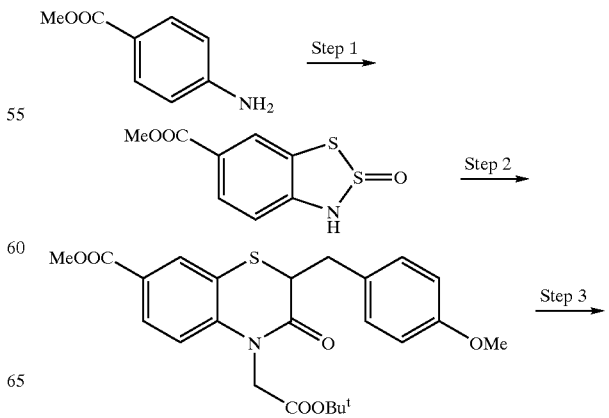

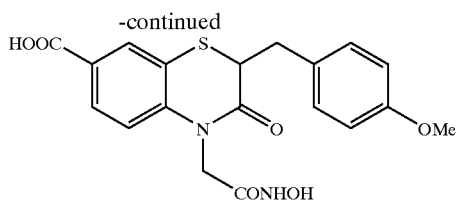

Step 1: 6-Methoxycarbonyl-3H-1,2,3-benzodithiazole-2-oxide

To sulphur monochloride (170 mL), a solution of methyl 4-aminobenzoate in acetic acid (200 mL) was slowly added at 0 to 10° C. The reaction mixture was stirred at 65° C. for 4 hrs. To the cooled mixture, toluene (300 mL) was added, the solid product was collected by filtration and washed with toluene three times. After drying under reduced pressure, this solid (30.888 g, 94%) was dissolved in 5% sodium acetate aq. and the solution was stirred at r.t. for 2 hrs. The solid product was collected by filtration and washed with water and toluene. After drying under reduced pressure, the product (28.028 g, 98%) was obtained.

:Sawhney's procedure (Indian J. chem. 33B, 280 (1994)).
Step 2: t-Butyl 7-Methoxycarbonyl-2H-2-(4-methoxybenzyl)-1,4-benzothiazin-3(4H)-one-4-ylacetate To a Solution of 6-methoxycarbonyl-3H-1,2,3-benzodithiazole-2-oxide (11.46 g) and 2-bromo-3-(4-methoxyphenyl)propionic acid (12.96 g) in 50% MeOH aq. (100 mL), triethylamine (50 mL) was slowly added at 70° C. The reaction mixture was stirred at 70° C. for 2 hrs. The mixture was cooled to r.t. and concentrated under reduced pressure. The residue was dissolved in EtOAc and washed with 5% Na$_2$CO$_3$ aq. and 1N HCl. The organic layer was dried over Na$_2$SO$_4$ and concentrated. The residue was purified by recrystallization from Et$_2$O and hexane to give the product (15.131 g, 88%) as a white powder.

To a solution of 7-methoxycarbonyl-2H-2-(4-methoxybenzyl)-1,4-benzothiazin-3(4H)-one (7.00 g) in DMF (40 mL), NaH (1.47 g, 60% in oil) was added at r.t. After minutes' stirring, t-buthyl bromoacetate (5.56 g) was slowly added. The reaction mixture was stirred at r.t. overnight. The solvent was removed under reduced pressure and the residue was dissolved in EtOAc and washed with water. The organic layer was dried over Na$_2$SO$_4$ and concentrated. The residue was purified with silica gel column chromatography (eluent: toluene/EtOAc, 20/1) to give the product (6.994 g, 64%).

Step 3: 7-Carboxy-2H-2-(4-methoxybenzyl)-1,4-benzothiazin-3(4H)-one-4-ylacetic Acid N-Hydroxamide t-Butyl 7-methoxycarbonyl-2H-2-(4-methoxybenzyl)-1,4-benzothiazin-3(4H)-one-4-ylacetate (4.81 g) was dissolved in TFA (19 mL) and ethanedithiol (1 mL). The mixture was stirred at r.t. for 2 hrs. The solvent was removed under reduced pressure, and the residue was diluted with 5% Na$_2$CO$_3$, washed with Et$_2$O. The aquaous layer was acidified with 4N HCl and extracted with EtOAc. The organic layer was dried over Na$_2$SO$_4$ and concentrated. The residue was purified with silica gel column chromatography (eluent: EtOAc) to give the product (3.522 g, 83%).

Isobutyl chloroformate (1.304 g) was added dropwise to a THF (20 mL) solution of 7-methoxycarbonyl-2H-2-(4-methoxybenzyl)-1,4-benzothiazin-3(4H)-one-4-ylacetic acid (3.484 g) and N-methylmorpholine (0.966 g) at −5° C. THF (1 mL) solution of O-TMS-hydoxylamine (1.096 g) was added after additional 20 minutes' stirring. The mixture was stirred at −5° C. for 2 hrs, gradually warmed to r.t. with stirring, and stood overnight. The reaction mixture was quenched with water and extracted with EtOAc. The organic layer was washed with 1N HCl and water, dried over Na$_2$SO$_4$ and concentrated under reduced pressure. The residue was purified with silica gel column chromatography (eluent: toluene/EtOAc, 3/1) to give the hydroxamic acid (2.943 g, 81%) as a white powder.

To a solution of 7-methoxycarbonyl-2H-2-(4-methoxybenzyl)-1,4-benzothiazin-3(4H)-one-4-ylacetic acid N-hydroxamide (2.827 g) in methanol (10 mL) and THF (10 mL) 1N NaOH (13.6 mL) was slowly added at 0° C. After 30 minutes' stirring, the mixture was warmed to room temperature and left overnight. The reaction mixture was concentrated under reduced pressure. The residue was dissolved in 5% Na$_2$CO$_3$ aq., and washed with Et$_2$O. The aqueous layer was acidified with 4N HCl, and the product was extracted with EtOAc. The organic layer was dried over Na$_2$SO$_4$ and concentrated. The residue was purified by recrystallization from EtOAc to give the hydroxamic acid (1.234 g, 45%) as a white solid.

The following compounds listed in the Tables 20, and 20' were prepared in a similar manner.

TABLE 20

| Example No. | RR$^1$ | RR$^2$ | NMR: $^1$H-NMR(DMSO-d6; δ) |
|---|---|---|---|
| 841 | —OMe | —CO2H | 2.67(1H, m), 3.09(1H, m), 3.72(3H, s), 3.89(1H, m), 4.52(2H, m), 6.84(2H, d, J=8.07Hz), 7.13(2H, d, J=8.25 Hz), 7.22(1H, d, J=10.26Hz), 7.85(2H, s), 9.00(1H, s), 10.80 (1H, s) |
| 842 | —OMe | —CO2Me | 2.67(1H, m), 3.08(1H, m), 3.73(3H, s), 3.84(3H, s), 3.92 (1H, m), 4.53(2H, m), 6.84 (2H, d, J=8.43Hz), 7.13(2H, d, J=8.61Hz), 7.25(1H, m), 7.84–7.90(2H, m), 9.01(1H, br-s), 10.81(1H, s) |
| 843 | —OMe | —COONa | 2.67(1H, m), 3.09(1H, m), 3.72(3H, s), 3.89(1H, m), 4.52 (2H, m), 6.84(2H, d, J=8.07 Hz), 7.13(2H, d, J=8.25Hz), 7.22(1H, d, J=10.26Hz), 7.85 (2H, s), 9.00(1H, s), 10.80(1H, s) |
| 844 | —Cl | —CO2H | 1H-NMR 2.75(1H, dd, J=13.9, 8.8Hz), 3.12(1H, dd, J=14.3 Hz, 6.2Hz), 3.98(1H, dd, J= 8.6Hz, 6.6Hz), [4.50(S), 4.69 (d, J=17.7Hz), 4.91(d, J= 17.7Hz)] 2H, [7.22(d, J=8.6 Hz), 7.02(d, J=8.4Hz)] 1H, 7.24(2H, d, J=8.6Hz), 7.32 (2H, d, J=8.6Hz), 7.83(1H, dd, J=8.4Hz, 1.8Hz), 7.86(1H, d, J=1.8Hz), [8.99(br), 9.39 (s)] 1H, [10.80(br), 10.38 (s)] 1H, 13.02(1H,(br). |
| 845 | —OPh | —CO2H | 2.76(1H, m), 3.13(1H, m), 4.02(1H, m), 4.53(2H, m), 6.91(2H, d, J=8.43Hz), 6.99 (2H, d, J=7.50Hz), 7.14(1H, m), 7.22–7.25(3H, m), 7.39 (2H, m), 7.85(1H, m), 7.88 (1H, d, J=2.01Hz), 9.02(1H, s), 10.82(1H, s) |

TABLE 20'

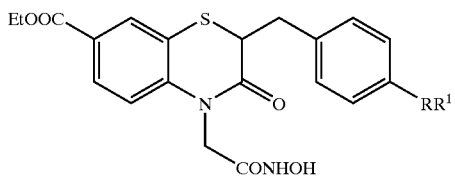

| Example No. | RR¹ | NMR: ¹H-NMR(DMSO-d6; δ) |
|---|---|---|
| 1005 | —Cl | 1.31(3H, t, J=7Hz), 2.77(1H, m), 3.14 (1H, m), 4.00(1H, m), 4.29(2H, dd, J=7, 13Hz), 4.52(2H, m), 7.25–7.35(5H, m), 7.84–7.90(2H, m), 9.03(1H, br-s), 10.86 (1H, br-s) |
| 1006 | —OPh | 1.31(3H, t, J=7.14Hz), 2.75(1H, m), 3.13 (1H, m), 3.97(1H, m), 4.29(2H, dd, J=7, 13Hz), 4.54(2H, m), 6.91(2H, d, J=8.43 Hz), 6.99(2H, d, J=7.68Hz), 7.14(1H, m), 7.22–7.27(3H, m), 7.37–7.42(2H, m), 7.85(1H, dd, J=2.0, 8.6Hz), 7.91(1H, d, J=1.86Hz) 9.03(1H, br-s), 10.83(1H, br-s) |

Example 846

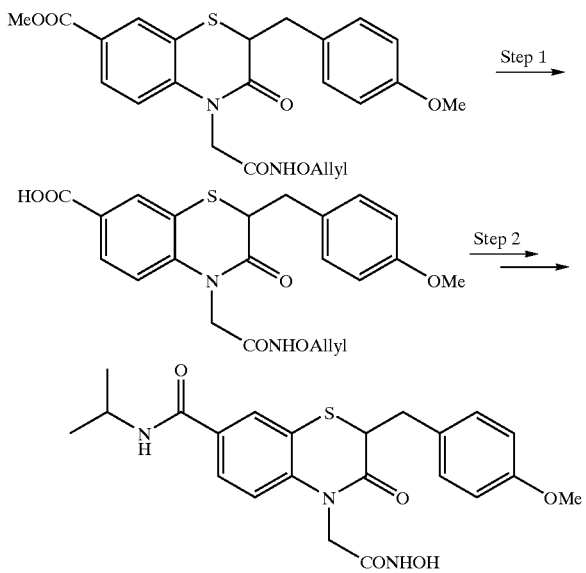

Step 1: 7-Carboxy-2H-2-(4-methoxybenzyl)-1,4-benzothiazin-3(4H)-one-4-ylacetic Acid N-Allyloxyamide To a solution of 7-methoxycarbonyl-2H-2-(4-methoxybenzyl)-1,4-benzothiazin-3(4H)-one-4-ylacetic acid N-allyloxyamide (5.067 g) in methanol (15 mL) and THF (15 mL), 1N NaOH (16.65 mL) was slowly added at 0° C. After 30 minutes' stirring, the mixture was warmed to room temperature and left overnight. The reaction mixture was concentrated under reduced pressure. The residue was dissolved in 5% Na₂CO₃ aq., and washed with Et₂O. The aqueous layer was acidified with 4N HCl, and the product was extracted with EtOAc. The organic layer was dried over Na₂SO₄ and concentrated to give the product (4.748 g, 97%) as a white solid.

Step 2: 7-Isopropylcarbamoyl-2H-2-(4-methoxybenzyl)-1,4-benzothiazin-3(4H)-one-4-ylacetic Acid N-Hydroxyamide To a solution of 7-carboxy-2H-2-(4-methoxybenzyl)-1,4-benzothiazin-3(4H)-one-4-ylacetic acid N-allyl-oxyamide (221 mg) and isopropylamine (36 mg) in DMF (10 mL), HOBt (552 mg) and 1-ethyl-3-(3-dimethylaminopropyl) carbodiimide.HCl(EDC.HCl) (690 mg) were added. The reaction mixture was stirred at r.t. overnight. The solvent was removed under reduced pressure. The residue was dissolved in EtOAc and washed with 1N HCl, 5% Na₂CO₃ aq. and brine. The organic layer was dried over Na₂SO₄ and concentrated. The crude product was used in the following step without purification.

To a solution of the crude product of 7-isopropylcarbamoyl-2H-2-(4-methoxybenzyl)-1,4-benzothiazin-3(4H)-one-4-ylacetic acid N-allyloxyamide in 80% ethanol aq. (8 mL), Pd(OAc)₂ (12 mg), PPh₃ (53 mg), and formic acid (69 mg) were added. The reaction mixture was heated at 80° C. under nitrogen for 1 hr. The solvent was removed and the residue was dissolved in EtOAc. The organic layer was washed with water, dried over Na₂SO₄ and concentrated under reduced pressure. The residue was purified by preparative thin layer chromatography on silica gel (chloroform/methanol, 8/1) to give the hydroxamic acid (207 mg, 93% in 2 steps) as a pale orange solid.

The following compounds listed in the Tables 21 were prepared in a similar manner.

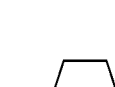

| | | | |
|---|---|---|---|
| 854 | —OMe | —NHCH2COOH | 2.67(1H, m), 3.09(1H, m), 3.73(3H, s), 3.87–3.92(3H, m), 4.53(2H, m), 6.84(2H, d, J=8.43Hz), 7.14(2H, d, J=8.58Hz), 7.22(1H, d, J=8.61Hz), 7.79(1H, dd, J=1.83, 8.61Hz), 7.89(1H, d, J=2.04Hz), 8.85(1H, m), 9.00(1H, s), 10.80(1H, s), 12.63(1H, br-s) |
| 855 | —OMe | —NHC(CH3)2COOH | 1.43(6H, s), 2.67(1H, m), 3.11(1H, m), 3.73(3H, s), 3.87(1H, m), 4.51(2H, m), 6.85(2H, d, J=8.61 Hz), 7.15(2H, d, J=8.61Hz), 7.20(1H, d, J=8.61Hz), 7.76(1H, d, J=8.43Hz), 7.91(1H, d, J=1.83 Hz), 8.44(1H, s), 9.00(1H, s), 10.79(1H, s), 12.11(1H, br-s) |
| 856 | —OMe | —NH—(S)—CH(iBu)COOH | 0.90(6H, m), 1.57–1.76(3H, m), 2.69(1H, m), 3.11(1H, m), 3.73(3H, s), 3.89(1H, m), 4.43(1H, m), 4.52(2H, m), 6.84(2H, d, J=8.43Hz), 7.15(2H, d, J=8.61Hz), 7.22(1H, d, J=8.61Hz), 7.80(1H, m), 7.94(1H, m), 8.57(1H, m), 9.00(1H, s), 10.80(1H, s) |
| 857 | —OMe | | 1.85–1.98(3H, m), 2.26(1H, m), 2.67(1H, m), 3.10(1H, m), 3.55(2H, m), 3.72(3H, s), 3.86(1H, m), 4.39(1H, m), 4.50(2H, m), 6.84(2H, d, J=8.43Hz), 7.13(2H, d, J=8.43Hz), 7.18(1H, d, J=8.22Hz), 7.47–7.50(2H, m), 9.01(1H, s), 10.80(1H, s) |

| 858 | —OMe | —NH(CH2)2CH(CH3)2 | 0.88(6H, d, 6.60Hz), 1.39(2H, m), 1.58(1H, m), 2.66(1H, m), 3.09(1H, m), 3.25(2H, m), 3.71(3H, s), 3.85(1H, m), 4.50(2H, m), 6.83(2H, d, J=8.61Hz), 7.12(2H, d, J=8.58Hz), 7.18(2H, d, J=8.61Hz), 7.74(1H, m), 7.83(1H, d, J=1.83Hz), 8.39(1H, m), 9.00(1H, s), 10.79(1H, s) |
|---|---|---|---|
| 859 | —OMe | —NH(CH2)2N(CH3)2 | 2.42(6H, s), 2.63–2.72(3H, m), 3.10(1H, m), 3.37(2H, m), 3.73(3H, s), 3.87(1H, m), 4.52(2H, m), 6.84(2H, d, J=8.61Hz), 7.14(2H, d, J=8.58Hz), 7.21(2H, d, J=8.61Hz), 7.78(1H, dd, J=2.01, 8.61Hz), 7.87(1H, d, J=2.01Hz), 8.15(1H, s), 8.55(1H, m), 10.82(1H, br-s) |
| 860 | —OMe | —NH(CH2)2NEt2 | 0.99(6H, t, J=7.14Hz), 2.55–2.70(7H, m), 3.10(1H, m), 3.35(2H, m), 3.73(3H, s), 3.88(1H, m), 4.52(2H, m), 6.84(2H, d, J=8.61Hz), 7.13(2H, d, J=8.43Hz), 7.20(2H, d, J=8.58Hz), 7.76(1H, d, J=2.01, 8.43Hz), 7.84(1H, s), 8.20(1H, s), 8.45(1H, ) m, 10.81(1H, br-s) |
| 861 | —OPh | —NH(CH2)2CH(CH3)2 | 0.89(6H, d, 6.60Hz), 1.39(2H, m), 1.60(1H, m), 2.74(1H, m), 3.17(1H, m), 3.26(2H, m), 3.93(1H, m), 4.52(2H, m), 6.91(2H, d, J=8.43Hz), 6.99(2H, d, J=7.50Hz), 7.11–7.26(4H, m), 7.40(2H, m), 7.76(1H, d, J=8.40Hz), 7.87(1H, s), 8.41(1H, m), 9.01(1H, s), 10.80(1H, s) |
| 862 | —OPh | —NH(CH2)2OMe | 2.74(1H, m), 3.15(1H, m), 3.26(3H, s), 3.33–3.44(4H, m), 3.93(1H, m), 4.52(2H, m), 6.91(2H, d, J=8.61Hz), 7.00(2H, d, J=8.79Hz), 7.16–7.26(4H, m), 7.37–7.42(2H, m), 7.78(1H, d, J=8.61 Hz), 7.89(1H, d, J=1.83Hz), 8.54(1H, m), 9.01(1H, s), 10.81(1H, s) |

TABLE 21

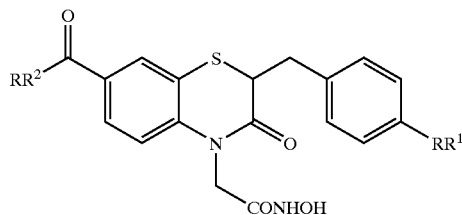

| Example No. | RR¹ | RR² | NMR: ¹H-NMR(DMSO-d6; δ) |
|---|---|---|---|
| 846 | —OMe | —NHiPr | 1.14(6H, m), 2.67(1H, m), 3.11(1H, m), 3.73(3H, s), 3.86(1H, m), 4.09(1H, m), 4.51 (2H, m), 6.85(2H, d, J=8.61Hz), 7.14(2H, d, J=8.40Hz), 7.18(1H, d, J=8.97Hz), 7.76 (1H, d, J=8.61Hz), 7.87(1H, s), 8.20(1H, d, J=7.68Hz), 9.00(1H, s), 10.79(1H, s) |
| 847 | —OMe | —NH2 | 2.65(1H, m), 3.12(1H, m), 3.71(3H, s), 3.86(1H, m), 4.50(2H, m), 6.83(2H, d, J=8.43 Hz), 7.13(2H, d, J=8.43Hz), 7.17(1H, d, J=8.79Hz), 7.36(1H, s), 7.78(1H, s), 7.86 (1H, d, J=1.65Hz), 7.95(1H, s), 8.99(1H, br-s), 10.79(1H, br-s) |
| 848 | —OMe | —NH-cyclopropyl | 0.56(2H, m), 0.67(2H, m), 2.65(1H, m), 2.83(1H, m), 3.11(1H, m), 3.73(3H, s), 3.86 (1H, m), 4.51(2H, m), 6.84(2H, d, J=8.43Hz), 7.13(2H, d, J=8.43Hz), 7.18(1H, m), 7.74 (1H, m), 7.82(1H, d, J=1.83Hz), 8.41(1H, d, J=4.05Hz), 9.00(1H, s), 10.79(1H, s) |
| 849 | —OMe | -morpholino | 2.67(1H, m), 3.12(1H, m), 3.32–3.60(8H, m), 3.72(3H, s), 3.87(1H, m), 4.50(2H, m), 6.84(2H, d, J=8.61Hz), 7.13(2H, d, J=8.58Hz), 7.17(1H, m), 7.35(1H, m), 7.41(1H, d, J=1.65Hz), 9.00(1H, s), 10.80(1H, s) |
| 850 | —OMe | -Piperadino-4-CHO | 2.68(1H, m), 3.15(1H, m), 3.17–3.44(8H, m), 3.72(3H, s), 3.87(1H, m), 4.51(2H, m), 6.84(2H, d, J=8.40Hz), 7.14(2H, d, J=8.04Hz), 7.18(1H, d, J=8.61Hz), 7.37(1H, d, J=8.22Hz), 7.44(1H, s), 8.06(1H, s), 9.01(1H, s), 10.81(1H, s) |
| 851 | —OMe | —NHCH(CH2OH)2 | 2.66(1H, m), 3.10(1H, m), 3.48(4H, m), 3.71(3H, s), 3.83–3.94(2H, m), 4.50(2H, m), 4.63(2H, m), 6.83(2H, d, J=8.43Hz), 7.13(2H, d, J=8.61Hz), 7.18(1H, d, J=8.43Hz), 7.76(1H, d, J=6.78Hz), 7.90(1H, s), 7.98(1H, d, J=8.2SHz), 8.98(1H, s), 10.78(1H, s) |
| 852 | —OMe | —N((CH2)20H)2 | 2.65(1H, m), 3.09(1H, m), 3.36–3.57(8H, m), 3.71(3H, s), 3.85(1H, m), 4.48(2H, m), 4.80(2H, m), 6.83(2H, d, J=8.61Hz), 7.10–7.15(3H, m), 7.33(1H, d, J=8.25Hz), 7.41 (1H, s), 9.00(1H, br-s), 10.78(1H, br-s) |
| 853 | —OMe | —NHC(Me)2CH2OH | 1.28(6H, s), 2.66(1H, m), 3.11(1H, m), 3.48(2H, d, J=6.03Hz), 3.71(3H, s), 3.84(1H, m), 4.49(2H, m), 4.85(1H, m), 6.83(2H, d, J=8.61Hz), 7.12–7.17(3H, m), 7.54(1H, s), 7.70 (1H, d, J=8.58Hz), 7.83(1H, d, J=1.83Hz), 8.98(1H, s), 10.78(1H, s) |
| 863 | —OPh | —NH(CH2)2OEt | 1.10(3H, t, J=6.96Hz), 2.74(1H, m), 3.14(1H, m), 3.31–3.42(6H, m), 3.93(1H, m), 4.52 (2H, m), 6.91(2H, d, J=8.61Hz), 6.99(2H, d, J=7.50Hz), 7.11–7.25(4H, m), 7.37–7.42 (2H, m), 7.78(1H, d, J=8.61Hz), 7.88(1H, s), 8.54(1H, m), 9.01(1H, s), 10.81(1H, s) |

TABLE 21-continued

[Structure: benzothiazinone core with $RR^2$-CO- substituent at position 7, $RR^1$ on the benzyl para position, and N-CH$_2$-CONHOH]

| Example No. | RR$^1$ | RR$^2$ | NMR: $^1$H-NMR(DMSO-d6; δ) |
|---|---|---|---|
| 864 | —OMe | [structure: —NH-CH(CH$_2$CH(CH$_3$)$_2$)-CH$_2$-O-C(=O)-CH$_3$] | 0.88(6H, m), 1.30(2H, m), 1.51(1H, m), 1.97(3H, s), 2.59(1H, m), 3.12(1H, m), 3.73 (3H, s), 3.88–3.92(2H, m), 4.07(1H, m), 4.27(1H, m), 4.52(2H, m), 6.85(2H, d, J=7.50 Hz), 7.1 5(2H, d, J=8.79Hz), 7.22(1H, m), 7.76(1H, d, J=8.61Hz), 7.86(1H, s), 8.20(1H, d, J=8.61Hz), 9.00(1H, s), 10.79(1H, s) |
| 865 | —OMe | [structure: —NH-CH(CH$_2$CH(CH$_3$)$_2$)-CH$_2$-OH] | 0.87(6H, m), 1.39(2H, m), 1 58(1H, m), 2.68(1H, m), 3.11(1H, m), 3.39(2H, m), 3.73 (3H, s), 3.87(1H, m), 4.03(1H, m), 4.52(3H, m), 6.84(2H, d, J=8.07Hz), 7.13–7.21(3H, m), 7.78(1H, m), 7.89(1H, m), 8.00(1H, d, J=8.61Hz), 9.00(1H, br-s), 10.80(1H, s) |
| 866 | —Cl | —NHCH2-2-furyl | 2.73(1H, dd, J=13.9Hz, 9.3Hz), 3.13(1H, d, J=14.4Hz, 6.6Hz), 3.94(1H, dd, J=8.8Hz, 6.4Hz), 4.46(2H, d, J=5.4Hz), [4.50(S), 4.72(d, J=17.9Hz), 4.95(d, J=17.9Hz)] 2H, 6.26(1H, d, J=2.7Hz), 6.38(1H, dd, J=3.0Hz, 1.6Hz), 7.20(1H, d, J=8.6Hz), 7.24(2H, d, J=8.4Hz), 7.32(2H, d, J=8.4Hz), 7.56(1H, t, J=0.9Hz), 7.79(1H, dd, J=8.4Hz, 2.0Hz), 7.87(1H, d, J=2.2Hz), 8.95(1H, t, J=5.4Hz), [8.99(br), 9.42(s)] 1H, [10.78(br), 10.35 (s)] 1H. |

Example 867

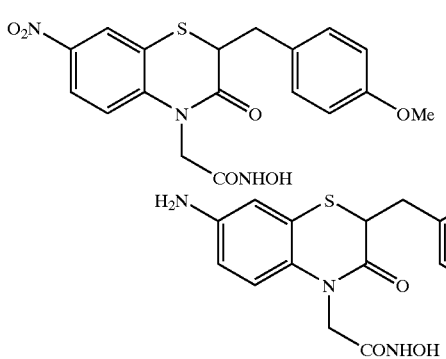

Step 1: 7-Amino-2H-2-(4-methoxybenzyl)-1,4-benzothiazin-3(4H)-one-4-ylacetic Acid N-Hydroxyamide The product in Example 757 (400 mg) was dissolved in MeOH (10 mL) and AcOH (1 mL). 10% Pd/C (200 mg) was added and the reaction mixture was vigorously stirred at r.t. for 5 hrs under H$_2$. The catalyst was removed by filtration, and the filtrate was concentrated under reduced pressure. The residue was purified by silica gel column chromatography (chloroform/MeOH, 30/1, 10/1) to give the product as a pale yellow solid (162 mg).

The following compounds listed in the Table 22 were prepared in a similar manner.

TABLE 22

[Structure: benzothiazinone core with $RR^3$ and $RR^2$ substituents on benzene ring, $RR^1$ on benzyl para position, N-CH$_2$-CONHOH]

| Example No. | RR$^1$ | RR$^2$ | RR$^3$ | NMR: $^1$H-NMR(DMSO-d6; δ) |
|---|---|---|---|---|
| 867 | —OMe | —H | —NH2 | 2.62(1H, m), 3.10(1H, m), 3.70(4H, m), 4.25–4.80(2H, m), 5.10(2H, bs), 6.46(2H, m), 6.82 (3H, m), 7.11(2H, d, J=7.5Hz), 8.93, 9.32(1H, bs), 10.24, 10.66(1H, bs). |
| 868 | —OMe | —NH2 | —H | 2.60(1H, dd, J=9.6, 14.2 Hz), 3.09(1H, dd, J=5.5, 9.5Hz), 3.63(1H, J=5.5, 9.5Hz), 3.72(3H, s), 4.25–4.40(2H, m), 5.29, 5.31(2H, bs), 6.20–6.36 (2H, m), 6.83(2H, m), 6.95(1H, m), 7.11(2H, d, J=8.6Hz), 8.96, 9.37(1H, bs), 10.30, 10.71(1H, bs). |

Example 869

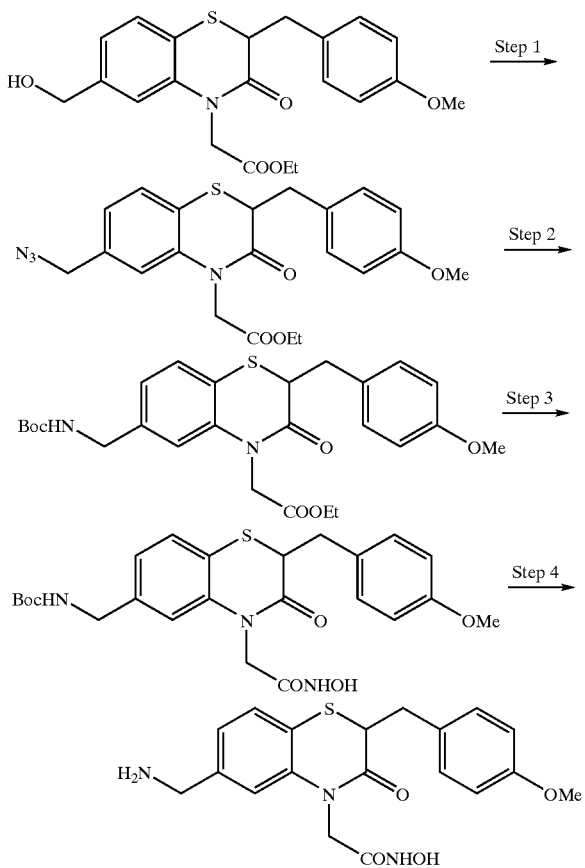

Step 1: Ethyl 6-Azidomethyl-2H-2-(4-methoxybenzyl)-1,4-benzothiazin-3(4H)-one-4-ylacetate Ethyl 6-hydroxymethyl-2H-2-(4-methoxybenzyl)-1,4-benzothiazin-3(4H)-one-4-ylacetate (1.75 g), prepared by the procedure described in Example 835 (Step 1), was dissolved in THF (16 mL), and triethylamine (0.93 ml) and methanesulfonyl chloride (0.51 ml) were slowly added at 0° C. The reaction mixture was stirred at 0° C. for 2 hrs. The reaction mixture was concentrated under reduced pressure. The residue was dissolved in DMF (30 ml), and sodium azide (636 mg) was added at 0° C. Stirring was continued for 1 hr at 0° C. and for 2 hrs at r.t. The reaction mixture was diluted with water and extracted with EtOAc. The organic layer was washed with brine, dried over $MgSO_4$ and concentrated under reduced pressure. The residue was purified with silica gel column chromatography (eluent: hexane:EtOAc=5:1, 3:1). 1.83 g of the product was obtained as oil.

Step 2: Ethyl 6-N-t-Butoxycarbonylaminomethyl-2H-2-(4-methoxybenzyl)-1,4-benzothiazin-3(4H)-one-4-ylacetate The compound obtained in Step 1 (1.07 g) was dissolved in methanol (20 mL) and EtOAc (5 mL). 10% Pd/C (300 mg) was added, and the reaction mixture was vigorously stirred at r.t. for 2 hrs under $H_2$. The catalyst was removed by filtration, and the filtrate was concentrated under reduced pressure. The residue was dissolved in MeOH (20 ml), di-t-butyldicarbonate (0.74 g) and $NaHCO_3$ (0.21 g) were added at 0° C. The reaction mixture was stirred at r.t. overnight. The reaction mixture was diluted with water and extracted with EtOAc. The organic layer was washed with brine, dried over $MgSO_4$ and concentrated under reduced pressure. The residue was purified with silica gel column chromatography (Eluent: Hexane/EtOAc, 5/1, 3/1, 2/1). 0.67 g of the product was obtained as oil.

Step 3: 6-N-t-Butoxycarbonylaminomethyl-2H-2-(4-methoxybenzyl)-1,4-benzothiazin-3(4H)-one-4-ylacetic Acid N-Hydroxyamide The compound in step 2 was converted to 600 mg of the hydroxamic acid by the reactions analogous to those described in Example 777.

Step 4: 6-Aminomethyl-2H-2-(4-methoxybenzyl)-1,4-benzothiazin-3(4H)-one-4-ylacetic Acid N-Hydroxyamide Hydrochloride To a solution of the compound in step 3 (485 mg) in 4N HCl/dioxane (3 mL) was stirred for 1 hr at 0° C. The reaction mixture was diluted with $Et_2O$ and the precipitate was filtered and washed with $Et_2O$. 300 mg of the product was obtained as pale yellow solid.

The following compounds listed in the Table 23 were prepared in a similar manner.

TABLE 23

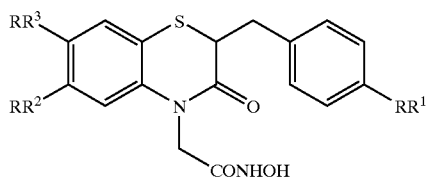

| Example No. | RR$^1$ | RR$^2$ | RR$^3$ | NMR: $^1$H-NMR(DMSO-d6; δ) |
|---|---|---|---|---|
| 869 | —OMe | —CH2NH2 | —H | 2.62(1H, dd, J=9Hz, 14Hz), 3.06(1H, dd, J=6, 14Hz), 3.71(3H, s), 3.80(1H, dd, J=6, 9Hz), 4.01(2H, m), 4.48–5.00(2H, m), 6.83(2H, d, J=8.6Hz), 7.09(2H, d, J=8.6Hz), 7.19(1H, m), 7.39(2H, m), 8.32(3H, bs), 8.95, 9.43(1H, bs), 10.30, 10.83(1H, bs). |
| 870 | —OMe | —CH2NHBoc | —H | 1.33(9H, s), 2.57(1H, m), 3.06(1H, m), 3.66(3H, s), 3.70(1H, dd, J=6, 9Hz), 4.05(2H, bd, J=5.7Hz), 4.3–4.9(2H, m), 6.76(2H, d, J=8.5Hz), 6.88(1H, d, J=8Hz), 6.97(1H, s), 7.05(2H, d, J=8.5Hz), 7.25(1H, d, J=8Hz), 7.34(1H, t, J=5.7Hz)m, 8.91, 9.33(1H, bs), 10.24, 10.69(1H, bs). |
| 871 | —H | —CH2NH2 | —H | 2.62(1H, dd, J=9.5, 14.2Hz), 3.09(1H, dd, J=5.7, 14.2Hz), 3.81(1H, m), 3.95, 3.98(2H, s), 4.44–4.88(2H, m), 7.10–7.24(6H, m), 7.35(2H, m), 8.33(3H, bs), 8.92, 9.40(1H, bs), 10.27, 10.81(1H, bs). |
| 872 | —OMe | —H | —CH2NH2 | 2.59(1H, m), 3.09(1H, dd, J=5.5, 14Hz), 3.72(3H, s), 3.83(1H, m), 3.96(2H, s), 6.83(2H, d, J=8.5Hz), 4.48–5.00(2H, m), 7.13(2H, d, J=8.5Hz), 7.17(1H, d, J=8.5Hz), 7.37(1H, d, J=8.5), 7.49(1H, s), 8.19(3H, bs), 9.43, 8.97(1H, bs), 10.80, 10.32(1H, bs). |

Example 873

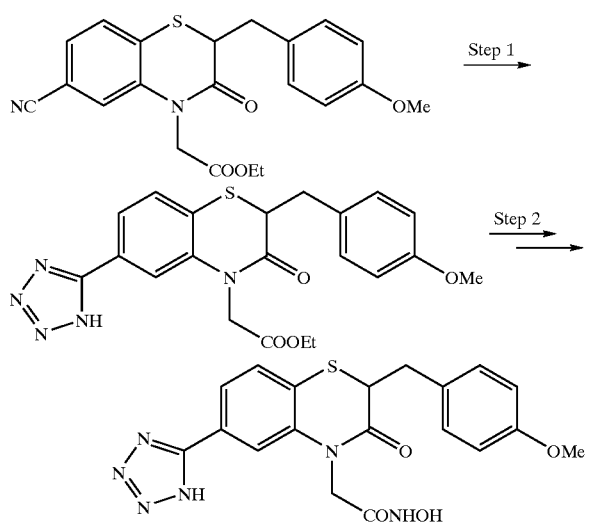

Step 1: Ethyl 6-Tetrazolyl-2H-2-(4-methoxybenzyl)-1,4-benzothiazin-3(4H)-one-4-ylacetate Ethyl 6-cyano-2H-2-(4-methoxybenzyl)-1,4-benzothiazin-3(4H)-one-4-ylacetate (700 mg) was dissolved in DMF (5 mL), and sodium azide (573 mg), ammonium chloride (641 mg) were added at r.t. The reaction mixture was stirred at 90° C. for 24 hrs, diluted with water (50 ml) and 1N HCl (5 ml), and extracted with EtOAc. The organic layer was washed with brine, dried over MgSO$_4$, and concentrated under reduced pressure. The residue was purified with silica gel column chromatography (Eluent: chloroform/MeOH, 30/1, 20/1, chloroform/MeOH/AcOH= 20/1/0.1). 800 mg of the product was obtained as oil.

Step 2: 6-Tetrazolyl-2H-2-benzyl-1,4-benzothiazin-3(4H)-one-4-ylacetic Acid N-Hydroxyamide The compound in step 1 was converted to 594 mg of the product by the procedure analogous to Example 777.

The following compounds listed in the Table 24 were prepared in a similar manner.

TABLE 24

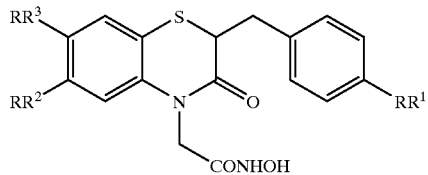

| Example No. | RR$^1$ | RR$^2$ | RR$^3$ | NMR: $^1$H-NMR(DMSO-d6; δ) |
|---|---|---|---|---|
| 873 | —OMe | -5-Tetrazolyl | —H | 2.70(1H, dd, J=9.3, 14.3Hz), 3.11(1H, dd, J=6.0, 14.3Hz), 3.05(3H, s), 3.94(dd, 1H, J=5.9, 9.1 Hz), 4.50–4.97(2H, m), 6.84(2H, d, J=8.6Hz), 7.14(2H, d, J=8.6Hz), 7.60–7.82(3H, m), 9.06, 9.49(1H, bs), 10.42, 10.86(1H, bs). |

TABLE 24-continued

[Structure with RR¹, RR², RR³ substituents on benzothiazinone with CONHOH group]

| Example No. | RR¹ | RR² | RR³ | NMR: ¹H-NMR(DMSO-d6; δ) |
|---|---|---|---|---|
| 874 | —H | -5-Tetrazolyl | —H | 2.75(1H, dd, J=8Hz, 14Hz), 3.20(1H, m), 3.98(1H, m), 4.50–5.10(2H, m), 7.30(5H, m), 7.70 (2H, m), 7.82(1H, s), 9.05, 9.55(1H, bs), 10.40, 10.85(1H, bs). |
| 875 | —OMe | —H | -5-Tetrazolyl | 2.69(1H, dd, J=9.2, 14Hz), 3.11(1H, dd, J=6, 14Hz), 3.72(3H, s), 3.94(1H, dd, J=6, 9.2Hz), 4.50–4.98(2H, m), 6.84(2H, d, J=8.5Hz), 7.14(2H, d, J=8.5Hz), 7.35(1H, d, J=8.8Hz), 7.94(1H, dd, J=2, 8.8Hz), 8.07(1H, d, J=2Hz), 9.42, 9.03(1H, bs), 10.83, 10.40(1H, bs). |

Example 876

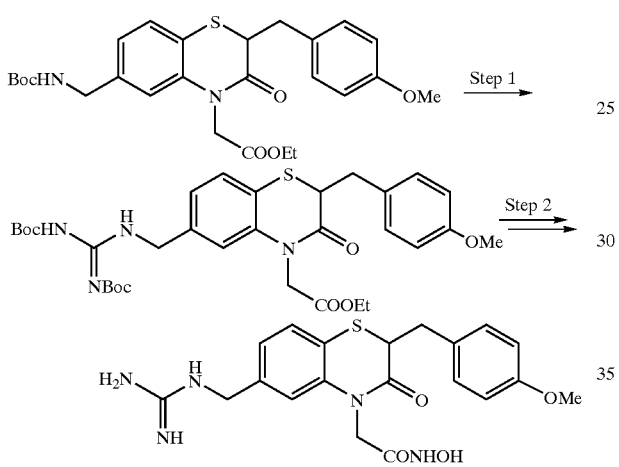

Step 1: Ethyl 6-(2,3-di-t-Butoxycarbonylguanidino)-methyl-2H-2-(4-methoxybenzyl)-1,4-benzothiazin-3(4H)-one-4-ylacetate The compound, obtained in Example 869 (Step 2), was dissolved in THF (2 mL) and H₂O (0.04 mL). The N,N'-di-t-butoxycarbonyl-S-methylisothiourea (369 mg) and triethylamine (89 ul) were added at r.t. and the stirring was continued for 2 hrs at 50° C. The reaction mixture was concentrated under reduced pressure, and the residue was purified with silica gel column chromatography (Eluent: hexane/EtOAc, 8/1, 6/1). 200 mg of the product was obtained as oil.

Step 2: 6-(2,3-Di-t-Butoxycarbonylguanidino)methyl-2H-2-(4-methoxybenzyl)-1,4-benzothiazin-3(4H)-one-4-yl-acetic Acid N-Hydroxyamide The compound in step 1 was converted to 510 mg of the hydroxamic acid by the procedure analogous to Example 777.

Step 3: 6-Guanidinomethyl-2H-2-(4-methoxybenzyl)-1,4-benzothiazin-3(4H)-one-4-ylacetic Acid Hydroxyamide The compound in Step 2 (110 mg) was dissolved in TFA (3 ml)-ethanedithiol (100 ul) at 0° C., and stirred at r.t. for 1 hr. The reaction mixture was diluted with Et₂O-Toluene (4:1) and, the product(29 mg) was obtained as precipitate.

¹H-NMR (DMSO-d₆, δ); 2.62 (1H, dd, J=9 Hz, 14 Hz), 3.08 (1H, dd, J=6, 14 Hz), 3.78 (3H, s), 3.78 (1H, dd, J=6 Hz, 9 Hz), 4.34 (2H, d, J=6 Hz), 4.45–4.90 (2H, m), 6.83 (2H, d, J=8.4 Hz), 6.98 (1H, d, J=8 Hz), 7.10 (2H, d, J=8.4 Hz), 7.16 (1H, s), 7.30 (4H, bs), 7.38 (1H, d, J=8 Hz), 8.00 (1H, t, J=6 Hz), 8.97, 9.42 (1H, bs), 10.31, 10.80 (1H, bs).

Example 877

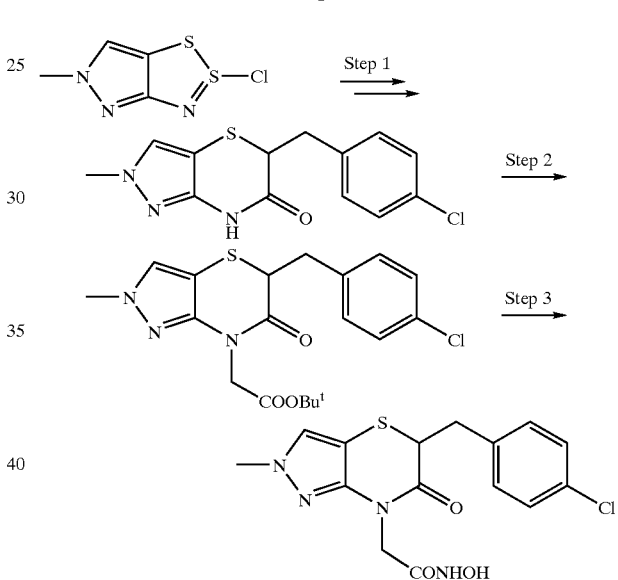

Step 1: 2-Methyl-5H-5-(4-chlorobenzyl)-pyrazolo[4,3-b]thiazin-6(7H)-one

A solution of 5-methylpyrazolo[3,4-d]dithiazolium chloride (930 mg), which was prepared by Chenard's procedure (J. Org. Chem. 49, 1224 (1984)), in 20% NaOH aq. (15 mL) was heated at 80° C. for 1 hr. A solution of 2-bromo-3-(4-chlorophenyl)propionic acid (1.05 g) in 20% NaOH aq. (10 ml) was added at 80° C. and the temperature was maintained at 80° C. for 1.5 hrs. The mixture was cooled to r.t. and concentrated under reduced pressure. The residue was dissolved in acetic acid (50 mL) and heated at 80° C. for 2.5 hours. The reaction mixture was cooled to r.t. and concentrated under reduced pressure. The residue was dissolved in EtOAc and washed with water, 5% Na₂CO₃ aq. and brine. The organic layer was dried over Na₂SO₄ and concentrated. The residue was purified by recrystallization from Et₂O to give the product (512 mg, 44%).

Step 2: t-Butyl 2-Methyl-5H-5-(4-chlorobenzyl)-pyrazolo[4,3-b]thiazin-6(7H)-one-7-ylacetate To a solution of the product of Step 1 (235 mg) in DMF (10 mL), NaH (52 mg, 60% in oil) was added. After 30 minutes' stirring, t-buthyl bromoacetate (203 mg) was slowly added. The reaction mixture was stirred at r.t. overnight. The solvent was removed under reduced pressure and the residue was dissolved in EtOAc and washed with 1N HCl, 5% Na$_2$CO$_3$ aq., and brine. The organic layer was dried over Na$_2$SO$_4$ and concentrated. The residue was purified with silica gel column chromatography (eluent: toluene/EtOAc, 20/1) to give the product(0.33 g, quant.).

Step 3: 2-Methyl-5H-5-(4-chlorobenzyl)-pyrazolo[4,3-b]thiazin-6(7H)-one-7-ylacetic Acid N-Hydroxyamide The product of Step 2 (0.32 g) was solved in TFA (15 mL) at r.t. The mixture was stirred for 2 hours. The solvent was removed under reduced pressure. The crude product (0.28 g) was used in the following step without purification.

Isobutyl chloroformate (120 mg) was added dropwise to a THF (10 mL) solution of 2-methyl-5H-5-(4-chlorobenzyl)-pyrazolo[4,3-b]thiazin-6(7H)-one-7-ylacetic acid (0.28 g) and N-methylmorpholine (170 mg) at −5° C. THF (1 mL) solution of O-TMS-hydoxylamine (101 mg) was added after additional 20 minutes' stirring. The mixture was stirred at −5° C. for 2 hrs, gradually warmed to r.t. with stirring, and stood overnight. The reaction mixture was quenched with water and extracted with EtOAc. The organic layer was washed with saturated NaHCO$_3$, 1N HCl, and brine, dried over Na$_2$SO$_4$ and concentrated under reduced pressure. The residue was purified by recrystallization from Et$_2$O to give the hydroxamic acid (221.3 mg, 77% in 2 steps) as a white powder.

The following compounds listed in the Table 25 were prepared in a similar manner.

TABLE 25

| Example No. | RR$^1$ | NMR: $^1$H-NMR(DMSO-d6; δ) |
|---|---|---|
| 877 | —Cl | 2.79(1H, m), 3.17(1H, m), 3.74(3H, s), 3.92(1H, m), 4.33(2H, m), 7.25(2H, d, J=8.40Hz), 7.34(2H, d, J=8.25Hz), 7.61 (1H, s), 8.88(1H, s), 10.62(1H, s) |
| 878 | —OPh | 2.77(1H, m), 3.17(1H, m), 3.74(3H, s), 3.90(1H, m), 4.34(2H, m), 6.92(2H, d, J=8.48Hz), 6.99(2H, d, J=8.60Hz), 7.14 (1H, m), 7.23(2H, d, J=8.56Hz), 7.37–7.42 (2H, m), 7.62(1H, s), 8.90(1H, s), 10.64 (1H, s) |

Example 879

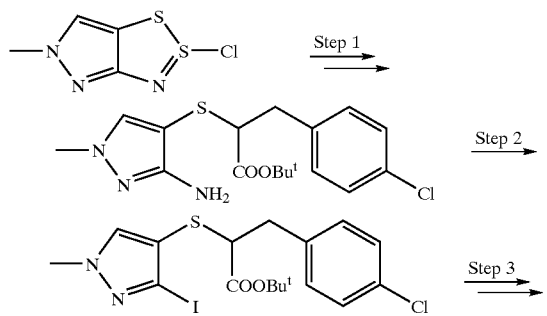

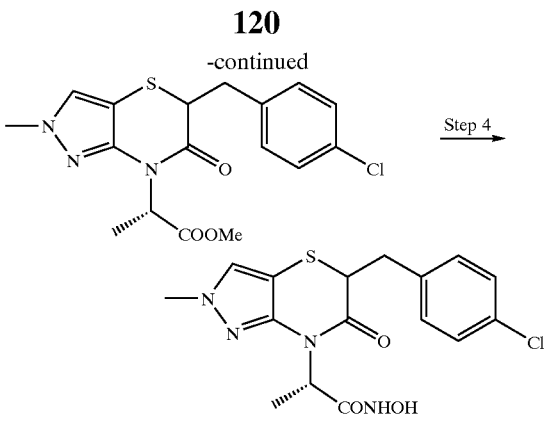

Step 1: t-Butyl 2-(3-Amino-1-methyl-4-pyrazolylthio)-3-(4-chlorophenyl)propanoate A solution of 5-methylpyrazolo[3,4-d]dithiazolium chloride (880 mg), which was prepared by Chenard's procedure (J. Org. Chem. 49, 1224 (1984)), in 20% NaOH aq. (15 mL) was heated at 90° C. for 1.5 hrs. The mixture was cooled to r.t. and the pH was adjusted to 6.0 with AcOH, and adjusted to 10 by Na$_2$CO$_3$ sat. To a mixture of the crude product and Na$_2$CO$_3$ (1.20 g), a solution of t-buthyl 2-bromo-3-(4-chlorophenyl)propionate (1.21 g) in DMF (20 mL) was added. The mixture was stirred at r.t. overnight and concentrated under reduced pressure. The residue was dissolved in EtOAc and washed with water and brine. The organic layer was dried over Na$_2$SO$_4$ and concentrated. The residue was purified with silica gel column chromatography (eluent: toluene/EtOAc, 2/1) to give the product (820 mg, 59%).

Step 2: t-Butyl 2-(3-Iodo-1-methyl-4-pyrazolylthio)-3-(4-chlorophenyl)propanoate To a solution of isoamyl nitrite (605 mg) in diiodomethane (5 ml) at 100° C., a solution of the product of Step 1 (380 mg) in dichloromethane (2 ml) were added dropwise. The reaction mixture was stirred at 100° C. for 1 hr. The solvent was removed under reduced pressure. The residue was purified with silica gel column chromatography (eluent: toluene/EtOAc, 20/1) to give the product (417 mg, 84%).

Step 3: Methyl 2-(S)-[2-Methyl-5H-5-(4-chlorobenzyl)-pyrazolo[4,3-b]thiazin-6(7H)-one-7-yl]-propanoate The product of Step 2 (335 mg) was dissolved in TFA (10 mL). The mixture was stirred at r.t. for 2 hrs. The solvent was removed under reduced pressure. To the solution of the residue (347 mg) and L-alanine methyl ester. HCl (215 mg) in DMF (10 mL), Et$_3$N (290 uL), HOBt (235 mg) and EDC.HCl (295 mg) were added. The reaction mixture was stirred at r.t. for 2 days. The solvent was removed under reduced pressure. The residue was dissolved in EtOAc and washed with 1N HCl, 5% Na$_2$CO$_3$ aq. And brine. The organic layer was dried over Na$_2$SO$_4$ and concentrated. The residue was purified with silica gel column chromatography (eluent: toluene/EtOAc, 2/1) to give the alanine derivative (316 mg, 89% in 2 steps).

To a solution of the alanine derivative (205 mg) and in DMF (10 mL), K$_2$CO$_3$ (112 mg), Cu powder (128 mg) were added. The reaction mixture was heated to 140° C. and stirred for 3 hrs. The mixture was diluted with EtOAc and filtered. The solvent was removed under reduced pressure. The residue was purified with silica gel column chromatography (eluent: toluene/EtOAc, 10/1) to give the product (128 mg, 83%).

121

Step 4: 2-(S)-[2-Methyl-5H-5-(4-chlorobenzyl)-pyrazolo[4,3-b]thiazin-6(7H)-one-7-yl]-propanoic Acid N-Hydroxyamide To a solution of the product of Step 3 (141 mg) in methanol (10 ml), 1N NaOH (2.0 mL) was slowly added at 0° C. After 30 minutes' stirring, the mixture was warmed to r.t. and left overnight. The reaction mixture was concentrated under reduced pressure. The residue was dissolved in EtOAc and water, washed with 1N HCl and water. The organic layer was dried over Na$_2$SO$_4$ and concentrated. To a THF (10 mL) solution of the crude product (151 mg) and N-methylmorpholine (45 mg), isobutyl chloroformate (61 mg) was added dropwise at −5° C. THF (0.5 mL) solution of O-TMS-hydoxylamine (51 mg) was added after additional 30 minutes' stirring. The mixture was stirred at −5° C. for 2 hrs, gradually warmed to r.t. with stirring, and stood overnight. The reaction mixture was quenched with water, concentrated under reduced pressure, and dissolved in EtOAc. The organic layer was washed with 1N HCl and brine, dried over Na$_2$SO$_4$ and concentrated under reduced pressure. The residue was purified by recrystallization from chloroform, Et$_2$O, and hexane to give the hydroxamic acid (110 mg, 78% in 2 steps) as a white powder.

The following compounds listed in the Table 33 were prepared in a similar manner.

TABLE 33

| Example No. | RR$^1$ | NMR: $^1$H-NMR(DMSO-d6; δ) |
|---|---|---|
| 1007 | (S) —Me | 1.45(3H, m), 2.76(1H, m), 3.14(0.5H, m), 3.26(0.5H, m), 3.73(1.5H, s), 3.75 (1.5H, s), 3.85(0.5H, m), 3.96(0.5H, m), 5.01(0.5H, m), 5.21(0.5H, m), 7.25(2H, d, J=8.43Hz), 7.32–7.37(2H, m), 7.59 (0.5H, s), 7.62(0.5H, s), 8.76(0.5H, s), 8.78(0.5H, s), 10.42(1H, s) |
| 1008 | (R) —Me | 1.45(3H, m), 2.76(1H, m), 3.14(0.5H, m), 3.25(0.5H, m), 3.73(1.5H, s), 3.74 (1.5H, s), 3.85(0.5H, m), 3.96(0.5H, m), 5.01(0.5H, m), 5.21(0.5H, m), 7.25(2H, d, J=8.43Hz), 7.33(2H, m), 7.59(0.5H, s), 7.61(0.5H, s), 8.76(0.5H, s), 8.78 (0.5H, s), 10.42(1H, s) |
| 1009 | (R) —iPr | 0.67(3H, m), 1.02(3H, m), 2.72–2.80 (2H, m), 3.23(1H, m), 3.74(1.5H, s), 3.77(1.5H, s), 3.91(1H, m), 4.62(0.5H, d, J=10.62Hz), 4.75(0.5H, d, J=10.62 Hz), 7.25(2H, m), 7.35(2H, m), 7.61 (0.5H, s), 7.63(0.5H, s), 8.78(0.5H, s), 8.81(0.5H, s), 10.40(1H, s) |

Example 880

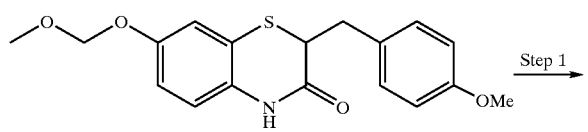

122

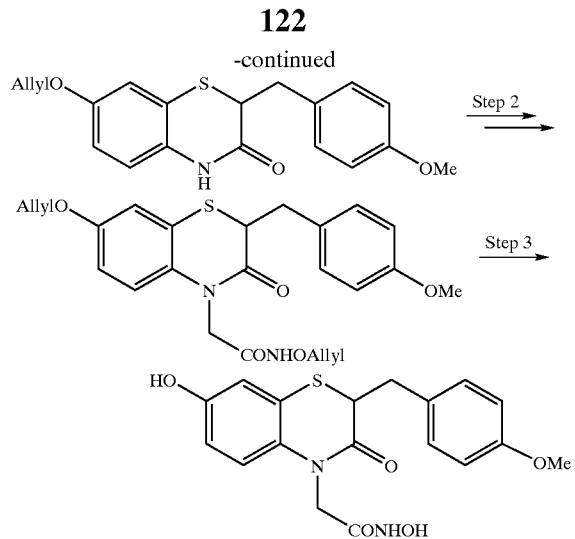

Step 1: 7-Allyloxy-2H-2-(4-methoxybenzyl)-1,4-benzothiazin-3(4H)-one

To a solution of 7-metoxymethyloxy-2H-2-(4-methoxybenzyl)-1,4-benzothiazin-3(4H)-one (1 g) in MeOH (20 ml), 4N HCl-dioxane (2 ml) was added at r.t. and stirring was continued for 24 hrs. The reaction mixture was concentrated and Et$_2$O was added. The colorless crystal (800 mg) was filtered.

The product was dissolved in DMF (5 mL), and allyl bromide (252 ul) and K$_2$CO$_3$ (366 mg) were added at 0° C. The reaction mixture was stirred at r.t. for 24 hrs, diluted with water, and extracted with EtOAc. The organic layer was washed with brine, dried over MgSO$_4$ and concentrated under reduced pressure. The residue was purified with silica gel column chromatography (Eluent: hexane/EtOAc, 4/1, 3/1). 560 mg of the product was obtained as oil.

Step 2: 7-Allyloxy-2H-2-(4-methoxybenzyl)-1,4-benzothiazin-3(4H)-one-4-ylacetic Acid N-Allyloxyamide The product of Step 1 (560 mg) was converted to 7-allyloxy-2H-2-(4-methoxybenzyl)-1,4-benzothiazin-3 (4H)-one-4-ylacetic acid N-allyloxyamide as described in Example 777. The product (650 mg) was obtained as oil.

Step 3: 7-Hydroxy-2H-2-(4-methoxybenzyl)-1,4-benzothiazin-3(4H)-one-4-ylacetic Acid N-Hydroxylamide To a solution of the product of Step 2 (650 mg) was dissolved in EtOH (8 ml) and H$_2$O (2 ml), tetrakis-triphenylphosphine palladium (175 mg) and formic acid (108 ul) were added at r.t. The mixture was stirred under reflux for 2 hrs. The reaction mixture was diluted with water and extracted with EtOAc. The organic layer was washed with sat.NaHCO$_3$, brine, 1N HCl, and brine, dried over MgSO$_4$ and concentrated under reduced pressure. The residue was purified with silica gel column chromatography (Eluent: chloroform/MeOH, 50/1, 30/1). The oily residue was crystalized in toluene-Et$_2$O, and the product (345 mg) was obtained as pale yellow crystal.

The following compounds listed in the Table 26 were prepared in a similar manner.

TABLE 26

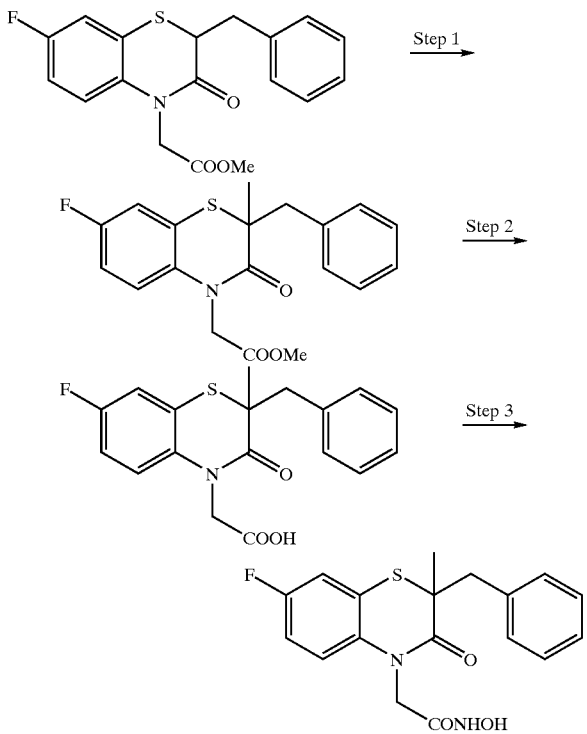

| Example No. | RR¹ | RR² | RR³ | NMR: ¹H-NMR(DMSO-d6; δ) |
|---|---|---|---|---|
| 880 | —OMe | —H | —OH | 2.62(1H, dd, J=9.3, 14 Hz), 3.09(1H, dd, J= 6.14Hz), 3.73(3H, s), 3.74(1H, m), 4.30–4.74 (2H, m), 6.67(2H, m), 6.82(2H, d, J=8.5Hz), 6.94(1H, d, J=9Hz), 7.10(2H, d, J=8.5Hz), 9.33, 8.95(1H, bs), 9.55 (1H, bs), 10.71, 10.28 (1H, bs). |
| 881 | —OMe | —OH | —H | 2.58(1H, dd, J=9.6, 14.5 Hz), 3.06(1H, dd, J=5.2, 14.5Hz), 3.69(3H, s), 3.69(1H, m), 4.2–4.9 (2H, m), 6.47(1H, dd, J=2, 8.4Hz), 6.53(1H, d, J=2Hz), 6.53(2H, d, J=8.8Hz), 7.09(3H, m), 8.97(1H, bs), 9.36, 9.72 (1H, s), 10.73, 10.32 (1H, bs). |

Example 882

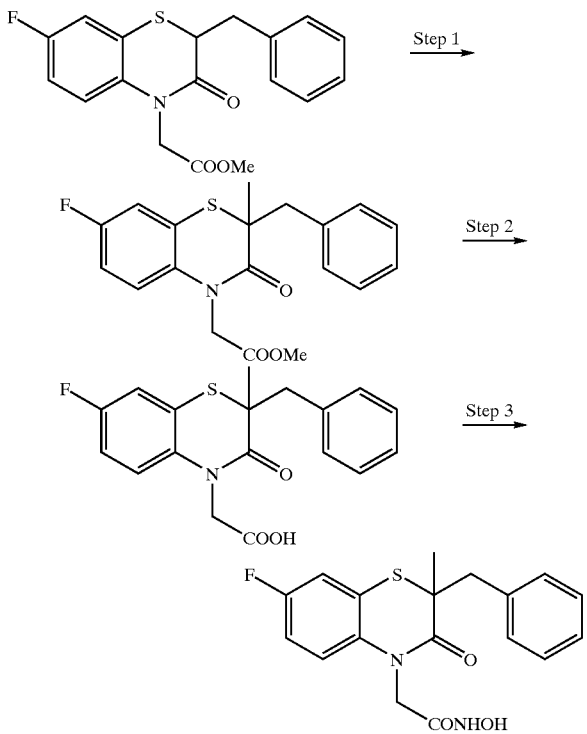

Step 1: Methyl 7-Fluoro-2H-2-benzyl-2-methyl-1,4-benzothiazin-3(4H)-one-4-yl-acetate Methyl 7-fluoro-2H-2-benzyl-1,4-benzothiazin-3(4H)-one-4-yl-acetate (100 mg, 0.29 mmol) was dissolved in THF (5 mL) at −78° C. and lithium hexamethyl disilazane 1M solution in THF (0.64 mmol, 0.64 ml) was added. The mixture was stirred for 1 hr and methyl iodide (39.7 ml, 0.64 mmol) was added. The mixture was allowed to warm to r.t., then poured into saturated solution of sodium carbonate (5 ml), diluted with EtOAc. The 2 layers were separated and the water layer extracted 2 additional times with ethyl acetate. The combined organic layers were dried with $MgSO_4$, evaporated and carried out to the next step with no further purification.

Step 2: 7-Fluoro-2H-2-benzyl-2-methyl-1,4-benzo-thiazin-3 (4H)-one-4-yl-acetic Acid Compound in step 1 was dissolved in dioxane (2 ml) and saturated solution of lithium hydroxide (2 ml). The mixture was stirred at room temperature for 12 hours, then acidified with conc.HCl and extracted with ethyl acetate, dried with $MgSO_4$ and evaporated to give product 3 as a solid.

Step 3: 7-Fluoro-2H-2-benzyl-2-methyl-1,4-benzo-thiazin-3 (4H)-one-4-yl-acetic Acid N-Hydroxyamide Acid obtained obtained in step 2 was dissolved in 1 ml of DCM and 1 ml of pyridine. Pentafluorophenol trifluoroacetate (74.7 ml, 0.43 mmol) was added and the mixture stirred at room temperature for 1 hour. Then, $O-TBDMSNH_2OH$ (129 mg, 0.87 mmol) was added, the mixture stirred for an additional 12 hours then acidified until pH=1 with cHCl, diluted with DCM (3 ml) and water (2 ml). The organic layer was separated and then evaporated, the solid obtained re-dissolved in DMSO and purified using reverse phase HPLC.

Retention time of HPLC analysis: 2.69 min; Mass: 361.2, 328.0 (M.W.=360).

Example 883

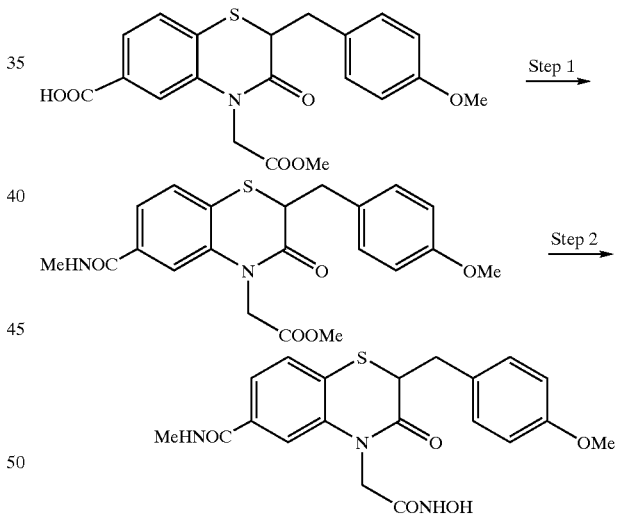

Step 1: Methyl [2H-2-Benzyl-6-N-methylcarbamoyl-3(4H)-oxo-1,4-benzothiazine-4-yl]-acetate Methyl [2H-2-benzyl-6-carboxyl-3(4H)-oxo-1,4-benzothiazine-4-yl]acetate (62 mg, 0.17 mmol), diisopropylethylamine (45 ml, 0.25 mmol), HOBT (35 mg, 0.25 mmol) and EDC.HCl (50 mg, 0.25 mmol) were dissolved in DCM (2 ml) and the reaction mixture was stirred at room temperature for 1 hour. Methylamine (64 ml, 0.51 mmol) (8.03 M in ethanol) was added to the mixture and stirring was continued for an additional 12 hours. The reaction mixture was diluted in DCM (5 ml) and washed with 1N HCl (2×2 ml), water (2 ml) and brine (2 ml). The organic layer was concentrated in vacuo and the crude amide was used directly in the next step.

Step 2: [2H-2-Benzyl-6-N-methylcarbamoyl-3(4H)-oxo-1,4-benzothiazine-4-yl]-acetic Acid N-Hydroxyamide Potassium hydroxide (109 mg, 1.93 mmol) and hydroxylamine hydrochloride (85 mg, 1.22 mmol) were dissolved in methanol (0.53 ml and 0.9 ml respectively) at room temperature. Once a solution was obtained the potassium hydroxide solution was poured into the hydroxylamine solution at 0° C. and the mixture was maintained at this temperature for 1 hour. The precipitate (potassium chloride) was filtered off, the liquid added into the solution of the methyl ester, obtained in step 1, (in methanol (1 ml) and stirring was continued for an additional 3 hours. Acetic acid (0.5 ml) was added to the mixture and the solvent was evaporated to dryness. The residue was then re-dissolved in water and extracted with ethyl acetate (2×3 ml). The combined organic extracts were evaporated to dryness, re-dissolved in DMSO and purified via reverse phase chromatography to yield the major product of the reaction together with small amount of the sulfoxide.

The following compounds listed in the Table 27 and 28 were prepared in a similar manner.

TABLE 27

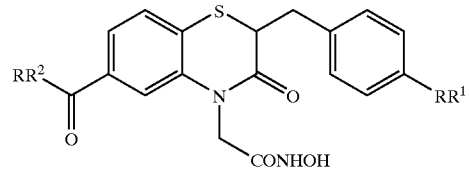

| Example No. | RR¹ | RR² | mol. weitht | Mass (m/e) | HPLC rt (min) |
|---|---|---|---|---|---|
| 883 | —OMe | —NHMe | 415.5 | 416.4, 383.2 | 2.88 |
| 884 | —H | —NH(CH2)2OMe | 429.5 | 430.2, 397 | 2.62 |
| 885 | —H | —morpholino | 441.5 | 442.2, 409.2 | 2.71 |
| 886 | —H | —NHCH2-cyclopropyl | 425.5 | 426.2, 393.2 | 2.91 |
| 887 | —H | —NHCH2-2-furyl | 451.5 | 452.2, 419.2 | 2.93 |
| 888 | —H | —NMe2 | 399.5 | 400.2, 366.8 | 2.71 |
| 889 | —H | —NHiPr | 413.5 | 414.2, 381.0 | 3.85 |
| 890 | —H | —NH-cyclopentyl | 439.5 | 440.4, 407.2, 379 | 3.99 |
| 891 | —H | —NH-3-isoxazolyl-5-Me | 452.5 | 453.2, 420.2 | 3.86 |
| 892 | —H | —piperidino | 439.5 | 440.4, 407.2 | 3.96 |
| 893 | —H | —NH-3-pyrazolyl | 437.5 | 438.2, 405 | 3.77 |
| 894 | —H | —NHCH2CF3 | 453.4 | 454.2, 421.0 | 3.97 |
| 895 | —H | —NH(CH2)2CH | 415.5 | 416.2, 383.0 | 3.70 |
| 896 | —H | —NHMe | 385.4 | 386.2, 353.0 | 3.77 |
| 897 | —H | —NH-2-pyridyl | 448.5 | 449.0 | 2.25 |
| 898 | —H | —NH2 | 371.4 | 372.2, 339.0 | 3.55 |
| 899 | —H | —NH-cyclopropyl | 411.5 | 412.2, 379.2 | 3.83 |
| 900 | —OMe | —NH-3-pyrazolyl | 467.5 | 468.4, 435.2 | 2.91 |
| 901 | —OMe | —NHPh | 477.5 | 478.2, 445.2 | 3.01 |
| 902 | —OMe | —NHCH2CF3 | 483.5 | 484.3, 451.0 | 2.84 |

TABLE 28

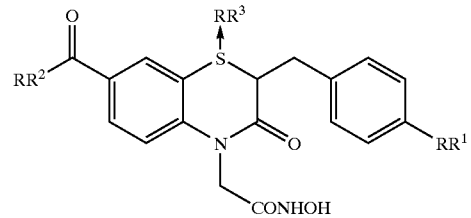

| Example No. | RR¹ | RR² | RR³ | mol. weitht | Mass (m/e) | HPLC rt (min) |
|---|---|---|---|---|---|---|
| 903 | —H | —NPr2 | — | 455.6 | 456.2, 423.2 | 2.86 |
| 904 | —H | —piperidino | — | 439.5 | 440.2, 407.2 | 4.02 |
| 905 | —H | —piperidino | O | 455.5 | 456.2, 437.9, 422.9, 405.2 | 3.95 |
| 906 | —H | —NMe2 | O | 415.5 | 416.2, 398.2, 383.2, 365.2 | 3.74 |
| 907 | —H | —NMe2 | — | 399.5 | 400.2, 367.2 | 3.73 |
| 908 | —H | —NH-cyclopropyl | O | 427.5 | 428.2, 410.2, 395.2 | 3.72 |
| 909 | —H | —NH-cyclopropyl | — | 411.5 | 412.2, 379.0 | 3.82 |
| 910 | —H | —NHMe | — | 385.4 | 386.2, 353.0 | 2.88 |
| 911 | —H | —NHiPr | — | 413.5 | 414.2, 381.2 | 3.97 |
| 912 | —H | —NH-cyclopentyl | O | 455.5 | 455.9, 438.2, 422.9 | 3.90 |
| 913 | —H | —NH-3-pyrazolyl | O | 453.5 | 454.2, 436.4, 421.4 | 3.78 |
| 914 | —H | —NH-3-pyrazolyl | — | 437.5 | 438.2, 405.2 | 3.80 |

TABLE 28-continued

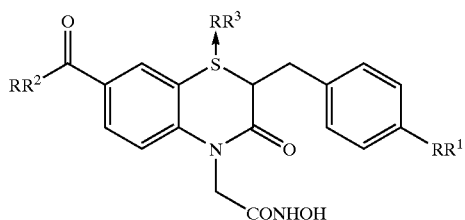

| Example No. | RR¹ | RR² | RR³ | mol. weitht | Mass (m/e) | HPLC rt (min) |
|---|---|---|---|---|---|---|
| 915 | —H | —NH2 | — | 371.4 | 372.0, 339.0 | 3.62 |
| 916 | —H | —NHiPr | O | 429.5 | 430.4, 412.2, 397.5 | 3.84 |
| 917 | —H | —morpholino | O | 457.5 | 458.1, 440.2, 425.2 | 3.59 |
| 918 | —H | —morpholino | — | 441.5 | 442.2, 409.2 | 3.72 |
| 919 | —H | —NHPh | O | 463.5 | 464.1, 446.2, 431.2, 413.2 | 4.03 |
| 920 | —H | —NHPh | — | 447.5 | 448.0, 415.2 | 4.10 |
| 921 | —H | —NH-2-pyridyl | — | 448.5 | 449.0, 416.2 | 3.80 |
| 922 | —H | —NHCH2-2-furyl | O | 467.5 | 467.9, 450.0, 434.9, 417.0 | 3.95 |
| 923 | —H | —NHCH2-2-furyl | — | 451.5 | 452.0, 419.2 | 4.04 |
| 924 | —H | —NH-3-isoxazolyl-5-Me | O | 468.5 | 469.3, 451.0, 436.4 | 2.43 |
| 925 | —H | —NH-3-isoxazolyl-5-Me | — | 452.5 | 453.0, 420.2 | 2.56 |
| 926 | —H | —NH-cyclopentyl | — | 439.5 | 440.2, 407.2 | 3.97 |
| 927 | —H | —NHCH2CF3 | O | 469.4 | 470.1, 452.0, 437.1 | 2.43 |
| 928 | —H | —NHCH2CF3 | — | 453.4 | 454.2, 421.0 | 2.54 |
| 929 | —H | —NHCH2-cyclopropyl | O | 441.5 | 442.4, 424.0, 409.4 | 2.39 |
| 930 | —H | —NHCH2-cyclopropyl | — | 425.5 | 426.2, 393.2 | 2.50 |
| 931 | —H | —NH(CH2)2OH | O | 431.5 | 432.2, 414.2, 399.0 | 1.89 |
| 932 | —H | —NH(CH2)2OH | — | 415.5 | 416.2, 383.2 | 2.01 |
| 933 | —H | —OH | — | 372.4 | 373.5, 340.0 | 2.23 |
| 934 | —H | —NH—(R)-2-butyl | O | 443.5 | 443.9, 426.2, 410.9 | 2.46 |
| 935 | —H | —NH—(R)-2-butyl | — | 427.5 | 428.2, 395.2 | 2.59 |
| 936 | —H | —NH—(S)—CH(Me)COOH | — | 443.5 | 444.2, 411.2 | 2.16 |
| 937 | —H | —NH—(S)—CH(iBu)COOH | — | 485.6 | 486.2, 453.2 | 2.56 |

Example 938

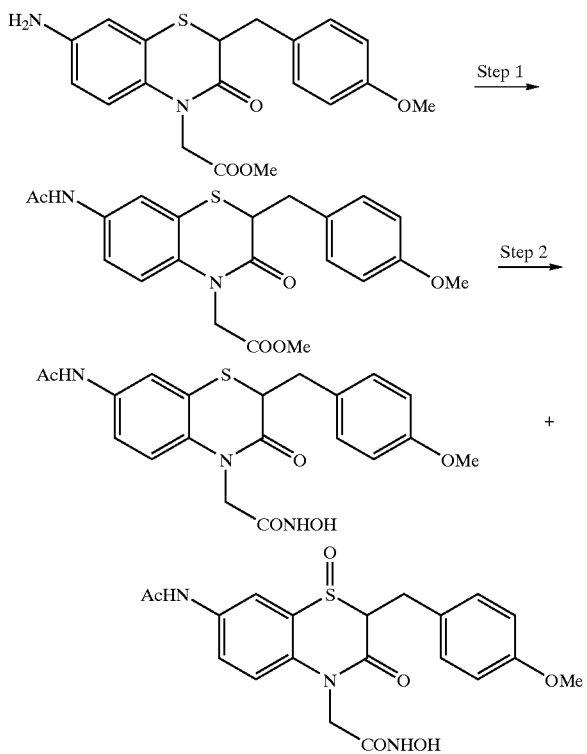

Step 1: Methyl 7-Acetoamino-2H-2-(4-methoxybenzyl)-3 (4H)-oxo-1,4-benzothiazine-4-yl-acetate Methyl 7-amino-2H-2-(4-methoxybenzyl)-3(4H)-oxo-1, 4-benzothiazine-4-yl-acetate (63 mg, 0.17 mmol), was dissolved in DCM (2 ml). Triethylamine (24 ml, 0.17 mmol) was added followed by acetyl chloride (12 ml, 0.17 mmol), and the reaction mixture was stirred at room temperature for 1 hour. The reaction mixture was diluted in DCM (5 ml) and washed with saturated $Na_2CO_3$ (2×2 ml), water (2 ml) and brine (2 ml). The organic layer was concentrated in vacuo and the crude amide was used directly in the next step.

Step 2: [7-Acetoamino-2H-2-benzyl-3(4H)-oxo-1,4-benzothiazine-4-yl]-acetic Acid N-Hydroxyamide Potassium hydroxide (109 mg, 1.93 mmol) and hydroxylamine hydrochloride (85 mg, 1.22 mmol) were dissolved in methanol (0.53 ml and 0.9 ml respectively) at room temperature. Once a solution was obtained the potassium hydroxide solution was poured into the hydroxylamine solution at 0° C. and the mixture was maintained at this temperature for 1 hour. The precipitate (potassium chloride) was filtered off, the liquid added into the solution of the methyl ester obtained in step 1 in methanol (1 ml) and stirring was continued for an additional 3 hours. Acetic acid (0.5 ml) was added to the mixture and the solvent was evaporated to dryness. The residue was then re-dissolved in water and extracted with ethyl acetate (2×3 ml). The combined organic extracts were evaporated to dryness, dissolved in DMSO and purified by reverse phase chromatography to yield the major product of the reaction together with small amount of the sulfoxide.

The following compounds listed in the Table 29 were prepared in a similar manner.

TABLE 29

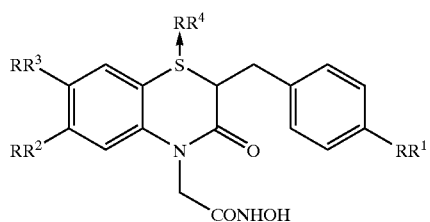

| Example No. | RR¹ | RR² | RR³ | RR⁴ | mol. weight | Mass (m/e) | HPLC rt (min) |
|---|---|---|---|---|---|---|---|
| 938 | —OMe | —H | —NHCOCH3 | O | 431.5 | 431.9, 414.2, 399.0 | 2.60 |
| 939 | —OMe | —NHCOEt | —H | — | 429.5 | 430.2, 397.0 | 2.88 |
| 940 | —H | —NHCOtBu | —H | — | 427.5 | 428.2, 395.2 | 2.98 |
| 941 | —H | —NHCOEt | —H | O | 415.5 | 416.2, 398.2, 383.2 | 2.31 |
| 942 | —H | —NHCO-2-pyrazinyl | —H | O | 465.5 | 466.4, 448.2 | 2.40 |
| 943 | —H | —NHCO-2-pyrazinyl | —H | — | 449.5 | 450.2, 417.2 | 2.53 |
| 944 | —H | —NHCOCH2—C6H4-4-Cl | —H | — | 496.0 | 496.2, 463.2 | 2.95 |
| 945 | —H | —NHAc | —H | O | 401.4 | 402.7, 384.2 | 2.17 |
| 946 | —H | —NHAc | —H | — | 385.4 | 386.2, 353.0 | 2.33 |
| 947 | —H | —NHBz | —H | O | 463.5 | 464.1, 446.2, 431.2 | 2.62 |
| 948 | —H | —NHBz | —H | — | 447.5 | 448.0, 415.2 | 2.75 |
| 949 | —H | —NHCO—CH2-2-thiophenyl | —H | — | 467.6 | 468.2, 435.2 | 2.72 |
| 950 | —H | —NHCOCH2—C6H4-4-OMe | —H | — | 491.6 | 492.2, 459.2 | 2.76 |
| 951 | —H | —NHCO-2-furyl | —H | — | 437.5 | 438.2, 405.2 | 2.60 |
| 952 | —H | —NHCOCH2Ph | —H | O | 477.5 | 478.3, 460.2, 445.4, 427.2 | 2.65 |
| 953 | —H | —NHCOCH2Ph | —H | — | 461.5 | 462.2, 429.2 | 2.77 |
| 954 | —H | —NHCOEt | —H | — | 399.5 | 400.2, 367.2 | 2.46 |
| 955 | —H | —NHCO-4-pyridyl | —H | O | 484.5 | 464.9, 447.2, 431.9 | 2.10 |
| 956 | —OMe | —H | —NHCOtBu | — | 457.6 | 458.2, 425.2 | 3.48 |
| 957 | —OMe | —H | —NHCOCH3 | — | 415.5 | 416.2, 383.2 | 2.33 |
| 958 | —OMe | —H | —NHCO-2-pyrazinyl | — | 479.5 | 480.2, 447.2 | 2.57 |

Example 959

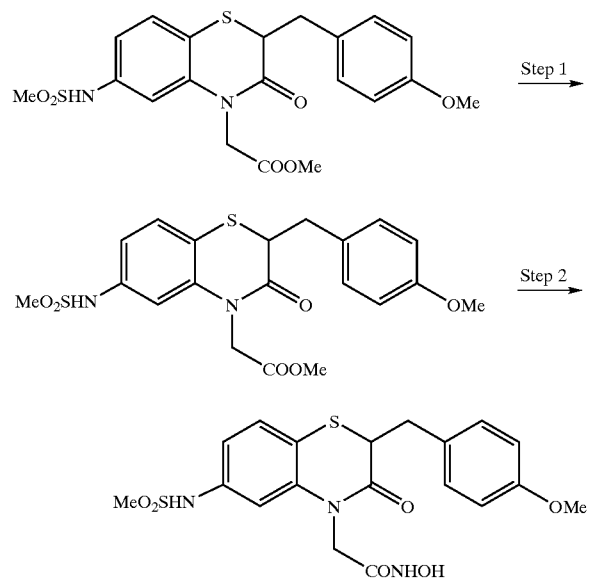

Step 1: Methyl 2H-2-(4-Methoxybenzyl)-6-methylsulfonylamino-3(4H)-oxo-1,4-benzothiazine-4-yl-acetate Methyl 6-amino-2H-2-(4-methoxybenzyl)-3(4H)-oxo-1,4-benzothiazine-4-yl-acetate (63 mg, 0.16 mmol), was dissolved in DCM (2 ml) and pyridine (0.5 ml). Methyl sulfonylchloride (20 ml, 0.26 mmol) was added and the reaction mixture was stirred at room temperature for 3 hour. The reaction mixture was diluted in DCM (5 ml) and washed with 1N HCl (2×2 ml), water (2 ml) and brine (2 ml). The organic layer was concentrated in vacuo and the crude sulfonamide was used directly in the next step.

Step 2: 2H-2-(4-Methoxybenzyl)-6-methylsulfonylamino-3(4H)-oxo-1,4-benzothiazine-4-yl-acetic Acid N-Hydroxyamide Potassium hydroxide (109 mg, 1.93 mmol) and hydroxylamine hydrochloride (85 mg, 1.22 mmol) were dissolved in methanol (0.53 ml and 0.9 ml respectively) at room temperature. Once a solution was obtained the potassium hydroxide solution was poured into the hydroxylamine solution at 0° C. and the mixture was maintained at this temperature for 1 hour. The precipitate (potassium chloride) was filtered off, the liquid added into the solution of the methyl ester in methanol (1 ml) and stirring was continued for an additional 3 hours. Acetic acid (0.5 ml) was added to the mixture and the solvent was evaporated to dryness. The residue was then dissolved in water and extracted with ethyl acetate (2×3 ml). The combined organic extracts were evaporated to dryness, re-dissolved in DMSO and purified by reverse phase chromatography.

The following compounds listed in the Table 30 were prepared in a similar manner.

TABLE 30

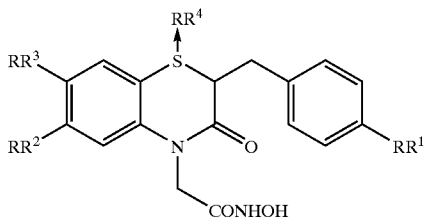

| Example No. | RR¹ | RR² | RR³ | RR⁴ | mol. weitht | Mass (m/e) | HPLC rt (min) |
|---|---|---|---|---|---|---|---|
| 959 | —OMe | —NHMs | —H | — | 451.5 | 452.0, 419.0 | 2.67 |
| 960 | —OMe | —NHTs | —H | — | 527.6 | 528.2, 495.2 | 3.09 |
| 961 | —H | —NHSO2—C6H4-4-Cl | —H | O | 534.0 | 534.5, 516.2, 501.5 | 2.81 |
| 962 | —H | —NHSO2-4-isoxazolyl-3,5-Me2 | —H | — | 502.6 | 503.2, 470.2 | 2.48 |
| 963 | —H | —NHMs | —H | — | 421.5 | 422.2, 389.2 | 2.40 |
| 964 | —H | —NHSO2Ph | —H | O | 499.6 | 500.1, 482.2, 467.1 | 2.59 |
| 965 | —H | —NHSO2Ph | —H | — | 483.6 | 484.2, 451.0 | 2.93 |
| 966 | —H | —NHSO2—C6H4-4-F | —H | — | 501.6 | 502.2, 469.2 | 2.80 |
| 967 | —H | —NHSO2—C6H4-4-OMe | —H | O | 529.6 | 530.0, 512.2, 497.1 | 2.64 |
| 968 | —H | —NHSO2—C6H4-4-OMe | —H | — | 513.6 | 514.3, 481.2 | 2.76 |
| 969 | —H | —NHSO2-2-thiophenyl | —H | O | 505.6 | 506.1, 488.2, 473.1, 455.2 | 2.56 |
| 970 | —H | —NHSO2iPr | —H | — | 449.6 | 450.2, 417.2 | 2.83 |
| 971 | —OMe | —H | —NHMs | — | 451.5 | 452.1, 419.2 | 2.47 |

Example 972

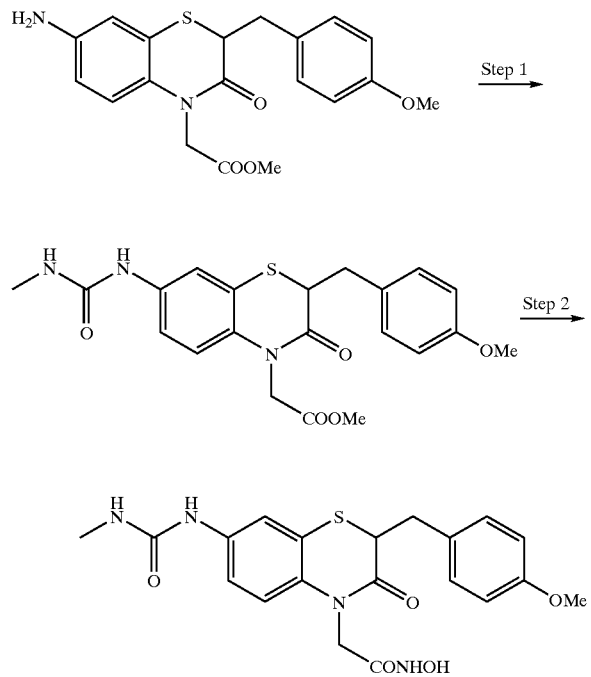

Step 1: Methyl 2H-2-(4-Methoxybenzyl)-7-(N'-methylureido)-3(4H)-oxo-1,4-benzothiazine-4-yl-acetate Methyl 7-amino-2H-2-(4-methoxybenzyl)-3(4H)-oxo-1,4-benzothiazine-4-yl-acetate (63 mg, 0.16 mmol) was dissolved in DCM (2 ml) and pyridine (0.5 ml). Methyl isocyanate (15 mg, 0.26 mmol) was added and the reaction mixture was stirred at room temperature for 3 hour. The reaction mixture was diluted in DCM (5 ml) and washed with saturated $Na_2CO_3$ (2×2 ml), water (2 ml) and brine (2 ml). The organic layer was concentrated in vacuo and the crude urea was carried directly to the next step.

Step 2: 2H-2-(4-Methoxybenzyl)-7-(N'-methylureido)-3 (4H)-oxo-1,4-benzothiazine-4-yl-acetic Acid N-Hydroxyamide Potassium hydroxide (109 mg, 1.93 mmol) and hydroxylamine hydrochloride (85 mg, 1.22 mmol) were dissolved in methanol (0.53 ml and 0.9 ml respectively) at room temperature. Once a solution was obtained the potassium hydroxide solution was poured into the hydroxylamine solution at 0° C. and the mixture was maintained at this temperature for 1 hour. The precipitate (potassium chloride) was filtered off, the liquid added into the solution of the methyl ester, obtained in Step 1, in methanol (1 ml) and stirring was continued for an additional 3 hours. Acetic acid (0.5 ml) was added to the mixture and the solvent was evaporated to dryness. The residue was then dissolved in water and extracted with ethyl acetate (2×3 ml). The combined organic extracts were evaporated to dryness, re-dissolved in DMSO and purified by reverse phase chromatography.

The following compounds listed in the Table 31 were prepared in a similar manner.

TABLE 31

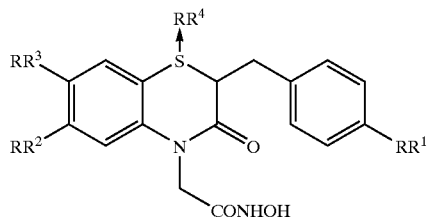

| Example No. | RR¹ | RR² | RR³ | RR⁴ | mol. weitht | Mass (m/e) | HPLC rt (min) |
|---|---|---|---|---|---|---|---|
| 972 | —OMe | —H | —NHCONHMe | — | 430.5 | 431.2, 398.2 | 2.68 |
| 973 | —OMe | —NHCONHPh | —H | — | 493.5 | 494.8, 477.0, 461.9 | 2.53 |
| 974 | —H | —NHCONH—C6H4-4-OMe | —H | O | 508.6 | 509.0, 491.2, 476.1 | 2.61 |
| 975 | —H | —NHCONH—C6H4-4-OMe | —H | — | 492.6 | 493.4, 460.2 | 2.73 |
| 976 | —H | —NHCONHCH2—C6H4-4-F | —H | O | 510.5 | 511.3, 493.4, 478.3, 460.2 | 2.66 |
| 977 | —H | —NHCONHCH2—C6H4-4-F | —H | — | 494.5 | 495.4, 462.2 | 2.77 |
| 978 | —H | —NHCONH—(R)—CH(Me)Ph | —H | — | 490.6 | 491.2, 458.2 | 2.80 |
| 979 | —H | —NHCONHBzl | —H | O | 492.6 | 493.3, 475.2, 460.4, 442.2 | 2.61 |
| 980 | —H | —NHCONHBzl | —H | — | 476.6 | 477.2, 444.2 | 2.74 |
| 981 | —H | —NHCONH—(R)—CH(Me)Ph | —H | O | 506.6 | 507.5, 489.2, 474.6 | 2.68 |
| 982 | —H | —NHCONHMe | —H | — | 400.5 | 401.2, 368.2 | 2.32 |
| 983 | —H | ←—NH—C(O)—NH—(cyclopropyl-Ph) | —H | O | 518.6 | 519.5, 501.2 | 2.73 |
| 984 | —OMe | —H | —NHCONHBu | O | 488.6 | 489.6, 471.2, 456.6 | 3.25 |
| 985 | —OMe | —H | —NHCONHBu | — | 472.6 | 473.2, 440.4 | 2.82 |

Example 986

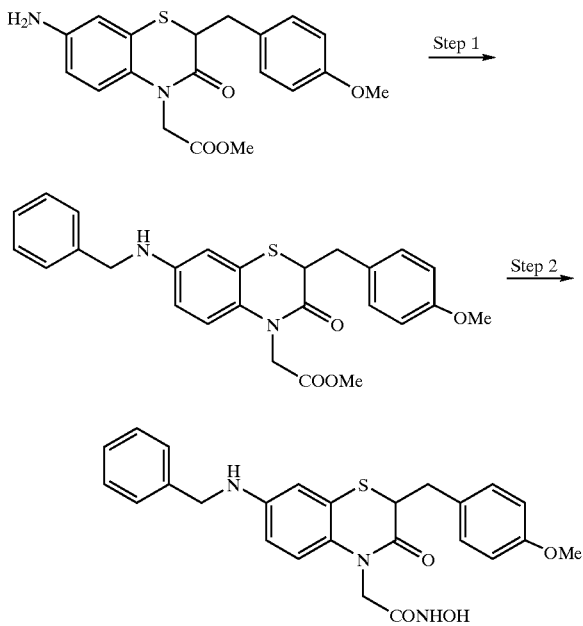

Step 1: Methyl 7-Benzylamino-2H-2-(4-methoxybenzyl)-3 (4H)-oxo-1,4-benzothiazine-4-yl-acetate Methyl 7-amino-2H-2-(4-methoxybenzyl)-3(4H)-oxo-1, 4-benzothiazine-4-yl-acetate (63 mg, 0.17 mmol) and diisopropylethylamine (45.5 ml, 0.27 mmol) were dissolved in DCM (2 ml. Benzaldehyde (27 ml, 0.26 mmol) and sodium triacetoxyborohydride (58 mg, 0.26 mmol) were added to the solution resulting in a suspension that was stirred at room temperature for 3 hour. The reaction mixture was diluted in DCM (5 ml) and washed with saturated $Na_2CO_3$ (2×2 ml), water (2 ml) and brine (2 ml). The organic layer was concentrated in vacuo and the crude amine was used directly in the next step.

Step 2: 7-Benzylamino-2H-2-(4-methoxybenzyl)-3(4H)-oxo-1,4-benzothiazine-4-yl-acetic Acid N-Hydroxyamide Potassium hydroxide (109 mg, 1.93 mmol) and hydroxylamine hydrochloride (85 mg, 1.22 mmol) were dissolved in methanol (0.53 ml and 0.9 ml respectively) at room temperature. Once a solution was obtained the potassium hydroxide solution was poured into the hydroxylamine solution at 0° C. and the mixture was maintained at this temperature for 1 hour. The precipitate (potassium chloride) was filtered off, the liquid added into the solution of the methyl ester, obtained in Step 1, in methanol (1 ml) and stirring was continued for an additional 3 hours. Acetic acid (0.5 ml) was added to the mixture and the solvent was evaporated to dryness. The residue was then dissolved in water and extracted with ethyl acetate (2×3 ml). The combined organic extracts were evaporated to dryness, re-dissolved in DMSO and purified by reverse phase chromatography.

The following compounds listed in the Table 32 were prepared in a similar manner.

TABLE 32

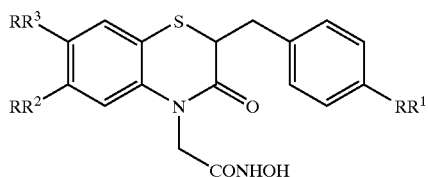

| Example No. | RR¹ | RR² | RR³ | mol. weitht | Mass (m/e) | HPLC rt (min) |
|---|---|---|---|---|---|---|
| 986 | —OMe | —H | —NHBzl | 463.6 | 464.2, 431.2 | 3.03 |
| 987 | —H | —NHBzl | —H | 433.5 | 434.2, 401.2 | 2.90 |

The results of biological testing of some compounds are described below.

BIOLOGICAL DATA

Metallo-proteinases used and inhibition assay protocols are described below.

MMP-2 and MMP-9

Both enzymes were commercially available as active forms (Yagai-Cosmobio) and were used for inhibition assays.

MMP-3 (Matrix Metalloproteinase-3, Stromelysin-1)

C-terminal truncated form of human prostromelysin cDNA (proMMP-3, cDNA sequence in *Nature*, 348, 699–704 (1990)) was subcloned, expressed in *E.coli* and purified as described previously (*Biochemistry* 30, 6476–6483 (1991)). Activation of proMMP-3 was achieved by treatment with 1 mM 4-aminophenylmercuric acetate at 37° C. for 60 min.

MMP-13 (Matrix Metalloproteinase-13, Collagenase-3)

To subclone C-terminal truncated form of procollagenase-3 (proMMP-13) cDNA (J.Biol.Chem., 269 (24), 16766–16773 (1994)), two synthetic oligonucleotide primer (5'-GGAATTC<u>CATATG</u>CTGCCGCTGCCGAG TGGTGGTGATGAAGATG-3' and 5'-TTT GGATCCTTAGCCGTACAGGCTTTGAATACCTTGTA CATCGTCATCAGG-3': the former incorporates sequences for a unique NdeI site (underlined) including initial methionine, and the latter has sequences for a stop codon and BamHI site (underlined)) were used with human chondrocyte cDNA library (CLONTECH) in PCR. With these primers and Pfu DNA polymerase (STRATAGENE) in PCR, 767 bp fragment was generated, which encodes 84 amino acid prosequence and 164 amino acids of mature MMP-13. The fragment was digested with NdaI and BamHI, ligated into the NdeI and BamHI sites of pET11a (STRATAGENE), transformed in *E.coli* BL21 (DE3) and cultured. The crude cell extract was prepared as described in *Biochemistry*. The extract was dialyzed against 20 mM Tris-HCl(pH7.2)/5 mM CaCl$_2$/0.02% NaN$_3$ and applied to a SP-Sepharose HP column (1.6×10 cm, Amersham-Pharmacia Biotech), and elution was performed with 50 mL linear gradient of 0 to 0.3 M NaCl (partially purified proMMP-13 was eluted at 0.2 M approximately). The fraction was dialyzed against 20 mM Tris-HCl(pH7.9)/5 mM CaCl$_2$/200 mM (NH$_4$)$_2$SO$_4$/0.02% NaN$_3$ and applied to a Phenyl Sepharose HP column (1.6×5 cm, Amersham-Pharmacia Biotech), and elution was performed with 20 mL linear gradient of 0.2 to 0 M (NH$_4$)$_2$SO$_4$ (pure proHMP-13 was eluted at 50 mM approximately). The fraction was concentrated by YM-5 ultrafiltration membrane and activated with 4-aminophenylmercuric acetate and active MMP-13 was separated from propeptide fragments by gel filtration chromatography as described in *Biochemistry*.

Inhibition Assays Against MMPs

Enzymatic assays were performed in accordance with C. G. Knight's method (*FEBS Lett.*, 296(3), 263–266 (1992)). The fluorescent MCA-labeled substrate, (7-methoxycumaline-4-yl)-Pro-Leu-Gly-Leu-L-[N-(2,4-dinitrophenyl)-L-2,3-diaminopropionyl]-Ala-Arg-NH$_2$ (Peptide Institute. Inc.) was used for measuring the kinetics of inhibition for each tested compound.

The substrate was incubated at 37° C. for 1.5 hours (MMP-1; for 24 hours) with active MMP (at 20 nM, except MMP-13 at 5 nM) and a test compound in assay buffer containing 100 mM Tris-HCl (pH7.5), 10 mM CaCl$_2$, 100 MM NaCl and 0.05% Brij-35. After the mixture was plated at 100 μL/well onto a 96-well microtiter plate and incubated at 37° C., enzymatic activity in the presence of the compound was estimated by measuring the fluorescence intensity ($\lambda_{ex}$ 320 nm, $\lambda_{em}$ 405 nm) and IC$_{50}$ was determined.

TABLE 10

| | IC50 (μM) | |
|---|---|---|
| Example No. | MMP3 | MMP13 |
| 10 | 31.6 | 5.3 |
| 13 | >50 | 13.2 |
| 19 | 1 | >50 |
| 42 | >10 | 0.759 |
| 46 | 0.894 | 0.134 |
| 71 | 9.071 | 0.249 |
| 88 | 3.798 | 0.062 |
| 92 | 0.794 | 0.048 |
| 105 | 6.717 | 0.231 |
| 109 | 0.599 | 0.043 |
| 121 | 2.547 | 0.128 |
| 130 | 1.141 | 0.056 |
| 143 | 1.268 | 0.064 |
| 175 | 1.140 | 0.112 |
| 176 | 1.057 | 0.100 |
| 195 | 1.892 | 0.119 |
| 211 | 0.895 | 0.108 |
| 218 | 0.422 | 0.056 |
| 239 | 0.274 | 0.035 |
| 255 | 1.203 | 0.106 |
| 257 | 0.267 | 0.023 |
| 262 | 0.850 | 0.066 |

TABLE 10-continued

| | IC50 (μM) | |
|---|---|---|
| Example No. | MMP3 | MMP13 |
| 283 | 0.614 | 0.037 |
| 306 | 0.987 | 0.122 |
| 316 | 0.442 | 0.026 |
| 324 | 0.733 | 0.063 |
| 329 | 0.155 | 0.011 |
| 330 | 0.745 | 0.066 |
| 333 | 0.794 | 0.070 |
| 361 | 0.446 | 0.053 |
| 368 | 1.5 | 0.036 |
| 370 | 1.2 | 0.035 |
| 371 | 0.88 | 0.036 |
| 378 | >50 | 16 |
| 388 | 23 | 1.6 |
| 389 | >50 | 29 |
| 406 | 3.228 | 0.257 |
| 407 | 0.433 | 0.024 |
| 409 | 0.279 | 0.012 |
| 419 | 0.514 | 0.063 |
| 422 | >10 | 4.815 |
| 423 | 5.134 | 1.216 |
| 426 | 0.375 | 0.038 |
| 429 | 5.616 | 3.601 |
| 431 | 0.238 | 0.013 |
| 436 | 0.938 | 0.671 |
| 438 | 1.665 | 0.375 |
| 441 | 2.959 | 0.118 |

TABLE 10'

| | IC50 (μM) | |
|---|---|---|
| Example No. | MMP3 | MMP13 |
| 740 | 0.459 | 0.012 |
| 479 | 0.27 | 0.019 |
| 739 | 0.301 | 0.017 |
| 785 | 0.026 | 0.001 |
| 865 | 0.053 | 0.0049 |

TABLE 11

| | IC50 (μM) | |
|---|---|---|
| Example No. | MMP-2 | MMP-9 |
| 21 | 1.0 | >1 |
| 365 | 0.32 | 0.11 |
| 368 | 0.30 | <0.01 |
| 369 | >1 | 0.20 |

Inhibition ELISA for Tumor Necrosis Factor-α (TNF-α) Release

RAW 267.4 (derived from mouse monocytes) was seeded in RPMI1640 containing 10% of FBS (GIBCO BRL) at 100 μL/well (5×10⁵ cells/mL) onto 96-well microplates and cultured at 37° C., 5% CO₂. After culturing for 4 hours, each test compound diluted in RPMI1640 was added at 50 μL/well. 15 minutes later, 4 μg/μL LPS (DIFCO) diluted in RPMI1640 was added at 50 μL/well and cultured for 24 hours.

TNF-α produced was measured by ELISA as usual. (For example; J. Cellular Physiol. 154, 479 (1993)) Absorbance at 450 nm (normalized at 620 nm) was measured and percentage of the amount of TNF-α release for each tested compound (n=2) was determined (0% for untreated control (n=4), and 100% for LPS stimulation (n=4)).

TABLE 12

| Inhibition of TNF production | |
|---|---|
| Example No. | at 5 μM (%) |
| 365 | 20 |
| 367 | 88 |
| 368 | 30 |
| 387 | 68 |

What is claimed is:

1. A compound represented by the formula (1), or a pharmaceutically acceptable salt thereof:

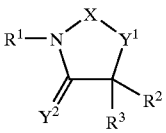

(1)

wherein

X is a group represented by the formula:

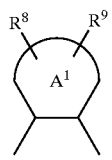

where $A^1$ is ortho-phenylene or monocyclic ortho-heteroarylene; and $R^8$ and $R^9$ are independently hydrogen, or substituents of the ortho-phenylene and the ortho-heteroarylene $Y^1$ is —O—, —S—, —S(O)— or —S(O)$_2$—;

$Y^2$ is —O— or —S—;

one of $R^1$ and $R^3$ is —(CHR$^4$)$_n$—(CR$^5$R$^6$)—CO—NHOH;

the other of $R^1$ and $R^3$ is hydrogen, optionally substituted alkyl, or optionally substituted cycloalkyl;

$R^2$ is hydrogen, optionally substituted alkyl, optionally substituted alkenyl, optionally substituted alkynyl, optionally substituted cycloalkyl, optionally substituted hetero-cycloalkyl; or $R^2$ and $R^3$ may be taken together to be optionally substituted $C_1$–$C_{10}$ alkylidene;

$R^4$, $R^5$ and $R^6$ are independently hydrogen, optionally substituted alkyl, optionally substituted alkenyl, optionally substituted alkynyl, optionally substituted alkoxy, optionally substituted alkylthio, optionally substituted cycloalkyl, optionally substituted heterocycloalkyl, optionally substituted aryl, or optionally substituted heteroaryl; or $R^5$ may be joined with $R^4$ or $R^6$ to form a ring with the carbon atom which they attach, wherein said ring is optionally substituted cycloalkane or optionally substituted heterocycloalkane;

n is an integer of 0 to 4;

wherein said cycloalkyl is C3–8 cycloalkyl containing a 0–2 carbonyl group;

said heterocycloalkyl is 5- or 6-membered heterocycloalkyl containing 1 to 5 atoms selected independently from nitrogen atoms, sulfur atoms, and oxygen atoms, wherein said sulfur atoms may be oxidized to form sulfoxide or sulfone;

said heteroaryl is mono or bicyclic 5- or 6-membered heteroaryl containing 1 to 5 atoms selected independently from nitrogen atoms, sulfur atoms, and oxygen atoms;

said ortho-heteroarylene is mono or bicyclic 5- or 6-membered ortho-heteroarylene containing 1 to 3 atoms selected independently from nitrogen atoms, sulfur atoms, and oxygen atoms;

said cycloalkane is C3–8 cycloalkane containing a 0–2 carbonyl group; said heterocycloalkane is 5- or 6-membered heterocycloalkane containing 1 to 5 atoms selected independently from nitrogen atoms, sulfur atoms, and oxygen atoms, wherein said sulfur atoms may be oxidized to form sulfoxide or sulfone;

a substituent of said substituted aryl and said substituted heteroaryl, and a substituent represented by $R^8$ and $R^9$ are selected from the group consisting of halogen; alkyl; alkenyl; alkynyl; halogenated alkyl; $-Z^1-Ar^3$; $-Z^1-Cy^1$; $-Z^1-N(Q^2)Q^1$; $-Z^1-N(Q^2)Ar^3$; $-Z^1-N(Q^2)Cy^1$; $-Z^1-NQ^4-C(NQ^3)N(Q^2)Q^1$; $-Z^1-NQ^4-C(NQ^3)N(Q^2)Ar^3$; $-Z^1-NQ^4-C(NQ^3)N(Q^2)Cy^1$; $-Z^1-NQ^3-CON(Q^2)Q^1$; $-Z^1-NQ^3-CON(Q^2)Ar^3$; $-Z^1-NQ^3-CON(Q^2)Cy^1$; $-Z^1-NQ^2-COOQ^1$; $-Z^1-NQ^2COOAr^3$; $-Z^1-NQ^2COOCy^1$; $-Z^1-OCON(Q^1)Q^2$; $-Z^1-OCON(Q^2)Ar^3$; $-Z^1-OCON(Q^2)Cy^1$; $-Z^1-OCOOQ^1$; $-Z^1-OCOOAr^3$; $-Z^1-OCOOCy^1$; $-Z^1-NQ^2-COQ^1$; $-Z^1-NQ^2COAr^3$; $-Z^1-NQ^2-COCy^1$; $-Z^1-NQ^2-SOQ^1$; $-Z^1-NQ^2-SOAr^3$; $-Z^1-NQ^2-SOCy^1$; $-Z^1-NQ^2-SO_2Q^1$; $-Z^1-NQ^2-SO_2Ar^3$; $-Z^1-NQ^2-SO_2Cy^1$; $-Z^1-OQ^1$; $-Z^1-OAr^3$; $-Z^1-O-Cy^1$; $-Z^1-OCOQ^1$; $-Z^1-OCOAr^3$; $-Z^1-OCOCy^1$; $-Z^1-COOQ^1$; $-Z^1-COOAr^3$; $-Z^1-COOCy^1$; $-Z^1-CON(Q^1)Q^2$; $-Z^1-CON(Q^2)Ar^3$; $-Z^1-CON(Q^2)Cy^1$; $-Z^1-CON(Q^2)OQ^1$; $-Z^1-CON(Q^2)OAr^3$; $-Z^1-CON(Q^2)Cy^1$; $-Z^1-COQ^1$; $-Z^1-COAr^3$; $-Z^1-CO-Cy^1$; $-Z^1-C(NQ^3)N(Q^1)Q^2$; $-C(NQ^3)N(Q^2)Ar^3$; $-Z^1-C(NQ^3)N(Q^2)Cy^1$; $-Z^1-SQ^1$; $-Z^1-SAr^3$; $-Z^1-S-Cy^1$; $-Z^1-SOQ^1$; $-Z^1-SOAr^3$; $-Z^1-SOCy^1$; $-Z^1-SO_2Q^1$; $-Z^1-SO_2Ar^3$; $-Z^1-SO_2Cy^1$; $-Z^1-SON(Q^1)Q^2$; $-Z^1-SON(Q^2)Ar^3$; $-Z^1-SON(Q^2)Cy^1$; $-Z^1-SO_2N(Q^1)Q^2$; $-Z^1-SO_2N(Q^2)Ar^3$; $-Z^1-SO_2N(Q^2)Cy^1$; $-Z^1-SO_3H$; $-Z^1-OSO_3H$; $-Z^1-NO_2$; $-Z^1-CN$; and $-CHO$;

wherein $Z^1$ is single bond, alkylene, alkenylene or alkynylene;

$Q^1$, $Q^2$, $Q^3$, $Q^4$ are independently hydrogen, alkyl, alkenyl, or alkynyl, wherein the alkyl, the alkenyl and the alkynyl are optionally substituted by one or more substituents selected from the group consisting of halogen; $-Ar^4$; $-Cy^2$; $-N(R^{21})R^{22}$; $-N(R^{22})Ar^4$; $-N(R^{22})Cy^2$; $-NR^{24}-C(NR^{23})N(R^{22})R^{21}$; $-NR^{24}-C(NR^{23})N(R^{22})Ar^4$; $-NR^{24}-C(NR^{23})N(R^{22})Cy^2$; $-NR^{23}-CON(R^{22})R^{21}$; $-NR^{23}-CON(R^{22})Ar^4$; $-NR^{23}-CON(R^{22})Cy^2$; $-NR^{22}-COOR^{21}$; $-NR^{22}-COOAr^4$; $-NR^{22}-COOCy^2$; $-OCON(R^{22})R^{21}$; $-OCON(R^{22})Ar^4$; $-OCON(R^{22})Cy^2$; $-OCOOR^{21}$; $-OCOOAr^4$; $-OCOOCy^2$; $-NR^{22}COR^{21}$; $-NR^{22}-COAr^4$; $-NR^{22}-COCy^2$; $-NR^{22}-SOR^{21}$; $-NR^{22}SOAr^4$; $-NR^{22}SOCy^2$; $-NR^{22}-SO_2R^{21}$; $-NR^{22}-SO_2Ar^4$; $-NR^{22}-SO_2Cy^2$; $-OR^{21}$; $-OAr^4$; $-OCy^2$; $-OCOR^{21}$; $-OCOAr^4$; $-OCOCy^2$; $-COOR^{21}$; $-COOAr^4$; $-COOCy^2$; $-CON(R^{21})R^{22}$; $-CON(R^{22})Ar^4$; $-CON(R^{22})Cy^2$; $-CON(R^{22})OR^{21}$; $-CON(R^{22})OAr^4$; $-CON(R^{22})OCy^2$; $-COR^{21}$; $-COAr^4$; $-COCy^2$; $-SR^{21}$; $-SAr^4$; $-SCy^2$; $-SOR^{21}$; $-SOAr^4$; $-SOCy^2$; $-SO_2R^{21}$; $SO_2Ar^4$; $-SO_2Cy^2$; $-SON(R^{22})R^{21}$; $-SON(R^{22})Ar^4$; $-SON(R^{22})Cy^2$; $-SO_2N(R^{22})R^{21}$; $-SO_2N(R^{22})Ar^4$; $-SO_2N(R^{22})Cy^2$; $SO_3H$; $-OSO_3H$; $-NO_2$; $-CN$; and $-CHO$;

or $Q^1$ may be joined with $Q^2$ or $Q^3$ to form optionally substituted heterocycloalkane, with the carbon atom with which they attach;

$Ar^3$ and $Ar^4$ are independently phenyl or heteroaryl, wherein the phenyl and the heteroaryl are optionally substituted by one or two substituents selected from the group consisting of halogen; alkyl; alkenyl; alkynyl; halogenated alkyl; $-Z^2-N(R^{25})R^{26}$; $-Z^2-NR^{28}-C(NR^{27})N(R^{26})R^{25}$; $-Z^2-NR^{27}-CON(R^{26})R^{25}$; $-Z^2NR^{26}-COOR^{25}$; $-Z^2-OCON(R^{26})R^{25}$; $-Z^2-NR^{26}-COR^{25}$; $-Z^2-NR^{26}-SOR^{25}$; $-Z^2-NR^{26}-SO_2R^{25}$; $-Z^2-OR^{25}$; $-Z^2COOR^{25}$; $-Z^2-OCOR^{25}$; $-Z^2-OCOOR^{25}$; $-Z^2-CON(R^{26})R^{25}$; $-Z^2-CON(R^{26})OR^{25}$; $-Z^2-COR^{25}$; $-Z^2-C(NR^{27})N(R^{26})R^{25}$; $-Z^2-SR^{25}$; $Z^2-SOR^{25}$; $-Z^2-SO_2R^{25}$; $-Z^2SON(R^{25})R^{26}$; $-Z^2-SO_2N(R^{26})R^{25}$; $-Z^2-SO_3H$; $-Z^2-OSO_3H$; $-Z^2-NO_2$; $-Z^2-CN$; $-CHO-O-CH_2-O-$; $-O-CH_2-CH_2-O-$; $-O-CH_2CH_2-$, $-CH_2-CH_2-O-CO-$, and $-CH_2-O-CO-$, wherein $Z^2$ is a single bond, alkylene, alkenylene or alkynylene;

$R^{21}$, $R^{22}$, $R^{23}$, $R^{24}$, $R^{25}$, $R^{26}$, $R^{27}$, and $R^{28}$ are independently hydrogen, alkyl, alkenyl, alkynyl, wherein $R^{21}$ may be joined with $R^{22}$ or $R^{23}$ to form heterocycloalkane with the carbon atom with which they attach, or $R^{25}$ may be joined with $R^{26}$ or $R^{27}$ to form heterocycloalkane with the carbon atom with which they attach;

$Cy^1$ and $Cy^2$ are independently cycloalkyl, cycloalkenyl, heterocycloalkyl, or heterocycloalkenyl, wherein the cycloalkyl, the cycloalkenyl, the heterocycloalkyl, and the heterocycloalkenyl are optionally substituted by one or two substituents which are selected from the same group as the substituents of $Ar^3$ and $Ar^4$;

a substituent of said substituted alkyl, said substituted alkenyl, said substituted alkynyl, said substituted alkoxy, said substituted alkylthio, said substituted cycloalkyl, said substituted heterocycloalkyl, and said substituted $C_1$–$C_{10}$ alkylidene is selected from the group consisting of halogen; $-Ar^5$; $-Cy^3$; $-N(Q^5)Q^6$; $-N(Q^6)Ar^5$; $-N(Q^6)Cy^3$; $-NQ^8-C(NQ^7)N(Q^6)Q^5$; $-NQ^8-C(NQ^7)-N(Q^6)Ar^5$; $-NQ^8-C(NQ^7)N(Q^6)Cy^3$; $-NQ^7-CON(Q^6)Q^5$; $-NQ^6-CON(Q^5)Ar^5$; $-NQ^7-CON(Q^6)Cy^3$; $-NQ^7-COOQ^5$; $-NQ^7-COOAr^5$; $-NQ^7-COOCy^3$; $-OCON(Q^6)^5$; $-OCON(Q^6)Ar^5$; $-OCON(Q^6)Cy^3$; $-NQ^6-COQ^5$; $-NQ^6-COAr^5$; $-NQ^6-COCy^3$; $-NQ^6SOQ^5$; $-NQ^6-SOAr^5$; $-NQ^6-SOCy^3$; $-NQ^6-SO_2Q^5$, $-NQ^6-SO_2Ar^5$; $-NQ^6-SO_2Cy^3$; $-OQ^5$; $-OAr^5$; $-OCy^3$;

—OCOQ$^5$; —OCOAr$^5$; —OCOCy$^3$; —COOQ$^5$; —COOAr$^5$; —COOCy$^3$; —OCOOQ$^5$; —OCOOAr$^5$; —OCOOCy$^3$; —CON(Q$^6$)Q$^5$; —CON(Q$^6$)Ar$^5$; —CON(Q$^6$)Cy$^3$; —CON(Q$^6$)OQ$^5$; —CON(Q$^6$)OAr$^5$; —CON(Q$^6$)OCy$^3$; —COQ$^5$; —COAr$^5$; —COCy$^3$; —SQ$^5$; —SAr$^5$; —SCy$^3$; —SOQ$^5$; —SOAr$^5$; —SOCy$^3$; —SO$_2$Q$^5$; —SO$_2$Ar$^5$; —SO$_2$Cy$^3$; —SON(Q$^6$)Q$^5$; —SON(Q$^6$)Ar$^5$; —SON(Q$^6$)Cy$^3$; —SO$_2$N(Q$^6$)Q$^5$; —SO$_2$N(Q$^6$)Ar$^5$; —SO$_2$N(Q$^6$)Cy$^3$; —SO$_3$H; —NO$_2$; and —CN;

wherein

Q$^5$, Q$^6$, Q$^7$, and Q$^8$ are independently hydrogen, alkyl, alkenyl and alkynyl wherein the alkyl, the alkenyl and the alkynyl are optionally substituted by one or more substituents selected from the group consisting of halogen; —Ar$^6$; —Cy$^4$; —N(R$^{29}$)R$^{30}$; —N(R$^{30}$)Ar$^6$; —N(R$^{30}$)Cy$^4$; —NR$^{32}$—C(NR$^{31}$)N(R$^{30}$)R$^{29}$; —NR$^{32}$—C(NR$^{31}$)N(R$^{30}$)Ar$^6$; —NR$^{32}$—C(NR$^{31}$)N(R$^{30}$)Cy$^4$; —NR$^{31}$—CON(R$^{30}$)R$^{29}$; —NR$^{31}$—CON(R$^{30}$)Ar$^6$; —NR$^{31}$—CON(R$^{30}$)Cy$^4$; —NR$^{30}$—COOR$^{29}$; —NR$^{30}$—COOAr$^6$; —NR$^{30}$—COOCy$^4$; —OCON(R$^{30}$)R$^{29}$; —OCON(R$^{30}$)Ar$^6$; —OCON(R$^{30}$)Cy$^4$; —NR$^{30}$—COR$^{29}$; —NR$^{30}$—COAr$^6$; —NR$^{30}$COCy$^4$; —NR$^{30}$—SOR$^{29}$; —NR$^{30}$—SOAr$^6$; —NR$^{30}$—SOCy$^4$; —NR$^{30}$—SO$_2$R$^{29}$; —NR$^{30}$—SO$_2$Ar$^6$; —NR$^{30}$—SO$_2$Cy$^4$; —OR$^{29}$; —OAr$^6$; —OCy$^4$; —COOR$^{29}$; —COOAr$^6$; —COOCy$^4$; —OCOR$^{29}$; —COAr$^5$; —OCOCy$^3$; —OCOOR$^{29}$; —OCOOAr$^6$; —Z$^1$—OCOOCy$^4$; —CON(R$^{30}$)R$^{29}$; —CON(R$^{30}$)Ar$^6$; —CON(R$^{30}$)Cy$^4$; —CON(R$^{30}$)OR$^{29}$; —CON(R$^{30}$)OAr$^6$; —CON(R$^{30}$)OCy$^4$; —COR$^{29}$; —COAr$^6$; —COCy$^4$; —SR$^{29}$; —SAr$^6$; —SCy$^4$; —SOR$^{29}$; —SOAr$^6$; —SOCy$^4$; —SO$_2$R$^{29}$; —SO$_2$Ar$^6$; —SO$_2$Cy$^4$; —SON(R$^{30}$)R$^{29}$; —SON(R$^{30}$)Ar$^6$; —SON(R$^{30}$)Cy$^4$; —SO$_2$N(R$^{30}$)R$^{29}$; —SO$_2$N(R$^{30}$)Ar$^6$; —SO$_2$N(R$^{30}$)Cy$^4$; —SO$_3$H; —NO$_2$; and —CN;

or Q$^5$ may be joined with Q$^6$ or Q$^7$ to form heterocycloalkane with the carbon atom with which they attach, wherein R$^{29}$, R$^{30}$, R$^{31}$, and R$^{32}$ are independently hydrogen, alkyl, alkenyl, or alkynyl;

Ar$^5$ and Ar$^6$ are independently optionally substituted aryl or optionally substituted heteroaryl;

Cy$^3$ and Cy$^4$ are independently cycloalkyl, cycloalkenyl, heterocycloalkyl, or heterocycloalkenyl, wherein the cycloalkyl, the cycloalkenyl, the heterocycloalkyl, and the heterocycloalkenyl are optionally substituted by one or two substituents which are the same as the substituent of Ar$^3$ or Ar$^4$;

a substituent of said substituted cycloalkane and said substituted heterocycloalkane is selected from the group consisting of halogen; —Ar$^5$; —Cy$^3$; —N(Q$^5$')Q$^6$'; —N(Q$^6$')Ar$^5$; —N(Q$^6$')Cy$^3$; —NQ$^8$'—C(NQ$^7$')N(Q$^6$')Q$^5$'; —NQ$^8$'—C(NQ$^7$')N(Q$^6$')Ar$^5$; —NQ$^8$'—C(NQ$^7$')N(Q$^6$')Cy$^3$; —NQ$^7$'—CON(Q$^6$')Q$^5$'; —NQ$^6$'—CON(Q$^5$')Ar$^5$; —NQ$^7$'—CON(Q$^6$')Cy$^3$; —NQ$^7$'—COOQ$^6$'; —NQ$^7$'—COOAr$^5$; —NQ$^7$'—COOCy$^3$; —OCON(Q$^6$')Q$^5$'; —OCON(Q$^6$')Ar$^5$; —OCON(Q$^6$')Cy$^3$; —NQ$^6$'—COQ$^5$'; —NQ$^6$'—COAr$^5$; —NQ$^6$'—COCy$^3$; —NQ$^6$'—SOQ$^5$'; —NQ$^6$'—SOAr$^5$; —NQ$^6$'SOCy$^3$; —NQ$^6$'—SO$_2$Q$^5$'; —NQ$^6$'—SO$_2$Ar$^5$; —NQ$^6$'—SO$_2$Cy$^3$; —OQ$^5$'; —OAr$^5$; —OCy$^3$; —OCOQ$^5$'; —OCOAr$^5$; —OCOCy$^3$; —COOQ$^5$'; —COOAr$^5$; —COOCy$^3$; —OCOOQ$^5$'; —OCOOAr$^5$; —OCOOCy$^3$; —CON(Q$^6$')Q$^5$'; —CON(Q$^6$')Ar$^5$; —CON(Q$^6$')Cy$^3$; —CON(Q$^6$')OQ$^5$'; —CON(Q$^6$')OAr$^5$; —CON(Q$^6$')OCy$^3$; —COQ$^5$'; —COAr$^5$; —COCy$^3$; —SQ$^5$'; —SAr$^5$; —SCy$^3$; —SOQ$^5$'; —SOAr$^5$; —SOCy$^3$; —SO$_2$Q$^5$'; —SO$_2$Ar$^5$; —SO$_2$Cy$^3$; —SON(Q$^6$')Q$^5$'; —SON(Q$^6$')Ar$^5$; —SON(Q$^6$')Cy$^3$; —SO$_2$N(Q$^6$')Q$^5$'; —SO$_2$N(Q$^6$')Ar$^5$; —SO$_2$N(Q$^6$')Cy$^3$; —SO$_3$H; —NO$_2$; and —CN;

wherein

Q$^{5'}$, Q$^{6'}$, Q$^{7'}$, and Q$^{8'}$ are independently hydrogen, alkyl, alkenyl or alkynyl;

Ar$^5$, Ar$^6$, Cy$^3$, and Cy$^4$ are the same as defined above.

2. The compound according to claim 1 or a pharmaceutically acceptable salt thereof, wherein Y$^1$ is —S—, —S(O)— or —S(O)$_2$—.

3. The compound according to claim 1 or a pharmaceutically acceptable salt thereof, wherein n is 0, 1 or 2.

4. The compound according to claim 1 or a pharmaceutically acceptable salt thereof, wherein n is 0.

5. The compound according to claim 1, or a pharmaceutically acceptable salt thereof, wherein Y$^2$ is —O—.

6. A pharmaceutical composition comprising a compound according to claim 1, or a pharmaceutically acceptable salt thereof, and a pharmaceutically acceptable carrier or diluent.

7. The compound according to claim 1, wherein

R$^1$ is —(CHR$^4$)$_n$—(CR$^5$R$^6$)—CONHOH;

R$^2$ is optionally substituted alkyl;

R$^3$ is hydrogen or optionally substituted alkyl; and n is 0, 1 or 2.

8. A method of treating osteo-arthritis or rheumatoid arthritis associated with increased levels of matrix metalloproteinases which comprises administering to a patient an effective amount of the compound of claim 1, or a pharmaceutically acceptable salt thereof, and a pharmaceutically acceptable carrier or diluent.

* * * * *